(12) United States Patent
Ogoshi

(10) Patent No.: US 7,640,115 B2
(45) Date of Patent: Dec. 29, 2009

(54) DIAGNOSTIC METHOD OF SELECTING APPROPRIATE CANCER TREATMENTS AND SCREENING METHOD OF MEASURING REAGENTS AND CURATIVE MEDICINES FOR CANCER PATIENTS

(76) Inventor: Kyoji Ogoshi, 408-26, Kamitsuruma, Sagamihara-shi, Kanagawa 228-0802 (JP)

(*) Notice: Subject to any disclaimer, the term of this patent is extended or adjusted under 35 U.S.C. 154(b) by 138 days.

(21) Appl. No.: 10/681,352

(22) Filed: Oct. 8, 2003

(65) Prior Publication Data
US 2004/0121378 A1  Jun. 24, 2004

Related U.S. Application Data

(63) Continuation of application No. PCT/JP02/02894, filed on Mar. 26, 2002.

(30) Foreign Application Priority Data

| Apr. 10, 2001 | (JP) | ............................. 2001-111856 |
| Sep. 4, 2001 | (JP) | ............................. 2001-267524 |

(51) Int. Cl.
| G06F 19/00 | (2006.01) |
| C12Q 1/00 | (2006.01) |
| G06F 17/50 | (2006.01) |
| G01N 33/48 | (2006.01) |

(52) U.S. Cl. .................. 702/20; 435/4; 435/3; 702/19; 703/1

(58) Field of Classification Search ..................... 435/4, 435/326, 455, 344; 424/573
See application file for complete search history.

(56) References Cited

U.S. PATENT DOCUMENTS

| 5,579,250 | A | * | 11/1996 | Balaji et al. .................... 702/19 |
| 5,642,292 | A | * | 6/1997 | Itai et al. ...................... 702/27 |
| 5,972,604 | A | * | 10/1999 | Santamaria et al. ............ 435/6 |
| 2004/0121378 | A1 | * | 6/2004 | Ogoshi .......................... 435/6 |

OTHER PUBLICATIONS

Sasazuki et al; New England Journal of Medicine; vol. 339(17), pp. 1177-1185; (Oct. 22, 1998).*
Rigas, B., Gastroenterology, vol. 111, pp. 523-526, 1996.*
Gorski et. al. J. Immunol., vol. 143, pp. 329-333, 1989.*
Hou et al. Curr. Pharmaceut. Design vol. 10, pp. 1011-1033, 2004.*
Kierzek et al., Biophys. Chem., vol. 91, pp. 1-20, 2001.*
Wiencek, Annu. Rev. Biomed. Eng., vol. 1, pp. 505-534, 1999.*
Ke & Doudna, Methods, vol. 34, pp. 408-414, 2004.*
Derewenda et al. Acta Crystallogr. D., vol. 62, pp. 116-124, 2006.*
Buts et al. Acta Crystallogr. D., vol. 61, pp. 1149-1159, 2005.*
López-Jaramillo et al. Acta Crystallogr. F., vol. 61, pp. 435-438, 2005.*
Skarzynski et al. Acta Crystallogr. D., vol. 62, pp. 102-107, 2006.*
Davies et al. J. Clinical Oncology, vol. 19, pp. 1279-1287, 2001.*
Lee et al. Gastroenterology, vol. 111, pp. 426-432, 1996.*
Toh et al. Protein Engineering, vol. 11, pp. 1027-1032, 1998.*
Gibbs et al. Science. vol. 287, pp. 1969-1973, 2000.*
Bateman et al., Human Leukocyte Antigens and Cancer: Is It In Our Genes?, 1999, Journal of Pathology, vol. 188, pp. 231-236.*
http://www.ncbi.nlm.nih.gov/entrez/viewer.fcgi?val=X97406.1.*
F. Lv et al., Identification of a novel HLA-DPB1 allele—DPB1*0102, Key Laboratory of Genetic Engineer of MOE, Department of Biochemistry, College of Life Sciences, 2004, 3 pages.*
International Search Report for PCT/JP02/02894.
Kyoji Ogoshi, "Atarashii Shuyo Maker", Japanese Journal of Clinical Medicine, Apr. 30, 2001, vol. 59, Suppl. 4, pp. 513-520.
Kyoji Ogoshi et al., "HLA Idenshi Joho ni Motozuita Geka Chiryo Senryaku", Journal of Japan Surgical Society, 2000, vol. 101, special extra issue, p. 56.
K. Ogoshi et al., HLA-A2 Antigen Status Predicts Metastasis and Response to Immunotherapy in Gastric Cancer, Cancer Immunol. Immunother., 1997, vol. 45, No. 1, pp. 53-59.
Kyogo Ito et al., "Genome Tayosei to Kino Kaiseki MHC-Tagata to Shikkan Kanjusei HLA-Tagata to Gan Chiryo Yadonushi Meneki Kino o Jushi sita Gan Chiryoho no Kakuritsu ni Mukete", Mol. Med., 2000, vol. 37, No. 5, pp. 590-596.
Kim, C.J., et al., Immunodominance across HLA Polymorphism: Implications for Cancer Immunotherapy, J. Immunother., 1998, vol. 21, No. 1, pp. 1-16.
Kyoji Ogose et al., "PSK no Shokakigan (Shokudo, I) ni okeru Rinsho Koka", Journal of Japan Surgical Society, p. 1443-1446, 1989.

* cited by examiner

Primary Examiner—Michael Borin
Assistant Examiner—Jason M Sims
(74) Attorney, Agent, or Firm—Kilyk & Bowersox, P.L.L.C.

(57) ABSTRACT

A method is provided to study gene function based on variations of the amino acids and the base sequences at specific positions on HLA genes which have polymorphisms and codon usage Medical industry applications for the method are also provided. The amino acid position(s) of the polymorphic amino acid(s) in amino acid sequence(s), including at least one of DRB1*gene, DQB1*gene, and DPB1*gene of HLA, is determined, the variation of the base sequences coding polymorphic positions of the amino acid and survival results with anticancer treatments after cancer resections, and survival results (prognosis, treatment effects) are analyzed, and the statistical relationship of the specific positions of the amino acids and the treatments is determined.

1 Claim, 129 Drawing Sheets

Fig. 1

| DQ | | Position 57 | | Position 67 | |
|---|---|---|---|---|---|
| | | Nucleotide | Amino Acid | Nucleotide | Amino Acid |
| | DQB1*0201 | GCC | A | ATC | I |
| | DQB1*03011 | GAC | D | GTC | V |
| | DQB1*03012 | GAC | D | GTC | V |
| | DQB1*0302 | GCC | A | GTC | V |
| | DQB1*03032 | GAC | D | GTC | V |
| | DQB1*03033 | GAC | D | GTC | V |
| | DQB1*0401 | GAC | D | ATC | I |
| | DQB1*0402 | GAC | D | ATC | I |
| | DQB1*0501 | GTT | V | GTC | V |
| | DQB1*0502 | AGC | S | GTC | V |
| | DQB1*05031 | GAC | D | GTC | V |
| | DQB1*05032 | GAT | D | GTC | V |
| | DQB1*06011 | GAC | D | ATC | I |
| | DQB1*06012 | GAC | D | ATC | I |
| | DQB1*06013 | GAC | D | ATC | I |
| | DQB1*0602 | GAT | D | GTC | V |
| | DQB1*0603 | GAT | D | GTC | V |
| | DQB1*06041 | GTT | V | GTC | V |
| | DQB1*06042 | GTT | V | GTC | V |
| | DQB1*06051 | GTT | V | GTC | V |
| | DQB1*06052 | GTT | V | GTC | V |

Fig. 2

| DRB1*0801 | AGC | S | TTC | F |
|---|---|---|---|---|
| DRB1*08021 | GAT | D | TTC | F |
| DRB1*08022 | GAT | D | TTC | F |
| DRB1*0803 | AGC | S | ATC | I |
| DRB1*08041 | GAT | D | TTC | F |
| DRB1*08042 | GAT | D | TTC | F |
| DRB1*08043 | GAT | D | TTC | F |
| DRB1*09012 | GTC | V | TTC | F |
| DRB1*10011 | GAT | D | CTC | L |
| DRB1*10012 | GAT | D | CTC | L |
| DRB1*111011 | GAT | D | TTC | F |
| DRB1*111012 | GAT | D | TTC | F |
| DRB1*111013 | GAT | D | TTC | F |
| DRB1*11102 | GAT | D | ATC | I |
| DRB1*11103 | GAT | D | TTC | F |
| DRB1*111041 | GAT | D | TTC | F |
| DRB1*111042 | GAT | D | TTC | F |
| DRB1*1201 | GTC | V | ATC | I |
| DRB1*12021 | GTC | V | TTC | F |
| DRB1*12022 | GTC | V | TTC | F |
| DRB1*1301 | GAT | D | ATC | I |
| DRB1*13021 | GAT | D | ATC | I |
| DRB1*13022 | GAT | D | ATC | I |

Fig. 3

| DRB1*1303 | AGC | S | ATC | I |
|---|---|---|---|---|
| DRB1*1304 | AGC | S | ATC | I |
| DRB1*1305 | GAT | D | TTC | F |
| DRB1*14011 | GCT | A | CTC | L |
| DRB1*14012 | GCT | A | CTC | L |
| DRB1*1402 | GAT | D | CTC | L |
| DRB1*1403 | GAT | D | CTC | L |
| DRB1*1404 | GCT | A | CTC | L |
| DRB1*1405 | GAT | D | CTC | L |
| DRB1*1406 | GAT | D | CTC | L |
| DRB1*1407 | GCT | A | CTC | L |
| DRB1*1408 | GAT | D | CTC | L |
| DRB1*15011 | GAC | D | TTC | F |
| DRB1*15012 | GAC | D | TTC | F |
| DRB1*15021 | GAC | D | ATC | I |
| DRB1*15022 | GCC | D | ATC | I |
| DRB1*15023 | GAC | D | ATC | I |
| DRB1*16011 | GAC | D | TTC | F |
| DRB1*16012 | GAC | D | TTC | F |
| DRB1*16021 | GAC | D | CTC | L |
| DRB1*16022 | GAC | D | CTC | L |

Fig. 41

5-year Survival Comparison

|   | DR |   |    | DQ |   |    | DP |   |
|---|---|---|---|---|---|---|---|---|
| % | APR_25 = RR | 0.8333 |   |   |   |   |   |   |
|   |   |   | * | AQP_21 = GG | 0.8782 |   |   |   |
| % | ARP_17 = AA | 0.8333 |   |   |   |   |   |   |
| % | ARP_16 = VV | 0.8333 | * | AQP_6 = TT | 0.8782 |   |   |   |
| % | ARP10 = YY | 0.7684 | * | AQP_4 = VV | 0.8782 |   |   |   |
| * | ARP11 = DS | 0.8394 | %@ | AQP3 = SS | 0.7644 |   |   |   |
| * | ARP13 = GH | 0.8375 | % | AQP23 = LR | 0.7789 |   |   |   |
| * | ARP26 = FL | 0.7981 | % | AQP30 = HH | 0.8247 |   |   |   |
| % | ARP32 = HH | 0.8228 | %@ | AQP37 = YY | 0.7661 |   |   |   |
|   |   |   | % | AQP53 = LL | 0.7965 |   | APP55 = AD | 0.8095 |
| @ | ARP57 = AV | 1 | % | AQP56 = LP | 0.7847 | % | APP65 = IL | 0.8618 |
| % | ARP67 = FF | 0.9444 | % | AQP66 = DE | 0.7786 | % | APP69 = EK | 0.7985 |
| * | ARP67 = IL | 0.8106 | %* | AQP66 = EE | 0.7535 |   |   |   |
| % | ARP73 = AA | 0.7554 | % | AQP67 = IV | 0.7786 |   |   |   |
| % | ARP78 = VV | 0.9 | % | AQP74 = ES | 0.799 |   |   |   |
| % | ARP86 = VV | 0.8618 | %@ | AQP75 = LV | 0.7963 |   |   |   |
| % | ARP96 = HY | 0.9 | % | AQP84 = QQ | 0.7965 | % | APP178 = LM | 0.8261 |
| * | ARP96 = HY | 0.79 | % | AQP85 = LL | 0.7965 |   |   |   |
| % | ARP98 = EK | 0.7846 | * | AQP87 = FY | 0.7922 |   |   |   |
| % | ARP104 = AA | 0.8355 | % | AQP89 = TT | 0.7965 |   |   |   |
| %@ | ARP133 = RR | 0.7774 | % | AQP90 = TT | 0.7965 |   |   |   |
| %@ | ARP142 = VV | 0.7774 | % | AQP125 = GS | 0.8179 |   |   |   |
| % | ARP189 = RR | 0.7328 | % | AQP140 = TT | 0.7957 |   |   |   |
|   |   |   | % | AQP182 = NN | 0.7957 |   |   |   |
|   |   |   | % | AQP185 = II | 0.8136 |   |   |   |
|   |   |   | %@ | AQP197 = SS | 0.7644 |   |   |   |
|   |   |   | % | AQP220 = HH | 0.7965 |   |   |   |
|   |   |   | % | AQP221 = HH | 0.7965 |   |   |   |

No marked   High survival rate
@   High survival rate and significant difference (+)
*   Low survival rate but significant difference (+)
%   Common in all cancer

Fig. 42

|   | DR |   |   | DQ |   |   | DP |   |
|---|---|---|---|---|---|---|---|---|
| % | APR_25 = RR | 0.8571 |   |   |   |   |   |   |
| % | ARP_17 = AA | 0.8571 |   |   |   |   |   |   |
| % | ARP_16 = VV | 0.8571 |   |   |   |   |   |   |
| % | APR9 = WW | 0.7109 | % | AQP3 = PS | 0.6237 |   |   |   |
| % | APR16 = YY | 0.6563 | %@ | AQP9 = LY | 0.6501 |   |   |   |
| * | ARP37 = LY | 0.7202 | % | AQP13 = AA | 0.6568 |   |   |   |
| @ | ARP57 = AV | 1 | %@ | AQP37 = DY | 0.628 |   |   |   |
| * | APR60 = YY | 0.5806 | % | AQP45 = EG | 0.6029 |   |   |   |
| * | APR67 = FI | 0.6366 | % | AQP56 = PP | 0.5597 | % | APP57 = DE | 0.6016 |
| % | APR70 = DD | 0.6583 | %@ | AQP66 = DE | 0.6298 |   |   |   |
| % | APR74 = LL | 0.7857 | %@ | AQP67 = IV | 0.6298 | % | APP84 = DG | 0.5565 |
| % | APR86 = GV | 0.5752 | % | AQP126 = HQ | 0.6046 | % | APP85 = EG | 0.5565 |
| % | APR120 = NN | 0.8 | % | AQP130 = RR | 0.5593 | % | APP87 = MV | 0.5565 |
|   |   |   |   |   |   |   |   |   |
| % | APR140 = TT | 0.6635 |   |   |   |   |   |   |
| % | APR149 = HH | 0.6717 | % | AQP167 = HH | 0.6568 |   |   |   |
|   |   |   | % | AQP185 = TT | 0.6213 |   |   |   |
|   |   |   | % | AQP197 = NS | 0.6237 |   |   |   |

No marked   High survival rate
@   High survival rate and significant difference (+)
*   Low survival rate but significant difference (+)
%   Common in all cancer

Fig. 43

| | DR | | | DQ | | | DP | |
|---|---|---|---|---|---|---|---|---|
| % | ARP_25 = RR | 0.7143 | % | AQP_21 = GG | 0.6208 | | | |
| %@ | ARP_17 = AA | 0.7143 | % | AQP_6 = TT | 0.6208 | | | |
| | | | %@ | AQP_5 = PP | 0.6208 | | | |
| % | ARR_1 = AA | 0.5833 | % | AQP_4 = VV | 0.6208 | | | |
| % | ARP4 = QR | 0.6692 | | | | | | |
| @ | ARP9 = KW | 0.8667 | * | AQP9 = YY | 0.6315 | | | |
| %@ | ARP11 = DP | 0.8462 | % | AQP13 = GG | 0.6271 | | | |
| * | ARP13 = FS | 0.7826 | % | AQP14 = LM | 0.6486 | | | |
| * | ARP26 = FL | 0.5386 | % | AQP23 = RR | 0.5781 | | | |
| * | ARP31 = FF | 0.5618 | %@ | AQP30 = HY | 0.6919 | % | APP36 = AV | 0.7225 |
| * | ARP31 = FI | 0.5981 | %@ | AQP57 = AA | 1 | | | |
| @ | ARP33 = HH | 0.8125 | @ | AQP66 = EE | 0.6043 | | | |
| @ | ARP37 = NS | 0.7281 | @ | AQP67 = VV | 0.6043 | | | |
| % | ARP38 = VV | 0.5842 | % | AQP71 = AT | 0.6808 | % | APP76 = IM | 0.667 |
| @ | ARP40 = FF | 0.5769 | % | AQP74 = ES | 0.5884 | | | |
| @ | ARP57 = AAV | 1 | % | AQP77 = RT | 0.6548 | | | |
| % | ARP60 = HS | 0.8 | % | AQP84 = QQ | 0.6117 | | | |
| * | ARP67 = FL | 0.6649 | @ | AQP86 = EG | 0.786 | | | |
| @ | ARP71 = ER | 0.7432 | @ | AQP87 = LY | 0.7151 | | | |
| @ | ARP74 = AE | 0.6849 | % | AQP116 = IV | 0.6486 | | | |
| % | ARP78 = VY | 0.6635 | | | | | | |
| % | ARP85 = VV | 0.581 | %@ | AQP130 = QR | 0.7567 | | | |
| % | ARP86 = GG | 0.5924 | | | | | | |
| % | ARP98 = EK | 0.6531 | | | | | | |
| % | ARP104 = AS | 0.6531 | % | AQP167 = RR | 0.6271 | | | |
| | | | % | AQP224 = QR | 0.6486 | | | |
| % | ARP120 = SS | 0.597 | | | | | | |
| % | ARP133 = RR | 0.592 | | | | | | |
| % | APR142 = VV | 0.592 | | | | | | |
| % | APR149 = HH | 0.619 | | | | | | |
| @ | ARP166 = RR | 0.5791 | | | | | | |
| %@ | ARP231 = QQ | 0.5848 | | | | | | |

No mark  High survival rate
@  High survival rate and significant difference (+)
*  Low survival rate but significant difference (+)
%  Common in all cancer

Fig. 44

| | | | | | No. | | Chemotherapy | Immunotherapy |
|---|---|---|---|---|---|---|---|---|
| Stomach Cancer | DP36 | A | | | | | | |
| Stomach Cancer | DP36 | V | | | | | | |
| Stomach Cancer | DP65 | I | | | | | | |
| Stomach Cancer | DP65 | L | | | | | | |
| Stomach Cancer | DP69 | E | | | Hetero>homo, (-) | | | (-), hetero>homo |
| Stomach Cancer | DP69 | K | | | Hetero>homo, (-) | | | (-), hetero>homo |
| Stomach Cancer | DP8 | L | DP9 | F | | | | |
| Stomach Cancer | DP8 | V | | | | | | |
| Stomach Cancer | DP9 | H | | | | | | (-) homo>hetero |
| | | | | | | | | |
| Other cancers | DP36 | A | | | | | | |
| Other cancers | DP36 | V | | | | | | |
| Other cancers | DP65 | I | | | | | | |
| Other cancers | DP65 | L | | | | | | |
| Other cancers | DP69 | E | | | Hetero>homo | | | |
| Other cancers | DP69 | K | | | | | | |
| Other cancers | DP8 | L | DP9 | F | DP11 | G | | |
| Other cancers | DP8 | V | | | DP11 | L | | |
| Other cancers | DP9 | H | | | homo, hetero>(+) | | | |
| | | | | | Hetero (-)>homo | | | |

Stomach and Other cancerss are at the same survival rate.

Fig. 45

| | | | | | | | | | No. | Chemotherapy | Immunotherapy |
|---|---|---|---|---|---|---|---|---|---|---|---|
| Stomach Cancer | DR_25 | K | | | | | | | | | |
| Stomach Cancer | DR_25 | R | | | | | | | | | |
| Stomach Cancer | DR_24 | F | | | | | | | | | |
| Stomach Cancer | DR_24 | L | | | | | | | | | |
| Stomach Cancer | DR_17 | A | | | | | | | | | |
| Stomach Cancer | DR_17 | T | | | | | | | | | |
| Stomach Cancer | DR_16 | A | | | | | | | | | |
| Stomach Cancer | DR_16 | V | | | | | | | | | |
| Stomach Cancer | DR_1 | S | | | | | | | | | |
| Stomach Cancer | DR_1 | A | | | | | | | | | |
| Stomach Cancer | DR4 | Q | | | | | | | | | |
| Stomach Cancer | DR4 | R | | | | | | | | | |
| Stomach Cancer | DR9 | K | | | | | | | | | |
| Stomach Cancer | DR9 | E | DR11 | D | DR26 | Y | DR28 | H | DR30 | G | homo,hetero>(-) | (-),homo>hetero | E homo,((-)>hetero |
| Stomach Cancer | DR10 | Q | | | | | | | | | |
| Stomach Cancer | DR10 | Y | | | | | | | | | |
| Stomach Cancer | DR10 | E | DR31 | V | DR38 | A | DR40 | Y | (DR166) | Q | (-)>hetero | Same | (-)>hetero |
| Stomach Cancer | | | | | | | | | (DR166) | R | (-)>hetero | Same | (-)>hetero |
| Stomach Cancer | DR11 | S | DR12 | K | | | | | | | | |
| Stomach Cancer | | | DR12 | T | | | | | | | | |
| Stomach Cancer | DR11 | G | DR13 | Y | DR14 | E | DR25 | Q | DR30 | L | | | |
| Stomach Cancer | | | | | DR14 | K | DR25 | R | | | | | |
| Stomach Cancer% | DR11 | V | | | | | | | | | Same | (-),homo>hetero | V homo>((-)>hetero |
| Stomach Cancer | DR11 | P | DR13 | R | | | | | | | | | |
| Stomach Cancer | DR13 | F | | | | | | | | | | | |
| Stomach Cancer | DR13 | F | DR31 | F | | | | | | | | | |
| Stomach Cancer | | | DR31 | I | | | | | | | | | |
| Stomach Cancer% | DR13 | H | | | | | | | | | Same | (-),homo>hetero | V homo>((-)>hetero |
| Stomach Cancer | DR13 | S | | | | | | | | | Same | Hetero,((+))>homo | Hetero,(+)>L.homo |
| Stomach Cancer | DR26 | L | | | | | | | | | | | |
| Stomach Cancer | DR26 | F | | | | | | | | | | | |
| Stomach Cancer | DR28 | H | DR30 | G | | | | | | | Homo>hetero,(-) | Hetero,((+))>homo | Hetero,(+)>E.homo |
| Stomach Cancer | DR28 | E | | | | | | | | | | | |
| Stomach Cancer | DR28 | D | | | | | | | | | | | |

Fig. 46

| | | | | | | | | | No. | Chemotherapy | Immunotherapy |
|---|---|---|---|---|---|---|---|---|---|---|---|
| Stomach Cancer | DR30 | H | DR37 | L | DR38 | L | DR85 | A | | | |
| Stomach Cancer | | | | | | | DR85 | V | | | |
| Stomach Cancer | DR31 | V | DR38 | A | DR40 | F | | | | | |
| Stomach Cancer | | | | | DR40 | Y | | | | | |
| Stomach Cancer | DR32 | H | | | | | | | | | |
| Stomach Cancer | DR32 | Y | | | | | | | Same | (-),homo>hetero | H homo,(-)>hetero |
| Stomach Cancer | DR33 | H | | | | | | | | | |
| Stomach Cancer | DR33 | N | | | | | | | Same | (-),homo>hetero | N homo,((-))>hetero |
| Stomach Cancer | DR37 | F | | | | | | | | | |
| Stomach Cancer | DR37 | S | | | | | | | | | |
| Stomach Cancer | DR47 | F | | | | | | | | | |
| Stomach Cancer | DR47 | Y | | | | | | | Same | (-)>hetero>homo | Hetero>(-) |
| Stomach Cancer | DR57 | A | | | | | | | Same | Hetero,((-))>homo | ((-),hetero)>homo |
| Stomach Cancer | DR57 | S | | | | | | | | | |
| Stomach Cancer | DR58 | A | | | | | | | | | |
| Stomach Cancer | DR58 | E | | | | | | | | | |
| Stomach Cancer | DR60 | H | | | | | | | | | |
| Stomach Cancer | DR67 | I | | | | | | | I homo>hetero,(-) | homo>hetero,(-) | (-)>homo,hetero |
| Stomach Cancer# | DR67 | L | | | | | | | Hetero,((-))>homo | L(-),homo>hetero | Homo>hetero,(-) |
| Stomach Cancer | DR70 | D | | | | | | | Hetero,(homo)>(-) | Homo>hetero,(-) | Homo>hetero,(-) |
| Stomach Cancer | DR73 | A | DR74 | R | DR77 | N | | | A homo>hetero | A homo>hetero | Hetero>homo |
| Stomach Cancer | DR73 | G | DR74 | N | DR77 | T | | | (-),homo>hetero | Same | Hetero,(-)>Ehomo |
| Stomach Cancer | DR74 | A | | | | | | | (-),homo>hetero | Same | Hetero,(-)>Ehomo |
| Stomach Cancer | DR78 | V | | | | | | | | | |
| Stomach Cancer | DR45 | Y | | | | | | | | | |
| Stomach Cancer | DR85 | A | | | | | | | | | |
| Stomach Cancer | DR85 | V | | | | | | | | | |
| Stomach Cancer | DR86 | G | | | | | | | | | |
| Stomach Cancer | DR86 | V | | | | | | | | | |
| Stomach Cancer | DR96 | Q | | | | | | | | | |
| Stomach Cancer | DR98 | E | DR10 | A | | | | | | | |
| Stomach Cancer | DR98 | K | DR10 | S | | | | | | | |
| Stomach Cancer | DR120 | S | | | | | | | | | |
| Stomach Cancer | DR120 | N | | | | | | | | | |

Fig. 47

| | | | | | | | | | No. | Chemotherapy | Immunotherapy |
|---|---|---|---|---|---|---|---|---|---|---|---|
| Stomach Cancer | DR133 | L | | | | | | | | | |
| Stomach Cancer | DR133 | R | DR14 | M | | | | | | | |
| Stomach Cancer | DR149 | H | DR14 | V | | | | | | | (-)>hetero |
| Stomach Cancer | DR149 | Q | | | | | | | | | (-)>hetero |
| Stomach Cancer | DR166 | Q | | | | | | | (-)>hetero | Same | |
| Stomach Cancer | DR166 | R | | | | | | | (-)>hetero | Same | |
| Stomach Cancer | DR180 | L | | | | | | | | | |
| Stomach Cancer | DR180 | V | | | | | | | | | |
| Stomach Cancer | DR189 | R | | | | | | | | | |
| Stomach Cancer | DR189 | S | | | | | | | | | |
| Stomach Cancer | DR231 | P | | | | | | | | | |
| Stomach Cancer | DR231 | Q | | | | | | | | | |
| Stomach Cancer | DR233 | R | | | | | | | | | |
| Stomach Cancer | DR233 | T | | | | | | | | | |
| Other cancers | DR_25 | K | | | | | | | | | |
| Other cancers | DR_25 | R | | | | | | | | | |
| Other cancers | DR_24 | F | | | | | | | | | |
| Other cancers | DR_24 | L | | | | | | | | | |
| Other cancers | DR_17 | A | | | | | | | | | |
| Other cancers | DR_17 | T | | | | | | | | | |
| Other cancers | DR_16 | A | | | | | | | | | |
| Other cancers | DR_16 | V | | | | | | | | | |
| Other cancers | DR_1 | S | | | | | | | | | |
| Other cancers | DR_1 | A | | | | | | | | | |
| Other cancers | DR4 | Q | | | | | | | | | |
| Other cancers | DR4 | R | | | | | | | | | |
| Other cancers | DR9 | K | DR11 | D | DR26 | Y | DR28 | H | DR30 | G | |
| Other cancers | DR9 | W | | | | | | | | hetero,(-)>homo | homo>hetero,(-) |
| Other cancers | DR10 | Q | | | | | | | | | hetero,(homo)>(-) |

Fig. 48

| | | | | | | | No. | Chemotherapy | Immunotherapy |
|---|---|---|---|---|---|---|---|---|---|
| Other cancers | DR10 | Y | | | | | | | |
| Other cancers | DR11 | S | DR12 | K | | | | | |
| Other cancers | | | DR12 | T | | | | | |
| Other cancers | DR11 | G | DR13 | Y | DR14 | E | | | |
| Other cancers | | | | | DR14 | K | | | |
| Other cancers% | DR11 | P | DR13 | R | | | hetero,(-)>homo | Same | homo>hetero,(-) |
| Other cancers | DR13 | S | | | | | homo,(-)>hetero | hetero,(-)>homo | hetero,(-)>homo |
| Other cancers | DR26 | F | | | | | Same | (-),(hetero)>homo | homo,hetero>(-) |
| Other cancers | DR28 | H | DR30 | G | | | | | |
| Other cancers | DR28 | D | | | | | Same | (-),hetero>homo | homo,(-)>hetero |
| Other cancers | DR30 | H | DR37 | L | DR38 | L | | | |
| Other cancers | DR31 | V | DR38 | A | DR40 | F | | | |
| Other cancers | | | | | DR40 | Y | | | |
| Other cancers | DR32 | H | | | | | homo,(-)>hetero | (-),(hetero)>homo | (-),(hetero)>homo |
| Other cancers | DR32 | Y | | | | | homo,(-)>hetero | (-),(hetero)>homo | (-),(hetero)>homo |
| Other cancers | DR33 | H | | | | | | | |
| Other cancers | DR33 | N | | | | | | | |
| Other cancers | DR37 | F | | | | | Same | (-)>hetero>homo | hetero>(-) |
| Other cancers | DR37 | S | | | | | (-),hetero>homo | homo>hetero,(-) | hetero,((-))>homo |
| Other cancers | DR38 | L | | | | | | | |
| Other cancers | DR38 | V | | | | | | | |
| Other cancers | DR47 | F | | | | | | | |
| Other cancers | DR47 | Y | | | | | | | |
| Other cancers | DR57 | A | | | | | Same | (-)>hetero>homo | hetero>(-) |
| Other cancers | DR57 | S | | | | | Same | hetero,((-))>homo | (-),(hetero)>homo |
| Other cancers | DR58 | A | | | | | | | |
| Other cancers | DR58 | E | | | | | | | |
| Other cancers | DR60 | H | | | | | Same | hetero,((-))>homo | hetero>(-) |
| Other cancers | DR71 | A | | | | | | | Same |
| Other cancers | DR73 | A | DR74 | R | DR77 | T | (-)>hetero>homo | (-)>hetero>homo | homo>hetero,(-) |
| Other cancers | DR73 | G | DR74 | N | DR77 | N | | | |
| Other cancers | DR74 | L | | | | | hetero,(-)>homo | homo,(-)>hetero | homo>hetero,(-) |
| Other cancers | DR78 | V | | | | | | | |
| Other cancers | DR78 | Y | DR85 | A | | | | | |
| Other cancers | DR85 | A | DR85 | V | | | | | |

Fig. 49

| | | | | | No. | Chemotherapy | Immunotherapy |
|---|---|---|---|---|---|---|---|
| Other cancers | DR85 | V | | | | | |
| Other cancers | DR86 | G | | | Same | hetero,homo>(-) | homo,hetero>(-) |
| Other cancers | DR86 | V | | | Same | hetero,homo>(-) | homo,hetero>(-) |
| Other cancers | DR96 | Q | | | (-)hetero>homo | Same | hetero,((-))>homo |
| Other cancers | DR98 | E | DR10 | A | hetero,(homo)>(-) | Same | (-),hetero>homo |
| Other cancers | DR98 | K | DR10 | S | hetero,(homo)>(-) | Same | (-),hetero>homo |
| Other cancers | DR120 | N | | | | | |
| Other cancers | DR120 | S | | | | | |
| Other cancers | DR133 | L | DR14 | V | (-)hetero>homo | Same | Same |
| Other cancers | DR133 | R | DR14 | M | (-)hetero>homo | Same | Same |
| Other cancers | DR149 | Q | | | | | |
| Other cancers | DR149 | H | | | | | |
| Other cancers | DR166 | Q | | | | | |
| Other cancers | DR166 | R | | | | | |
| Other cancers | DR180 | L | | | | | |
| Other cancers | DR180 | V | | | | | |
| Other cancers | DR189 | R | | | | | |
| Other cancers | DR189 | S | | | | | |
| Other cancers | DR231 | P | | | | | |
| Other cancers | DR231 | Q | | | | | |
| Other cancers | DR233 | R | | | Same | hetero,(-)>homo | |
| Other cancers | DR233 | T | | | | | (-),hetero>homo |

Fig. 50

| | | | | | | | | | No. | Chemotherapy | Immunotherapy |
|---|---|---|---|---|---|---|---|---|---|---|---|
| Stomach Cancer | DQ14 | L | | | | | | | | | |
| Stomach Cancer | DQ14 | M | | | | | | | | | |
| Stomach Cancer | DQ23 | L | | | | | | | | | |
| Stomach Cancer | DQ23 | R | | | | | | | | | |
| Stomach Cancer | DQ28 | S | DQ30 | S | DQ37 | I | | | | | |
| Stomach Cancer | DQ28 | T | | | DQ37 | L | | | | | |
| Stomach Cancer | DQ3 | P | DQ9 | | (Although there are not much samples, it is almost the same) | D | DQ46 | V | DQ47 | F | DQ52 | P |
| Stomach Cancer | DQ3 | | | | | | DQ46 | E | DQ47 | Y | DQ52 | L | DQ55 | L |
| Stomach Cancer | DQ30 | Y | | | | | | | | | |
| Stomach Cancer | DQ30 | H | | | | | | | | | |
| Stomach Cancer | DQ38 | A | | | | | | | | hetero>(-) homo | |
| Stomach Cancer | DQ38 | V | | | | | | | | hetero>(-) homo | hetero>(-)>homo |
| Stomach Cancer | DQ45 | E | | | | | | | | | Hetero>(->homo (Differs from 30Y) |
| Stomach Cancer | DQ45 | G | | | | | | | | | |
| Stomach Cancer | DQ53 | L | | | | | | | | | |
| Stomach Cancer | DQ53 | Q | | | | | | | | | |
| Stomach Cancer | DQ55 | P | | | | | | | | | |
| Stomach Cancer | DQ55 | R | | | | | | | | | |
| Stomach Cancer | DQ56 | L | | | | | | | | | |
| Stomach Cancer | DQ56 | P | | | | | | | | | |
| Stomach Cancer | DQ57 | V | | | | | | | | hetero>(-) homo | hetero>(-)>homo |
| Stomach Cancer | DQ66 | D | DQ67 | I | | | | | | hetero>(-) homo | |
| Stomach Cancer | DQ66 | E | DQ67 | V | | | | | | | |
| Other cancers | DQ14 | L | | | | | | | | | |
| Other cancers | DQ14 | M | | | | | | | | | |

Fig. 51

| | | | | | | | | | | | | No. | Chemotherapy | Immunotherapy |
|---|---|---|---|---|---|---|---|---|---|---|---|---|---|---|
| Other cancers | DQ23 | L | | | | | | | | | | | | |
| Other cancers | DQ23 | R | | | | | | | | | | | | |
| Other cancers | DQ28 | S | DQ30 | S | DQ37 | I | DQ46 | E | DQ47 | F | DQ52 | L | DQ55 | L | | | |
| Other cancers | DQ28 | T | | | DQ37 | D | DQ46 | V | DQ47 | Y | DQ52 | P | | | |
| Other cancers | DQ3 | P | DQ9 | L | | | | | | | | | (-) hetero>homo | | |
| Other cancers | DQ3 | S | | | | | | | | | | | (-) hetero>homo | | |
| Other cancers | DQ9 | F | | | | | | | | | | | | | |
| Other cancers | DQ9 | Y | | | | | | | | | | | hetero,homo>(-) | hetero,homo>(-) | |
| Other cancers | DQ38 | A | | | | | | | | | | | hetero,hoo>(-) | | |
| Other cancers | DQ38 | V | | | | | | | | | | | hetero,homo>(-) | | |
| Other cancers | DQ45 | E | | | | | | | | | | | | | |
| Other cancers | DQ45 | G | | | | | | | | | | | | | |
| Other cancers | DQ53 | L | | | | | | | | | | | | | |
| Other cancers | DQ53 | Q | | | | | | | | | | | | | |
| Other cancers | DQ55 | P | | | | | | | | | | | | | hetero,(-)>homo |
| Other cancers | DQ55 | R | | | | | | | | | | | | | |
| Other cancers | DQ56 | L | | | | | | | | | | | | | |
| Other cancers | DQ56 | P | | | | | | | | | | | | | |
| Other cancers | DQ66 | D | DQ67 | I | | | | | | | | | | hetero,(-)>homo | |
| Other cancers | DQ66 | E | DQ67 | V | | | | | | | | | | hetero,(-)>homo | |

Fig. 52

| | DR | Diversity | Equivalence | Prognosis Total (+) Vs (-) Total | Prognosis Total (homo) | Prognosis Total | Prognosis Total (+) vs (-) Stomach | Prognosis Total (homo) Stomach | Prognosis Stomach | Prognosis Total (+) vs (-) Other cancers | Prognosis Total (homo) Other cancers |
|---|---|---|---|---|---|---|---|---|---|---|---|
| 5 | arp_25 | KR | K=R | | | RR78.8 | Stomach | | RR71.4 | | Other cancers |
| 6 | arp_24 | FL | F=L | | | FI66.7 | F(-)>(+) | | LL60.9 | | |
| 13 | arp_17 | AT | A=T | | A:homo>hetero, T:>hetero | AA76.6 | | | AA67.8 | | |
| 14 | arp_16 | AV | A=V | | A:>hetero V:homo>hetero | VV78.8 | | | VV71.4 | | |
| 29 | arp_1 | AS | A=S | | | SS83.36 | | | SS100 | A(+)>(-), S:(+)>(-) | A:, S:homo>hetero (-) |
| 33 | arp4 | QR | Q=R | | | QR68.3 | | | RR68.1 | | |
| 38 | arp9 | EKW | 9K=11D=26Y=28H=30G | | | KW74.2 | | | KW75.8 | | |
| 39 | arp10 | EQY | 10E=31V=38A=40Y= (16Q)=(16R) | | | EY83.3 | | | EY75 | | |
| 40 | arp11 | DGLPSV | 11G=13Y=14E=14=K25 Q=25R=30L, 11S=12K=12T, 11P=13R | | V:>hetero | GV100, LL100O | | V:hetero>(-) | LL100 | | P:hetero>homo |
| 41 | arp12 | KT | | | | KK66.5 | | | TT70.7 | | |
| 42 | arp13 | FGHRSY | 13F=31F=31I | | | HY100, FR71.6 | | | SY100, GR75.4 | F(+)>(-) | F:hetero>(-), R:hetero>homo S:hetero,(-)>homo |
| 43 | arp14 | EK | E=K | | | EE66.2 | | | EK80 | | |
| 45 | arp16 | HQY | | | | HQ71.SO | | Q:hetero>homo | HQ8O | | |
| 55 | arp25 | QR | Q=R | | | | | | | | |
| | arp26 | FLY | | | | LY70.2 | | L:hetero>homo | LY80.3 | | F:hetero>homo |
| 57 | arp28 | DEH | 28H=30G | | | DE69.2 | | | DE69.4 | | |
| 59 | arp30 | CDHLRY | 30H=37L=38L=85A=85V | | | CC100O | | | CC100O | | |
| 60 | arp31 | FIV | 31V=38A=40F=40Y, 31 (F=I) | | | FV77.8 | | | FV76.2 | I(+)>(-) | F:hetero>homo I:hetero,(-) |

Fig. 53

| | DR | Diversity | Equivalence | Prognosis Total (+) vs (-) Total | Prognosis Total (homo) Total | Prognosis Total | Prognosis Total (+) vs (-) Stomach | Prognosis Total (homo) Stomach | Prognosis Total (+) vs (-) Other cancers | Prognosis Total (homo) Other cancers |
|---|---|---|---|---|---|---|---|---|---|---|
| 61 | arp32 | HY | H=Y | | | HY66.9 | Stomach | YY68 | | |
| 62 | arp33 | HN | H=N | | | NN66.7 | | HH71.4 | | |
| 66 | arp37 | FLNSY | F=S | | | LL80O | | FS73.4 | | F(-), hetero>homo |
| 67 | arp38 | ALV | | | | LL80O | | AV78.8 | | |
| 69 | arp40 | FY | F=Y | | | FY73.1 | | FY71.6 | | |
| 76 | arp47 | FY | F=Y | | | FY67.4 | | YY68.9 | | |
| 86 | arp57 | ADSV | | | S=hetero,(+)>homo | AV73.70 | | AD72.5, SV72.5 | | S=hetero,(+)>homo |
| 87 | arp58 | AE | A=E | | | AE67 | | AE71.1 | | |
| 89 | arp60 | HAY | | | | HS73.7 | | HY68.4 | | |
| 96 | arp67 | FIL | | | | FI69.5 | | FI72.2 | | |
| 99 | arp70 | DQR | | | | DD69.4 | | DD72.7 | | |
| 100 | arp71 | AEKR | | | K(-)>hetero | AR63.5, ER67.2, AE72.6 | K(-)>(+) | EK75O | | A,E,hetero> homo |
| | | AG | 73A=73G=74R=74N= 77N=77T | | | AA66.3 | | AA68.1 | | |
| 103 | arp74 | AELQR | R=N | | | LR80 | | AQ100.O | | |
| 106 | arp77 | NT | N=T | | | TT66.4 | | TT68.2 | | |
| 107 | arp78 | VY | V=Y | | | VY67.1 | | VY68.6 | | |

Fig. 54

| | DR | Diversity | Equivalence | Prognosis Total (+) Vs (-) Total | Prognosis Total (homo) | Prognosis Total (+) vs (-) Total | Prognosis Total (homo) Stomach | Prognosis Stomach | Prognosis Total (+) vs (-) Other cancers | Prognosis Total (homo) Other cancers |
|---|---|---|---|---|---|---|---|---|---|---|
| | | Diversity | | | | | | | | |
| 114 | arp85 | AV | A=V | | | Stomach | Stomach | | | |
| 115 | arp86 | GV | G=V | | | | | VV68.1 | | |
| 125 | arp96 | EHQY | | | | | | VV69.4 EE100 | | Q(-) hetero>homo |
| 127 | arp98 | EK | 98E=98K=104A=142V | | | | | EK72.1 | | |
| 133 | arp104 | AS | A=S | | | | | AS72.1 | | |
| 149 | arp120 | NS | S=N | | N(-) >hetero,Shomo>h etero | | | NN72.9 | | |
| 162 | arp133 | LR | 133L=133R=142M=142V | | | | | LL69.7 | R(+)>(-) | |
| 169 | arp140 | AT | | | | | | TT74.1 | | |
| 171 | arp142 | MV | M=V | | | | | MM69.7 | V(+)>(-) | |
| 178 | arp149 | HQY | H=Q | | | | | HH70.8 | | |
| 195 | arp166 | QR | Q=R | | | | | QR68.6, RR68.6 | | |
| 209 | arp180 | LV | L=V | | | | | LL70.1 | | |
| 210 | arp181 | MT | | | | | | TT69 | | |
| 218 | arp189 | RS | R=S | | | | | SS100 | | |
| 260 | arp231 | PQ | P=Q | | | | | QQ67.9 | | |
| 262 | arp233 | RT | R=T | | | T(+)>(+) | R.Thomo-h etero,(-) | RR78.2 | | R.Thetero(-) >homo |
| | | All survived | | DR11GLGV LL(5) | | | | DR30CLC C(4) | | |

Fig. 55

| DR | Diversity | Equivalence | Prognosis Other cancers | Treatment Effect Total (+) vs (-) | Treatment Effect Total (hetero) | Treatment Effect All cases | Treatment Effect Total (+) vs (-) | Treatment Effect Total (homo) | Treatment Effect |
|---|---|---|---|---|---|---|---|---|---|
| arp_25 | KR | K=R | RR100 | | | | | | Stomach cancer |
| arp_24 | FL | F=L | FL100 | | | | Stomach | Stomach | |
| arp_17 | AT | A=T | AA100 | | | | | | |
| arp16 | AV | A=V | VV100 | | | Immunotherapy AA 71.4 | | | |
| arp1 | AS | A=S | AA90,90 | | | | | | |
| arp4 | QR | Q=R | QQ69.3 | | | | | | |
| arp9 | EKW | 9K=11D=26Y=28 H=30G | KW71.2 | | | Immunotherapy KW (86.7) | | Immunotherapy E(-), (homo)>hetero | Immunotherapy KW B&G |
| arp10 | EQY | 10E=31V=38A=40Y=(166Q)=(166R) | EY100 | Immunotherapy E(-)>(+) | Immunotherapy V>hetero | | Immunotherapy E(-)>(+) | Immunotherapy E(-)>hetero | |
| arp11 | DGLPSV | 11G=13Y=14E=14=K25Q=25R=30L 11S=12K=12T, 11P=13R | LL100O | | Immunotherapy V>homo,((-))>homo | no adjuvant therapy DS(83.4)DV(79.6); Immunotherapy DP (84.6) | | Immunotherapy V>homo,((-))>hetero | |
| arp12 | KT | | KK64.2 | | | | | | |
| arp13 | FGHRSY | 13F=19F=31I | FR74.20 | Immunotherapy S>hetero>(-)>homo | | no adjuvant therapy GH(89.9); Immunotherapy FS(81.9) | | Immunotherapy H>homo, (-)>hetero | |
| arp14 | EK | E=K | EE63.5 | | | | | | |
| arp16 | HQY | | QY100 | | | | | | |
| arp25 | QR | Q=R | | | | | | | |
| arp26 | FLY | | LL100 | Chemotherapy L>hetero>(-)>(+), Immunotherapy R(+)>(-) | Chemotherapy L>hetero>(-)>homo, Immunotherapy L>hetero>(-)>homo | no adjuvant therapy FL(67); immunotherapy FL(61.4) | | Chemotherapy L>hetero, (-)>homo, Immunotherapy L>hetero, (-)>homo | Immunotherapy LY66.7 |
| arp28 | DEH | 28H=30G | EE83.3 | no adjuvant therapy H(+)>(-), Immunotherapy R(-)>(+) | Chemotherapy E>hetero, Immunotherapy R(-)>hetero | | immunotherapy R(-)>(+) | Immunotherapy E>hetero, (-)>homo | Immunotherapy EH (88.8) |
| arp30 | CGHLRY | 30H=37L=38L=85A=85V | CC100 | | | | | | |
| arp31 | FIV | 31V=38A=40F=40Y, 31(F=I) | FV80 | Immunotherapy V(-)>(+), >hetero | Immunotherapy V>hetero | Immunotherapy FF 55.5, FI(60.7) | Immunotherapy V(-)>(+), V(+)>(-) | Immunotherapy V(-)>homo, V>hetero | |

Fig. 56

| DR | Diversity | Diversity | Equivalence | Prognosis Other cancers | Treatment Effect Total (+) vs (-) | Treatment Effect Total (homo) | Treatment Effect All cases | Treatment Effect Total (+) vs. (-) Stomach | Treatment Effect Total (homo) Stomach | Treatment Effect Stomach cancer |
|---|---|---|---|---|---|---|---|---|---|---|
| arp32 | HY | | H=Y | HY64.6 | | Total | | | | |
| arp33 | HN | | H=N | HN84.5 | | | | Immunotherapy NI(>(+) | Immunotherapy H(homo>(-),hetero, Immunotherapy NI,->(homo), hetero | Immunotherapy HH(87.5) |
| arp37 | FLNSY | | F=S | FL93.30 | Chemotherapy F(->(+), no adjuvant therapy L(+)>(-), Immunotherapy N(+)>(-) | Chemotherapy F(-)>hetero,homo, Immunotherapy N>hetero (homo)>(-) | Chemotherapy I,V(70.9), Immunotherapy NS(72.5) | | | Immunotherapy AS(69.1) |
| arp38 | ALV | | | LL100 | Immunotherapy A(-)>(+), no adjuvant therapy L(+)>(-) | Immunotherapy A(-)>hetero | | Immunotherapy A(-)>(+) | Immunotherapy A(-)>hetero | |
| arp40 | FY | | F=Y | FY75 | Immunotherapy Y(-)>(+) | Immunotherapy F,homo>hetero, Immunotherapy Y(-)>hetero | Immunotherapy FF(67.5) | | Immunotherapy Y(-)>hetero | |
| arp47 | FY | | F=Y | FY67.3 | | | no adjuvant therapy S(92.2), Chemotherapy ED(56.3), Immunotherapy AD(76.2) | | | Chemotherapy FF(74.5) |
| arp57 | ADSV | | | AV88.90 | Chemotherapy A(>)>(+) | no adjuvant therapy S,hetero,(+)>homo | | | | no adjuvant therapy SX(100) Immunotherapy AD(83.3) |
| arp58 | AE | | A=E | AA63.5 | | | | | | |
| arp60 | HAY | | | HS88.9 | | | Chemotherapy YY, (56.8) | | | |
| arp67 | FIL | | | FF72.4 | Chemotherapy H (-)>(+), Immunotherapy L(-)->(+), Chemotherapy I(-)>(+) | Immunotherapy H(-)>homo, hetero, no adjuvant therapy L,hetero>(-), Chemotherapy L(-)>hetero | no adjuvant therapy H,(82.8), Chemotherapy F,I(63.4), Immunotherapy FL(88) | | | Chemotherapy I(74.8) |
| arp70 | DQR | | | RR69.4 | Chemotherapy R(-)>(+) | | | | | |
| arp71 | AEKR | | | KR78.80 | no adjuvant therapy K(-)>(+) | no adjuvant therapy A,hetero, E(hetero,(+)>homo, Ehetero,(+)>homo | no adjuvant therapy RRR(81.8), Immunotherapy ER(73.7) | no adjuvant therapy K(-)>(+) | no adjuvant therapy D,hetero>homo,(+) | no adjuvant therapy DQ (86.5) |
| arp73 | AG | | 73A=73G=74 R=74N=77N=77T | AG65.6 | | | | Chemotherapy G,(-)>(+) | Chemotherapy A,homo>hetero | no adjuvant therapy ER(91.7), Chemotherapy AA(77.9) |
| arp74 | AELQR | | R=N | ER100.0 | Chemotherapy E(-)>(+), Immunotherapy E(-)>(+) | Immunotherapy A,hetero,(-)>homo, Immunotherapy E,hetero,homo>(-) | Immunotherapy AE(67.9) | Chemotherapy R(-)>(+) | Chemotherapy G(-)>hetero Chemotherapy A,hetero,(-)>homo, Immunotherapy E,homo, Chemotherapy homo>hetero | Chemotherapy AA (58) no adjuvant therapy A(-), Chemotherapy AE(67.5) Immunotherapy EL(90.8) no adjuvant therapy A,L(66.1) |
| arp77 | NT | | N=T | NT83.3 | | | | Chemotherapy NI(-)>(+) | Chemotherapy N(-)>hetero, Chemotherapy T,homo>hetero | Chemotherapy NN(68) |
| arp78 | VY | | V=Y | VV69.3 | | | | | | Chemotherapy TT(58) |

Fig. 57

| DR | Diversity | Equivalence | Prognosis Other cancers | Treatment Effect Total (+) vs (-) | Treatment Effect Total | Treatment Effect All cases | Treatment Effect Total (+) vs (-) | Treatment Effect Total (homo) | Treatment Effect |
|---|---|---|---|---|---|---|---|---|---|
| | Diversity | | | | | | | | Stomach cancer |
| arp85 | AV | A=V | AA100 | Total | Total | | Stomach | Stomach | |
| | GV | G=V | GG64 | no adjuvant therapy A(+)>(-) | | | | | |
| arp86 | EHQY | | EE100Q | | | no adjuvant therapy HY(61 B) | | | |
| arp96 | | | | | no adjuvant therapy Q(-)hetero>homo | | | | |
| arp98 | EK | 98E=98K=104A=104S | ED68.2 | | | | | | |
| arp104 | AS | A=S | AS68.2 | | | | | | |
| arp120 | NS | S=N | NN85.7 | | immunotherapy N homo<(-)hetero, Immunotherapy S(-)(homo),hetero | | | | |
| arp133 | LR | 133L=133R=142M=142V | LR67.6 | | | no adjuvant therapy RR(73.9) | | | |
| arp140 | AT | | TT67.4 | | | | | | |
| arp142 | MV | M=V | MV67.6 | | | no adjuvant therapy VV(79.9) | | | |
| arp149 | HQY | H=Q | QQ64.7 | | | | | | |
| arp164 | FV | | | | | | | | |
| arp166 | QR | Q=R | RR64.2 | Immunotherapy Q(+)>(-) | Immunotherapy Q(-)>hetero, Immunotherapy R(-)>hetero | Immunotherapy RR(57.5) | | Immunotherapy(-)>hetero, Immunotherapy R(-)>hetero(Same) | Immunotherapy RR(65.2) |
| arp180 | LV | L=V | LL83.3 | | | | | | |
| arp181 | MT | | MM68.1 | | | | | | |
| arp189 | RS | R=S | SS100 | | | | | | |
| arp231 | PQ | P=Q | QQ64.7 | Immunotherapy P(-)hetero, Immunotherapy Q hetero>homo | Immunotherapy P(-)>hetero, Immunotherapy Q hetero>homo | Immunotherapy QQ(57.5) | | Immunotherapy P(-)>hetero, Immunotherapy Q hetero>homo | |
| arp233 | RT | R=T | RT65.9 | | | | | | |
| | All survived | V=Y | DR96EE(3) | | | | | | |

Fig. 58

| | Diversity | Diversity | Equivalence | Treatment Effect Total (+) vs (-) Other cancers | Treatment Effect Total (homo) Other cancers | Treatment Effect Other cancers | DR Cancer in Family | DR Metastases | DR Total t(ratio of advanced cancer) | DR Smoking |
|---|---|---|---|---|---|---|---|---|---|---|
| DR | | | | | | | | | | |
| arp_25 | | KR | K=R | | | | | | | |
| arp_24 | | FL | F=L | | | | | | | |
| arp_17 | | AT | A=T | | | | | | | |
| arp_16 | | AV | A=V | | | | | | | |
| arp_1 | | AS | A=S | | | | | | FL30,LL22,9O | |
| arp.4 | | QR | Q=R | | | | | | | AS73.3, AA44.4O |
| arp9 | | EKW | 9K=11D=26Y =28H=30G | | no adjuvant therapy W(hetero,(-) >homo | no adjuvant therapy AA(100) | | | | |
| arp10 | | EQY | 10E=31V=38A =40Y=(16Q) =(16R) | | | no adjuvant therapy KW(88.9) | | | | |
| arp11 | | DGLPSV | 11G=13Y=14 E=14=K25Q= 25R=30L, 11S=12K=12T ,11P=13R | | no adjuvant therapy P(hetero,(-) >homo | | | | | |
| arp12 | | KT | | | | | | | | |
| arp13 | | FGHRSY | 13F=31F=31I | | no adjuvant therapy R(hetero,( ->homo, Chemotherapy S(hetero,(-)>homo Immunotherapy S(hetero,(-) homo | no adjuvant therapy FR(80), Chemotherapy FR(72), Immunotherapy FS(100) | | | FT22.6, FF0, GR0. O | |
| arp14 | | EK | E=K | | | | | # | | |
| arp16 | | HQY | | | | | | | | |
| arp25 | | QR | Q=R | | | | | # | QQ100, YY6, 3O | |
| arp26 | | FLY | | | Chemotherapy F(-) (hetero)>homo | | | # | | |
| arp28 | | DEH | 28H=30G | | Chemotherapy (hetero,(-)>homo | Chemotherapy EE100 | | | | |
| arp30 | | CDHLRY | 30H=27L=38L =85A=85V, | | | | | | | |
| arp31 | | FIV | 31V=38A=40F =40Y,31(F=I) | | | | | | | |

Fig. 59

| | Diversity | Equivalence | Treatment Effect Total (+) vs (-) Other cancers | Treatment Effect Total (homo) Other cancers | Treatment Effect Other cancers | DR Cancer in Family | DR Metastases | DR Total t(ratio of advanced cancer) | DR Smoking |
|---|---|---|---|---|---|---|---|---|---|
| DR | Diversity | | | | | | | | |
| arp32 | HY | H=Y | Chemotherapy Y(+)>(-) Immunotherapy Y(+)>(-) Chemotherapy H(+)>(-) | Chemotherapy H(-),hetero>homo, Immunotherapy H(hetero>-), (>homo Chemotherapy (hetero>homo(-), Immunotherapy Y(hetero>homo(+) | Chemotherapy HY(35.6), Immunotherapy HY(33.6) | | | | |
| arp33 | HN | H=N | | Chemotherapy F(-), (hetero>-homo no adjuvant therapy S(hetero(-)>homo | no adjuvant therapy YY(61.3), Chemotherapy FS(102), Immunotherapy NS(80) | | | | |
| arp37 | FLNSY | F=S | | | | | | RR18.3, RR9.80 | |
| arp38 | ALV | | | | | | | | |
| arp40 | FY | F=Y | | | | | | | |
| arp47 | FY | F=Y | | | | | | | |
| arp57 | ADSV | | Chemotherapy A(+)>(+) | Chemotherapy A(+)> hetero>homo Immunotherapy S(hetero(-) >homo | no adjuvant therapy SV(81.8), Chemotherapy VV(85.7), Immunotherapy DS(78.8) | | | | |
| arp58 | AE | A=E | | | | # | | | |
| arp60 | HAY | | | Chemotherapy H(-) p(hetero), homo | Chemotherapy SS(85.7), Immunotherapy HY(75) | | | | |
| arp67 | FIL | | | | no adjuvant therapy FF35.7 IL63.3 | | | | |
| arp70 | DQR | | | | | | | | |
| arp71 | AEKR | | | no adjuvant therapy A(=hetero, (-))homo | no adjuvant therapy AR(74.9) | | | | |
| arp73 | AG | 73A=73G=74 R=74N=77N= 77T | | | | | | | |
| arp74 | AELQR | R=N | no adjuvant therapy L(-) P(+) | no adjuvant therapy A(hetero (-))=homo | no adjuvant therapy (AE81), Chemotherapy (AE54.4) | | | | |
| arp77 | NT | N=T | | | | | | | |
| arp78 | VY | V=Y | | | | | | | |

Fig. 60

| DR | Diversity | Equivalence | Treatment Effect Total (+) vs (-) | Treatment Effect Total (homo) | Treatment Effect Other cancers | DR Cancer in Family | DR Metastases | DR Total (ratio of advanced cancer) | DR Smoking |
|---|---|---|---|---|---|---|---|---|---|
| | Diversity | | Other cancers | Other cancers | | | | | |
| arp85 | AV | A=V | Chemotherapy G(+)>(-) | Chemotherapy Ghomo>(-) | Chemotherapy VV(90) | | | | |
| arp86 | GV | G=V | | no adjuvant therapy Q(-) hetero>homo | no adjuvant therapy RY(66.4) | AV38.7, MX0.0 | # | # | |
| arp93 | EHQY | | | | | | | | |
| arp98 | EK | 98E=98K=104 A=104S | immunotherapy K(+)>(-) | immunotherapy Ehetero,(-) phomo, immunotherapy Khetero, homo>(-) | immunotherapy EK(66.4) | | | | |
| arp104 | AS | A=S | immunotherapy S(+)>(-) | immunotherapy Ahetero phomo, immunotherapy Shetero,homo>(-) | immunotherapy AS(81.9) | | | | |
| arp120 | NS | S=N | | | | | | | |
| arp133 | LR | 133L=133R=1 42M=142V | no adjuvant therapy R(+)>(-) | no adjuvant therapy Lhetero,(-)>homo, no adjuvant therapy Rhomo,hetero>(-) | no adjuvant therapy RR(89.1) | # | | | |
| arp140 | AT | | | | | | | | |
| arp142 | MV | M=V | no adjuvant therapy V(+)>(-) | no adjuvant therapy Mhetero,(-)>homo, no adjuvant therapy Vhomo,hetero>(-) | no adjuvant therapy VV(59.1) | | | | |
| arp149 | HQY | H=Q | | | | | | | |
| arp164 | FV | | | | | | | | # |
| arp166 | QR | Q=R | | | | | | | |
| arp180 | LV | L=V | | | no adjuvant therapy LV(100) | # | | | |
| arp181 | MT | | | | | | | | |
| arp189 | RS | R=S | | | | | | | |
| arp231 | PQ | P=Q | | | | | | | |
| arp233 | RT | R=T | immunotherapy T(+)>(-) | immunotherapy Rhetero,(-) phomo, immunotherapy hetero,homo>(-) | immunotherapy RT(77.9) | | | | |
| | All survived | | | | | | | | |

Fig. 61

| | DP | Diversity | Equivalence | Prognosis Total (+) vs (-) Total | Prognosis Total (homo) Total | Prognosis Total | Prognosis Total (+) vs (-) Stomach | Prognosis Total (homo) Stomach | Prognosis Stomach | Prognosis Total (+) vs (-) Other cancers | Prognosis Total (homo) Other cancers | Prognosis Other cancers | Treatment Effect Total (+) vs (-) Total | Treatment Effect Total (homo) Total | Treatment Effect All cases |
|---|---|---|---|---|---|---|---|---|---|---|---|---|---|---|---|
| 37 | app8 | LV | 8L=8V=9F =11G=11L | | | LV67.4 | | | VV77.8 | | | LV54.7O | | | |
| 38 | app9 | FHY | | | | FY68.2 | | | YY85.7 | | | FY65.8O | | | |
| 40 | app11 | GL | G=L | | | GL67.3 | | | LL77.8 | | | GG94 GL64.7O | | | |
| 64 | app35 | FLY | | | | FF68 | | | FY78.9O | | | LL68.8 LY68.8 | | | |
| 65 | app36 | AV | A=V | | | AA85.7 | | | AA80 | | | AA100 | | | |
| 84 | app55 | ADE | | | | AAE85.7 | | | AA80 | | | AA100 | | | |
| 85 | app56 | AE | | | | EE67.5 | | | EE70.8 | | | AA67.3 | | | |
| 86 | app57 | DE | | | | DD68.5 | | | DD76 | | | EE64.2 | | | |
| 94 | app65 | FIL | 65L=25L | | | LL85.7 | | | LL85.7 | | | IL64.6 | | | no adjuvant therapy AD(79) |
| 98 | app69 | EK | E=K | | | EK66.6 | | | EK69.4 | | | EK67.9O | no adjuvant therapy Chemo-r(), homo, no adjuvant therapy Chemo-h omo(LL) | | no adjuvant therapy EK (81.4) |
| 105 | app76 | IMV | | | | II100 | | | IV100 | | | IM67.7O | | | |
| 113 | app84 | DG | | | | DG66.9 | | | GG70.8 | | | DG65.9 | | | |
| 114 | app85 | EG | | | | EG65.9 | | | GG70.8 | | | EG65.9 | | | |
| 115 | app86 | AP | | | | AP66.9 | | | PP70.8 | | | AP65.9 | | | |

Fig. 62

| | DP | Diversity | Equivalence | Prognosis Total (+) vs (-) Total | Prognosis Total (homo) Total | Prognosis Total | Prognosis Total (+) vs (-) Stomach | Prognosis Total (homo) Stomach | Prognosis Total (+) Vs (-) Stomach | Prognosis Total (homo) Other cancers | Prognosis Total (+) Vs (-) Other cancers | Prognosis Other cancers | Treatment Effect Total (+) Vs (-) Total | Treatment Effect Total (homo) Total | Treatment Effect All cases |
|---|---|---|---|---|---|---|---|---|---|---|---|---|---|---|---|
| 116 | app87 | MV | | | | MV66.9 | | | MM70.8 | | | MV65.9 | | | |
| 125 | app96 | KR | | | | KK100 | | | KK100 | | | KR65.3 | | | |
| 199 | app170 | IT | | | | IT100 | | | IT100 | | | IT65.3 | | | |
| 207 | app178 | LM | | | | LM70.6 | | | MM75 | | | LM70.5 | | | |
| | Overall Prognosis | More than 3, all survived | | | | DP9YY(5) | | | DP65LL(5) | | | | | | |

Fig. 63

| DP | Diversity | Treatment Effect Total (+) vs (-) Stomach | Treatment (homo) Stomach | Treatment Effect Stomach cancer | Treatment Effect Total (+) vs (-) Other cancers | Treatment Effect Total (homo) Other cancers | Treatment Effect Other cancers | DP Category (name of malignancy) | DP Metastases |
|---|---|---|---|---|---|---|---|---|---|
| app8 | LV | | | | | | | VV95.2 LL89.60 | |
| app9 | FHY | Immunotherapy E(+)(+) | Immunotherapy H(+,homo)>hetero | Immunotherapy FY(16/71)FF(65) | | no adjuvant therapy F(+)>(+), no adjuvant therapy H(-) hetero>homo(-), no adjuvant therapy H(-) hetero>homo | no adjuvant therapy E(+), homo | no adjuvant therapy F(+) | # | |
| app11 | GL | | | | no adjuvant therapy G(+)>(-) | no adjuvant therapy G(+)>(-), no adjuvant therapy L(-) hetero>homo | no adjuvant therapy (GL) | VV95.2 LL89.60 | |
| app35 | FLY | | Chemotherapy (FF) | Chemotherapy (FF) | | | Chemotherapy (LY) | | # |
| app36 | AV | | Chemotherapy A(-), homo>hetero, Chemotherapy V(homo)(-)>hetero | | | | | | |
| app55 | ADE | | Chemotherapy A(-), homo>hetero | | no adjuvant therapy A(+)>(-) | no adjuvant therapy D(hetero)(-), homo, no adjuvant therapy A(hetero)(-), homo | no adjuvant therapy DE(76.3) | | AE44.6 AA10 |
| app56 | AE | | | | | no adjuvant therapy A(hetero)(-), homo, no adjuvant therapy E(hetero)(-), homo | no adjuvant therapy AE(74.6) | | O |
| app57 | DE | | | | no adjuvant therapy E(+)>(-) | no adjuvant therapy D(hetero)(-), homo, no adjuvant therapy E(hetero)(-), homo | no adjuvant therapy DE(76.8) | VV96.3 LL89.10 | O |
| app65 | FIL | | | | no adjuvant therapy L(+)>(-) | no adjuvant therapy L(hetero)>homo, no adjuvant therapy F(hetero)>homo, no adjuvant therapy I(-) hetero>homo, no adjuvant therapy E(-) hetero>homo | no adjuvant therapy IL(100) | | |
| app69 | EK | no adjuvant therapy E(-)(+) Immunotherapy E(-), homo>hetero, no adjuvant therapy K(hetero)>(-) Immunotherapy Khomo>hetero | Immunotherapy EK(8.5,4) Immunotherapy KK(58.3) | | no adjuvant therapy K(+)>(-) | | no adjuvant therapy EK(71.7) | | |
| app76 | IMV | Chemotherapy I(-), homo>hetero | Chemotherapy MV(64) | | | no adjuvant therapy V(hetero)>homo | no adjuvant therapy MV(79) | VV95.6 II66.70 | |
| app84 | DG | | | | | | | DD92.1 GG87.60 | |
| app85 | EG | | | | | | | EE92.1 GG87.60 | |
| app86 | AP | | | | | | | VV92.1 MM87.60 | |

Fig. 64

| DP | Diversity | Treatment Effect Total (+) vs (-) | Treatment Effect Total (homo) | Treatment Effect Stomach cancer | Treatment Effect Total (+) vs (-) Other cancers | Treatment Effect Total (homo) Other cancers | Treatment Effect Other cancers | DP Category (rate of malignancy) | DP Metastases |
|---|---|---|---|---|---|---|---|---|---|
| app87 | MV | Stomach | Stomach | | Other cancers | Other cancers | | VV92.1, MM87.6O | |
| app96 | KR | | | | | | | | |
| app170 | IT | | | | | | | | |
| app178 | LM | | | | | | | | |
| Overall Prognosis | More than 3, all survived | | | | | | | | |

Fig. 65

| DP | Diversity | DP Smoking | DP Age 50 (ratio, -49) | | |
|---|---|---|---|---|---|
| app8 | LV | | | | |
| app9 | FHY | | | | |
| app11 | GL | | | | |
| app35 | FLY | | | | |
| app36 | AV | | # | | |
| app55 | ADE | | AA45.5 | AE15.6 | O |
| app56 | AE | | # | | |
| app57 | DE | | | | |
| app65 | FIL | | | | |
| app69 | EK | EK58.5 KK50.30 | KK23.9 | EE17.5 | O |
| app76 | IMV | | | | |
| app84 | DG | | | | |
| app85 | EG | | | | |
| app86 | AP | | | | |

Fig. 66

| DP | | DP<br>Smoking | DP<br>Age 50 (ratio, −49) | |
|---|---|---|---|---|
| | Diversity | | | |
| app87 | MV | | | |
| app96 | KR | | | |
| app170 | IT | | | |
| app178 | LM | # | | |
| Overall Prognosis | More than 3, all survived | | | |

Fig. 67

| | DQ | Diversity | Equivalence | Prognosis Total (+) vs (-) | Prognosis Total (homo) | Prognosis Total | Prognosis Total (+) Vs (-) Stomach | Prognosis Total (homo) Stomach | Prognosis Stomach | Prognosis Total (+) vs (-) Other cancers | Prognosis Total (homo) Other cancers | Prognosis Other cancers | Treatment Effect Total (+) Vs (-) Total |
|---|---|---|---|---|---|---|---|---|---|---|---|---|---|
| 12 | aqp_27 | AS | | Total | Total | | Stomach | Stomach | | Other cancers | Other cancers | | Total |
| | aqp_21 | DG | | | | GG66.7 | | | DG57.7 | | | DD87.5 | no adjuvant therapy D(+):P(+) |
| 24 | aqp_10 | AS | | | | | | | | | | | |
| 27 | aqp_9 | IM | | | | I80 | | | IM75.2 | | | II100 | |
| | aqp_6 | ST | | | | TT66.7 | | | ST67.7 | | | SS67.5 | no adjuvant therapy S(+);P(+) |
| 28 | aqp_5 | LPS | | | | LL80, SS80 | L(+):(+) | L(+):hetero | LL100 | | | LS100, SS100 | |
| 29 | aqp_4 | LV | | | | VV66.9 | | | LV67.7 | | | LL87.5 | no adjuvant therapy LL(+);(+) |
| 35 | aqp3 | PS | | | | PS68 | | | PS69.4 | | | PS65.3 | |
| 41 | aqp9 | FLY | | Y(+):(+) | Yhetero(+) | LY71.60 | | LY:hetero | LY720 | Y(+):(+) | Yhetero(-) | LY70.80 | no adjuvant therapy Y(+);(+) immunotherapy Y(+):(+) |
| 45 | aqp13 | AG | | | | AA67 | | | AG68.4 | | | AA65.3 | |
| 46 | aqp14 | LM | L=M | | | LM70.1 | | | LM72.4 | | | LL70 | |
| 55 | aqp23 | LR | L=R | | | LR67.4 | | | RR68.1 | R(+):(+) | Lhetero (-) Rhetero ho mo(+) | LR67.30 | |
| 60 | aqp26 | GLY | 28S=28T= 30S=37I=4 6V=46E=4 7F=47Y=5 2P=52L=5 5L | | | ST68.2 | | | ST77.8 | | | TT63.4 | |
| | aqp28 | ST | | | | | | | | | | | |
| 62 | aqp30 | HSY | | | | SY75 | | | HS100 | | | SY100 | immunotherapy H(+):(+) |
| 69 | aqp37 | DIY | | | | DY68 | | | IY83.3 | | | DY65.3 | |

Fig. 68

| | DQ | Diversity | Equivalence | Prognosis Total (+) vs (-) Total | Prognosis Total (homo) Total | Prognosis Total | Prognosis Total (+) vs (-) Stomach | Prognosis Total (homo) Stomach | Prognosis Stomach | Prognosis Total (+) vs (-) Other cancers | Prognosis Total (homo) Other cancers | Prognosis Other cancers | Treatment Effect Total (+) vs (-) Total |
|---|---|---|---|---|---|---|---|---|---|---|---|---|---|
| 70 | aqp38 | AV | A=V | | | VV69.4 | | | VV71.7 | | | AV64.7 | |
| 77 | aqp45 | EG | E=G | | | EG67 | | | EG68.6 | | | EG64.2 | |
| 78 | aqp46 | EV | E=V | | | EV68.2 | | | EV77.8 | | | VV63.4 | |
| 79 | aqp47 | FY | F=Y | | | FY68.2 | | | FY77.8 | | | YY63.4 | |
| 84 | aqp52 | LPS | 52P=52L | | | LP68.2 | | | LP77.8 | | | PP63.4 | |
| 85 | aqp53 | LQ | L=Q | | | QQ66.5 | | | LQ68.5 | | | QQ64.9 | |
| 87 | aqp55 | LPR | 55P=55R | | | LP100O | | | LR75O | | | PR66.3 | |
| 88 | aqp56 | LP | L=P | | | LP47.3O | | | LP68.4 | P(+)>(-) | Lhetero>(-),phomo,Phetero>homo>(-) | LP65.8 | |
| 89 | aqp57 | ADSV | | | Ahomo>(-)hetero>hetero | AA84.7O | | | AS100 | | | SV60 | |
| 98 | aqp66 | DE | 66D=66E=67I=66V | E(+)>(-) | Dhetero>(-),phomo,Ehetero-homo>(-) | DE70.1 | E(+)>p(-) | Dhetero>(-),phomo,Ehetero-homo>(-) | DE77.0O | E(+)>(-) | Dhetero>(-),phomo,Ehetero-homo>(-) | DE67O | no adjuvant therapy E(+)>(-), Chemotherapy E(+)>(-), Immunotherapy E(+)>(-) |
| 99 | aqp67 | IV | I=V | V(+)>(-) | Ihetero>(-),phomo,Vhetero-homo>(-) | IV70.1O | V(+)>p(-) | Ihetero>(-),phomo,Vhetero-homo>(-) | IV72O | V(+)>(-) | Ihetero>(-),phomo,Vhetero-homo>(-) | IV67O | no adjuvant therapy V(+)>p(-), Chemotherapy V(+)>(-), Immunotherapy V(+)>(-) |
| 102 | aqp70 | EGR | | | | GG68.1O | | | GR69.6 | | | GG72.7O | |
| 103 | aqp71 | ADKT | | | | AA100O | | | KT83.3 | | | AA70O | |
| 106 | aqp74 | AES | | | | AS80O | | | AE83.3 | | | AS100 | |
| 107 | aqp75 | LV | | | | LV69.6 | | | LV71.5 | | | LV66.4 | |
| 109 | aqp77 | RT | | | | RT69.7 | | | RT72.4 | | | RR82.7 | |
| 116 | aqp84 | EQ | | | | EE66.5 | | | EQ68.5 | | | EE64.9 | |
| 117 | aqp85 | LV | | | | VV66.5 | | | LV68.5 | | | VV64.9 | |
| 118 | aqp86 | AEG | | | | AG67.8 | | | EG76.1 | | | AG86.8O | |

Fig. 69

| | DQ | Diversity | Equivalence | Prognosis Total (+) vs (-) Total | Prognosis Total (homo) Total | Prognosis Total | Prognosis Total (+) vs (-) Stomach | Prognosis Total (homo) Stomach | Prognosis Stomach | Prognosis Total (+) vs (-) Other cancers | Prognosis Total (homo) Other cancers | Prognosis Other cancers | Prognosis Total (+) vs (-) Total immunotherapy |
|---|---|---|---|---|---|---|---|---|---|---|---|---|---|
| 199 | aqp87 | FLY | | | | FY72.1 | | | LY72.1 | | Pheteo lymphoma | FY75.9 | immunotherapy X(3.3) Total |
| 121 | aqp89 | GT | | | | GG66.5 | | | GT68.5 | | | GG64.9 | |
| 122 | aqp90 | IT | | | | II66.5 | | | IT68.5 | | | II64.9 | |
| 148 | aqp116 | IV | | | | | | | | | | | |
| 157 | aqp125 | AGS | | | | GS74.4 | | | GS75.3 | | | GS72.5 | |
| 158 | aqp126 | HQ | | | | HQ71.4 | | | QQ67.9 | | | HQ71.5 | |
| 162 | aqp130 | QR | | | | QR68.9 | | | RR68.2 | | | QR67.2 | immunotherapy R(+)(+) |
| 172 | aqp140 | AT | | | | AA66.4 | | | AT68.4 | | | AA64.1 | |
| 199 | aqp167 | HR | | | | HH67 | | | HR68.4 | | | HH65.3 | |
| 214 | aqp182 | NS | | | | SS66.4 | | | NS68.4 | | | SS64.1 | |
| 217 | aqp185 | IT | | | | II67.8 | | | II69.4 | | | II65 | |
| 229 | aqp197 | NS | | | | NS68 | | | NS69.4 | | | NS65.3 | |
| 235 | aqp203 | IV | | | | IV67.5 | | | IV70.7 | | | VV66.9 | |
| 252 | aqp220 | HR | | | | RR66.5 | | | HR68.5 | | | RR64.9 | |
| 253 | aqp221 | HQ | | | | QQ66.5 | | | HQ68.5 | | | QQ64.9 | |
| 256 | aqp224 | QR | | | | QR70.1 | | | QR72.4 | | | RR70 | |
| | | All survived | DQ71AKDK(3) | | | | DQ74AS(3) | | | | | | |

Fig. 70

| | Diversity | Treatment Effect Total (homo) | Treatment Effect Total (hetero) | Treatment Effect All cases | Treatment Effect Total (+) Vs (-) Stomach | Treatment Effect Total (homo) Stomach | Treatment Effect Stomach cancer | Treatment Effect Total (+) Vs (-) Other cancers | Treatment Effect Total (homo) Other cancers | Treatment Effect Other cancers |
|---|---|---|---|---|---|---|---|---|---|---|
| DG | AS | | | | | | | | | |
| aqp_27 | DG | no adjuvant therapy D(- );hetero (homo), no adjuvant therapy (hetero) | | no adjuvant therapy GG87.0 | no adjuvant therapy D(+);(+) | no adjuvant therapy D(- );hetero (homo), no adjuvant therapy Chemo(hetero) (- ) | no adjuvant therapy GG92.0 | | | |
| aqp_10 | AS | | | | | | | | | |
| aqp_9 | IM | | | | | | | | | |
| aqp_6 | ST | no adjuvant therapy S(- );hetero (homo), no adjuvant therapy Thermo(hetero) (- ) | | no adjuvant therapy TT87.8 | NS S(-);(+) | no adjuvant therapy S(- );hetero (homo), no adjuvant therapy Thermo(hetero) (- ) | no adjuvant therapy TT92.6 | | | |
| aqp_5 | LPS | no adjuvant therapy L(+ );hetero (homo), no adjuvant therapy Thermo(hetero) (- ) | | Immunotherapy PP62 | no adjuvant therapy L(+);(+) | no adjuvant therapy L(hetero) (+ ), no adjuvant therapy Thermo(hetero) (- ) | no adjuvant therapy PP92.6 | no adjuvant therapy L(+);(+) | | |
| aqp_4 | LV | no adjuvant therapy L(+);hetero (homo), no adjuvant therapy Vitamin(hetero) (- ) | | no adjuvant therapy VV87.8 | no adjuvant therapy L(+);(+) | no adjuvant therapy N(+);hetero (homo), no adjuvant therapy Thermo(hetero) (- ) | no adjuvant therapy VV92.8 | | | |
| aqp3 | PS | | | no adjuvant therapy SS(78) | | | | NI S(+);(+) | no adjuvant therapy P(+ );hetero (homo), no adjuvant therapy Stomach; hetero(- ) | SS(63.5) |
| aqp9 | FLY | no adjuvant therapy F(hetero);homo, immunotherapy Y(hetero);homo | | Chemotherapy LY(64.5) Immunotherapy LY(63.9) | Immunotherapy Y(+);(+) | | Immunotherapy YY(52.9) | no adjuvant therapy Y(+);(+) Chemotherapy Y(+);(+) | F(hetero);homo, no adjuvant therapy Y(hetero); homo, Chemotherapy Y(hetero);homo | no adjuvant therapy LY(75.1) Chemotherapy LY(65.6) Immunotherapy LY(58.1) |
| aqp13 | AG | | | | | | | | | |
| aqp14 | LM | | | | | | | | | |
| aqp23 | LR | | | | | | | | | |
| aqp26 | GLY | | | | | | | | | |
| aqp28 | ST | | | | | | | | | |
| aqp30 | HSY | Immunotherapy H(hetero);homo, Immunotherapy Y(hetero);homo | | Immunotherapy HY(69.6) | | Immunotherapy H(hetero);homo, Immunotherapy Y(hetero);homo | Immunotherapy HY(66.2) | | | |
| aqp37 | DY | | | no adjuvant therapy YY(78.2), Chemotherapy DY(62.5) | no adjuvant therapy Y(+);(+) | | | no adjuvant therapy Y(+);(+) | no adjuvant therapy D(+);(hetero)>homo, no adjuvant therapy Y(homo, hetero)(- ) | no adjuvant therapy YY(69.7) |

Fig. 71

| ID | Diversity | Treatment Effect Total (homo) | Treatment Effect All cases | Treatment Effect Total (+) Vs. (-) Stomach | Treatment Effect Total (homo) Stomach | Treatment Effect Stomach cancer | Treatment Effect Total (+) Vs (-) Other cancers | Treatment Effect Total (homo) Other cancers | Treatment Effect Other cancers |
|---|---|---|---|---|---|---|---|---|---|
| DQ | | Total | | | | | | | |
| aqp38 | AV | | | | Chemotherapy, hetero>(+),homo, Chemotherapy, Vhetero>(+),homo | Chemotherapy AV(65.2) | Chemotherapy K (+)(+) | no adjuvant therapy, V(-),hetero>homo, no adjuvant therapy, hetero>(+),homo | no adjuvant therapy AV(71.3) |
| aqp45 | EG | | | | | | | | |
| aqp46 | EV | | | | | | | | |
| aqp47 | FY | | | | | | | | |
| aqp52 | LPS | | | | | | | | |
| aqp53 | LQ | | | | | | | | |
| aqp55 | LPR | | | | | | | | |
| aqp56 | LP | | | | | | | | |
| aqp57 | ADSV | Immunotherapy A homo (all subjects)(+) hetero | Immunotherapy AA (100) | | Immunotherapy Vhetero(-),homo | Immunotherapy AA(100) | | | |
| aqp66 | DE | no adjuvant therapy Dhetero(-),homo, Chemotherapy Dhetero>(+), homo, Immunotherapy Dhetero(-),homo, no adjuvant therapy, Ehetero(+),homo, Chemotherapy, Ehetero(-),homo, Immunotherapy Ehetero(-),homo | no adjuvant therapy EE(77.7), Chemotherapy DE(62.1), Immunotherapy EE(60.3) | | Chemotherapy Dhetero(-),homo, Chemotherapy Ehetero>(+),homo | Chemotherapy DE(65.1) | | Chemotherapy Dhetero>(+),homo, Chemotherapy Ehetero(homo)(+) | Chemotherapy DE(99.1) |
| aqp67 | IV | Immunotherapy Ihetero(-),homo, no adjuvant therapy Vhetero(-),homo, Chemotherapy Vhetero>(+),homo, Immunotherapy Vhetero(-),homo | no adjuvant therapy IV(73.4), Chemotherapy DE(65.1), Immunotherapy EE(60.3) | | Chemotherapy Ihetero(-),homo, Chemotherapy Vhetero>(+),homo | Chemotherapy IV(65.1) | | Chemotherapy Ihetero(-),homo, Chemotherapy Vhetero(-),homo | Chemotherapy IV(65.1) |
| aqp70 | EGR | Immunotherapy Ghetero>(+),homo | Immunotherapy EG(75.2) | Immuno therapy E(+)(+) | | | | | |
| aqp71 | ADKT | | | | | | | | Chemotherapy AV(59.8), no adjuvant therapy AD(41.7), Chemotherapy TT(58.9) |
| aqp74 | AES | | | | | | | | |
| aqp75 | LV | | | | | | | | |
| aqp77 | RT | | | | | | | | |
| aqp84 | EQ | | | | | | | | |
| aqp85 | LV | | | | | | | | |
| aqp86 | AEG | | Chemotherapy AA 70.8, Immunotherapy EG(63.8) | | no adjuvant therapy Ahetero(-),homo | Chemotherapy AA 70.8 | | no adjuvant therapy AG(67.5) |

Fig. 72

| DQ | Diversity | Treatment Effect<br>Total (homo) | Treatment Effect<br>All cases | Treatment Effect<br>Total (+) Vs (-) | Treatment Effect<br>Total (homo) | Treatment Effect<br>Stomach cancer | Treatment Effect<br>Total (+) Vs (-) Other cancers | Treatment Effect<br>Total (homo) Other cancers | Treatment Effect<br>Other cancers |
|---|---|---|---|---|---|---|---|---|---|
| | | Total | All cases | Stomach | Stomach | Stomach cancer | Other cancers | Other cancers | Other cancers |
| aqp67 | FLY | Immunotherapy<br>\>hetero>homo(-) | no adjuvant<br>therapy<br>FY(82.3),<br>Immunotherapy<br>LY(71.2) | Immunother<br>apy F(+)(+) | Immunotherapy,At<br>(>homo)<br>Chemotherapy<br>F>homo-hetero(-) | Chemotherapy<br>F(61.3),<br>Immunotherapy<br>LY(68.1) | | no adjuvant<br>therapy F>hetero,+<br>>homo | no adjuvant<br>therapy FY(76),<br>LY(75) |
| aqp89 | GT | | | | | | | | |
| aqp90 | IT | | | | | | | | |
| aqp116 | IV | | | | | | | | |
| aqp125 | AGS | | | | | | | | no adjuvant<br>therapy AS(73.7) |
| aqp126 | HQ | | | | | | | | |
| aqp130 | QR | Immunotherapy<br>Q>hetero+(-)>homo<br>Immunotherapy<br>R>hetero>homo(+,-) | Immunotherapy<br>QR(75) | | | | | | |
| aqp140 | AT | | | | | | | | |
| aqp167 | HR | | | | | | | | |
| aqp182 | NS | | | | | | | | |
| aqp185 | IT | | | | | | | | |
| aqp197 | NS | | no adjuvant<br>therapy SS(70) | | | N(S,SS(70)) | no adjuvant<br>therapy S(+)>(-) | no adjuvant<br>therapy N,+<br>,hetero>homo, no<br>adjuvant therapy<br>S>homo,hetero(-) | no adjuvant<br>therapy Ss(68.8) |
| aqp203 | IV | | | | | | | | |
| aqp220 | HR | | | | | | | | |
| aqp221 | HQ | | | | | | | | |
| aqp224 | QR | | | | | | | | |
| | All<br>survived | | | | | | | | |

Fig. 73

| DQ | Diversity | DQ Cancer in Family | DQ Category | DQ Metastases | DQ Alcohol | DQ Smoking |
|---|---|---|---|---|---|---|
| aqp_27 | AS | | | | | |
| aqp_21 | DG | | | | | |
| aqp_10 | AS | | | | | |
| aqp_9 | IM | | | | | |
| aqp_6 | ST | | | | | |
| aqp_5 | LPS | | | | | |
| aqp_4 | LV | | | | | |
| aqp_3 | PS | | | # | | |
| aqp9 | FLY | | | | | |
| aqp13 | AG | | | | | |
| aqp14 | LM | | | LL100, LM23.2O | | |
| aqp23 | LR | | | | | |
| aqp26 | GLY | | | # | | |
| aqp28 | ST | | | | | |
| aqp30 | HSY | | | | | |
| aqp37 | DIY | | | | | # |

Fig. 74

| DQ | DQ Diversity | DQ Cancer in Family | DQ Category | DQ Metastases | DQ Alcohol | DQ Smoking |
|---|---|---|---|---|---|---|
| aqp38 | AV | | | | | |
| aqp45 | EG | EE50, GG19.4 O | | | # AV24.1, VV15.6 O | # |
| aqp46 | EV | | | | | |
| aqp47 | FY | | | | | |
| aqp52 | LPS | | | | | |
| aqp53 | LQ | LQ26.4, QQ12.5 O | | | | |
| aqp55 | LPR | PR29.7, LR0 O | | | | |
| aqp56 | LP | | | | | |
| aqp57 | ADSV | | | | | |
| aqp66 | DE | | | | | |
| aqp67 | IV | | | | | |
| aqp70 | EGR | | | | | |
| aqp71 | ADKT | | | | | |
| aqp74 | AES | | | | | |
| aqp75 | LV | | | # | | |
| aqp77 | RT | | | RR100, RT22.5 O | | |
| aqp84 | EQ | EQ26.4, EE12.5 O | | | | |
| aqp85 | LV | LV26.4, VV12.5 | GG84.4, EG82.8 O | | | |
| aqp86 | AEG | | | | | |

Fig. 75

| DQ | DQ Diversity | DQ Cancer in Family | DQ Category | DQ Metastases | DQ Alcohol | DQ Smoking |
|---|---|---|---|---|---|---|
| aqp87 | FLY | | | YY50, LL20 O | | |
| aqp89 | GT | GT26.4, GG12.5 | | | | |
| aqp90 | IT | IT26.4, II12.5 | | | | |
| aqp166 | IV | | | II100, IV23.2 | | |
| aqp125 | AGS | | | SS100, AA20 O | | |
| aqp126 | HQ | | | | | |
| aqp130 | QR | | # | | | |
| aqp140 | AT | AT26.8, AA12.2 O | | | | |
| aqp167 | HR | | | | | |
| aqp182 | NS | NS26.8, SS12.2 O | | | | |
| aqp158 | IT | | | | | |
| aqp197 | NS | # | | # | | |
| aqp203 | IV | | | VV32, II22.2 | | DI66.7, DD39.1 O |
| aqp220 | HR | HR26.4, RR12.5 O | | | | |
| aqp221 | HQ | HQ26.4, QQ12.5 O | | RR100, QR23.2 O | | |
| aqp224 | QR | | | | | |
| All survived | | | | | | |

Fig. 76

| DR Nucleic Acid | No. of Diversity | Total Total | Total Stomach | Total Other cancers | All cases Treatment Effect | Stomach Cancer Treatment Effect | Other cancers Treatment Effect |
|---|---|---|---|---|---|---|---|
| 16 | 3 | | aGCCaGCG> aGCGaGCU | | | | |
| 4 | 3 | | | | | | |
| 12 | 5 | | | | Immunotherapy: kAAAkAAA>kAAGkAAG> kAAAkAAG | Immunotherapy: kAAAkAAA>kAAGkAAG> kAAAkAAG | no adjuvant therapy: kAAAkAAG>kAAGkAAG |
| 14 | 3 | | | | | | |
| 19 | 2 | | | | | | |
| 26 | 5 | | | | | | |
| 28 | 4 | | hCACeGAA> hCACeGAG | | | | |
| 34 | 3 | | | | | | no adjuvant therapy: qCAAqCAA> qCAAgCAG |
| 53 | 2 | | | | | | |
| 57 | 7 | | | dGACdGAU> dGAUdGAU | | | no adjuvant therapy: dGACdGAU, dGAUdGAU>dGACdGAC, Chemotherapy: aGCCaGCU>aGCCaGCU, aGCGaGCU>aGCGaGCG |
| 58 | 6 | | | eGAGaGCC> eGAGaGCU | no adjuvant therapy: aGCCaGCC>aCGUaGCU, Chemotherapy: aGCUaGCU, aGCGaGCU>aGCGaGCG | | |
| 69 | 3 | | | | | no adjuvant therapy: | |
| 72 | 5 | | rGGrCGG> rGGrCGG | | no adjuvant therapy: rCGrCGG>rCGGrCGU | no adjuvant therapy: rCGrCGG>rCGGrCGU Chemotherapy: rCGgrCGU, rCGGrCGG, rCGGrCGG>rCGrCGC | |
| 78 | 3 | | | | Chemotherapy: yUACyUAC> yUAUyUAU | | |
| 90 | 2 | | | | | | |
| 93 | 2 | | | | | | Chemotherapy: |

Fig. 77

| DR | | Total | | | | All cases | Stomach Cancer | |
|---|---|---|---|---|---|---|---|---|
| Nucleic Acid | No. of Diversity | Total | Stomach | Other cancers | | Treatment Effect | Treatment Effect | Other cancers Treatment Effect |
| 95 | | | | | | | | |
| 101 | 2 | | | | | | | no adjuvant therapy, vGUGvGUG, vGUAvGUG> vGUAvGUA |
| 104 | 2 | aGCAaGCC> aGCAaGCA | | | | | | |
| 106 | 3 | | | | | | | |
| 112 | 2 | | | | | | | |
| 117 | 2 | | | | | | | |
| 145 | 2 | | | | | | | |
| 152 | 2 | | | | | | | |
| 166 | 3 | | | | | no adjuvant therapy, rCGGrCGG> rCGArCGA | | no adjuvant therapy, rCGGrCGG, rCGArCGG> rCGArCGA |
| 169 | 2 | | | tACAmAUG> tAGCmAUG | | | | |
| 179 | 2 | | | | | | | |
| 181 | 3 | | | | | | | |
| 206 | 2 | | | | | | | |
| 217 | 2 | | | | | | | |

Fig. 78

| DR | | | | | |
|---|---|---|---|---|---|
| Nucleic Acid | No. of Diversity | Cancer in Family | Alcohol | Metastases | Smoking |
| -16 | 3 | | | | |
| 4 | 3 | | | | |
| 12 | 5 | | | | |
| 14 | 3 | | | | |
| 19 | 2 | | | | |
| 26 | 5 | | | | |
| 28 | 4 | | eGAGeGAG(55.6), eGAAeGAG(0), eGAAeGAA(16.7) | | |
| 34 | 3 | | | | |
| 53 | 2 | | | | |
| 57 | 7 | | | | |
| 58 | 6 | | | | |
| 69 | 3 | | | | |
| 72 | 5 | rCGGrCGU(50), rCGCrCGG(40), rCGCrCGC(0) | | | |
| 78 | 3 | | | | |
| 90 | 2 | | | | |
| 30 | 2 | | | | |

Fig. 79

| DR Nucleic Acid | No. of Diversity | Cancer in Family | Alcohol | Metastases | Smoking |
|---|---|---|---|---|---|
| 95 | 2 | | | vGUCvGUC(33.2), vGUCvGUU(23.5), vGUUvGUU(42.9) | |
| 101 | 2 | | | | |
| 104 | 3 | | | | |
| 106 | 2 | | | | |
| 112 | 2 | | | | |
| 117 | 2 | | | | |
| 145 | 2 | | | | |
| 152 | 2 | | | | |
| 166 | 3 | | | | |
| 169 | 2 | | | | |
| 179 | 2 | | | | |
| 181 | 3 | | | | |
| 206 | 2 | | | | |
| 217 | 2 | | | | |

Fig. 80

| DR Nucleic Acid | No. of Diversity | Total Total | Total Stomach | Other cancers | All cases Treatment Effect | Stomach Cancer Treatment Effect |
|---|---|---|---|---|---|---|
| -29 | 2 | | | | | no adjuvant therapy: pCCUpCCU>pCCCpCCU, pCCCpCCC |
| -23 | 2 | | | | | Same curve as DQ_23 pCCUpCCU>pCCCpCCU, pCCCpCCC |
| -15 | 2 | | | | | |
| DQNP19 | 2 | | | tACGtACC, tACGtACG>tACCtACC | | |
| DQNP21 | 3 | | | | | |
| DQNP25 | 2 | | | | | |
| DQNP27 | 2 | | | | Immunotherapy. vGUAvGUG, vGUGvGUG>vGUAvGUA | |
| DQNP35 | 2 | | | aGCAaGCG>aGCGaGCG | | |
| DQNP38 | 3 | | | | | |
| DQNP47 | 3 | | | | | |
| DQNP48 | 2 | | | | | |
| DQNP49 | 3 | | | | | |
| DQNP57 | 6 | | | | | |
| DQNP62 | 2 | | | nAACnAAC, nAACnAAU>nAAU | | |
| DQNP72 | 2 | | | | | |
| DQNP77 | 4 | | | tACCACG, tACGtACG>tACCtACC | | |
| DQNP78 | 2 | | | vGUAvGUG, vGUGvGUG>vGUAvGUA | | |
| DQNP91 | 2 | | | | | |
| DQNP93 | 2 | | | | | |
| DQNP94 | 2 | | | | | |

Fig. 81

| DR | Total | | | | All cases Treatment Effect | Stomach Cancer Treatment Effect |
|---|---|---|---|---|---|---|
| Nucleic Acid | No. of Diversity | Total | Stomach | Other cancers | | |
| DQNP118 | 2 | | | | | |
| DQNP135 | 3 | | | | | |
| DQNP140 | 4 | | | | | |
| DQNP147 | 2 | | | | | |
| DQNP150 | 2 | | | | | |
| DQNP154 | 2 | | | | | |
| DQNP169 | 2 | | | | | |
| DQNP191 | 2 | | | | | |
| DQNP210 | 2 | | | | | |
| DQNP213 | 2 | | | | | |
| DQNP215 | 2 | | | | | |
| DQNP218 | 2 | | | | | |
| DQNP235 | 2 | | | | | |

Fig. 82

| DR Nucleic Acid | No. of Diversity | Other cancers Treatment Effect | Cancer in Family | Alcohol | Metastases | Smoking |
|---|---|---|---|---|---|---|
| -29 | | | | | | |
| -23 | 2 | | | | | |
| -15 | 2 | | | | | |
| DQNP19 | 2 | no adjuvant therapy: nAACnAAC, nAACnAAU> nAAunAAu | | | | nAACnAAC(54.7), nAACnAAU(59.8), nAAUnAAU(39.1) |
| DQNP 21 | 3 | no adjuvant therapy: tACCtACG>tACAtACG | | | | |
| DQNP25 | 2 | | | | | |
| DQNP27 | 2 | | | | | |
| DQNP35 | 2 | | | | | |
| DQNP38 | 3 | Chemotherapy: aGCAaGCG>aGCGaGCG | | | | |
| DQNP47 | 3 | | | | | |
| DQNP48 | 2 | | | | | |
| DQNP49 | 3 | | | | | |
| DQNP57 | 6 | | | | | |
| DQNP62 | 2 | | | | | |
| DQNP72 | 2 | The Same curve with DQ19 rCGGrCGG, rCGArCGG>rCGArCGA | | | | rCGArCGA(39.1), rCGrCGG(59.8), rCGGrCGG(54.7) |
| DQNP77 | 4 | Chemotherapy: rAGGrAGG>rAGArAGG, rAGArAGA | | | | |
| DQNP78 | 2 | | | | | |
| DQNP91 | 2 | | | | ICUGICUG, ICUGIUUG, IUUGIUUG | ICUGICUG(39.7), ICUGIUUG(26.8), IUUGIUUG(31.8) |
| DQNP93 | 2 | | | | | |
| DQNP94 | 2 | | | | | |

Fig. 83

| DR Nucleic Acid | No. of Diversity | Other cancers Treatment Effect | Cancer in Family | Alcohol | Metastases | Smoking |
|---|---|---|---|---|---|---|
| DQNP118 | 2 | | | | | |
| DQNP135 | 3 | | | | dGACdGAC(32.6), dGACdGAU(27.1), dGAUdGAU(34.4) | |
| DQNP140 | 4 | no adjuvant therapy: aGCCaGCC>aCGUaGCU Immunotherapy: tACCaGCU>tACCaGCC | | TACCtACC(50), tACCtACU(21.3), tACUtACU(20.5) | | |
| DQNP147 | 2 | | | | ICUCICUC(47.8), ICUCICUU(24.5), ICUUICUU(32.1) | |
| DQNP150 | 2 | | | | | |
| DQNP154 | 2 | | | | | |
| DQNP169 | 2 | | | | dGACdGAC(32.6), dGACdGAU(27.1), dGAUdGAU(34.4) | |
| DQNP191 | 2 | | | | | |
| DQNP210 | 2 | | | ICUCICUC(50), ICUCICUG(18.6), ICUGICUG(22.5) | | |
| DQNP213 | 2 | | | | ICUCICUC(32.6), ICUCICUU(27.1), ICUUICUU(34.4) | |
| DQNP215 | 2 | | | | LCUUICUU(47.8), ICUGICUU(24.5), ICUGICUG(32.1) | |
| DQNP218 | 2 | | | | | |
| DQNP235 | 2 | | | | | |

Fig. 84

| DP | | Total | | | All Cases | Stomach Cancer | Other cancers |
|---|---|---|---|---|---|---|---|
| Nucleic Acid | No. of Diversity | Total | Stomach | Other cancers | Treatment Effect | Treatment Effect | Treatment Effect |
| 98 | 2 | All same with the survival curve | | | | | |
| 107 | 2 | All same with the survival curve | | | | | |
| 118 | 2 | All same with the survival curve | | | | | |
| 167 | 2 | All same with the survival curve | | | | | |
| 179 | 2 | All same with the survival curve | | | | | |
| | | | | | | | |
| | | All NS | | | | | |

Fig. 85

| Position | Diverse Amino Acid | | | | | | no adjuvant therapy | Chemotherapy | Immunotherapy | |
|---|---|---|---|---|---|---|---|---|---|---|
| 29 | M | | | | | | M | M | M | |
| 28 | M | | | | | | M | M | M | |
| 27 | V | | | | | | V | V | V | |
| 26 | L | | | | | | L | L | L | |
| 25 | Q | | | | | | Q | Q | Q | |
| 24 | V | | | | | | V | V | V | |
| 23 | S | | | | | | S | S | S | |
| 22 | A | | | | | | A | A | A | |
| 21 | A | | | | | | A | A | A | |
| 20 | P | | | | | | P | P | P | |
| 19 | Q | | | | | | R | R | R | |
| 18 | T | | | | | | T | T | T | |
| 17 | V | | | | | | V | V | V | |
| 16 | A | | | | | | A | A | A | |
| 15 | L | | | | | | L | L | L | |
| 14 | T | | | | | | T | T | T | |
| 13 | A | | | | | | A | A | A | |
| 12 | L | | | | | | L | L | L | |
| 11 | L | | | | | | L | L | L | |
| 10 | M | | | | | | M | M | M | |
| 9 | V | | | | | | V | V | V | |
| 8 | L | | | | | | L | L | L | |
| 7 | L | | | | | | L | L | L | |
| 6 | T | | | | | | T | T | T | |
| 5 | S | | | | | | S | S | S | |
| 4 | V | | | | | | V | V | V | |
| 3 | V | | | | | | V | V | V | |
| 2 | Q | | | | | | Q | Q | Q | |
| 1 | G | | | | | | G | G | G | |
| 1 | R | | | | | | R | R | R | |
| 2 | A | | | | | | A | A | A | |
| 3 | T | | | | | | T | T | T | |
| 4 | P | | | | | | P | P | P | |
| 5 | E | | | | | | E | E | E | |
| 6 | N | | | | | | N | N | N | |
| 7 | Y | | | | | | Y | Y | Y | |
| 8 | L | V | | | | | L or V | L or V | L or V | |
| 9 | F | H | Y | | | | () | () | () | DP8 LV and DP F |
| 10 | Q | | | | | | Q | Q | Q | |
| 11 | G | L | | | | | G or L | G or L | G or L | |
| 12 | R | | | | | | R | R | R | |
| 13 | Q | | | | | | Q | Q | Q | |
| 14 | E | | | | | | E | E | E | |
| 15 | C | | | | | | C | C | C | |
| 16 | Y | | | | | | Y | Y | Y | |
| 17 | A | | | | | | A | A | A | |
| 18 | F | | | | | | F | F | F | |
| 19 | N | | | | | | N | N | N | |
| 20 | G | | | | | | G | G | G | |
| 21 | T | | | | | | T | T | T | |
| 22 | Q | | | | | | Q | Q | Q | |
| 23 | R | | | | | | R | R | R | |
| 24 | F | | | | | | F | F | F | |
| 25 | L | | | | | | L | L | L | |
| 26 | E | | | | | | E | E | E | |
| 27 | R | | | | | | R | R | R | |
| 28 | Y | | | | | | Y | Y | Y | |

Fig. 86

| Position | Diverse Amino Acid | | | | | no adjuvant therapy | Chemotherapy | Immunotherapy | |
|---|---|---|---|---|---|---|---|---|---|
| 29 | I | | | | | I | I | I | |
| 30 | Y | | | | | Y | Y | Y | |
| 31 | N | | | | | N | N | N | |
| 32 | R | | | | | R | R | R | |
| 33 | E | | | | | E | E | E | |
| 34 | E | | | | | E | E | E | |
| 35 | F | L | Y | | | () | () | () | |
| 36 | A | V | | | | A or V | A or V | AV | |
| 37 | R | | | | | R | R | R | |
| 38 | F | | | | | F | F | F | |
| 39 | D | | | | | D | D | D | |
| 40 | S | | | | | S | S | S | |
| 41 | D | | | | | D | D | D | |
| 42 | V | | | | | V | V | V | |
| 43 | G | | | | | G | G | G | |
| 44 | E | | | | | E | E | E | |
| 45 | F | | | | | F | F | F | |
| 46 | R | | | | | R | R | R | |
| 47 | A | | | | | A | A | A | |
| 48 | V | | | | | V | V | V | |
| 49 | T | | | | | T | T | T | |
| 50 | E | | | | | E | E | E | |
| 51 | L | | | | | L | L | L | |
| 52 | G | | | | | G | G | G | |
| 53 | R | | | | | R | R | R | |
| 54 | P | | | | | P | P | P | |
| 55 | A | D | E | | | AD | () | () | |
| 56 | A | E | | | | () | () | () | |
| 57 | D | E | | | | () | DE | () | |
| 58 | Y | | | | | Y | Y | Y | |
| 59 | W | | | | | W | W | W | |
| 60 | N | | | | | N | N | N | |
| 61 | S | | | | | S | S | S | |
| 62 | Q | | | | | Q | Q | Q | |
| 63 | K | | | | | K | K | K | |
| 64 | D | | | | | D | D | D | |
| 65 | F | I | L | | | IL | I or L | I or L | |
| 66 | L | | | | | L | L | L | |
| 67 | E | | | | | E | E | E | |
| 68 | E | | | | | E | E | E | |
| 69 | E | K | | | | EK | E or K | E or K | |
| 70 | R | | | | | R | R | R | |
| 71 | A | | | | | A | A | A | |
| 72 | V | | | | | V | V | V | |
| 73 | P | | | | | P | P | P | |
| 74 | D | | | | | D | D | D | |
| 75 | R | | | | | R | R | R | |
| 76 | I | M | V | | | () | () | IM | |
| 77 | C | | | | | C | C | C | |
| 78 | R | | | | | R | R | R | |
| 79 | H | | | | | H | H | H | |
| 80 | N | | | | | N | N | N | |
| 81 | Y | | | | | Y | Y | Y | |
| 82 | E | | | | | E | E | E | |
| 83 | L | | | | | L | L | L | |
| 84 | D | G | | | | () | DG | () | |
| 85 | E | G | | | | () | EG | () | |

Fig. 87

| Position | Diverse Amino Acid | | | | | no adjuvant therapy | Chemotherapy | Immunotherapy | |
|---|---|---|---|---|---|---|---|---|---|
| 86 | A | P | | | | () | () | () | |
| 87 | M | V | | | | () | MV | () | |
| 88 | T | | | | | T | T | T | |
| 89 | L | | | | | L | L | L | |
| 90 | Q | | | | | Q | Q | Q | |
| 91 | R | | | | | R | R | R | |
| 92 | R | | | | | R | R | R | |
| 93 | V | | | | | V | V | V | |
| 94 | Q | | | | | Q | Q | Q | |
| 95 | P | | | | | P | P | P | |
| 96 | K | R | | | | () | () | () | |
| 97 | V | | | | | V | V | V | |
| 98 | N | | | | | N | N | N | |
| 99 | V | | | | | V | V | V | |
| 100 | S | | | | | S | S | S | |
| 101 | P | | | | | P | P | P | |
| 102 | S | | | | | S | S | S | |
| 103 | K | | | | | K | K | K | |
| 104 | K | | | | | K | K | K | |
| 105 | G | | | | | G | G | G | |
| 106 | P | | | | | P | P | P | |
| 107 | L | | | | | L | L | L | |
| 108 | Q | | | | | Q | Q | Q | |
| 109 | H | | | | | H | H | H | |
| 110 | H | | | | | H | H | H | |
| 111 | N | | | | | N | N | N | |
| 112 | L | | | | | L | L | L | |
| 113 | L | | | | | L | L | L | |
| 114 | V | | | | | V | V | V | |
| 115 | C | | | | | C | C | C | |
| 116 | H | | | | | H | H | H | |
| 117 | V | | | | | V | V | V | |
| 118 | T | | | | | T | T | T | |
| 119 | D | | | | | D | D | D | |
| 120 | F | | | | | F | F | F | |
| 121 | Y | | | | | Y | Y | Y | |
| 122 | P | | | | | P | P | P | |
| 123 | G | | | | | G | G | G | |
| 124 | S | | | | | S | S | S | |
| 125 | I | | | | | I | I | I | |
| 126 | Q | | | | | Q | Q | Q | |
| 127 | V | | | | | V | V | V | |
| 128 | R | | | | | R | R | R | |
| 129 | W | | | | | W | W | W | |
| 130 | F | | | | | F | F | F | |
| 131 | L | | | | | L | L | L | |
| 132 | N | | | | | N | N | N | |
| 133 | G | | | | | G | G | G | |
| 134 | Q | | | | | Q | Q | Q | |
| 135 | E | | | | | E | E | E | |
| 136 | E | | | | | E | E | E | |
| 137 | T | | | | | T | T | T | |
| 138 | A | | | | | A | A | A | |
| 139 | G | | | | | G | G | G | |
| 140 | V | | | | | V | V | V | |
| 141 | V | | | | | V | V | V | |
| 142 | S | | | | | S | S | S | |
| 143 | T | | | | | T | T | T | |
| 144 | N | | | | | N | N | N | |

Fig. 88

| Position | Diverse Amino Acid | | | | | no adjuvant therapy | Chemotherapy | Immunotherapy | |
|---|---|---|---|---|---|---|---|---|---|
| 145 | L | | | | | L | L | L | |
| 146 | I | | | | | I | I | I | |
| 147 | R | | | | | R | R | R | |
| 148 | N | | | | | N | N | N | |
| 149 | G | | | | | G | G | G | |
| 150 | D | | | | | D | D | D | |
| 151 | W | | | | | W | W | W | |
| 152 | T | | | | | T | T | T | |
| 153 | F | | | | | F | F | F | |
| 154 | Q | | | | | Q | Q | Q | |
| 155 | I | | | | | I | I | I | |
| 156 | L | | | | | L | L | L | |
| 157 | V | | | | | V | V | V | |
| 158 | M | | | | | M | M | M | |
| 159 | L | | | | | L | L | L | |
| 160 | E | | | | | E | E | E | |
| 161 | M | | | | | M | M | M | |
| 162 | T | | | | | T | T | T | |
| 163 | P | | | | | P | P | P | |
| 164 | Q | | | | | Q | Q | Q | |
| 165 | Q | | | | | Q | Q | Q | |
| 166 | G | | | | | G | G | G | |
| 167 | D | | | | | D | D | D | |
| 168 | V | | | | | V | V | V | |
| 169 | Y | | | | | Y | Y | Y | |
| 170 | I | T | | | | () | () | () | |
| 171 | C | | | | | C | C | C | |
| 172 | Q | | | | | Q | Q | Q | |
| 173 | V | | | | | V | V | V | |
| 174 | E | | | | | E | E | E | |
| 175 | H | | | | | H | H | H | |
| 176 | T | | | | | T | T | T | |
| 177 | S | | | | | S | S | S | |
| 178 | L | M | | | | LM | () | () | |
| 179 | D | | | | | D | D | D | |
| 180 | S | | | | | S | S | S | |
| 181 | P | | | | | P | P | P | |
| 182 | V | | | | | V | V | V | |
| 183 | T | | | | | T | T | T | |
| 184 | V | | | | | V | V | V | |
| 185 | E | | | | | E | E | E | |
| 186 | W | | | | | W | W | W | |
| 187 | K | | | | | K | K | K | |
| 188 | A | | | | | A | A | A | |
| 189 | Q | | | | | Q | Q | Q | |
| 190 | S | | | | | S | S | S | |
| 191 | D | | | | | D | D | D | |
| 192 | S | | | | | S | S | S | |
| 193 | A | | | | | A | A | A | |
| 194 | R | | | | | R | R | R | |
| 195 | S | | | | | S | S | S | |
| 196 | K | | | | | K | K | K | |
| 197 | T | | | | | T | T | T | |
| 198 | L | | | | | L | L | L | |
| 199 | T | | | | | T | T | T | |
| 200 | G | | | | | G | G | G | |
| 201 | A | | | | | A | A | A | |
| 202 | G | | | | | G | G | G | |
| 203 | G | | | | | G | G | G | |

Fig. 89

| Position | Diverse Amino Acid | | | | | | no adjuvant therapy | Chemotherapy | Immunotherapy | |
|---|---|---|---|---|---|---|---|---|---|---|
| 204 | F | | | | | | F | F | F | |
| 205 | V | | | | | | V | V | V | |
| 206 | L | | | | | | L | L | L | |
| 207 | G | | | | | | G | G | G | |
| 208 | L | | | | | | L | L | L | |
| 209 | I | | | | | | I | I | I | |
| 210 | I | | | | | | I | I | I | |
| 211 | C | | | | | | C | C | C | |
| 212 | G | | | | | | G | G | G | |
| 213 | V | | | | | | V | V | V | |
| 214 | G | | | | | | G | G | G | |
| 215 | I | | | | | | I | I | I | |
| 216 | F | | | | | | F | F | F | |
| 217 | M | | | | | | M | M | M | |
| 218 | H | | | | | | H | H | H | |
| 219 | R | | | | | | R | R | R | |
| 220 | R | | | | | | R | R | R | |
| 221 | S | | | | | | S | S | S | |
| 222 | K | | | | | | K | K | K | |
| 223 | K | | | | | | K | K | K | |
| 224 | V | | | | | | V | V | V | |
| 225 | Q | | | | | | Q | Q | Q | |
| 226 | R | | | | | | R | R | R | |
| 227 | G | | | | | | G | G | G | |
| 228 | S | | | | | | S | S | S | |
| 229 | A | | | | | | A | A | A | |

"or" – expected to be the same antigen

Fig. 90

| Position | Diverse Amino Acid | | | | | no adjuvant therapy | Chemotherapy | Immunotherapy | |
|---|---|---|---|---|---|---|---|---|---|
| 32 | M | | | | | M | M | M | |
| 31 | S | | | | | S | S | S | |
| 30 | W | | | | | W | W | W | |
| 29 | K | | | | | K | K | K | |
| 28 | K | | | | | K | K | K | |
| 27 | A | S | | | | () | () | () | |
| 26 | L | | | | | L | L | L | |
| 25 | R | | | | | R | R | R | |
| 24 | I | | | | | I | I | I | |
| 23 | P | | | | | P | P | P | |
| 22 | G | | | | | G | G | G | |
| 21 | D | G | | | | GG | () | GG | |
| 20 | L | | | | | L | L | L | |
| 19 | R | | | | | R | R | R | |
| 18 | A | V | | | | () | () | () | |
| 17 | A | | | | | A | A | A | |
| 16 | T | | | | | T | T | T | |
| 15 | V | | | | | V | V | V | |
| 14 | T | | | | | T | T | T | |
| 13 | L | | | | | L | L | L | |
| 12 | M | | | | | M | M | M | |
| 11 | L | | | | | L | L | L | |
| 10 | A | S | | | | () | () | () | |
| 9 | I | M | | | | () | () | () | |
| 8 | L | | | | | L | L | L | |
| 7 | S | | | | | S | S | S | |
| 6 | S | T | | | | TT | () | TT | |
| 5 | L | P | S | | | () | () | PP | |
| 4 | L | V | | | | VV | () | VV | |
| 3 | A | | | | | A | A | A | |
| 2 | E | | | | | E | E | E | |
| 1 | G | | | | | G | G | G | |
| 1 | R | | | | | R | R | R | |
| 2 | D | | | | | D | D | D | |
| 3 | P | S | | | | SS | PS | P or S | |
| 4 | P | | | | | P | P | P | |
| 5 | E | | | | | E | E | E | |
| 6 | D | | | | | D | D | D | |
| 7 | F | | | | | F | F | F | |
| 8 | V | | | | | V | V | V | |
| 9 | F | L | Y | | | () | LY | YY | DQ3 PS is same as DQ9 L |
| 10 | Q | | | | | Q | Q | Q | |
| 11 | F | | | | | F | F | F | |
| 12 | K | | | | | K | K | K | |
| 13 | A | G | | | | () | AA | GG | |
| 14 | L | M | | | | L or M | L or M | LM | |
| 15 | C | | | | | C | C | C | |
| 16 | Y | | | | | Y | Y | Y | |
| 17 | F | | | | | F | F | F | |
| 18 | T | | | | | T | T | T | |
| 19 | N | | | | | N | N | N | |
| 20 | G | | | | | G | G | G | |
| 21 | T | | | | | T | T | T | |
| 22 | E | | | | | E | E | E | |
| 23 | L | R | | | | LR | L or R | RR | |
| 24 | V | | | | | V | V | V | |
| 25 | R | | | | | R | R | R | |
| 26 | G | L | Y | | | () | () | () | |
| 27 | V | | | | | V | V | V | |

Fig. 91

| Position | Diverse Amino Acid | | | | no adjuvant therapy | Chemotherapy | Immunotherapy | |
|---|---|---|---|---|---|---|---|---|
| 28 | S | T | | | S or T | S or T | S or T | |
| 29 | R | | | | R | R | R | |
| 30 | H | S | Y | | HH | () | HY | |
| 31 | I | | | | I | I | I | |
| 32 | Y | | | | Y | Y | Y | |
| 33 | N | | | | N | N | N | |
| 34 | R | | | | R | R | R | |
| 35 | E | | | | E | E | E | |
| 36 | E | | | | E | E | E | |
| 37 | D | I | Y | | YY | DY | () | DQ28 ST is same as DQ37I |
| 38 | A | V | | | A or V | A or V | A or V | |
| 39 | R | | | | R | R | R | |
| 40 | F | | | | F | F | F | |
| 41 | D | | | | D | D | D | |
| 42 | S | | | | S | S | S | |
| 43 | D | | | | D | D | D | |
| 44 | V | | | | V | V | V | |
| 45 | E | G | | | E or G | EG | E or G | |
| 46 | E | V | | | () | () | () | DQ28 ST is same as DQ46VE |
| 47 | F | Y | | | () | () | () | DQ28 ST is same as DQ47FY |
| 48 | R | | | | R | R | R | |
| 49 | A | | | | A | A | A | |
| 50 | V | | | | V | V | V | |
| 51 | T | | | | T | T | T | |
| 52 | L | P | | | () | () | () | DQ28 ST is same as DQ52PL |
| 53 | L | Q | | | LL | L or Q | L or Q | |
| 54 | G | | | | G | G | G | |
| 55 | L | P | R | | P or R | P or R | P or R | DQ28 ST is same as DQ55L |
| 56 | L | P | | | LP | PP | L or P | |
| 57 | A | D | S | V | () | () | AA | |
| 58 | A | | | | A | A | A | |
| 59 | E | | | | E | E | E | |
| 60 | Y | | | | Y | Y | Y | |
| 61 | W | | | | W | W | W | |
| 62 | N | | | | N | N | N | |
| 63 | S | | | | S | S | S | |
| 64 | Q | | | | Q | Q | Q | |
| 65 | K | | | | K | K | K | |
| 66 | D | E | | | DE | DE | EE | |
| 67 | I | V | | | IV | IV | VV | |
| 68 | L | | | | L | L | L | |
| 69 | E | | | | E | E | E | |
| 70 | E | G | R | | () | () | () | |
| 71 | A | D | K | T | () | () | AT | |
| 72 | R | | | | R | R | R | |
| 73 | A | | | | A | A | A | |
| 74 | A | E | S | | ES | () | ES | |
| 75 | L | V | | | LV | () | () | |
| 76 | D | | | | D | D | D | |
| 77 | R | T | | | () | () | RT | |
| 78 | V | | | | V | V | V | |
| 79 | C | | | | C | C | C | |
| 80 | R | | | | R | R | R | |
| 81 | H | | | | H | H | H | |
| 82 | N | | | | N | N | N | |
| 83 | Y | | | | Y | Y | Y | |
| 84 | E | Q | | | QQ | () | QQ | |
| 85 | L | V | | | LL | () | () | |
| 86 | A | E | G | | () | () | EG | |

Fig. 92

| Position | Diverse Amino Acid | | | | | | no adjuvant therapy | Chemotherapy | Immunotherapy | |
|---|---|---|---|---|---|---|---|---|---|---|
| 87 | F | L | Y | | | | FY | () | LY | |
| 88 | R | | | | | | R | R | R | |
| 89 | G | T | | | | | TT | () | () | |
| 90 | I | T | | | | | TT | () | () | |
| 91 | L | | | | | | L | L | L | |
| 92 | Q | | | | | | Q | Q | Q | |
| 93 | R | | | | | | R | R | R | |
| 94 | R | | | | | | R | R | R | |
| 95 | V | | | | | | V | V | V | |
| 96 | E | | | | | | E | E | E | |
| 97 | P | | | | | | P | P | P | |
| 98 | T | | | | | | T | T | T | |
| 99 | V | | | | | | V | V | V | |
| 100 | T | | | | | | T | T | T | |
| 101 | I | | | | | | I | I | I | |
| 102 | S | | | | | | S | S | S | |
| 103 | P | | | | | | P | P | P | |
| 104 | S | | | | | | S | S | S | |
| 105 | R | | | | | | R | R | R | |
| 106 | T | | | | | | T | T | T | |
| 107 | E | | | | | | E | E | E | |
| 108 | A | | | | | | A | A | A | |
| 109 | L | | | | | | L | L | L | |
| 110 | N | | | | | | N | N | N | |
| 111 | H | | | | | | H | H | H | |
| 112 | H | | | | | | H | H | H | |
| 113 | N | | | | | | N | N | N | |
| 114 | L | | | | | | L | L | L | |
| 115 | L | | | | | | L | L | L | |
| 116 | I | V | | | | | () | () | IV | |
| 117 | C | | | | | | C | C | C | |
| 118 | S | | | | | | S | S | S | |
| 119 | V | | | | | | V | V | V | |
| 120 | T | | | | | | T | T | T | |
| 121 | D | | | | | | D | D | D | |
| 122 | F | | | | | | F | F | F | |
| 123 | Y | | | | | | Y | Y | Y | |
| 124 | P | | | | | | P | P | P | |
| 125 | A | G | S | | | | GS | () | () | |
| 126 | H | Q | | | | | () | HQ | () | |
| 127 | I | | | | | | I | I | I | |
| 128 | K | | | | | | K | K | K | |
| 129 | V | | | | | | V | V | V | |
| 130 | Q | R | | | | | () | RR | QR | |
| 131 | W | | | | | | W | W | W | |
| 132 | F | | | | | | F | F | F | |
| 133 | R | | | | | | R | R | R | |
| 134 | N | | | | | | N | N | N | |
| 135 | D | | | | | | D | D | D | |
| 136 | Q | | | | | | Q | Q | Q | |
| 137 | E | | | | | | E | E | E | |
| 138 | E | | | | | | E | E | E | |
| 139 | T | | | | | | T | T | T | |
| 140 | A | T | | | | | TT | () | () | |
| 141 | G | | | | | | G | G | G | |
| 142 | V | | | | | | V | V | V | |
| 143 | V | | | | | | V | V | V | |
| 144 | S | | | | | | S | S | S | |
| 145 | T | | | | | | T | T | T | |

Fig. 93

| Position | Diverse Amino Acid | | | | | no adjuvant therapy | Chemotherapy | Immunotherapy | |
|---|---|---|---|---|---|---|---|---|---|
| 146 | P | | | | | P | P | P | |
| 147 | L | | | | | L | L | L | |
| 148 | I | | | | | I | I | I | |
| 149 | T | | | | | T | T | T | |
| 150 | N | | | | | N | N | N | |
| 151 | G | | | | | G | G | G | |
| 152 | D | | | | | D | D | D | |
| 153 | W | | | | | W | W | W | |
| 154 | T | | | | | T | T | T | |
| 155 | F | | | | | F | F | F | |
| 156 | Q | | | | | Q | Q | Q | |
| 157 | I | | | | | I | I | I | |
| 158 | L | | | | | L | L | L | |
| 159 | V | | | | | V | V | V | |
| 160 | M | | | | | M | M | M | |
| 161 | L | | | | | L | L | L | |
| 162 | E | | | | | E | E | E | |
| 163 | M | | | | | M | M | M | |
| 164 | T | | | | | T | T | T | |
| 165 | P | | | | | P | P | P | |
| 166 | Q | | | | | Q | Q | Q | |
| 167 | H | R | | | | () | HH | RR | |
| 168 | G | | | | | G | G | G | |
| 169 | D | | | | | D | D | D | |
| 170 | V | | | | | V | V | V | |
| 171 | Y | | | | | Y | Y | Y | |
| 172 | T | | | | | T | T | T | |
| 173 | C | | | | | C | C | C | |
| 174 | H | | | | | H | H | H | |
| 175 | V | | | | | V | V | V | |
| 176 | E | | | | | E | E | E | |
| 177 | H | | | | | H | H | H | |
| 178 | P | | | | | P | P | P | |
| 179 | S | | | | | S | S | S | |
| 180 | L | | | | | L | L | L | |
| 181 | Q | | | | | Q | Q | Q | |
| 182 | N | S | | | | NN | () | () | |
| 183 | P | | | | | P | P | P | |
| 184 | I | | | | | I | I | I | |
| 185 | I | T | | | | II | TT | () | |
| 186 | V | | | | | V | V | V | |
| 187 | E | | | | | E | E | E | |
| 188 | W | | | | | W | W | W | |
| 189 | R | | | | | R | R | R | |
| 190 | A | | | | | A | A | A | |
| 191 | Q | | | | | Q | Q | Q | |
| 192 | S | | | | | S | S | S | |
| 193 | E | | | | | E | E | E | |
| 194 | S | | | | | S | S | S | |
| 195 | A | | | | | A | A | A | |
| 196 | Q | | | | | Q | Q | Q | |
| 197 | N | S | | | | SS | NS | () | |
| 198 | K | | | | | K | K | K | |
| 199 | M | | | | | M | M | M | |
| 200 | L | | | | | L | L | L | |
| 201 | S | | | | | S | S | S | |
| 202 | G | | | | | G | G | G | |
| 203 | I | V | | | | () | () | () | |
| 204 | G | | | | | G | G | G | |

Fig. 94

| Position | Diverse Amino Acid | | | | | | no adjuvant therapy | Chemotherapy | Immunotherapy | |
|---|---|---|---|---|---|---|---|---|---|---|
| 205 | G | | | | | | G | G | G | |
| 206 | F | | | | | | F | F | F | |
| 207 | V | | | | | | V | V | V | |
| 208 | L | | | | | | L | L | L | |
| 209 | G | | | | | | G | G | G | |
| 210 | L | | | | | | L | L | L | |
| 211 | I | | | | | | I | I | I | |
| 212 | F | | | | | | F | F | F | |
| 213 | L | | | | | | L | L | L | |
| 214 | G | | | | | | G | G | G | |
| 215 | L | | | | | | L | L | L | |
| 216 | G | | | | | | G | G | G | |
| 217 | L | | | | | | L | L | L | |
| 218 | I | | | | | | I | I | I | |
| 219 | I | | | | | | I | I | I | |
| 220 | H | R | | | | | HH | () | () | |
| 221 | H | Q | | | | | HH | () | () | |
| 222 | R | | | | | | R | R | R | |
| 223 | S | | | | | | S | S | S | |
| 224 | Q | R | | | | | () | () | QR | |
| 225 | K | | | | | | K | K | K | |
| 226 | G | | | | | | G | G | G | |
| 227 | P | | | | | | P | P | P | |
| 228 | Q | | | | | | Q | Q | Q | |
| 229 | G | | | | | | G | G | G | |
| 230 | P | | | | | | P | P | P | |
| 231 | P | | | | | | P | P | P | |
| 232 | P | | | | | | P | P | P | |
| 233 | A | | | | | | A | A | A | |
| 234 | G | | | | | | G | G | G | |
| 235 | L | | | | | | L | L | L | |
| 236 | L | | | | | | L | L | L | |
| 237 | H | | | | | | H | H | H | |

Fig. 95

| Position | Diverse Amino Acid | | | | | | no adjuvant therapy | Chemotherapy | Immunotherapy | |
|---|---|---|---|---|---|---|---|---|---|---|
| -29 | M | | | | | | M | M | M | |
| -28 | V | | | | | | V | V | V | |
| -27 | C | | | | | | C | C | C | |
| -26 | L | | | | | | L | L | L | |
| -25 | K | R | | | | | RR | RR | RR | |
| -24 | F | L | | | | | F or L | F or L | F or L | |
| -23 | P | | | | | | P | P | P | |
| -22 | G | | | | | | G | G | G | |
| -21 | G | | | | | | G | G | G | |
| -20 | S | | | | | | S | S | S | |
| -19 | C | | | | | | C | C | C | |
| -18 | M | | | | | | M | M | M | |
| -17 | A | T | | | | | AA | AA | AA | |
| -16 | A | V | | | | | VV | VV | A or V | |
| -15 | L | | | | | | L | L | L | |
| -14 | T | | | | | | T | T | T | |
| -13 | V | | | | | | V | V | V | |
| -12 | T | | | | | | T | T | T | |
| -11 | L | | | | | | L | L | L | |
| -10 | M | | | | | | M | M | M | |
| -9 | V | | | | | | V | V | V | |
| -8 | L | | | | | | L | L | L | |
| -8 | S | | | | | | S | S | S | |
| -6 | S | | | | | | S | S | S | |
| -5 | P | | | | | | P | P | P | |
| -4 | L | | | | | | L | L | L | |
| -3 | A | | | | | | A | A | A | |
| -2 | L | | | | | | L | L | L | |
| -1 | A | S | | | | | A or S | A or S | AA | |
| 1 | G | | | | | | G | G | G | |
| 2 | D | | | | | | D | D | D | |
| 3 | T | | | | | | T | T | T | |
| 4 | Q | R | | | | | Q or R | Q or R | QR | |
| 5 | P | | | | | | P | P | P | |
| 6 | R | | | | | | R | R | R | |
| 7 | F | | | | | | F | F | F | |
| 8 | L | | | | | | L | L | L | |
| 9 | E | K | W | | | | () | WW | KW | |
| 10 | E | Q | Y | | | | YY | () | () | |
| 11 | D | G | L | P | S | V | DS | () | DP | |
| 12 | K | T | | | | | K or T | K or T | K or T | |
| 13 | F | G | H | R | S | Y | GH | () | FS | |
| 14 | E | K | | | | | E or K | E or K | E or K | |
| 15 | C | | | | | | C | C | C | |
| 16 | H | Q | Y | | | | () | YY | () | |
| 17 | F | | | | | | F | F | F | |
| 18 | F | | | | | | F | F | F | |
| 19 | N | | | | | | N | N | N | |
| 20 | G | | | | | | G | G | G | |
| 21 | T | | | | | | T | T | T | |
| 22 | E | | | | | | E | E | E | |
| 23 | R | | | | | | R | R | R | |
| 24 | V | | | | | | V | V | V | |
| 25 | Q | R | | | | | Q or R | Q or R | Q or R | |
| 26 | F | L | Y | | | | FL | () | FL | |
| 27 | L | | | | | | L | L | L | |
| 28 | D | E | H | | | | () | () | () | |
| 29 | R | | | | | | R | R | R | |
| 30 | C | G | H | L | R | Y | () | () | () | |

Fig. 96

| Position | Diverse Amino Acid | | | | | | no adjuvant therapy | Chemotherapy | Immunotherapy | |
|---|---|---|---|---|---|---|---|---|---|---|
| 31 | F | I | V | | | | F or I | F or I | FI | |
| 32 | H | Y | | | | | HH | () | () | |
| 33 | H | N | | | | | () | () | HH | |
| 34 | Q | | | | | | Q | Q | Q | |
| 35 | E | | | | | | E | E | E | |
| 36 | E | | | | | | E | E | E | |
| 37 | F | L | N | S | Y | | () | LY | NS | |
| 38 | A | L | V | | | | () | () | VV | |
| 39 | R | | | | | | R | R | R | |
| 40 | F | Y | | | | | F or Y | F or Y | FF | |
| 41 | D | | | | | | D | D | D | |
| 42 | S | | | | | | S | S | S | |
| 43 | D | | | | | | D | D | D | |
| 44 | V | | | | | | V | V | V | |
| 45 | G | | | | | | G | G | G | |
| 46 | E | | | | | | E | E | E | |
| 47 | F | Y | | | | | F or Y | F or Y | F or Y | |
| 48 | R | | | | | | R | R | R | |
| 49 | A | | | | | | A | A | A | |
| 50 | V | | | | | | V | V | V | |
| 51 | T | | | | | | T | T | T | |
| 52 | E | | | | | | E | E | E | |
| 53 | L | | | | | | L | L | L | |
| 54 | G | | | | | | G | G | G | |
| 55 | R | | | | | | R | R | R | |
| 56 | P | | | | | | P | P | P | |
| 57 | A | D | S | V | | | AV | AV | AV | |
| 58 | A | E | | | | | A or E | A or E | A or E | |
| 59 | E | | | | | | E | E | E | |
| 60 | H | S | Y | | | | () | YY | HS | |
| 61 | W | | | | | | W | W | W | |
| 62 | N | | | | | | N | N | N | |
| 63 | S | | | | | | S | S | S | |
| 64 | Q | | | | | | Q | Q | Q | |
| 65 | K | | | | | | K | K | K | |
| 66 | D | | | | | | D | D | D | |
| 67 | F | I | L | | | | FF | FI | FL | |
| 68 | L | | | | | | L | L | L | |
| 69 | E | | | | | | E | E | E | |
| 70 | D | Q | R | | | | () | DD | () | |
| 71 | A | E | K | R | | | A | A | A | |
| 72 | R | | | | | | R | R | R | |
| 73 | A | G | | | | | AA | A or G | A or G | |
| 74 | A | E | L | Q | R | | () | LL | AE | |
| 75 | V | | | | | | V | V | V | |
| 76 | D | | | | | | D | D | D | |
| 77 | N | T | | | | | N or T | N or T | N or T | |
| 78 | V | Y | | | | | VV | V or Y | VY | |
| 79 | C | | | | | | C | C | C | |
| 80 | R | | | | | | R | R | R | |
| 81 | H | | | | | | H | H | H | |
| 82 | N | | | | | | N | N | N | |
| 83 | Y | | | | | | Y | Y | Y | |
| 84 | G | | | | | | G | G | G | |
| 85 | A | V | | | | | A or V | A or V | VV | |
| 86 | G | V | | | | | VV | GV | GG | |
| 87 | E | | | | | | E | E | E | |
| 88 | S | | | | | | S | S | S | |
| 89 | F | | | | | | F | F | F | |

Fig. 97

| Position | Diverse Amino Acid | | | | | no adjuvant therapy | Chemotherapy | Immunotherapy | |
|---|---|---|---|---|---|---|---|---|---|
| 90 | T | | | | | T | T | T | |
| 91 | V | | | | | V | V | V | |
| 92 | Q | | | | | Q | Q | Q | |
| 93 | R | | | | | R | R | R | |
| 94 | R | | | | | R | R | R | |
| 95 | V | | | | | V | V | V | |
| 96 | E | H | Q | Y | | EQ | () | () | |
| 97 | P | | | | | P | P | P | |
| 98 | E | K | | | | EK | E or K | EK | |
| 99 | V | | | | | V | V | V | |
| 100 | T | | | | | T | T | T | |
| 101 | V | | | | | V | V | V | |
| 102 | Y | | | | | Y | Y | Y | |
| 103 | P | | | | | P | P | P | |
| 104 | A | S | | | | AA | A or S | AK | O |
| 105 | K | | | | | K | K | K | |
| 106 | T | | | | | T | T | T | |
| 107 | Q | | | | | Q | Q | Q | |
| 108 | P | | | | | P | P | P | |
| 109 | L | | | | | L | L | L | |
| 110 | Q | | | | | Q | Q | Q | |
| 111 | H | | | | | H | H | H | |
| 112 | H | | | | | H | H | H | |
| 113 | N | | | | | N | N | N | |
| 114 | L | | | | | L | L | L | |
| 115 | L | | | | | L | L | L | |
| 116 | V | | | | | V | V | V | |
| 117 | C | | | | | C | C | C | |
| 118 | S | | | | | S | S | S | |
| 119 | V | | | | | V | V | V | |
| 120 | N | S | | | | S or N | NN | SS | |
| 121 | F | | | | | F | F | F | |
| 122 | G | | | | | G | G | G | |
| 123 | Y | | | | | Y | Y | Y | |
| 124 | P | | | | | P | P | P | |
| 125 | G | | | | | G | G | G | |
| 126 | S | | | | | S | S | S | |
| 127 | I | | | | | I | I | I | |
| 128 | E | | | | | E | E | E | |
| 129 | V | | | | | V | V | V | |
| 130 | R | | | | | R | R | R | |
| 131 | W | | | | | W | W | W | |
| 132 | F | | | | | F | F | F | |
| 133 | L | R | | | | RR | L or R | RR | |
| 134 | N | | | | | N | N | N | |
| 135 | G | | | | | G | G | G | |
| 136 | Q | | | | | Q | Q | Q | |
| 137 | E | | | | | E | E | E | |
| 138 | E | | | | | E | E | E | |
| 139 | K | | | | | K | K | K | |
| 140 | A | T | | | | () | TT | () | |
| 141 | G | | | | | G | G | G | |
| 142 | M | V | | | | VV | M or V | VV | |
| 143 | V | | | | | V | V | V | |
| 144 | S | | | | | S | S | S | |
| 145 | T | | | | | T | T | T | |
| 146 | G | | | | | G | G | G | |
| 147 | L | | | | | L | L | L | |
| 148 | I | | | | | I | I | I | |

Fig. 98

| Position | Diverse Amino Acid | | | | | no adjuvant therapy | Chemotherapy | Immunotherapy | |
|---|---|---|---|---|---|---|---|---|---|
| 149 | H | Q | | | | H or Q | HH | HH | |
| 150 | N | | | | | N | N | N | |
| 151 | G | | | | | G | G | G | |
| 152 | D | | | | | D | D | D | |
| 153 | W | | | | | W | W | W | |
| 154 | T | | | | | T | T | T | |
| 155 | F | | | | | F | F | F | |
| 156 | Q | | | | | Q | Q | Q | |
| 157 | T | | | | | T | T | T | |
| 158 | L | | | | | L | L | L | |
| 159 | V | | | | | V | V | V | |
| 160 | M | | | | | M | M | M | |
| 161 | L | | | | | L | L | L | |
| 162 | E | | | | | E | E | E | |
| 163 | T | | | | | T | T | T | |
| 164 | F | V | | | | () | () | () | |
| 165 | P | | | | | P | P | P | |
| 166 | Q | R | | | | Q or R | Q or R | RR | |
| 167 | S | | | | | S | S | S | |
| 168 | G | | | | | G | G | G | |
| 169 | E | | | | | E | E | E | |
| 170 | V | | | | | V | V | V | |
| 171 | Y | | | | | Y | Y | Y | |
| 172 | T | | | | | T | T | T | |
| 173 | C | | | | | C | C | C | |
| 174 | Q | | | | | Q | Q | Q | |
| 175 | V | | | | | V | V | V | |
| 176 | E | | | | | E | E | E | |
| 177 | H | | | | | H | H | H | |
| 178 | P | | | | | P | P | P | |
| 179 | S | | | | | S | S | S | |
| 180 | L | V | | | | L or V | L or V | L or V | |
| 181 | M | T | | | | () | () | () | |
| 182 | S | | | | | S | S | S | |
| 183 | P | | | | | P | P | P | |
| 184 | L | | | | | L | L | L | |
| 185 | T | | | | | T | T | T | |
| 186 | V | | | | | V | V | V | |
| 187 | E | | | | | E | E | E | |
| 188 | W | | | | | W | W | W | |
| 189 | R | S | | | | RR | R or S | R or S | |
| 190 | A | | | | | A | A | A | |
| 191 | R | | | | | R | R | R | |
| 192 | S | | | | | S | S | S | |
| 193 | E | | | | | E | E | E | |
| 194 | S | | | | | S | S | S | |
| 195 | A | | | | | A | A | A | |
| 196 | Q | | | | | Q | Q | Q | |
| 197 | S | | | | | S | S | S | |
| 198 | K | | | | | K | K | K | |
| 199 | M | | | | | M | M | M | |
| 200 | L | | | | | L | L | L | |
| 201 | S | | | | | S | S | S | |
| 202 | G | | | | | G | G | G | |
| 203 | V | | | | | V | V | V | |
| 204 | G | | | | | G | G | G | |
| 205 | G | | | | | G | G | G | |
| 206 | F | | | | | F | F | F | |
| 207 | V | | | | | V | V | V | |

Fig. 99

| Position | Diverse Amino Acid | | | | | | no adjuvant therapy | Chemotherapy | Immunotherapy | |
|---|---|---|---|---|---|---|---|---|---|---|
| 208 | L | | | | | | L | L | L | |
| 209 | G | | | | | | G | G | G | |
| 210 | L | | | | | | L | L | L | |
| 211 | L | | | | | | L | L | L | |
| 212 | F | | | | | | F | F | F | |
| 213 | L | | | | | | L | L | L | |
| 214 | G | | | | | | G | G | G | |
| 215 | A | | | | | | A | A | A | |
| 216 | G | | | | | | G | G | G | |
| 217 | L | | | | | | L | L | L | |
| 218 | F | | | | | | F | F | F | |
| 219 | I | | | | | | I | I | I | |
| 220 | Y | | | | | | Y | Y | Y | |
| 221 | F | | | | | | F | F | F | |
| 222 | R | | | | | | R | R | R | |
| 223 | N | | | | | | N | N | N | |
| 224 | Q | | | | | | Q | Q | Q | |
| 225 | K | | | | | | K | K | K | |
| 226 | G | | | | | | G | G | G | |
| 227 | H | | | | | | H | H | H | |
| 228 | S | | | | | | S | S | S | |
| 229 | G | | | | | | G | G | G | |
| 230 | L | | | | | | L | L | L | |
| 231 | P | Q | | | | | P or Q | P or Q | QQ | |
| 232 | P | | | | | | P | P | P | |
| 233 | R | T | | | | | R or T | R or T | R or T | |
| 234 | G | | | | | | G | G | G | |
| 235 | F | | | | | | F | F | F | |
| 236 | L | | | | | | L | L | L | |
| 237 | S | | | | | | S | S | S | |

Fig. 100

| Position | Diverse Amino Acid | | | | | Amino Acid Configuration to Inhibit Metastases |
|---|---|---|---|---|---|---|
| 29 | M | | | | | M |
| 28 | M | | | | | M |
| 27 | V | | | | | V |
| 26 | L | | | | | L |
| 25 | Q | | | | | Q |
| 24 | V | | | | | V |
| 23 | S | | | | | S |
| 22 | A | | | | | A |
| 21 | A | | | | | A |
| 20 | P | | | | | P |
| 19 | R | | | | | R |
| 18 | T | | | | | T |
| 17 | V | | | | | V |
| 16 | A | | | | | A |
| 15 | L | | | | | L |
| 14 | T | | | | | T |
| 13 | A | | | | | A |
| 12 | L | | | | | L |
| 11 | L | | | | | L |
| 10 | M | | | | | M |
| 9 | V | | | | | V |
| 8 | L | | | | | L |
| 7 | L | | | | | L |
| 6 | T | | | | | T |
| 5 | S | | | | | S |
| 4 | V | | | | | V |
| 3 | V | | | | | V |
| 2 | Q | | | | | Q |
| 1 | G | | | | | G |
| 1 | R | | | | | R |
| 2 | A | | | | | A |
| 3 | T | | | | | T |
| 4 | P | | | | | P |
| 5 | E | | | | | E |
| 6 | N | | | | | N |
| 7 | Y | | | | | Y |
| 8 | L | V | | | | () |
| 9 | F | H | Y | | | () |
| 10 | Q | | | | | Q |
| 11 | G | L | | | | () |
| 12 | R | | | | | R |
| 13 | Q | | | | | Q |
| 14 | E | | | | | E |
| 15 | C | | | | | C |
| 16 | Y | | | | | Y |
| 17 | A | | | | | A |
| 18 | F | | | | | F |
| 19 | N | | | | | N |
| 20 | G | | | | | G |
| 21 | T | | | | | T |
| 22 | Q | | | | | Q |
| 23 | R | | | | | R |
| 24 | F | | | | | F |
| 25 | L | | | | | L |
| 26 | E | | | | | E |
| 27 | R | | | | | R |
| 28 | Y | | | | | Y |
| 29 | I | | | | | I |
| 30 | Y | | | | | Y |

Fig. 101

| Position | Diverse Amino Acid | | | | | Amino Acid Configuration to Inhibit Metastases |
|---|---|---|---|---|---|---|
| 31 | N | | | | | N |
| 32 | R | | | | | R |
| 33 | E | | | | | E |
| 34 | E | | | | | E |
| 35 | F | L | Y | | | () |
| 36 | A | V | | | | () |
| 37 | R | | | | | R |
| 38 | F | | | | | F |
| 39 | D | | | | | D |
| 40 | S | | | | | S |
| 41 | D | | | | | D |
| 42 | V | | | | | V |
| 43 | G | | | | | G |
| 44 | E | | | | | E |
| 45 | F | | | | | F |
| 46 | R | | | | | R |
| 47 | A | | | | | A |
| 48 | V | | | | | V |
| 49 | T | | | | | T |
| 50 | E | | | | | E |
| 51 | L | | | | | L |
| 52 | G | | | | | G |
| 53 | R | | | | | R |
| 54 | P | | | | | P |
| 55 | A | D | E | | | AA |
| 56 | A | E | | | | () |
| 57 | D | E | | | | () |
| 58 | Y | | | | | Y |
| 59 | W | | | | | W |
| 60 | N | | | | | N |
| 61 | S | | | | | S |
| 62 | Q | | | | | Q |
| 63 | K | | | | | K |
| 64 | D | | | | | D |
| 65 | F | I | L | | | () |
| 66 | L | | | | | L |
| 67 | E | | | | | E |
| 68 | E | | | | | E |
| 69 | E | K | | | | () |
| 70 | R | | | | | R |
| 71 | A | | | | | A |
| 72 | V | | | | | V |
| 73 | P | | | | | P |
| 74 | D | | | | | D |
| 75 | R | | | | | R |
| 76 | I | M | V | | | () |
| 77 | C | | | | | C |
| 78 | R | | | | | R |
| 79 | H | | | | | H |
| 80 | N | | | | | N |
| 81 | Y | | | | | Y |
| 82 | E | | | | | E |
| 83 | L | | | | | L |
| 84 | D | G | | | | () |
| 85 | E | G | | | | () |
| 86 | A | P | | | | () |
| 87 | M | V | | | | () |
| 88 | T | | | | | T |
| 89 | L | | | | | L |

Fig. 102

| Position | Diverse Amino Acid | | | | | Amino Acid Configuration to Inhibit Metastases |
|---|---|---|---|---|---|---|
| 90 | Q | | | | | Q |
| 91 | R | | | | | R |
| 92 | R | | | | | R |
| 93 | V | | | | | V |
| 94 | Q | | | | | Q |
| 95 | P | | | | | P |
| 96 | K | R | | | | () |
| 97 | V | | | | | V |
| 98 | N | | | | | N |
| 99 | V | | | | | V |
| 100 | S | | | | | S |
| 101 | P | | | | | P |
| 102 | S | | | | | S |
| 103 | K | | | | | K |
| 104 | K | | | | | K |
| 105 | G | | | | | G |
| 106 | P | | | | | P |
| 107 | L | | | | | L |
| 108 | Q | | | | | Q |
| 109 | H | | | | | H |
| 110 | H | | | | | H |
| 111 | N | | | | | N |
| 112 | L | | | | | L |
| 113 | L | | | | | L |
| 114 | V | | | | | V |
| 115 | C | | | | | C |
| 116 | H | | | | | H |
| 117 | V | | | | | V |
| 118 | T | | | | | T |
| 119 | D | | | | | D |
| 120 | F | | | | | F |
| 121 | Y | | | | | Y |
| 122 | P | | | | | P |
| 123 | G | | | | | G |
| 124 | S | | | | | S |
| 125 | I | | | | | I |
| 126 | Q | | | | | Q |
| 127 | V | | | | | V |
| 128 | R | | | | | R |
| 129 | W | | | | | W |
| 130 | F | | | | | F |
| 131 | L | | | | | L |
| 132 | N | | | | | N |
| 133 | G | | | | | G |
| 134 | Q | | | | | Q |
| 135 | E | | | | | E |
| 136 | E | | | | | E |
| 137 | T | | | | | T |
| 138 | A | | | | | A |
| 139 | G | | | | | G |
| 140 | V | | | | | V |
| 141 | V | | | | | V |
| 142 | S | | | | | S |
| 143 | T | | | | | T |
| 144 | N | | | | | N |
| 145 | L | | | | | L |
| 146 | I | | | | | I |
| 147 | R | | | | | R |
| 148 | N | | | | | N |

Fig. 103

| Position | Diverse Amino Acid | | | | | Amino Acid Configuration to Inhibit Metastases |
|---|---|---|---|---|---|---|
| 149 | G | | | | | G |
| 150 | D | | | | | D |
| 151 | W | | | | | W |
| 152 | T | | | | | T |
| 153 | F | | | | | F |
| 154 | Q | | | | | Q |
| 155 | I | | | | | I |
| 156 | L | | | | | L |
| 157 | V | | | | | V |
| 158 | M | | | | | M |
| 159 | L | | | | | L |
| 160 | E | | | | | E |
| 161 | M | | | | | M |
| 162 | T | | | | | T |
| 163 | P | | | | | P |
| 164 | Q | | | | | Q |
| 165 | Q | | | | | Q |
| 166 | G | | | | | G |
| 167 | D | | | | | D |
| 168 | V | | | | | V |
| 169 | Y | | | | | Y |
| 170 | I | T | | | | () |
| 171 | C | | | | | C |
| 172 | Q | | | | | Q |
| 173 | V | | | | | V |
| 174 | E | | | | | E |
| 175 | H | | | | | H |
| 176 | T | | | | | T |
| 177 | S | | | | | S |
| 178 | L | M | | | | () |
| 179 | D | | | | | D |
| 180 | S | | | | | S |
| 181 | P | | | | | P |
| 182 | V | | | | | V |
| 183 | T | | | | | T |
| 184 | V | | | | | V |
| 185 | E | | | | | E |
| 186 | W | | | | | W |
| 187 | K | | | | | K |
| 188 | A | | | | | A |
| 189 | Q | | | | | Q |
| 190 | S | | | | | S |
| 191 | D | | | | | D |
| 192 | S | | | | | S |
| 193 | A | | | | | A |
| 194 | R | | | | | R |
| 195 | S | | | | | S |
| 196 | K | | | | | K |
| 197 | T | | | | | T |
| 198 | L | | | | | L |
| 199 | T | | | | | T |
| 200 | G | | | | | G |
| 201 | A | | | | | A |
| 202 | G | | | | | G |
| 203 | G | | | | | G |
| 204 | F | | | | | F |
| 205 | V | | | | | V |
| 206 | L | | | | | L |
| 207 | G | | | | | G |

Fig. 104

| Position | Diverse Amino Acid | Amino Acid Configuration to Inhibit Metastases |
|---|---|---|
| 208 | L | L |
| 209 | I | I |
| 210 | I | I |
| 211 | C | C |
| 212 | G | G |
| 213 | V | V |
| 214 | G | G |
| 215 | I | I |
| 216 | F | F |
| 217 | M | M |
| 218 | H | H |
| 219 | R | R |
| 220 | R | R |
| 221 | S | S |
| 222 | K | K |
| 223 | K | K |
| 224 | V | V |
| 225 | Q | Q |
| 226 | R | R |
| 227 | G | G |
| 228 | S | S |
| 229 | A | A |

Fig. 105

| Position | Diverse Amino Acid | | | | | Amino Acid Configuration to Inhibit Metastases |
|---|---|---|---|---|---|---|
| -32 | M | | | | | M |
| -31 | S | | | | | S |
| -30 | W | | | | | W |
| -29 | K | | | | | K |
| -28 | K | | | | | K |
| -27 | A | S | | | | () |
| -26 | L | | | | | L |
| -25 | R | | | | | R |
| -24 | I | | | | | I |
| -23 | P | | | | | P |
| -22 | G | | | | | G |
| -21 | D | G | | | | () |
| -20 | L | | | | | L |
| -19 | R | | | | | R |
| -18 | A | V | | | | () |
| -17 | A | | | | | A |
| -16 | T | | | | | T |
| -15 | V | | | | | V |
| -14 | T | | | | | T |
| -13 | L | | | | | L |
| -12 | M | | | | | M |
| -11 | L | | | | | L |
| -10 | A | S | | | | () |
| -9 | I | M | | | | () |
| -8 | L | | | | | L |
| -7 | S | | | | | S |
| -6 | S | T | | | | () |
| -5 | L | P | S | | | () |
| -4 | L | V | | | | () |
| -3 | A | | | | | A |
| -2 | E | | | | | E |
| -1 | G | | | | | G |
| 1 | R | | | | | R |
| 2 | D | | | | | D |
| 3 | P | S | | | | () |
| 4 | P | | | | | P |
| 5 | E | | | | | E |
| 6 | D | | | | | D |
| 7 | F | | | | | F |
| 8 | V | | | | | V |
| 9 | F | L | Y | | | () |
| 10 | Q | | | | | Q |
| 11 | F | | | | | F |
| 12 | K | | | | | K |
| 13 | A | G | | | | () |
| 14 | L | M | | | | LM |
| 15 | C | | | | | C |
| 16 | Y | | | | | Y |
| 17 | F | | | | | F |
| 18 | T | | | | | T |
| 19 | N | | | | | N |
| 20 | G | | | | | G |
| 21 | T | | | | | T |
| 22 | E | | | | | E |
| 23 | L | R | | | | () |
| 24 | V | | | | | V |
| 25 | R | | | | | R |
| 26 | G | L | Y | | | () |
| 27 | V | | | | | V |

Fig. 106

| Position | Diverse Amino Acid | | | | | Amino Acid Configuration to Inhibit Metastases |
|---|---|---|---|---|---|---|
| 28 | S | T | | | | () |
| 29 | R | | | | | R |
| 30 | H | S | Y | | | () |
| 31 | I | | | | | I |
| 32 | Y | | | | | Y |
| 33 | N | | | | | N |
| 34 | R | | | | | R |
| 35 | E | | | | | E |
| 36 | E | | | | | E |
| 37 | D | I | Y | | | () |
| 38 | A | V | | | | () |
| 39 | R | | | | | R |
| 40 | F | | | | | F |
| 41 | D | | | | | D |
| 42 | S | | | | | S |
| 43 | D | | | | | D |
| 44 | V | | | | | V |
| 45 | E | G | | | | () |
| 46 | E | V | | | | () |
| 47 | F | Y | | | | () |
| 48 | R | | | | | R |
| 49 | A | | | | | A |
| 50 | V | | | | | V |
| 51 | T | | | | | T |
| 52 | L | P | | | | () |
| 53 | L | Q | | | | () |
| 54 | G | | | | | G |
| 55 | L | P | R | | | () |
| 56 | L | P | | | | () |
| 57 | A | D | S | V | | () |
| 58 | A | | | | | A |
| 59 | E | | | | | E |
| 60 | Y | | | | | Y |
| 61 | W | | | | | W |
| 62 | N | | | | | N |
| 63 | S | | | | | S |
| 64 | Q | | | | | Q |
| 65 | K | | | | | K |
| 66 | D | E | | | | () |
| 67 | I | V | | | | () |
| 68 | L | | | | | L |
| 69 | E | | | | | E |
| 70 | E | G | R | | | () |
| 71 | A | D | K | T | | () |
| 72 | R | | | | | R |
| 73 | A | | | | | A |
| 74 | A | E | S | | | () |
| 75 | L | V | | | | () |
| 76 | D | | | | | D |
| 77 | R | T | | | | RT |
| 78 | V | | | | | V |
| 79 | C | | | | | C |
| 80 | R | | | | | R |
| 81 | H | | | | | H |
| 82 | N | | | | | N |
| 83 | Y | | | | | Y |
| 84 | E | Q | | | | () |
| 85 | L | V | | | | () |
| 86 | A | E | G | | | () |

Fig. 107

| Position | Diverse Amino Acid | | | | | Amino Acid Configuration to Inhibit Metastases |
|---|---|---|---|---|---|---|
| 87 | F | L | Y | | | LL |
| 88 | R | | | | | R |
| 89 | G | T | | | | () |
| 90 | I | T | | | | () |
| 91 | L | | | | | L |
| 92 | Q | | | | | Q |
| 93 | R | | | | | R |
| 94 | R | | | | | R |
| 95 | V | | | | | V |
| 96 | E | | | | | E |
| 97 | P | | | | | P |
| 98 | T | | | | | T |
| 99 | V | | | | | V |
| 100 | T | | | | | T |
| 101 | I | | | | | I |
| 102 | S | | | | | S |
| 103 | P | | | | | P |
| 104 | S | | | | | S |
| 105 | R | | | | | R |
| 106 | T | | | | | T |
| 107 | E | | | | | E |
| 108 | A | | | | | A |
| 109 | L | | | | | L |
| 110 | N | | | | | N |
| 111 | H | | | | | H |
| 112 | H | | | | | H |
| 113 | N | | | | | N |
| 114 | L | | | | | L |
| 115 | L | | | | | L |
| 116 | I | V | | | | IV |
| 117 | C | | | | | C |
| 118 | S | | | | | S |
| 119 | V | | | | | V |
| 120 | T | | | | | T |
| 121 | D | | | | | D |
| 122 | F | | | | | F |
| 123 | Y | | | | | Y |
| 124 | P | | | | | P |
| 125 | A | G | S | | | AA |
| 126 | H | Q | | | | () |
| 127 | I | | | | | I |
| 128 | K | | | | | K |
| 129 | V | | | | | V |
| 130 | Q | R | | | | () |
| 131 | W | | | | | W |
| 132 | F | | | | | F |
| 133 | R | | | | | R |
| 134 | N | | | | | N |
| 135 | D | | | | | D |
| 136 | Q | | | | | Q |
| 137 | E | | | | | E |
| 138 | E | | | | | E |
| 139 | T | | | | | T |
| 140 | A | T | | | | () |
| 141 | G | | | | | G |
| 142 | V | | | | | V |
| 143 | V | | | | | V |
| 144 | S | | | | | S |
| 145 | T | | | | | T |

Fig. 108

| Position | Diverse Amino Acid | | | | | Amino Acid Configuration to Inhibit Metastases |
|---|---|---|---|---|---|---|
| 146 | P | | | | | P |
| 147 | L | | | | | L |
| 148 | I | | | | | I |
| 149 | R | | | | | R |
| 150 | N | | | | | N |
| 151 | G | | | | | G |
| 152 | D | | | | | D |
| 153 | W | | | | | W |
| 154 | T | | | | | T |
| 155 | F | | | | | F |
| 156 | Q | | | | | Q |
| 157 | I | | | | | I |
| 158 | L | | | | | L |
| 159 | V | | | | | V |
| 160 | M | | | | | M |
| 161 | L | | | | | L |
| 162 | E | | | | | E |
| 163 | M | | | | | M |
| 164 | T | | | | | T |
| 165 | P | | | | | P |
| 166 | Q | | | | | Q |
| 167 | H | R | | | | () |
| 168 | G | | | | | G |
| 169 | D | | | | | D |
| 170 | V | | | | | V |
| 171 | Y | | | | | Y |
| 172 | T | | | | | T |
| 173 | C | | | | | C |
| 174 | H | | | | | H |
| 175 | V | | | | | V |
| 176 | E | | | | | E |
| 177 | H | | | | | H |
| 178 | P | | | | | P |
| 179 | S | | | | | S |
| 180 | L | | | | | L |
| 181 | Q | | | | | Q |
| 182 | N | S | | | | () |
| 183 | P | | | | | P |
| 184 | I | | | | | I |
| 185 | I | T | | | | () |
| 186 | V | | | | | V |
| 187 | E | | | | | E |
| 188 | W | | | | | W |
| 189 | R | | | | | R |
| 190 | A | | | | | A |
| 191 | Q | | | | | Q |
| 192 | S | | | | | S |
| 193 | E | | | | | E |
| 194 | S | | | | | S |
| 195 | A | | | | | A |
| 196 | Q | | | | | Q |
| 197 | N | S | | | | () |
| 198 | K | | | | | K |
| 199 | M | | | | | M |
| 200 | L | | | | | L |
| 201 | S | | | | | S |
| 202 | G | | | | | G |
| 203 | I | V | | | | () |
| 204 | G | | | | | G |

Fig. 109

| Position | Diverse Amino Acid | | | | | Amino Acid Configuration to Inhibit Metastases |
|---|---|---|---|---|---|---|
| 205 | G | | | | | G |
| 206 | F | | | | | F |
| 207 | V | | | | | V |
| 208 | L | | | | | L |
| 209 | G | | | | | G |
| 210 | L | | | | | L |
| 211 | I | | | | | I |
| 212 | F | | | | | F |
| 213 | L | | | | | L |
| 214 | G | | | | | G |
| 215 | L | | | | | L |
| 216 | G | | | | | G |
| 217 | L | | | | | L |
| 218 | I | | | | | I |
| 219 | I | | | | | I |
| 220 | H | R | | | | () |
| 221 | H | Q | | | | () |
| 222 | R | | | | | R |
| 223 | S | | | | | S |
| 224 | Q | R | | | | QR |
| 225 | K | | | | | K |
| 226 | G | | | | | G |
| 227 | P | | | | | P |
| 228 | Q | | | | | Q |
| 229 | G | | | | | G |
| 230 | P | | | | | P |
| 231 | P | | | | | P |
| 232 | P | | | | | P |
| 233 | A | | | | | A |
| 234 | G | | | | | G |
| 235 | L | | | | | L |
| 236 | L | | | | | L |
| 237 | H | | | | | H |

Fig. 110

| Position | Diverse Amino Acid | | | | | | Amino Acid Configuration to Inhibit Metastases |
|---|---|---|---|---|---|---|---|
| _29 | M | | | | | | M |
| _28 | V | | | | | | V |
| _27 | C | | | | | | C |
| _26 | L | | | | | | L |
| _25 | K | R | | | | | () |
| _24 | F | L | | | | | LL |
| _23 | P | | | | | | P |
| _22 | G | | | | | | G |
| _21 | G | | | | | | G |
| _20 | S | | | | | | S |
| _19 | C | | | | | | C |
| _18 | M | | | | | | M |
| _17 | A | T | | | | | () |
| _16 | A | V | | | | | () |
| _15 | L | | | | | | L |
| _14 | T | | | | | | T |
| _13 | V | | | | | | V |
| _12 | T | | | | | | T |
| _11 | L | | | | | | L |
| _10 | M | | | | | | M |
| _9 | V | | | | | | V |
| _8 | L | | | | | | L |
| _8 | S | | | | | | S |
| _6 | S | | | | | | S |
| _5 | P | | | | | | P |
| _4 | L | | | | | | L |
| _3 | A | | | | | | A |
| _2 | L | | | | | | L |
| _1 | A | S | | | | | () |
| 1 | G | | | | | | G |
| 2 | D | | | | | | D |
| 3 | T | | | | | | T |
| 4 | Q | R | | | | | () |
| 5 | P | | | | | | P |
| 6 | R | | | | | | R |
| 7 | F | | | | | | F |
| 8 | L | | | | | | L |
| 9 | E | K | W | | | | () |
| 10 | E | Q | Y | | | | () |
| 11 | D | G | L | P | S | V | () |
| 12 | K | T | | | | | () |
| 13 | F | G | H | R | S | Y | () |
| 14 | E | K | | | | | () |
| 15 | C | | | | | | C |
| 16 | H | Q | Y | | | | () |
| 17 | F | | | | | | F |
| 18 | F | | | | | | F |
| 19 | N | | | | | | N |
| 20 | G | | | | | | G |
| 21 | T | | | | | | T |
| 22 | E | | | | | | E |
| 23 | R | | | | | | R |
| 24 | V | | | | | | V |
| 25 | Q | R | | | | | () |
| 26 | F | L | Y | | | | () |
| 27 | L | | | | | | L |
| 28 | D | E | H | | | | () |
| 29 | R | | | | | | R |
| 30 | C | G | H | L | R | Y | () |

Fig. 111

| Position | Diverse Amino Acid | | | | | Amino Acid Configuration to Inhibit Metastases |
|---|---|---|---|---|---|---|
| 31 | F | I | V | | | () |
| 32 | H | Y | | | | () |
| 33 | H | N | | | | () |
| 34 | Q | | | | | Q |
| 35 | E | | | | | E |
| 36 | E | | | | | E |
| 37 | F | L | N | S | Y | () |
| 38 | A | L | V | | | () |
| 39 | R | | | | | R |
| 40 | F | Y | | | | () |
| 41 | D | | | | | D |
| 42 | S | | | | | S |
| 43 | D | | | | | D |
| 44 | V | | | | | V |
| 45 | G | | | | | G |
| 46 | E | | | | | E |
| 47 | F | Y | | | | () |
| 48 | R | | | | | R |
| 49 | A | | | | | A |
| 50 | V | | | | | V |
| 51 | T | | | | | T |
| 52 | E | | | | | E |
| 53 | L | | | | | L |
| 54 | G | | | | | G |
| 55 | R | | | | | R |
| 56 | P | | | | | P |
| 57 | A | D | S | V | | () |
| 58 | A | E | | | | () |
| 59 | E | | | | | E |
| 60 | H | S | Y | | | () |
| 61 | W | | | | | W |
| 62 | N | | | | | N |
| 63 | S | | | | | S |
| 64 | Q | | | | | Q |
| 65 | K | | | | | K |
| 66 | D | | | | | D |
| 67 | F | I | L | | | () |
| 68 | L | | | | | L |
| 69 | E | | | | | E |
| 70 | D | Q | R | | | () |
| 71 | A | E | K | R | | () |
| 72 | R | | | | | R |
| 73 | A | G | | | | () |
| 74 | A | E | L | Q | R | () |
| 75 | V | | | | | V |
| 76 | D | | | | | D |
| 77 | N | T | | | | () |
| 78 | V | Y | | | | () |
| 79 | C | | | | | C |
| 80 | R | | | | | R |
| 81 | H | | | | | H |
| 82 | N | | | | | N |
| 83 | Y | | | | | Y |
| 84 | G | | | | | G |
| 85 | A | V | | | | () |
| 86 | G | V | | | | () |
| 87 | E | | | | | E |
| 88 | S | | | | | S |
| 89 | F | | | | | F |

Fig. 112

| Position | Diverse Amino Acid | | | | | Amino Acid Configuration to Inhibit Metastases |
|---|---|---|---|---|---|---|
| 90 | T | | | | | T |
| 91 | V | | | | | V |
| 92 | Q | | | | | Q |
| 93 | R | | | | | R |
| 94 | R | | | | | R |
| 95 | V | | | | | V |
| 96 | E | H | Q | Y | | () |
| 97 | P | | | | | P |
| 98 | E | K | | | | () |
| 99 | V | | | | | V |
| 100 | T | | | | | T |
| 101 | V | | | | | V |
| 102 | Y | | | | | Y |
| 103 | P | | | | | P |
| 104 | A | S | | | | () |
| 105 | K | | | | | K |
| 106 | T | | | | | T |
| 107 | Q | | | | | Q |
| 108 | P | | | | | P |
| 109 | L | | | | | L |
| 110 | Q | | | | | Q |
| 111 | H | | | | | H |
| 112 | H | | | | | H |
| 113 | N | | | | | N |
| 114 | L | | | | | L |
| 115 | L | | | | | L |
| 116 | V | | | | | V |
| 117 | C | | | | | C |
| 118 | S | | | | | S |
| 119 | V | | | | | V |
| 120 | N | S | | | | () |
| 121 | F | | | | | F |
| 122 | G | | | | | G |
| 123 | Y | | | | | Y |
| 124 | P | | | | | P |
| 125 | G | | | | | G |
| 126 | S | | | | | S |
| 127 | I | | | | | I |
| 128 | E | | | | | E |
| 129 | V | | | | | V |
| 130 | R | | | | | R |
| 131 | W | | | | | W |
| 132 | F | | | | | F |
| 133 | L | R | | | | () |
| 134 | N | | | | | N |
| 135 | G | | | | | G |
| 136 | Q | | | | | Q |
| 137 | E | | | | | E |
| 138 | E | | | | | E |
| 139 | K | | | | | K |
| 140 | A | T | | | | () |
| 141 | G | | | | | G |
| 142 | M | V | | | | () |
| 143 | V | | | | | V |
| 144 | S | | | | | S |
| 145 | T | | | | | T |
| 146 | G | | | | | G |
| 147 | L | | | | | L |
| 148 | I | | | | | I |

Fig. 113

| Position | Diverse Amino Acid | | | | | | Amino Acid Configuration to Inhibit Metastases |
|---|---|---|---|---|---|---|---|
| 149 | H | Q | | | | | () |
| 150 | N | | | | | | N |
| 151 | G | | | | | | G |
| 152 | D | | | | | | D |
| 153 | W | | | | | | W |
| 154 | T | | | | | | T |
| 155 | F | | | | | | F |
| 156 | Q | | | | | | Q |
| 157 | T | | | | | | T |
| 158 | L | | | | | | L |
| 159 | V | | | | | | V |
| 160 | M | | | | | | M |
| 161 | L | | | | | | L |
| 162 | E | | | | | | E |
| 163 | T | | | | | | T |
| 164 | F | V | | | | | () |
| 165 | P | | | | | | P |
| 166 | Q | R | | | | | () |
| 167 | S | | | | | | S |
| 168 | G | | | | | | G |
| 169 | E | | | | | | E |
| 170 | V | | | | | | V |
| 171 | Y | | | | | | Y |
| 172 | T | | | | | | T |
| 173 | C | | | | | | C |
| 174 | Q | | | | | | Q |
| 175 | V | | | | | | V |
| 176 | E | | | | | | E |
| 177 | H | | | | | | H |
| 178 | P | | | | | | P |
| 179 | S | | | | | | S |
| 180 | L | V | | | | | () |
| 181 | M | T | | | | | () |
| 182 | S | | | | | | S |
| 183 | P | | | | | | P |
| 184 | L | | | | | | L |
| 185 | T | | | | | | T |
| 186 | V | | | | | | V |
| 187 | E | | | | | | E |
| 188 | W | | | | | | W |
| 189 | R | S | | | | | () |
| 190 | A | | | | | | A |
| 191 | R | | | | | | R |
| 192 | S | | | | | | S |
| 193 | E | | | | | | E |
| 194 | S | | | | | | S |
| 195 | A | | | | | | A |
| 196 | Q | | | | | | Q |
| 197 | S | | | | | | S |
| 198 | K | | | | | | K |
| 199 | M | | | | | | M |
| 200 | L | | | | | | L |
| 201 | S | | | | | | S |
| 202 | G | | | | | | G |
| 203 | V | | | | | | V |
| 204 | G | | | | | | G |
| 205 | G | | | | | | G |
| 206 | F | | | | | | F |
| 207 | V | | | | | | V |

Fig. 114

| Position | Diverse Amino Acid | | | | | Amino Acid Configuration to Inhibit Metastases |
|---|---|---|---|---|---|---|
| 208 | L | | | | | L |
| 209 | G | | | | | G |
| 210 | L | | | | | L |
| 211 | L | | | | | L |
| 212 | F | | | | | F |
| 213 | L | | | | | L |
| 214 | G | | | | | G |
| 215 | A | | | | | A |
| 216 | G | | | | | G |
| 217 | L | | | | | L |
| 218 | F | | | | | F |
| 219 | I | | | | | I |
| 220 | Y | | | | | Y |
| 221 | F | | | | | F |
| 222 | R | | | | | R |
| 223 | N | | | | | N |
| 224 | Q | | | | | Q |
| 225 | K | | | | | K |
| 226 | G | | | | | G |
| 227 | H | | | | | H |
| 228 | S | | | | | S |
| 229 | G | | | | | G |
| 230 | L | | | | | L |
| 231 | P | Q | | | | () |
| 232 | P | | | | | P |
| 233 | R | T | | | | () |
| 234 | G | | | | | G |
| 235 | F | | | | | F |
| 236 | L | | | | | L |
| 237 | S | | | | | S |

Fig. 115

| Position | Diverse Amino Acid | | | | | Amino Acid Configuration With Less Tendency to Malignancy |
|---|---|---|---|---|---|---|
| 29 | M | | | | | M |
| 28 | M | | | | | M |
| 27 | V | | | | | V |
| 26 | L | | | | | L |
| 25 | Q | | | | | Q |
| 24 | V | | | | | V |
| 23 | S | | | | | S |
| 22 | A | | | | | A |
| 21 | A | | | | | A |
| 20 | P | | | | | P |
| 19 | R | | | | | R |
| 18 | T | | | | | T |
| 17 | V | | | | | V |
| 16 | A | | | | | A |
| 15 | L | | | | | L |
| 14 | T | | | | | T |
| 13 | A | | | | | A |
| 12 | L | | | | | L |
| 11 | L | | | | | L |
| 10 | M | | | | | M |
| 9 | V | | | | | V |
| 8 | L | | | | | L |
| 7 | L | | | | | L |
| 6 | T | | | | | T |
| 5 | S | | | | | S |
| 4 | V | | | | | V |
| 3 | V | | | | | V |
| 2 | Q | | | | | Q |
| 1 | G | | | | | G |
| 1 | R | | | | | R |
| 2 | A | | | | | A |
| 3 | T | | | | | T |
| 4 | P | | | | | P |
| 5 | E | | | | | E |
| 6 | N | | | | | N |
| 7 | Y | | | | | Y |
| 8 | L | V | | | | LL |
| 9 | F | H | Y | | | () |
| 10 | Q | | | | | Q |
| 11 | G | L | | | | LL |
| 12 | R | | | | | R |
| 13 | Q | | | | | Q |
| 14 | E | | | | | E |
| 15 | C | | | | | C |
| 16 | Y | | | | | Y |
| 17 | A | | | | | A |
| 18 | F | | | | | F |
| 19 | N | | | | | N |
| 20 | G | | | | | G |
| 21 | T | | | | | T |
| 22 | Q | | | | | Q |
| 23 | R | | | | | R |
| 24 | F | | | | | F |
| 25 | L | | | | | L |
| 26 | E | | | | | E |
| 27 | R | | | | | R |
| 28 | Y | | | | | Y |
| 29 | I | | | | | I |
| 30 | Y | | | | | Y |

Fig. 116

| Position | Diverse Amino Acid | | | | | Amino Acid Configuration With Less Tendency to Malignancy |
|---|---|---|---|---|---|---|
| 31 | N | | | | | N |
| 32 | R | | | | | R |
| 33 | E | | | | | E |
| 34 | E | | | | | E |
| 35 | F | L | Y | | | () |
| 36 | A | V | | | | () |
| 37 | R | | | | | R |
| 38 | F | | | | | F |
| 39 | D | | | | | D |
| 40 | S | | | | | S |
| 41 | D | | | | | D |
| 42 | V | | | | | V |
| 43 | G | | | | | G |
| 44 | E | | | | | E |
| 45 | F | | | | | F |
| 46 | R | | | | | R |
| 47 | A | | | | | A |
| 48 | V | | | | | V |
| 49 | T | | | | | T |
| 50 | E | | | | | E |
| 51 | L | | | | | L |
| 52 | G | | | | | G |
| 53 | R | | | | | R |
| 54 | P | | | | | P |
| 55 | A | D | E | | | () |
| 56 | A | E | | | | () |
| 57 | D | E | | | | EE |
| 58 | Y | | | | | Y |
| 59 | W | | | | | W |
| 60 | N | | | | | N |
| 61 | S | | | | | S |
| 62 | Q | | | | | Q |
| 63 | K | | | | | K |
| 64 | D | | | | | D |
| 65 | F | I | L | | | () |
| 66 | L | | | | | L |
| 67 | E | | | | | E |
| 68 | E | | | | | E |
| 69 | E | K | | | | () |
| 70 | R | | | | | R |
| 71 | A | | | | | A |
| 72 | V | | | | | V |
| 73 | P | | | | | P |
| 74 | D | | | | | D |
| 75 | R | | | | | R |
| 76 | I | M | V | | | II |
| 77 | C | | | | | C |
| 78 | R | | | | | R |
| 79 | H | | | | | H |
| 80 | N | | | | | N |
| 81 | Y | | | | | Y |
| 82 | E | | | | | E |
| 83 | L | | | | | L |
| 84 | D | G | | | | GG |
| 85 | E | G | | | | GG |
| 86 | A | P | | | | MM |
| 87 | M | V | | | | MM |
| 88 | T | | | | | T |
| 89 | L | | | | | L |

Fig. 117

| Position | Diverse Amino Acid | | | | | Amino Acid Configuration With Less Tendency to Malignancy |
|---|---|---|---|---|---|---|
| 90 | Q | | | | | Q |
| 91 | R | | | | | R |
| 92 | R | | | | | R |
| 93 | V | | | | | V |
| 94 | Q | | | | | Q |
| 95 | P | | | | | P |
| 96 | K | R | | | | Q |
| 97 | V | | | | | V |
| 98 | N | | | | | N |
| 99 | V | | | | | V |
| 100 | S | | | | | S |
| 101 | P | | | | | P |
| 102 | S | | | | | S |
| 103 | K | | | | | K |
| 104 | K | | | | | K |
| 105 | G | | | | | G |
| 106 | P | | | | | P |
| 107 | L | | | | | L |
| 108 | Q | | | | | Q |
| 109 | H | | | | | H |
| 110 | H | | | | | H |
| 111 | N | | | | | N |
| 112 | L | | | | | L |
| 113 | L | | | | | L |
| 114 | V | | | | | V |
| 115 | C | | | | | C |
| 116 | H | | | | | H |
| 117 | V | | | | | V |
| 118 | T | | | | | T |
| 119 | D | | | | | D |
| 120 | F | | | | | F |
| 121 | Y | | | | | Y |
| 122 | P | | | | | P |
| 123 | G | | | | | G |
| 124 | S | | | | | S |
| 125 | I | | | | | I |
| 126 | Q | | | | | Q |
| 127 | V | | | | | V |
| 128 | R | | | | | R |
| 129 | W | | | | | W |
| 130 | F | | | | | F |
| 131 | L | | | | | L |
| 132 | N | | | | | N |
| 133 | G | | | | | G |
| 134 | Q | | | | | Q |
| 135 | E | | | | | E |
| 136 | E | | | | | E |
| 137 | T | | | | | T |
| 138 | A | | | | | A |
| 139 | G | | | | | G |
| 140 | V | | | | | V |
| 141 | V | | | | | V |
| 142 | S | | | | | S |
| 143 | T | | | | | T |
| 144 | N | | | | | N |
| 145 | L | | | | | L |
| 146 | I | | | | | I |
| 147 | R | | | | | R |
| 148 | N | | | | | N |

Fig. 118

| Position | Diverse Amino Acid | | | | | | Amino Acid Configuration With Less Tendency to Malignancy |
|---|---|---|---|---|---|---|---|
| 149 | G | | | | | | G |
| 150 | D | | | | | | D |
| 151 | W | | | | | | W |
| 152 | T | | | | | | T |
| 153 | F | | | | | | F |
| 154 | Q | | | | | | Q |
| 155 | I | | | | | | I |
| 156 | L | | | | | | L |
| 157 | V | | | | | | V |
| 158 | M | | | | | | M |
| 159 | L | | | | | | L |
| 160 | E | | | | | | E |
| 161 | M | | | | | | M |
| 162 | T | | | | | | T |
| 163 | P | | | | | | P |
| 164 | Q | | | | | | Q |
| 165 | Q | | | | | | Q |
| 166 | G | | | | | | G |
| 167 | D | | | | | | D |
| 168 | V | | | | | | V |
| 169 | Y | | | | | | Y |
| 170 | I | T | | | | | () |
| 171 | C | | | | | | C |
| 172 | Q | | | | | | Q |
| 173 | V | | | | | | V |
| 174 | E | | | | | | E |
| 175 | H | | | | | | H |
| 176 | T | | | | | | T |
| 177 | S | | | | | | S |
| 178 | L | M | | | | | () |
| 179 | D | | | | | | D |
| 180 | S | | | | | | S |
| 181 | P | | | | | | P |
| 182 | V | | | | | | V |
| 183 | T | | | | | | T |
| 184 | V | | | | | | V |
| 185 | E | | | | | | E |
| 186 | W | | | | | | W |
| 187 | K | | | | | | K |
| 188 | A | | | | | | A |
| 189 | Q | | | | | | Q |
| 190 | S | | | | | | S |
| 191 | D | | | | | | D |
| 192 | S | | | | | | S |
| 193 | A | | | | | | A |
| 194 | R | | | | | | R |
| 195 | S | | | | | | S |
| 196 | K | | | | | | K |
| 197 | T | | | | | | T |
| 198 | L | | | | | | L |
| 199 | T | | | | | | T |
| 200 | G | | | | | | G |
| 201 | A | | | | | | A |
| 202 | G | | | | | | G |
| 203 | G | | | | | | G |
| 204 | F | | | | | | F |
| 205 | V | | | | | | V |
| 206 | L | | | | | | L |
| 207 | G | | | | | | G |

Fig. 119

| Position | Diverse Amino Acid | | | | | | Amino Acid Configuration With Less Tendency to Malignancy |
|---|---|---|---|---|---|---|---|
| 208 | L | | | | | | L |
| 209 | I | | | | | | I |
| 210 | I | | | | | | I |
| 211 | C | | | | | | C |
| 212 | G | | | | | | G |
| 213 | V | | | | | | V |
| 214 | G | | | | | | G |
| 215 | I | | | | | | I |
| 216 | F | | | | | | F |
| 217 | M | | | | | | M |
| 218 | H | | | | | | H |
| 219 | R | | | | | | R |
| 220 | R | | | | | | R |
| 221 | S | | | | | | S |
| 222 | K | | | | | | K |
| 223 | K | | | | | | K |
| 224 | V | | | | | | V |
| 225 | Q | | | | | | Q |
| 226 | R | | | | | | R |
| 227 | G | | | | | | G |
| 228 | S | | | | | | S |
| 229 | A | | | | | | A |

Fig. 120

| Position | Diverse Amino Acid | | | | | Amino Acid Configuration With Less Tendency to Malignancy |
|---|---|---|---|---|---|---|
| 32 | M | | | | | M |
| 31 | S | | | | | S |
| 30 | W | | | | | W |
| 29 | K | | | | | K |
| 28 | K | | | | | K |
| 27 | A | S | | | | ( ) |
| 26 | L | | | | | L |
| 25 | R | | | | | R |
| 24 | I | | | | | I |
| 23 | P | | | | | P |
| 22 | G | | | | | G |
| 21 | D | G | | | | ( ) |
| 20 | L | | | | | L |
| 19 | R | | | | | R |
| 18 | A | V | | | | ( ) |
| 17 | A | | | | | A |
| 16 | T | | | | | T |
| 15 | V | | | | | V |
| 14 | T | | | | | T |
| 13 | L | | | | | L |
| 12 | M | | | | | M |
| 11 | L | | | | | L |
| 10 | A | S | | | | ( ) |
| 9 | I | M | | | | ( ) |
| 8 | L | | | | | L |
| 7 | S | | | | | S |
| 6 | S | T | | | | ( ) |
| 5 | L | P | S | | | ( ) |
| 4 | L | V | | | | ( ) |
| 3 | A | | | | | A |
| 2 | E | | | | | E |
| 1 | G | | | | | G |
| 1 | R | | | | | R |
| 2 | D | | | | | D |
| 3 | P | S | | | | ( ) |
| 4 | P | | | | | P |
| 5 | E | | | | | E |
| 6 | D | | | | | D |
| 7 | F | | | | | F |
| 8 | V | | | | | V |
| 9 | F | L | Y | | | ( ) |
| 10 | Q | | | | | Q |
| 11 | F | | | | | F |
| 12 | K | | | | | K |
| 13 | A | G | | | | ( ) |
| 14 | L | M | | | | ( ) |
| 15 | C | | | | | C |
| 16 | Y | | | | | Y |
| 17 | F | | | | | F |
| 18 | T | | | | | T |
| 19 | N | | | | | N |
| 20 | G | | | | | G |
| 21 | T | | | | | T |
| 22 | E | | | | | E |
| 23 | L | R | | | | ( ) |
| 24 | V | | | | | V |
| 25 | R | | | | | R |
| 26 | G | L | Y | | | ( ) |
| 27 | V | | | | | V |

Fig. 121

| Position | Diverse Amino Acid | | | | | | Amino Acid Configuration With Less Tendency to Malignancy |
|---|---|---|---|---|---|---|---|
| 28 | S | T | | | | | S or () |
| 29 | R | | | | | | R |
| 30 | H | S | Y | | | | () |
| 31 | I | | | | | | I |
| 32 | Y | | | | | | Y |
| 33 | N | | | | | | N |
| 34 | R | | | | | | R |
| 35 | E | | | | | | E |
| 36 | E | | | | | | E |
| 37 | D | I | Y | | | | () |
| 38 | A | V | | | | | () |
| 39 | R | | | | | | R |
| 40 | F | | | | | | F |
| 41 | D | | | | | | D |
| 42 | S | | | | | | S |
| 43 | D | | | | | | D |
| 44 | V | | | | | | V |
| 45 | E | G | | | | | () |
| 46 | E | V | | | | | () |
| 47 | F | Y | | | | | () |
| 48 | R | | | | | | R |
| 49 | A | | | | | | A |
| 50 | V | | | | | | V |
| 51 | T | | | | | | T |
| 52 | L | P | | | | | () |
| 53 | L | Q | | | | | () |
| 54 | G | | | | | | G |
| 55 | L | P | R | | | | () |
| 56 | L | P | | | | | () |
| 57 | A | D | S | V | | | () |
| 58 | A | | | | | | A |
| 59 | E | | | | | | E |
| 60 | Y | | | | | | Y |
| 61 | W | | | | | | W |
| 62 | N | | | | | | N |
| 63 | S | | | | | | S |
| 64 | Q | | | | | | Q |
| 65 | K | | | | | | K |
| 66 | D | E | | | | | () |
| 67 | I | V | | | | | () |
| 68 | L | | | | | | L |
| 69 | E | | | | | | E |
| 70 | E | G | R | | | | () |
| 71 | A | D | K | T | | | () |
| 72 | R | | | | | | R |
| 73 | A | | | | | | A |
| 74 | A | E | S | | | | () |
| 75 | L | V | | | | | () |
| 76 | D | | | | | | D |
| 77 | R | T | | | | | () |
| 78 | V | | | | | | V |
| 79 | C | | | | | | C |
| 80 | R | | | | | | R |
| 81 | H | | | | | | H |
| 82 | N | | | | | | N |
| 83 | Y | | | | | | Y |
| 84 | E | Q | | | | | () |
| 85 | L | V | | | | | () |
| 86 | A | E | G | | | | EG |

Fig. 122

| Position | Diverse Amino Acid | | | | | | Amino Acid Configuration With Less Tendency to Malignancy |
|---|---|---|---|---|---|---|---|
| 87 | F | L | Y | | | | () |
| 88 | R | | | | | | R |
| 89 | G | T | | | | | () |
| 90 | I | T | | | | | () |
| 91 | L | | | | | | L |
| 92 | Q | | | | | | Q |
| 93 | R | | | | | | R |
| 94 | R | | | | | | R |
| 95 | V | | | | | | V |
| 96 | E | | | | | | E |
| 97 | P | | | | | | P |
| 98 | T | | | | | | T |
| 99 | V | | | | | | V |
| 100 | T | | | | | | T |
| 101 | I | | | | | | I |
| 102 | S | | | | | | S |
| 103 | P | | | | | | P |
| 104 | S | | | | | | S |
| 105 | R | | | | | | R |
| 106 | T | | | | | | T |
| 107 | E | | | | | | E |
| 108 | A | | | | | | A |
| 109 | L | | | | | | L |
| 110 | N | | | | | | N |
| 111 | H | | | | | | H |
| 112 | H | | | | | | H |
| 113 | N | | | | | | N |
| 114 | L | | | | | | L |
| 115 | L | | | | | | L |
| 116 | I | V | | | | | () |
| 117 | C | | | | | | C |
| 118 | S | | | | | | S |
| 119 | V | | | | | | V |
| 120 | T | | | | | | T |
| 121 | D | | | | | | D |
| 122 | F | | | | | | F |
| 123 | Y | | | | | | Y |
| 124 | P | | | | | | P |
| 125 | A | G | S | | | | () |
| 126 | H | Q | | | | | () |
| 127 | I | | | | | | I |
| 128 | K | | | | | | K |
| 129 | V | | | | | | V |
| 130 | Q | R | | | | | () |
| 131 | W | | | | | | W |
| 132 | F | | | | | | F |
| 133 | R | | | | | | R |
| 134 | N | | | | | | N |
| 135 | D | | | | | | D |
| 136 | Q | | | | | | Q |
| 137 | E | | | | | | E |
| 138 | E | | | | | | E |
| 139 | T | | | | | | T |
| 140 | A | T | | | | | () |
| 141 | G | | | | | | G |
| 142 | V | | | | | | V |
| 143 | V | | | | | | V |
| 144 | S | | | | | | S |
| 145 | T | | | | | | T |

Fig. 123

| Position | Diverse Amino Acid | | | | | | Amino Acid Configuration With Less Tendency to Malignancy |
|---|---|---|---|---|---|---|---|
| 146 | P | | | | | | P |
| 147 | L | | | | | | L |
| 148 | I | | | | | | I |
| 149 | R | | | | | | R |
| 150 | N | | | | | | N |
| 151 | G | | | | | | G |
| 152 | D | | | | | | D |
| 153 | W | | | | | | W |
| 154 | T | | | | | | T |
| 155 | F | | | | | | F |
| 156 | Q | | | | | | Q |
| 157 | I | | | | | | I |
| 158 | L | | | | | | L |
| 159 | V | | | | | | V |
| 160 | M | | | | | | M |
| 161 | L | | | | | | L |
| 162 | E | | | | | | E |
| 163 | M | | | | | | M |
| 164 | T | | | | | | T |
| 165 | P | | | | | | P |
| 166 | Q | | | | | | Q |
| 167 | H | R | | | | | () |
| 168 | G | | | | | | G |
| 169 | D | | | | | | D |
| 170 | V | | | | | | V |
| 171 | Y | | | | | | Y |
| 172 | T | | | | | | T |
| 173 | C | | | | | | C |
| 174 | H | | | | | | H |
| 175 | V | | | | | | V |
| 176 | E | | | | | | E |
| 177 | H | | | | | | H |
| 178 | P | | | | | | P |
| 179 | S | | | | | | S |
| 180 | L | | | | | | L |
| 181 | Q | | | | | | Q |
| 182 | N | S | | | | | () |
| 183 | P | | | | | | P |
| 184 | I | | | | | | I |
| 185 | I | T | | | | | () |
| 186 | V | | | | | | V |
| 187 | E | | | | | | E |
| 188 | W | | | | | | W |
| 189 | R | | | | | | R |
| 190 | A | | | | | | A |
| 191 | Q | | | | | | Q |
| 192 | S | | | | | | S |
| 193 | E | | | | | | E |
| 194 | S | | | | | | S |
| 195 | A | | | | | | A |
| 196 | Q | | | | | | Q |
| 197 | N | S | | | | | () |
| 198 | K | | | | | | K |
| 199 | M | | | | | | M |
| 200 | L | | | | | | L |
| 201 | S | | | | | | S |
| 202 | G | | | | | | G |
| 203 | I | V | | | | | () |
| 204 | G | | | | | | G |

Fig. 124

| Position | Diverse Amino Acid | | | | | Amino Acid Configuration With Less Tendency to Malignancy |
|---|---|---|---|---|---|---|
| 205 | G | | | | | G |
| 206 | F | | | | | F |
| 207 | V | | | | | V |
| 208 | L | | | | | L |
| 209 | G | | | | | G |
| 210 | L | | | | | L |
| 211 | I | | | | | I |
| 212 | F | | | | | F |
| 213 | L | | | | | L |
| 214 | G | | | | | G |
| 215 | L | | | | | L |
| 216 | G | | | | | G |
| 217 | L | | | | | L |
| 218 | I | | | | | I |
| 219 | I | | | | | I |
| 220 | H | R | | | | () |
| 221 | H | Q | | | | () |
| 222 | R | | | | | R |
| 223 | S | | | | | S |
| 224 | Q | R | | | | () |
| 225 | K | | | | | K |
| 226 | G | | | | | G |
| 227 | P | | | | | P |
| 228 | Q | | | | | Q |
| 229 | G | | | | | G |
| 230 | P | | | | | P |
| 231 | P | | | | | P |
| 232 | P | | | | | P |
| 233 | A | | | | | A |
| 234 | G | | | | | G |
| 235 | L | | | | | L |
| 236 | L | | | | | L |
| 237 | H | | | | | H |

Fig. 125

| Position | Diverse Amino Acid | | | | | | Amino Acid Configuration to Inhibit Metastases | Amino Acid Configuration to Inhibit Metastases |
|---|---|---|---|---|---|---|---|---|
| 29 | M | | | | | | M | M |
| 28 | V | | | | | | V | V |
| 27 | C | | | | | | C | C |
| 26 | L | | | | | | L | L |
| 25 | K | R | | | | | () | () |
| 24 | F | L | | | | | () | () |
| 23 | P | | | | | | P | P |
| 22 | G | | | | | | G | G |
| 21 | G | | | | | | G | G |
| 20 | S | | | | | | S | S |
| 19 | C | | | | | | C | C |
| 18 | M | | | | | | M | M |
| 17 | A | T | | | | | () | () |
| 16 | A | V | | | | | () | () |
| 15 | L | | | | | | L | L |
| 14 | T | | | | | | T | T |
| 13 | V | | | | | | V | V |
| 12 | T | | | | | | T | T |
| 11 | L | | | | | | L | L |
| 10 | M | | | | | | M | M |
| 9 | V | | | | | | V | V |
| 8 | L | | | | | | L | L |
| 7 | S | | | | | | S | S |
| 6 | S | | | | | | S | S |
| 5 | P | | | | | | P | P |
| 4 | L | | | | | | L | L |
| 3 | A | | | | | | A | A |
| 2 | L | | | | | | L | L |
| 1 | A | S | | | | | () | () |
| 1 | G | | | | | | G | G |
| 2 | D | | | | | | D | D |
| 3 | T | | | | | | T | T |
| 4 | Q | R | | | | | () | () |
| 5 | P | | | | | | P | P |
| 6 | R | | | | | | R | R |
| 7 | F | | | | | | F | F |
| 8 | L | | | | | | L | L |
| 9 | E | K | W | | | | () | () |
| 10 | E | Q | Y | | | | () | () |
| 11 | D | G | L | P | S | V | () | () |
| 12 | K | T | | | | | () | () |
| 13 | F | G | H | R | S | Y | () | FF or GR |
| 14 | E | K | | | | | () | () |
| 15 | C | | | | | | C | C |
| 16 | H | Q | Y | | | | () | YY |
| 17 | F | | | | | | F | F |
| 18 | F | | | | | | F | F |
| 19 | N | | | | | | N | N |
| 20 | G | | | | | | G | G |
| 21 | T | | | | | | T | T |
| 22 | E | | | | | | E | E |
| 23 | R | | | | | | R | R |
| 24 | V | | | | | | V | V |
| 25 | Q | R | | | | | () | () |
| 26 | F | L | Y | | | | () | () |
| 27 | L | | | | | | L | L |
| 28 | D | E | H | | | | () | () |
| 29 | R | | | | | | R | R |
| 30 | C | G | H | L | R | Y | () | () |

Fig. 126

| Position | Diverse Amino Acid | | | | | | Amino Acid Configuration to Inhibit Metastases | Amino Acid Configuration to Inhibit Metastases |
|---|---|---|---|---|---|---|---|---|
| 31 | F | I | V | | | | () | () |
| 32 | H | Y | | | | | () | () |
| 33 | H | N | | | | | () | NN |
| 34 | Q | | | | | | Q | Q |
| 35 | E | | | | | | E | E |
| 36 | E | | | | | | E | E |
| 37 | F | L | N | S | Y | | () | () |
| 38 | A | L | V | | | | () | () |
| 39 | R | | | | | | R | R |
| 40 | F | Y | | | | | () | () |
| 41 | D | | | | | | D | D |
| 42 | S | | | | | | S | S |
| 43 | D | | | | | | D | D |
| 44 | V | | | | | | V | V |
| 45 | G | | | | | | G | G |
| 46 | E | | | | | | E | E |
| 47 | F | Y | | | | | () | () |
| 48 | R | | | | | | R | R |
| 49 | A | | | | | | A | A |
| 50 | V | | | | | | V | V |
| 51 | T | | | | | | T | T |
| 52 | E | | | | | | E | E |
| 53 | L | | | | | | L | L |
| 54 | G | | | | | | G | G |
| 55 | R | | | | | | R | R |
| 56 | P | | | | | | P | P |
| 57 | A | D | S | V | | | () | () |
| 58 | A | E | | | | | () | () |
| 59 | E | | | | | | E | E |
| 60 | H | S | Y | | | | () | () |
| 61 | W | | | | | | W | W |
| 62 | N | | | | | | N | N |
| 63 | S | | | | | | S | S |
| 64 | Q | | | | | | Q | Q |
| 65 | K | | | | | | K | K |
| 66 | D | | | | | | D | D |
| 67 | F | I | L | | | | () | () |
| 68 | L | | | | | | L | L |
| 69 | E | | | | | | E | E |
| 70 | D | Q | R | | | | () | () |
| 71 | A | E | K | R | | | () | () |
| 72 | R | | | | | | R | R |
| 73 | A | G | | | | | () | () |
| 74 | A | E | L | Q | R | | () | () |
| 75 | V | | | | | | V | V |
| 76 | D | | | | | | D | D |
| 77 | N | T | | | | | () | () |
| 78 | V | Y | | | | | () | () |
| 79 | C | | | | | | C | C |
| 80 | R | | | | | | R | R |
| 81 | H | | | | | | H | H |
| 82 | N | | | | | | N | N |
| 83 | Y | | | | | | Y | Y |
| 84 | G | | | | | | G | G |
| 85 | A | V | | | | | () | () |
| 86 | G | V | | | | | () | () |
| 87 | E | | | | | | E | E |
| 88 | S | | | | | | S | S |
| 89 | F | | | | | | F | F |

Fig. 127

| Position | Diverse Amino Acid | | | | Amino Acid Configuration to Inhibit Metastases | Amino Acid Configuration to Inhibit Metastases |
|---|---|---|---|---|---|---|
| 90 | T | | | | T | T |
| 91 | V | | | | V | V |
| 92 | Q | | | | Q | Q |
| 93 | R | | | | R | R |
| 94 | R | | | | R | R |
| 95 | V | | | | V | V |
| 96 | E | H | Q | Y | ( ) | ( ) |
| 97 | P | | | | P | P |
| 98 | E | K | | | ( ) | ( ) |
| 99 | V | | | | V | V |
| 100 | T | | | | T | T |
| 101 | V | | | | V | V |
| 102 | Y | | | | Y | Y |
| 103 | P | | | | P | P |
| 104 | A | S | | | ( ) | ( ) |
| 105 | K | | | | K | K |
| 106 | T | | | | T | T |
| 107 | Q | | | | Q | Q |
| 108 | P | | | | P | P |
| 109 | L | | | | L | L |
| 110 | Q | | | | Q | Q |
| 111 | H | | | | H | H |
| 112 | H | | | | H | H |
| 113 | N | | | | N | N |
| 114 | L | | | | L | L |
| 115 | L | | | | L | L |
| 116 | V | | | | V | V |
| 117 | C | | | | C | C |
| 118 | S | | | | S | S |
| 119 | V | | | | V | V |
| 120 | N | S | | | ( ) | ( ) |
| 121 | F | | | | F | F |
| 122 | G | | | | G | G |
| 123 | Y | | | | Y | Y |
| 124 | P | | | | P | P |
| 125 | G | | | | G | G |
| 126 | S | | | | S | S |
| 127 | I | | | | I | I |
| 128 | E | | | | E | E |
| 129 | V | | | | V | V |
| 130 | R | | | | R | R |
| 131 | W | | | | W | W |
| 132 | F | | | | F | F |
| 133 | L | R | | | ( ) | ( ) |
| 134 | N | | | | N | N |
| 135 | G | | | | G | G |
| 136 | Q | | | | Q | Q |
| 137 | E | | | | E | E |
| 138 | E | | | | E | E |
| 139 | K | | | | K | K |
| 140 | A | T | | | ( ) | ( ) |
| 141 | G | | | | G | G |
| 142 | M | V | | | ( ) | ( ) |
| 143 | V | | | | V | V |
| 144 | S | | | | S | S |
| 145 | T | | | | T | T |
| 146 | G | | | | G | G |
| 147 | L | | | | L | L |
| 148 | I | | | | I | I |

Fig. 128

| Position | Diverse Amino Acid | | | | | | Amino Acid Configuration to Inhibit Metastases | Amino Acid Configuration to Inhibit Metastases |
|---|---|---|---|---|---|---|---|---|
| 149 | H | Q | | | | | () | () |
| 150 | N | | | | | | N | N |
| 151 | G | | | | | | G | G |
| 152 | D | | | | | | D | D |
| 153 | W | | | | | | W | W |
| 154 | T | | | | | | T | T |
| 155 | F | | | | | | F | F |
| 156 | Q | | | | | | Q | Q |
| 157 | T | | | | | | T | T |
| 158 | L | | | | | | L | L |
| 159 | V | | | | | | V | V |
| 160 | M | | | | | | M | M |
| 161 | L | | | | | | L | L |
| 162 | E | | | | | | E | E |
| 163 | T | | | | | | T | T |
| 164 | F | V | | | | | () | () |
| 165 | P | | | | | | P | P |
| 166 | Q | R | | | | | () | () |
| 167 | S | | | | | | S | S |
| 168 | G | | | | | | G | G |
| 169 | E | | | | | | E | E |
| 170 | V | | | | | | V | V |
| 171 | Y | | | | | | Y | Y |
| 172 | T | | | | | | T | T |
| 173 | C | | | | | | C | C |
| 174 | Q | | | | | | Q | Q |
| 175 | V | | | | | | V | V |
| 176 | E | | | | | | E | E |
| 177 | H | | | | | | H | H |
| 178 | P | | | | | | P | P |
| 179 | S | | | | | | S | S |
| 180 | L | V | | | | | () | () |
| 181 | M | T | | | | | () | () |
| 182 | S | | | | | | S | S |
| 183 | P | | | | | | P | P |
| 184 | L | | | | | | L | L |
| 185 | T | | | | | | T | T |
| 186 | V | | | | | | V | V |
| 187 | E | | | | | | E | E |
| 188 | W | | | | | | W | W |
| 189 | R | S | | | | | () | () |
| 190 | A | | | | | | A | A |
| 191 | R | | | | | | R | R |
| 192 | S | | | | | | S | S |
| 193 | E | | | | | | E | E |
| 194 | S | | | | | | S | S |
| 195 | A | | | | | | A | A |
| 196 | Q | | | | | | Q | Q |
| 197 | S | | | | | | S | S |
| 198 | K | | | | | | K | K |
| 199 | M | | | | | | M | M |
| 200 | L | | | | | | L | L |
| 201 | S | | | | | | S | S |
| 202 | G | | | | | | G | G |
| 203 | V | | | | | | V | V |
| 204 | G | | | | | | G | G |
| 205 | G | | | | | | G | G |
| 206 | F | | | | | | F | F |
| 207 | V | | | | | | V | V |

Fig. 129

| Position | Diverse Amino Acid | | | | | | Amino Acid Configuration to Inhibit Metastases | Amino Acid Configuration to Inhibit Metastases |
|---|---|---|---|---|---|---|---|---|
| 208 | L | | | | | | L | L |
| 209 | G | | | | | | G | G |
| 210 | L | | | | | | L | L |
| 211 | L | | | | | | L | L |
| 212 | F | | | | | | F | F |
| 213 | L | | | | | | L | L |
| 214 | G | | | | | | G | G |
| 215 | A | | | | | | A | A |
| 216 | G | | | | | | G | G |
| 217 | L | | | | | | L | L |
| 218 | F | | | | | | F | F |
| 219 | I | | | | | | I | I |
| 220 | Y | | | | | | Y | Y |
| 221 | F | | | | | | F | F |
| 222 | R | | | | | | R | R |
| 223 | N | | | | | | N | N |
| 224 | Q | | | | | | Q | Q |
| 225 | K | | | | | | K | K |
| 226 | G | | | | | | G | G |
| 227 | H | | | | | | H | H |
| 228 | S | | | | | | S | S |
| 229 | G | | | | | | G | G |
| 230 | L | | | | | | L | L |
| 231 | P | Q | | | | | () | () |
| 232 | P | | | | | | P | P |
| 233 | R | T | | | | | () | () |
| 234 | G | | | | | | G | G |
| 235 | F | | | | | | F | F |
| 236 | L | | | | | | L | L |
| 237 | S | | | | | | S | S |

DIAGNOSTIC METHOD OF SELECTING APPROPRIATE CANCER TREATMENTS AND SCREENING METHOD OF MEASURING REAGENTS AND CURATIVE MEDICINES FOR CANCER PATIENTS

This application is a continuation of International Application No. PCT/JP02/02894 filed Mar. 26, 2002, designating the United States, and further claims priority under 35 U.S.C. § 119 to Japanese Patent Application Nos. 2001-111856 filed Apr. 10, 2001, and 2001-267524 filed Sep. 4, 2001.

TECHNICAL FIELD

The field relates to using identified amino acids at specific regions of genes and corresponding base sequences as markers to screen for cancer treatments.

BACKGROUND OF THE INVENTION

When a gene characteristic that is controlled by a single locus has several phenotypes, which are genetically balanced, it is called a polymorphism. Each variable of the polymorphism is called an allele. A polymorphism is attributed not only by phenotype characteristics, or variety of amino acid sequences constructing proteins, but also by DNA base sequences where an amino acid sequence does not have varieties. In most cases, it is detected as cleavage positions of DNA, created by restriction enzymes, that differ from the others.

The HLA molecule of Human MHC molecule (major histocompatibility complex) was found as an antigen against the antibody that reacts in leukoagglutinin during serum treatment, in 1952. The HLA molecule is a gene product controlled by a gene cluster coded by the MHC region, within about 4000 kbp on the $6^{th}$ chromosome short arm, 6p21.3. The MHC region includes the following 3 regions: 1) Class I gene region controlling HLA-A, B, and C and antigens, which are found on eucaryotic cell membranes, 2) Class II region controlling cell-specific HLA-DP, DQ, and DR antigens, which are found on particular tissues or cells, such as B-cell and macrophage, and 3) Class III gene region controlling complement ingredients and 21-hydroxyilaze.

The Class II molecule is a non-covalent cell membrane antigen made of glycoprotein of 34 kDa ($\alpha$-chain) and glycoprotein of 29 kDa ($\beta$-chain). 7 pieces of $\alpha$-chain gene and 9 to 12 pieces of $\beta$-chain (16 kinds) form clusters to construct a multigene family. On the Class II gene region, each gene lines up as DP-DN-DM-DO-DQ-DR from the centromere side. HLA-DP, DQ, and DR antigens include multiple alloantigens, and mainly the sequences of amino acids of the $\beta$-chain (B1) cause a polymorphism. DR and DQ antigens are epitope that reactwith antibodiesproduced from B-cells.

Each HLA molecule includes a form of domain construction with 260 to 370 amino acids. $\alpha1(\beta1)$, $\alpha2(\beta2)$ domain, compounded peptide (CP), TM, and CY regions construct the Class II molecule, and $\alpha1$ and $\beta1$ domains configure polymorphism while $\alpha2$ and $\beta2$ domains compose the base of the Class II molecule.

A genetic polymorphism of the HLA molecule is caused by different amino acid sequences coded by the corresponding HLA gene (Gene information regulating the amino acid sequences is written as the base sequence on DNA. A group of three bases, called a "Codon," is connected as one unit to form a single amino acid.). This is a reflection of an alloantigen with different base sequences, and currently most of the base sequences for alloantigens have been identified. (Tissue Antigen, 45, 258-280, 1995) Regions of polymorphism are found mainly in the $\alpha1$ and $\alpha2$ domains of the Class I molecule, and single common variable regions exist on each $\alpha1$ C-terminal domain and $\alpha2$ N-terminal domain. In the Class II molecule, the variable regions are found mainly in the $\alpha1$ domain of the DQ$\alpha$-chain and the $\beta1$ domain of DR$\beta$, DQ$\beta$, DP$\beta$-chains. (Proc. Natl. Acad. Sci. USA, 84, 6234-6238, 1987). Substitution of the amino acid residue on the variable regions or differences in alloantigens have a direct effect on the affinity of HLA molecules against antigens. Substitution of the amino acid residue on the variable regions or differences in alloantigens also effects an affinity of TCR, which changes the ability of antigen presentations. The fact differentiates immune responses against an exogenous antigen and an autoantigen among individuals with diverse HLA antigens and can induce variety of immune responses.

Brief Description One object of this invention is to elucidate functions controlled by variations of the amino acids on particular positions of particular regions on the HLA genes and the base sequences and to provide usages of the functions in medical field.

This invention has clarified the relationship of particular positions of the amino acids and base sequences and cancer by analysis of clinical phenomenon of cancer patients based on analysis of polymorphisms of the HLA gene.

The following method is provided:
1. A screening method to determine effective cancer curative medicines, comprising:
   (1) determining position(s) of polymorphic amino acid(s) in amino acids sequence(s), including at least one of DRB1*gene, DQB1*gene, and DPB1*gene of HLA,
   (2) analyzing variations of the polymorphic position(s) of the amino acid(s), and survival results (prognosis, treatment effects) by the cancer treatments [the cancer resection alone (no adjuvant therapy), the anticancer chemotherapy after the cancer resection (Chemotherapy), and the anticancer immunotherapy after the cancer resection (Immunotherapy)],
   (3) determining positions of the amino acids and the amino acid(s), which have been estimated to have a statistically significant relationship with the treatments,
   (4) creating a three-dimensional structure of amino acid sequences including the amino acids, and
   (5) using the interactions of candidate compounds with the three-dimensional structure as a marker.
2. The method according to topic 1, wherein cancer is analyzed by distinguishing stomach cancer and others.
3. The method according to topic 1 or 2, which is carried out by using drug designing techniques based on comparison with the three-dimensional structure of the candidate compounds.
4. The method according to topic 1 to 3, wherein effective cancer curative medicines can suppress and control metastasis of cancer.
5. The method according to topic 1 to 3, wherein effective cancer curative medicines are immunological medicines.
6. The method according to topic 1 to 3, wherein effective cancer curative medicines are chemotherapeutic medicines.
7. The method according to topic 1 to 6, wherein the effectiveness of the cancer curative medicines is measured by:
   (1) contacting the candidate compounds and the three-dimensional structure by alignment and variation of each amino acid under a condition in which the interaction is possible, (2) evaluating the interaction of the three-dimensional structure with the candidate compounds, and detecting a signal of the interaction.
8. The method according to topic 1 to 7, wherein cancer is analyzed by distinguishing stomach cancer and others.
9. The method according to topic 1 to 8, wherein both effectiveness of the anticancer treatments and the variations of the base sequences coding the polymorphic amino acids on any one of DRB1*gene, DQB1*gene, and DPB1*gene of HLA, are analyzed.
10. The method according to topic 1 to 9, wherein both effectiveness of the anticancer treatments and the variations of the base sequences coding the polymorphic amino acids on any one of DRB1*gene, DQB1*gene, and DPB1*gene of HLA, are analyzed.
11. A measuring method for evaluating anticancer treatments, comprising:
   (1) determining position(s) of polymorphic amino acid(s) in amino acids sequence(s), including at least one of DRB1*gene, DQB1*gene, and DPB1*gene of HLA,
   (2) analyzing variations of the polymorphic position(s) of the amino acid(s), and survival results (prognosis, treatment effects) by the cancer treatments [the cancer resection alone (no adjuvant therapy), the anticancer chemotherapy after the cancer resection (Chemotherapy), the anticancer immunotherapy after the cancer resection (Immunotherapy)],
   (3) determining positions of the amino acids and the amino acids, which have been estimated to have a statistically significant relationship with the treatments, and
   (4) using the specified positions and the corresponding amino acid(s) as a marker.
12. The method of topic 11, wherein cancer is analyzed by distinguishing stomach cancer and others.
13. A measuring method for evaluating cancer treatments, comprising:
   (1) confirming position(s) of polymorphic amino acid(s) in amino acids sequence(s), including at least one of, DRB1*gene, DQB1*gene, and DPB1*gene of HLA,
   (2) analyzing variations of the base sequences coding the polymorphic positions of the amino acid, and survival results (prognosis, treatment effects) by the cancer treatments [the cancer resection alone (no adjuvant therapy), the anticancer chemotherapy after the cancer resection (Chemotherapy), the anticancer immunotherapy after the cancer resection (Immunotherapy)],
   (3) determining position(s) of the amino acids and the amino acid(s) which have been estimated to have a statistically significant relationship with the treatments, and the corresponding base sequences, and
   (4) using the specified positions and the amino acids together with the corresponding base sequences as a marker.
14. The method according to topic 13, wherein cancer is analyzed by distinguishing stomach cancer and others.
15. Clinical measuring reagents comprising a composition:
   (1) wherein positions of polymorphic amino acid(s) in amino acids sequence(s), that include at least one of, DRB1*gene, DQB1*gene, and DPB1*gene of HLA have been determined,
   (2) wherein the variation of the polymorphic positions of the amino acid, and survival results (prognosis, treatment effects) by the cancer treatments [the cancer resection alone (no adjuvant therapy), the anticancer chemotherapy after the cancer resection (Chemotherapy), the anticancer immunotherapy after the cancer resection (Immunotherapy)] have been analyzed,
   (3) wherein the positions of the amino acids and the amino acids, which have been estimated to have a statistically significant relationship with the treatments, have been determined, and
   (4) wherein the specified positions and the corresponding amino acids have been used as a marker.
16. The method according to topic 15, wherein cancer is analyzed by distinguishing stomach cancer and others.
17. Clinical measuring reagents comprising a composition:
   (1) wherein position(s) of polymorphic amino acid(s) in amino acids sequence(s), that include at least one of DRB1*gene, DQB1*gene, and DPB1*gene of HLA have been confirmed,
   (2) wherein the variations of the base sequences coding the polymorphic positions of the amino acid, and survival results (prognosis, treatment effects) by the cancer treatments [the cancer resection alone (no adjuvant therapy), the anticancer chemotherapy after the cancer resection (Chemotherapy), the anticancer immunotherapy after the cancer resection (Immunotherapy)] have been analyzed,
   (3) wherein the positions of the amino acids and the base sequences of amino acids which have been estimated to have a statistically significant relationship with the treatments, and the corresponding base sequences have been determined, and
   (4) wherein the specified positions and the amino acids together with the base sequences have been used as a marker.
18. The method according to topic 17, wherein cancer is analyzed by distinguishing stomach cancer and others.

BRIEF DESCRIPTION OF THE DRAWINGS

FIG. 1: Base sequence at Position 57 and 67 of DQB1*gene cluster and corresponding amino acids;

FIG. 2: Base sequence at Position 57 and 67 of DRB1*gene cluster and corresponding amino acids;

FIG. 3: Base sequence at Position 57 and the 67 of DRB1*gene cluster and corresponding amino acids;

FIG. 41: Table showing effectiveness of the cancer resection alone (no adjuvant therapy) in Working Example 7;

FIG. 42: Table showing effectiveness of the anticancer chemotherapy after the cancer resection (Chemotherapy) in Working Example 7;

FIG. 43: Table showing effectiveness of the anticancer immunotherapy after cancer resection (Immunotherapy) in Working Example 7;

FIG. 44: Analysis of DPB1*gene equivalence (1) in Working Example 8;

FIG. 45: Analysis of DRB1*gene equivalence (1) in Working Example 8;

FIG. 46: Analysis of DRB1*gene equivalence (2) in Working Example 8;

FIG. 47: Analysis of DRB1*gene equivalence (3) in Working Example 8;

FIG. 48: Analysis of DRB1*gene equivalence (4) in Working Example 8;

FIG. 49: Analysis of DRB1*gene equivalence (5) in Working Example 8;

FIG. 50: Analysis of DQB1*gene equivalence (1) in Working Example 8;

FIG. 51: Analysis of DQB1*gene equivalence (2) in Working Example 8;

FIG. 52: Prognosis and treatment effect in patients with DRB1*gene (1) in Working Example 9;
FIG. 53: Prognosis and treatment effect in patients with DRB1*gene (2) in Working Example 9;
FIG. 54: Prognosis and treatment effect in patients with DRB1*gene (3) in Working Example 9;
FIG. 55: Prognosis and treatment effect in patients with DRB1*gene (4) in Working Example 9;
FIG. 56: Prognosis and treatment effect in patients with DRB1*gene (5) in Working Example 9;
FIG. 57: Prognosis and treatment effect in patients with DRB1*gene (6) in Working Example 9;
FIG. 58: Prognosis and treatment effect in patients with DRB1*gene (7) in Working Example 9;
FIG. 59: Prognosis and treatment effect in patients with DRB1*gene (8) in Working Example 9;
FIG. 60: Prognosis and treatment effect in patients with DRB1*gene (9) in Working Example 9;
FIG. 61: Prognosis and treatment effect in patients with DPB1*gene (1) in Working Example 9;
FIG. 62: Prognosis and treatment effect in patients with DPB1*gene (2) in Working Example 9;
FIG. 63: Prognosis and treatment effect in patients with DPB1*gene (3) in Working Example 9;
FIG. 64: Prognosis and treatment effect in patients with DPB1*gene (4) in Working Example 9;
FIG. 65: Prognosis and treatment effect in patients with DPB1*gene (5) in Working Example 9;
FIG. 66: Prognosis and treatment effect in patients with DPB1*gene (6) in Working Example 9;
FIG. 67: Prognosis and treatment effect in patients with DQB1*gene (1) in Working Example 9;
FIG. 68: Prognosis and treatment effect in patients with DQB1*gene (2) in Working Example 9;
FIG. 69: Prognosis and treatment effect in patients with DQB1*gene (3) in Working Example 9;
FIG. 70: Prognosis and treatment effect in patients with DQB1*gene (4) in Working Example 9;
FIG. 71: Prognosis and treatment effect in patients with DQB1*gene (5) in Working Example 9;
FIG. 72: Prognosis and treatment effect in patients with DQB1*gene (6) in Working Example 9;
FIG. 73: Prognosis and treatment effect in patients with DQB1*gene (7) in Working Example 9;
FIG. 74: Prognosis and treatment effect in patients with DQB1*gene (8) in Working Example 9;
FIG. 75: Prognosis and treatment effect in patients with DQB1*gene (9) in Working Example 9;
FIG. 76: Base sequence analysis in patients with DRB1*gene (1) in Working Example 10;
FIG. 77: Base sequence analysis in patients with DRB1*gene (2) in Working Example 10;
FIG. 78: Base sequence analysis in patients with DRB1*gene (3) in Working Example 10;
FIG. 79: Base sequence analysis in patients with DRB1*gene (4) in Working Example 10;
FIG. 80: Base sequence analysis in patients with DQB1*gene (1) in Working Example 10;
FIG. 81: Base sequence analysis in patients with DQB1*gene (2) in Working Example 10;
FIG. 82: Base sequence analysis in patients with DQB1*gene (3) in Working Example 10;
FIG. 83: Base sequence analysis in patients with DQB1*gene (4) in Working Example 10;
FIG. 84: Base sequence analysis in patients with DPB1*gene (1) in Working Example 10;
FIG. 85: Optimum amino acid sequence in patients with DPB1*gene (1) in Working Example 11;
FIG. 86: Optimum amino acid sequence in patients with DPB1*gene (2) in Working Example 11;
FIG. 87: Optimum amino acid sequence in patients with DPB1*gene (3) in Working Example 11;
FIG. 88: Optimum amino acid sequence in patients with DPB1*gene (4) in Working Example 11;
FIG. 89: Optimum amino acid sequence in patients with DPB1*gene (5) in Working Example 11;
FIG. 90: Optimum amino acid sequence in patients with DQB1*gene (1) in Working Example 11;
FIG. 91: Optimum amino acid sequence in patients with DQB1*gene (2) in Working Example 11;
FIG. 92: Optimum amino acid sequence in patients with DQB1*gene (3) in Working Example 11;
FIG. 93: Optimum amino acid sequence in patients with DQB1*gene (4) in Working Example 11;
FIG. 94: Optimum amino acid sequence in patients with DQB1*gene (5) in Working Example 11;
FIG. 95: Optimum amino acid sequence in patients with DRB1*gene (1) in Working Example 11;
FIG. 96: Optimum amino acid sequence in patients with DRB1*gene (2) in Working Example 11;
FIG. 97: Optimum amino acid sequence in patients with DRB1*gene (3) in Working Example 11;
FIG. 98: Optimum amino acid sequence in patients with DRB1*gene (4) in Working Example 11;
FIG. 99: Optimum amino acid sequence in patients with DRB1*gene (5) in Working Example 11;
FIG. 100: Relationship between DPB1*gene and cancer metastases (1) in Working Example 12;
FIG. 101: Relationship between DPB1*gene and cancer metastases (2) in Working Example 12;
FIG. 102: Relationship between DPB1*gene and cancer metastases (3) in Working Example 12;
FIG. 103: Relationship between DPB1*gene and cancer metastases (4) in Working Example 12;
FIG. 104: Relationship between DPB1*gene and cancer metastases (5) in Working Example 12;
FIG. 105: Relationship between DQB1*gene and cancer metastases (1) in Working Example 12;
FIG. 106: Relationship between DQB1*gene and cancer metastases (2) in Working Example 12;
FIG. 107: Relationship between DQB1*gene and cancer metastases (3) in Working Example 12;
FIG. 108: Relationship between DQB1*gene and cancer metastases (4) in Working Example 12;
FIG. 109: Relationship between DQB1*gene and cancer metastases (5) in Working Example 12;
FIG. 110: Relationship between DRB1*gene and cancer metastases (1) in Working Example 12;
FIG. 111: Relationship between DRB1*gene and cancer metastases (2) in Working Example 12;
FIG. 112: Relationship between DRB1*gene and cancer metastases (3) in Working Example 12;
FIG. 113: Relationship between DRB1*gene and cancer metastases (4) in Working Example 12;
FIG. 114: Relationship between DRB1*gene and cancer metastases (5) in Working Example 12;
FIG. 115: Relationship between DPB1*gene and tumor advancement (1) in Working Example 12;
FIG. 116: Relationship between DPB1*gene and tumor advancement (2) in Working Example 12;
FIG. 117: Relationship between DPB1*gene and tumor advancement (3) in Working Example 12;

FIG. 118: Relationship between DPB1*gene and tumor advancement (4) in Working Example 12;
FIG. 119: Relationship between DPB1*gene and tumor advancement (5) in Working Example 12;
FIG. 120: Relationship between DQB1*gene and tumor advancement (1) in Working Example 12;
FIG. 121: Relationship between DQB1*gene and tumor advancement (2) in Working Example 12;
FIG. 122: Relationship between DQB1*gene and tumor advancement (3) in Working Example 12;
FIG. 123: Relationship between DQB1*gene and tumor advancement (4) in Working Example 12;
FIG. 124: Relationship between DQB1*gene and tumor advancement (5) in Working Example 12;
FIG. 125: Relationship between DRB1*gene and tumor advancement (1) in Working Example 12;
FIG. 126: Relationship between DRB1*gene and tumor advancement (2) in Working Example 12;
FIG. 127: Relationship between DRB1*gene and tumor advancement (3) in Working Example 12;
FIG. 128: Relationship between DRB1*gene and tumor advancement (4) in Working Example 12; and
FIG. 129: Relationship between DRB1*gene and tumor advancement (5) in Working Example 12.

LEGEND FOR SYMBOLS AND MARKERS

FIG. 1
A, D, V, S, I: Single character codes for the amino acid

FIG. 2
D, S, V, F, I, L, A: Single character codes for the amino acid

FIG. 3
D, S, V, F, I, L, A: Single character codes for the amino acid

Figure 4:
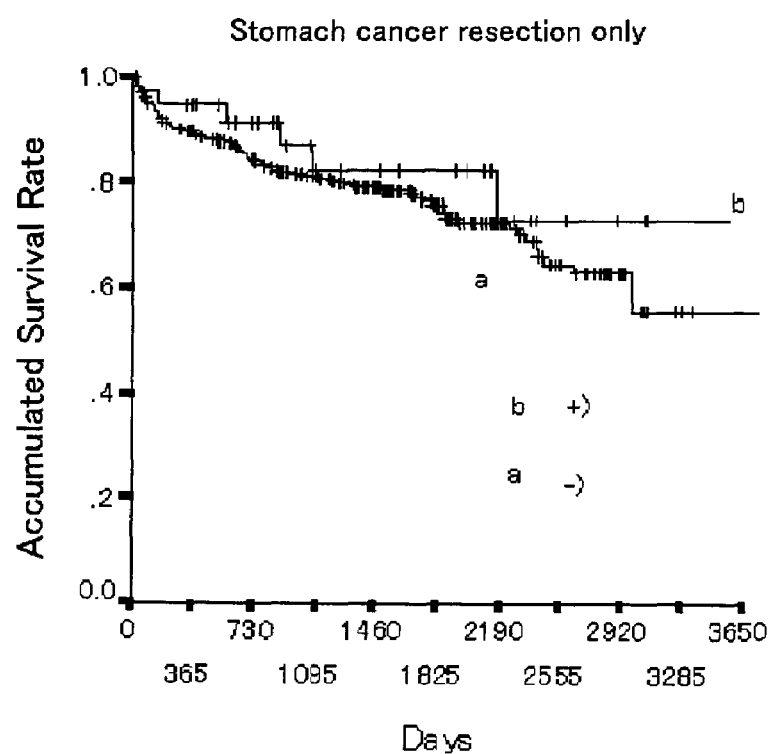
FIG. 4: Result of the stomach cancer resection alone in patients a) with DQB1*05031 gene (Asp at Position 57, Val at Position 67) and b) without DQB1*05031 gene.

FIG. 4
a: patients without DQRB1*05031 gene
b: patients with DQRB1*05031 gene (Asp at Position 57, Val at Position 67)

Figure 5:
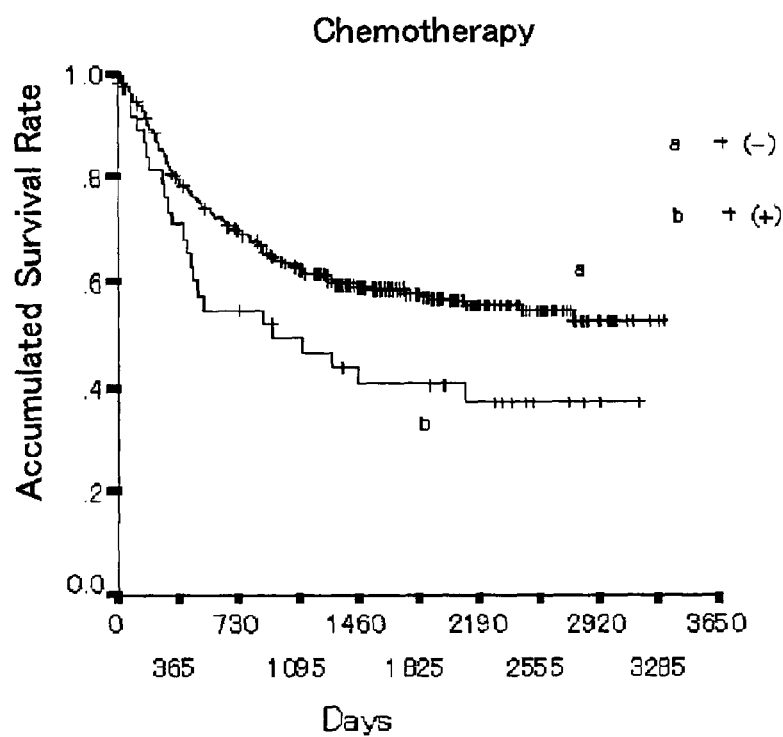
FIG. 5: Result of the anticancer chemotherapy after the stomach cancer resection in patients a) with DQB1*05031 gene (Asp at Position 57, Val at Position 67) and b) without DQB1*05031 gene.

FIG. 5
a: patients without DQRB1*05031 gene
b: patients with DQRB1*05031 gene (Asp at Position 57, Val at Position 67)

Figure 6:
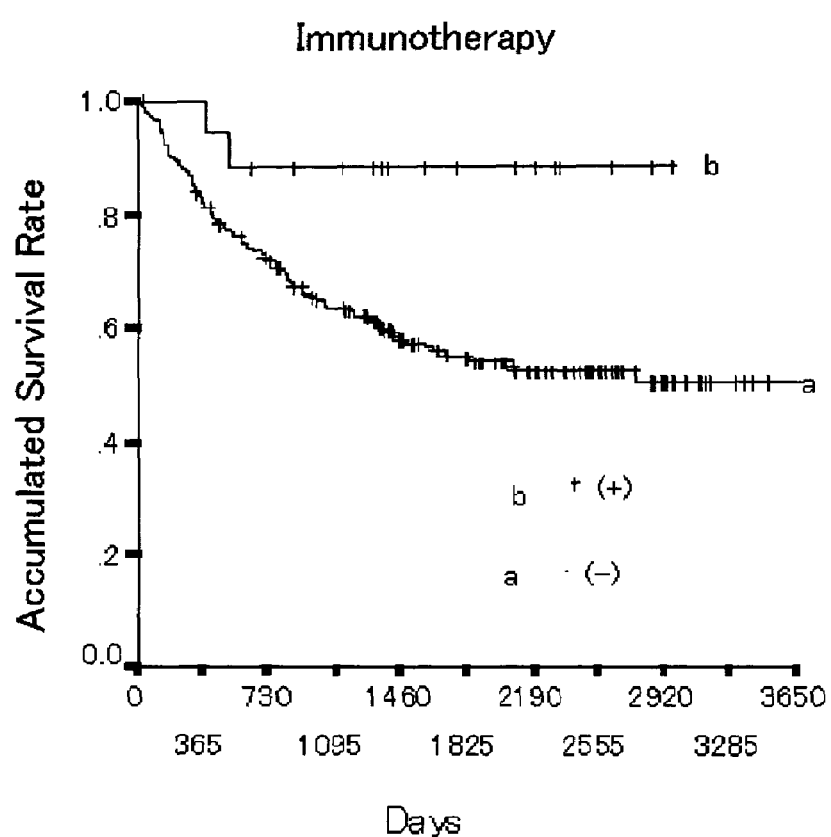
FIG. 6: Result of the anticancer immunotherapy after the stomach cancer resection in patients in patients a) with DQB1*05031 gene (Asp at Position 57, Val at Position 67) and b) without DQB1*05031 gene.

FIG. 6
a: patients without DQRB1*05031 gene
b: patients with DQRB1*05031 gene (Asp at Position 57, Val at Position 67)

Figure 7:
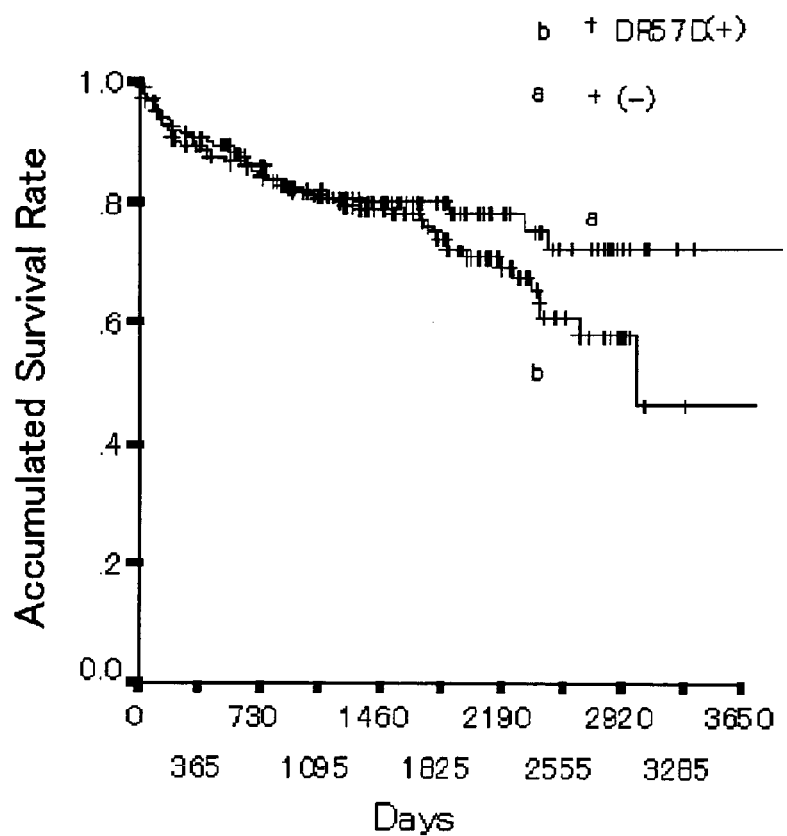
FIG. 7: Result of the resections of stomach cancer in patients a) with Asp at Position 57 of DRB1*gene cluster (+) and b) without Asp at Position 57 of DRB*1 gene cluster (−)

FIG. 7
a: patients without Asp at Position 57 of DRB1* (−)
b: patients with Asp at Position 57 of DRB1* (+)

Figure 8:
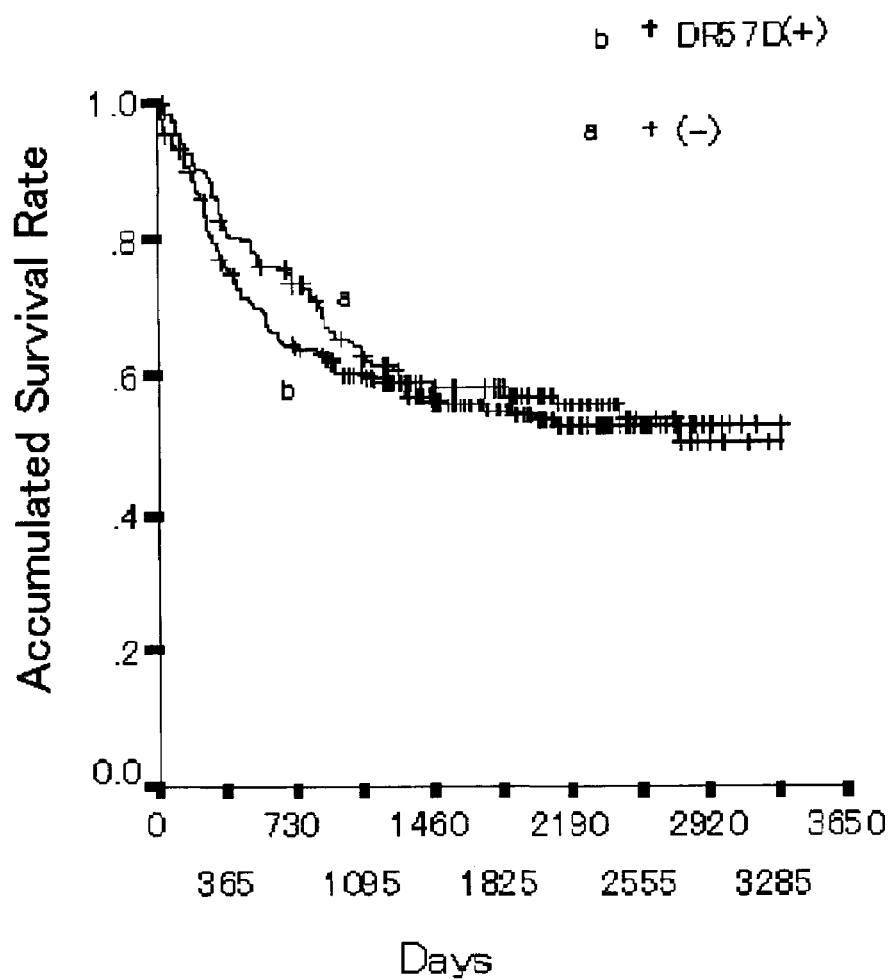
FIG. 8: Result of the anticancer chemotherapy after the stomach cancer resection in patients a) with Asp at Position 57 of DRB1*gene cluster (+) and b) without Asp at Position 57 of DRB1*gene cluster (−)

FIG. 8
a: patients without Asp at Position 57 of DRB1* (−)
b: patients with Asp at Position 57 of DRB1* (+)

Figure 9:
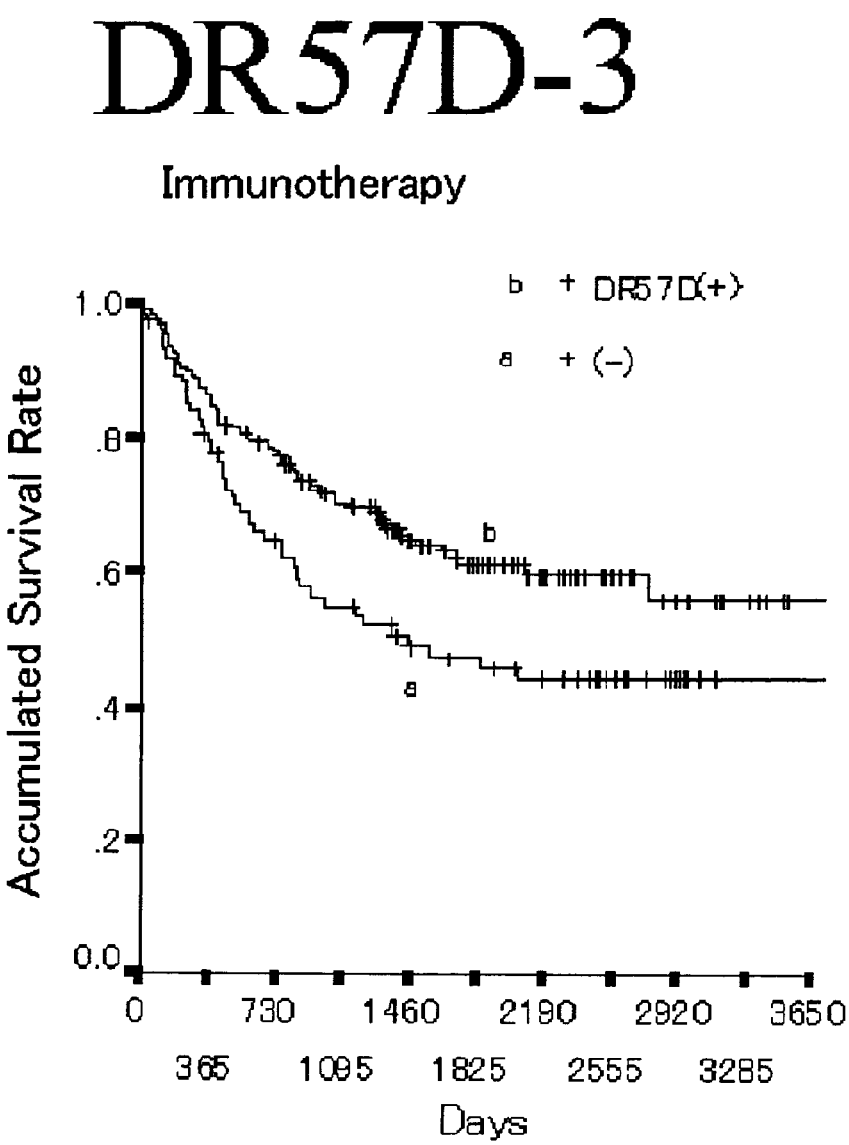
FIG. 9: Result of the anticancer immunotherapy after the stomach cancer resection in patients a) with Asp at Position 57 Asp of the DRB1*gene cluster (+) and b) without Asp at Position 57 on the DRB1*gene cluster (−)

FIG. 9
a: patients without Asp at Position 57 of DRB1* (−)
b: patients with Asp at Position 57 of DRB1* (+)

Figure 10:
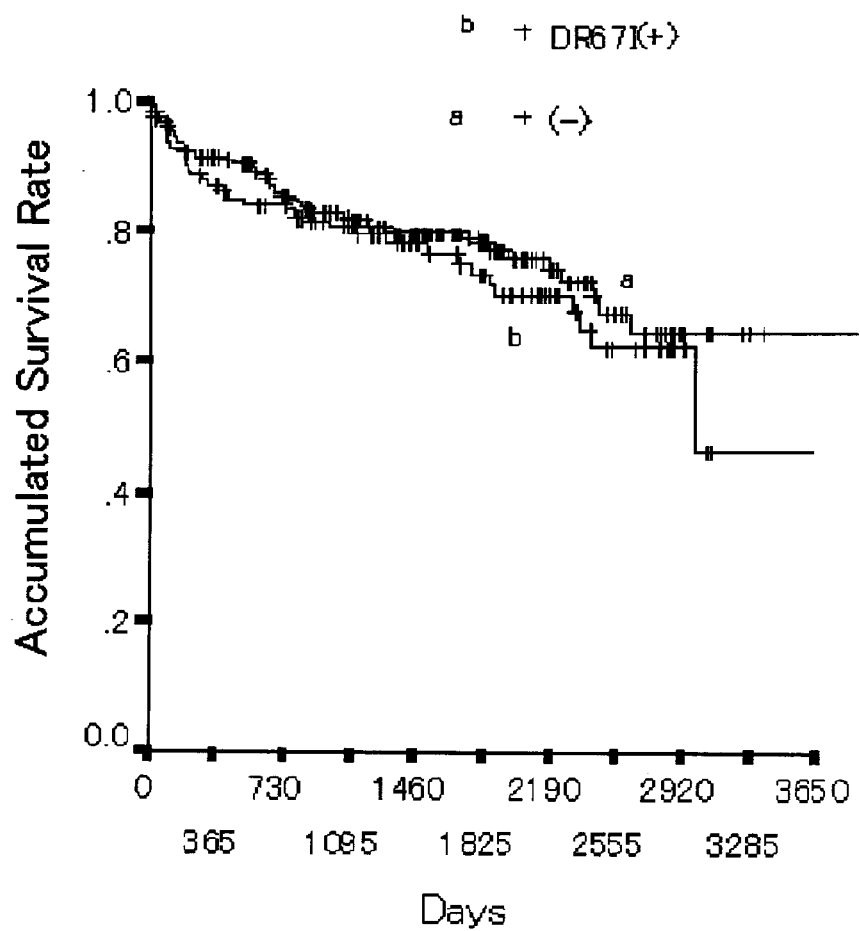
FIG. 10: Result of the stomach cancer resection alone in patients a) with Ile at Position 67 of DRB1*gene cluster (+) and b) without Ile at Position 67 of DRB1*gene cluster (−)

FIG. 10
a: patients without Ile at Position 67 of DRB1* (−)
b: patients with Ile at Position 67 of DRB1* (+)

Figure 11:
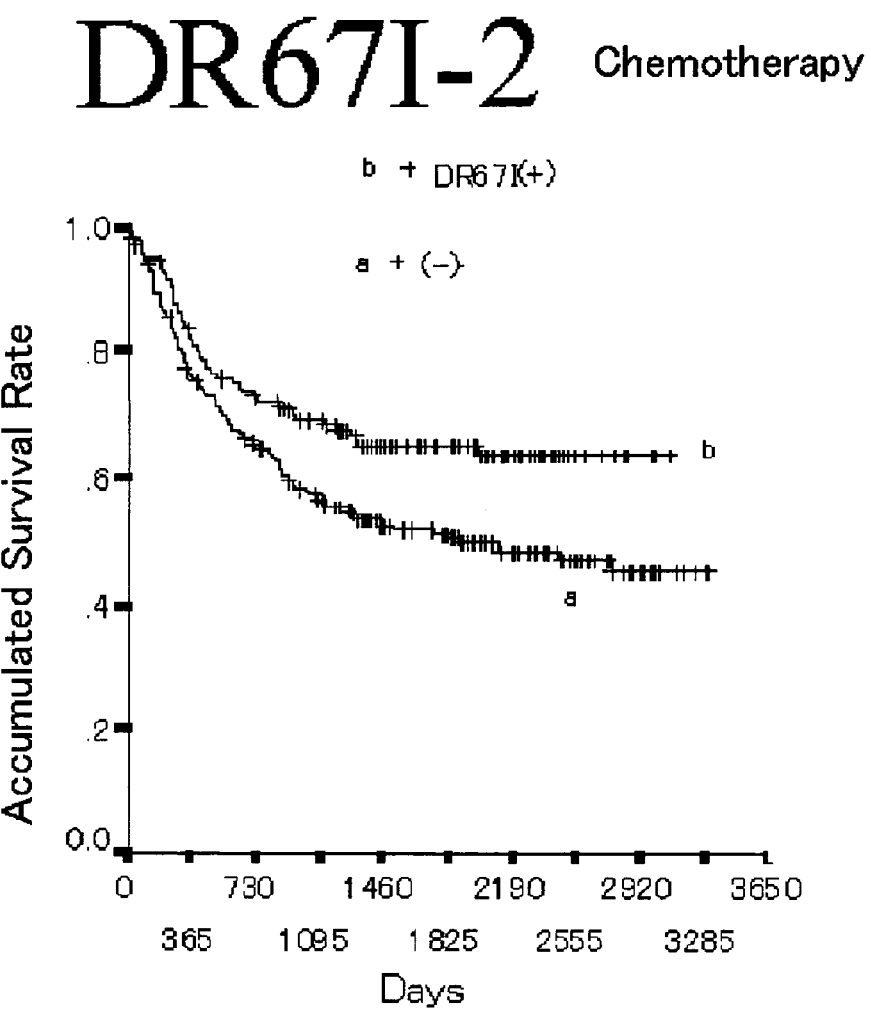
FIG. 11: Result of the anticancer chemotherapy after the stomach cancer resection in patients a) with Ile at Position 67 of DRB1*gene cluster (+) and b) without Ile at Position 67 of DRB1*gene cluster (−)

FIG. 11
a: patients without Ile at Position 67 of DRB1* (−)
b: patients with Ile at Position 67 of DRB1* (+)

Figure 12:
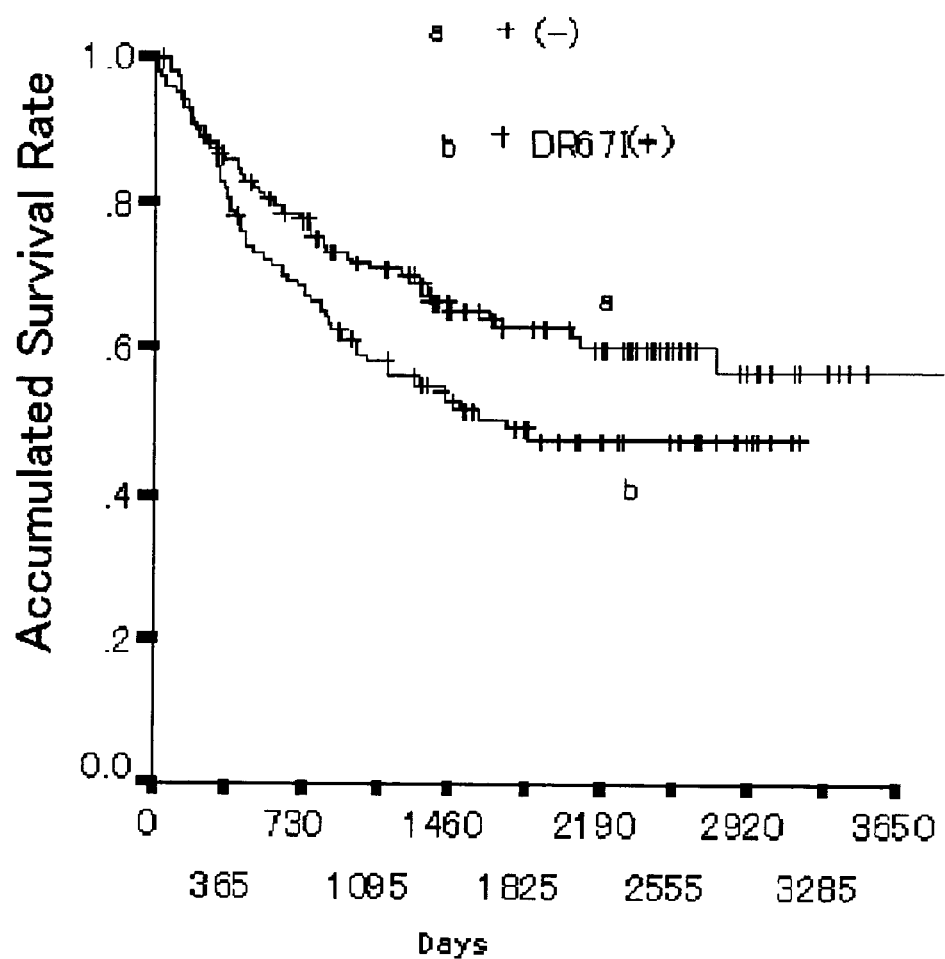
FIG. 12: Result of the anticancer immunotherapy after the stomach cancer resection in patients a) with Ile at Position 67 of DRB1*gene cluster (+) and b) without Ile at Position 67 of DRB1*gene cluster (−)

FIG. 12
a: patients without ile at Position 67 of DRB1* (−)
b: patients with Ile at Position 67 of DRB1* (+)

Figure 13:
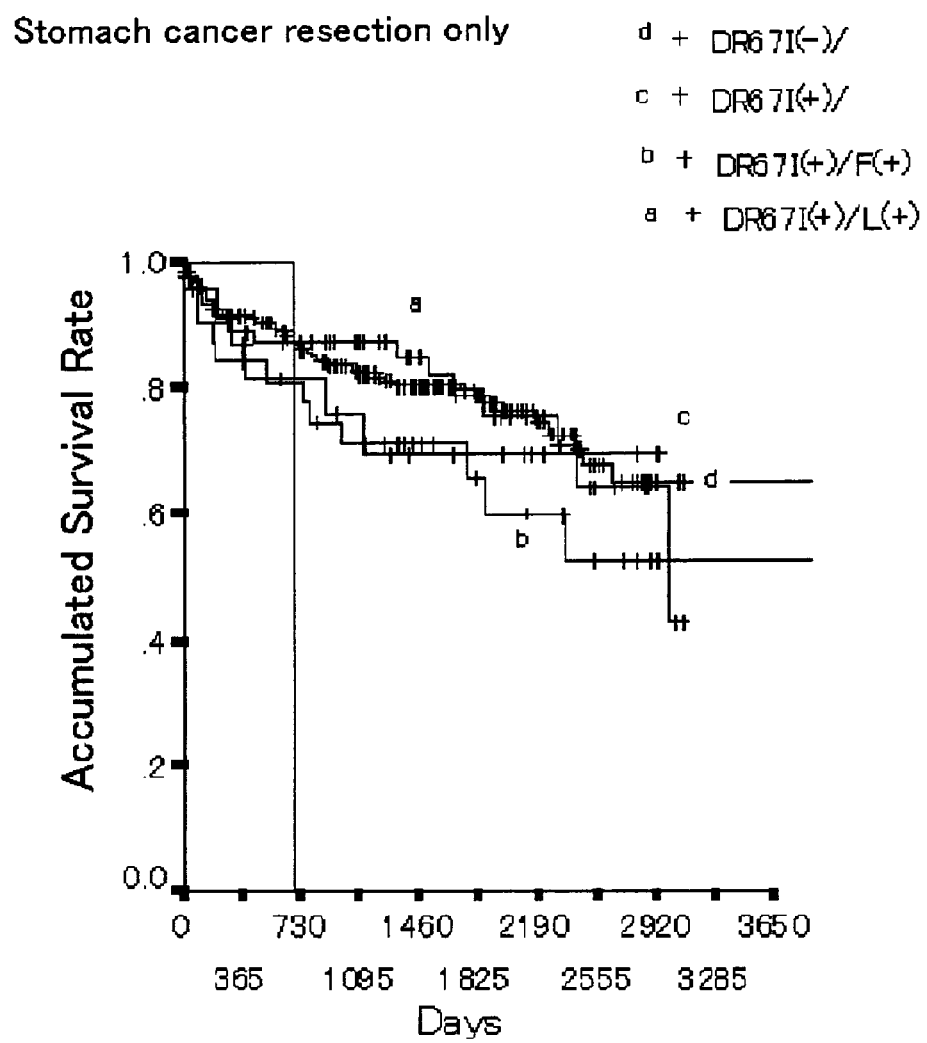
FIG. 13: Result of the stomach cancer resection alone in patients a) with Ile at Position 67 of DRB1*gene cluster (+), b) without Ile at Position 67 of DRB1*gene cluster (−), c) with Ile and Phe at Position 67 of DRB1*gene cluster "DR67I (+)/F(+)", and d) with Ile and Leu at Position 67 of DRB1*gene cluster "DR67I(+)/L(+)

FIG. 13
a: DR67I(+)/L(+) patients with Ile and Leu at Position 67 of DRB1*
b: DR67I(+)/F(+) patients with Ile and Phe at Position 67 of DRB1*
c: DR67I(+) patients with Ile at Position 67 of DRB1*
d: DR67I(−) patients with no Ile at Position 67 of DRB1*

Figure 14:
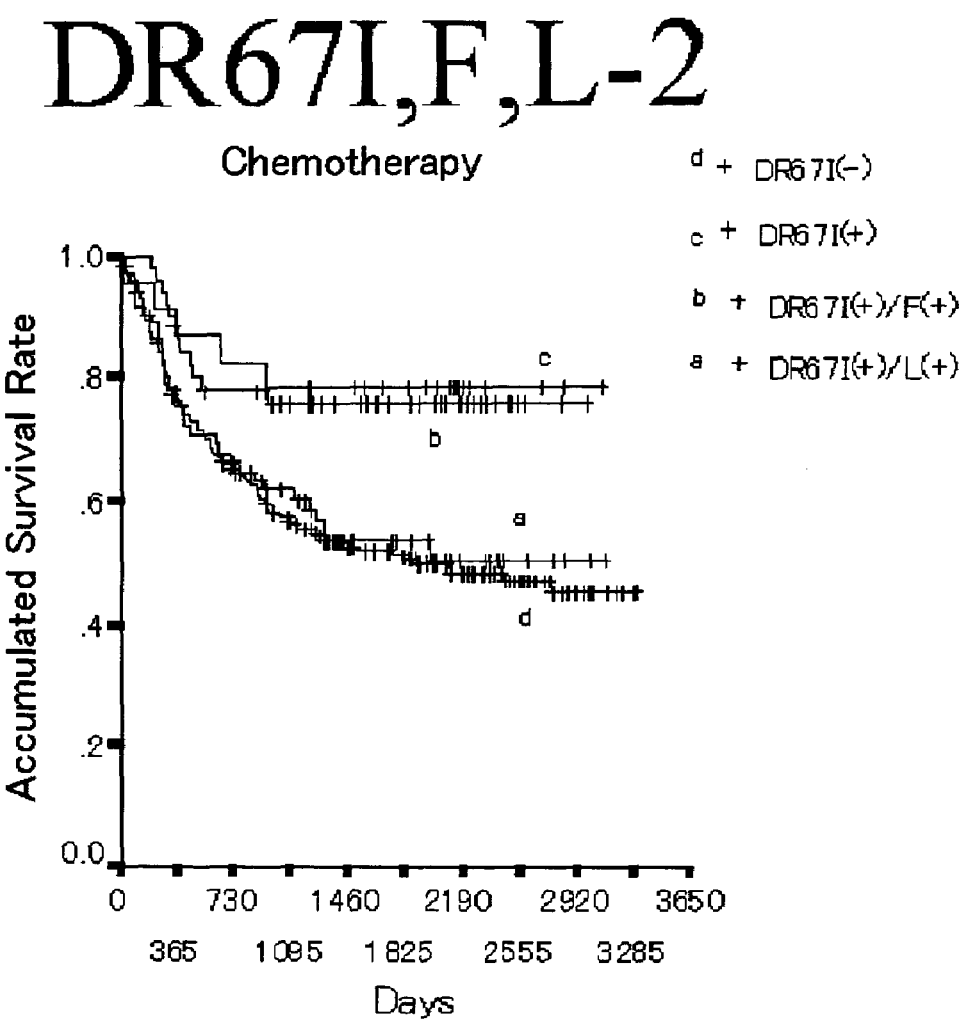
FIG. 14: Result of the anticancer chemotherapy after the stomach cancer resection in patients a) with Ile at Position 67 of DRB1*, "DR67I(+)", b) without Ile, "DR67I(−)", c) with Ile and Phe "DR67I(+)/F(+)", and d) with Ile and Leu "DR67I (+)/L(+)

FIG. 14
a: DR67I(+)/L(+) patients with Ile and Leu at Position 67 of DRB1*
b: DR67I(+)/F(+) patients with Ile and Phe at Position 67 of DRB1*
c: DR67I(+) patients with Ile at Position 67 of DRB1*
d: DR67I(−) patients with no Ile at Position 67 of DRB1*

Figure 15:
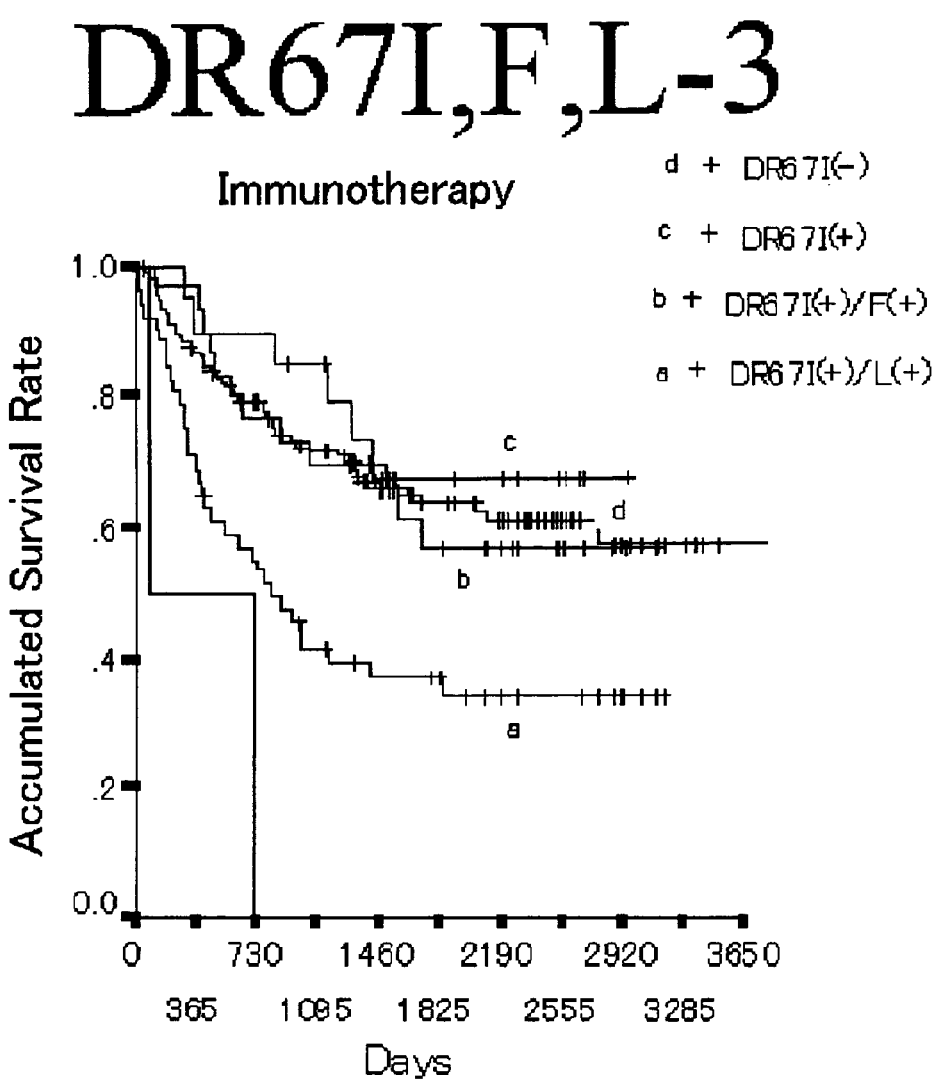
FIG. 15: Result of the anticancer immunotherapy after the stomach cancer resection in patients a) with Ile at Position 67 of DRB1*, "DR67I(+)", b) the patient group without Ile, "DR67I(−)", c) the patient group with Ile and Phe "DR67I (+)/F(+)", and d) the patient group with Iie and Leu "DR67I (+)/L(+)

FIG. 15
a: DR67I(+)/L(+) patients with Ile and Leu at Position 67 of DRB1*
b: DR67I(+)/F(+) patients with Ile and Phe at Position 67 of DRB1*
c: DR67I(+) patients with Ile at Position 67 of DRB1*
d: DR67I(−) patients with no Ile at Position 67 of DRB1*

Figure 16:
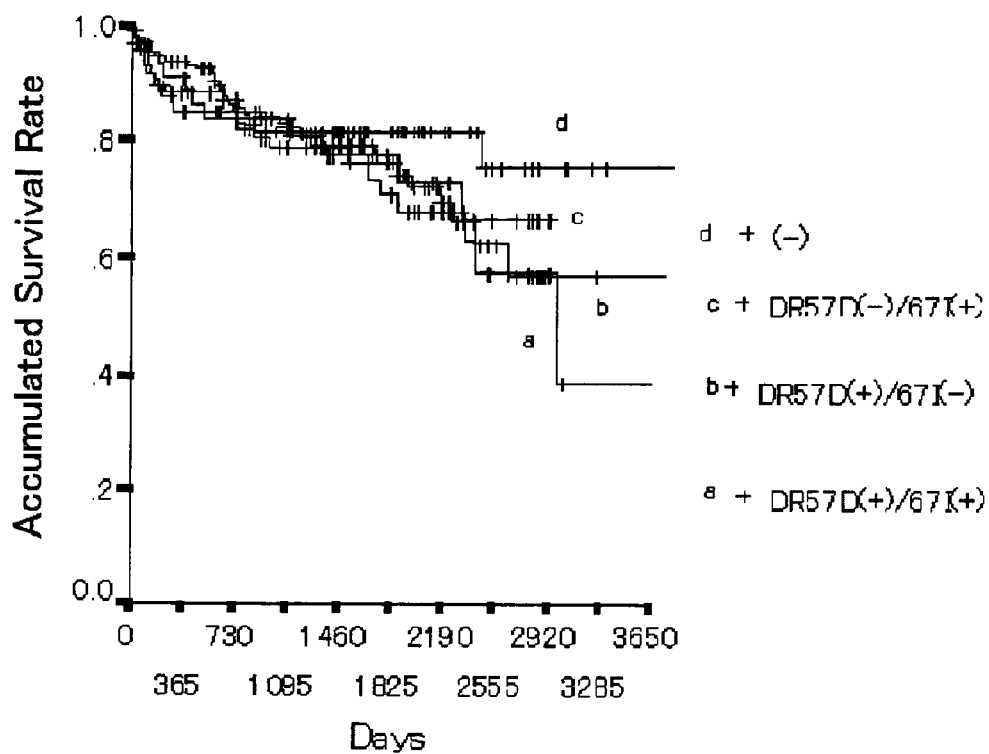
FIG. 16: Result of the stomach cancer resection alone in patients with Asp at Position 57 and with Ile at Position 67 on DRB1*.

FIG. 16
a: patients with Asp at Position 57 and Ile at Position 67 of DRB1*
b: patients with Asp at Position 57 and no Ile at Position 67 of DRB1*
c: patients with no Asp at Position 57 and Ile at Position 67 of DRB1*
d: patients with neither Asp at Position 57 nor Ile at the 67 of DRB1*

Figure 17:
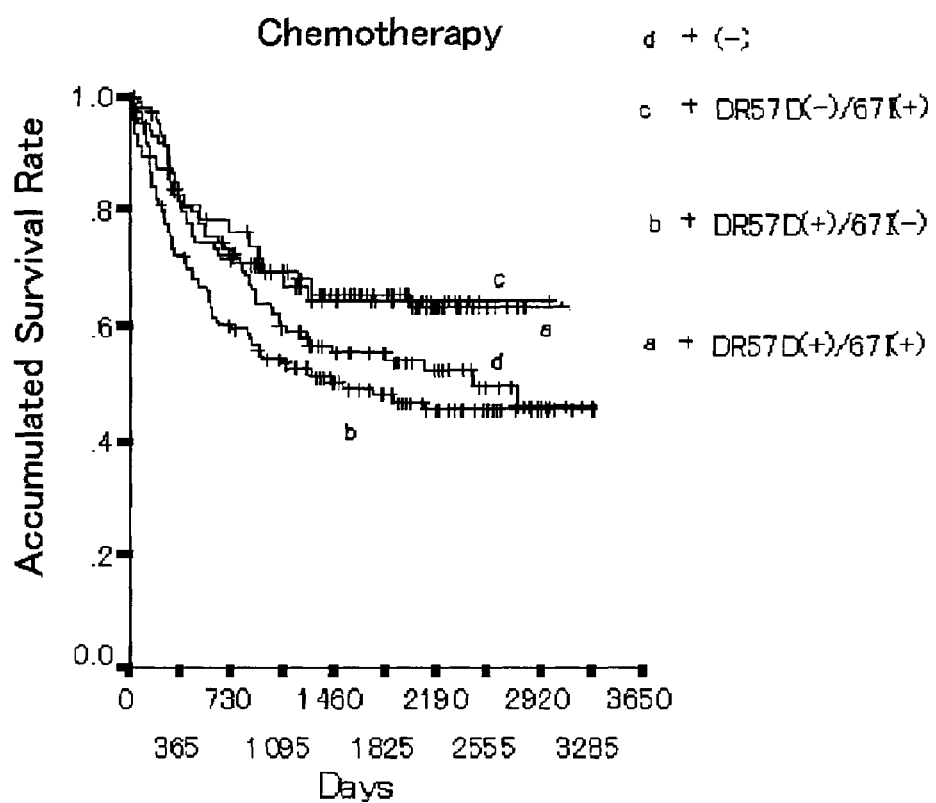
FIG. 17: Result of the anticancer chemotherapy after the stomach cancer resection in patients with Asp at Position 57 and with Ile at Position 67 on DRB1*.

FIG. 17
a: patients with Asp at Position 57 and Ile at Position 67 of DRB1*
b: patients with Asp at Position 57 and no Ile at Position 67 of DRB1*
c: patients with no Asp at Position 57 and Ile at Position 67 of DRB1*
d: patients with neither Asp at Position 57 nor Ile at Position 67 of DRB1*

Figure 18:
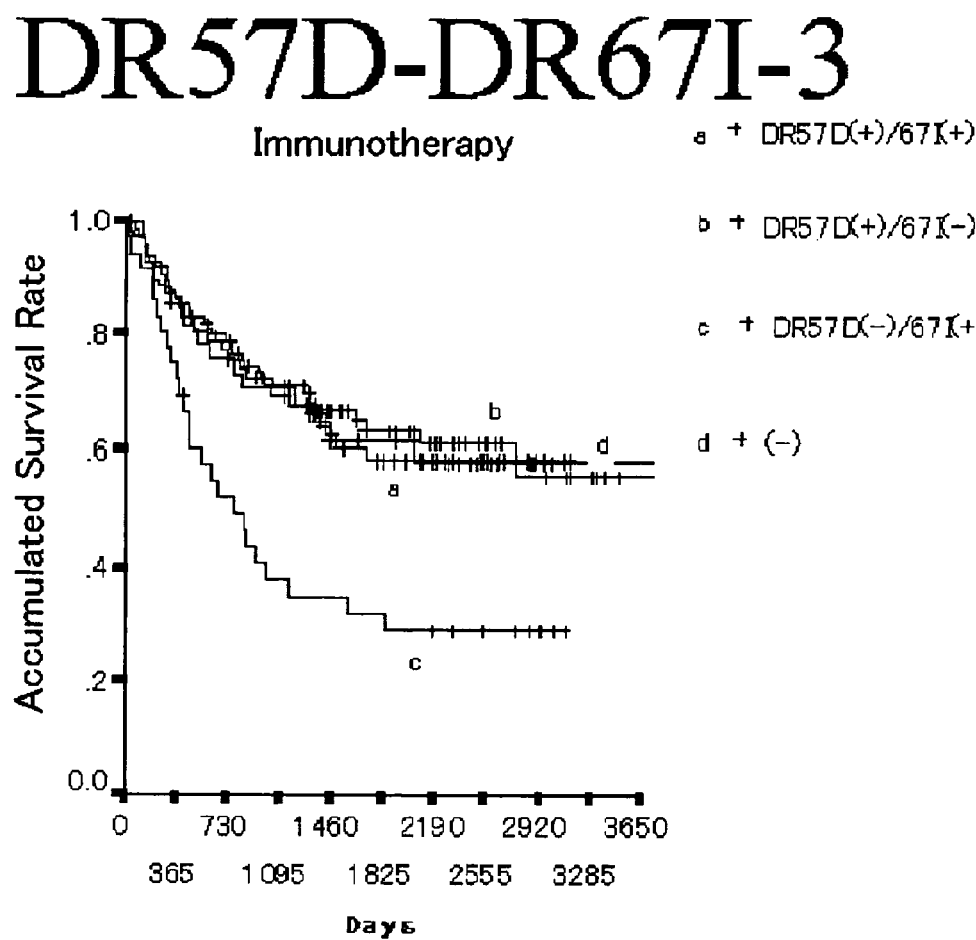
FIG. 18: Result of the anticancer immunotherapy after the stomach cancer resection in patients with Asp at Position 57 and Ile at Position 67 on DRB1*.

FIG. 18
a: patients with Asp at Position 57 and Ile at Position 67 of DRB1*
b: patients with Asp at Position 57 and no Ile at Position 67 of DRB1*
c: patients with no Asp at Position 57 and Ile at Position 67 of DRB1*
d: patients with neither Asp at Position 57 nor Ile at Position 67 of DRB1*

Figure 19:
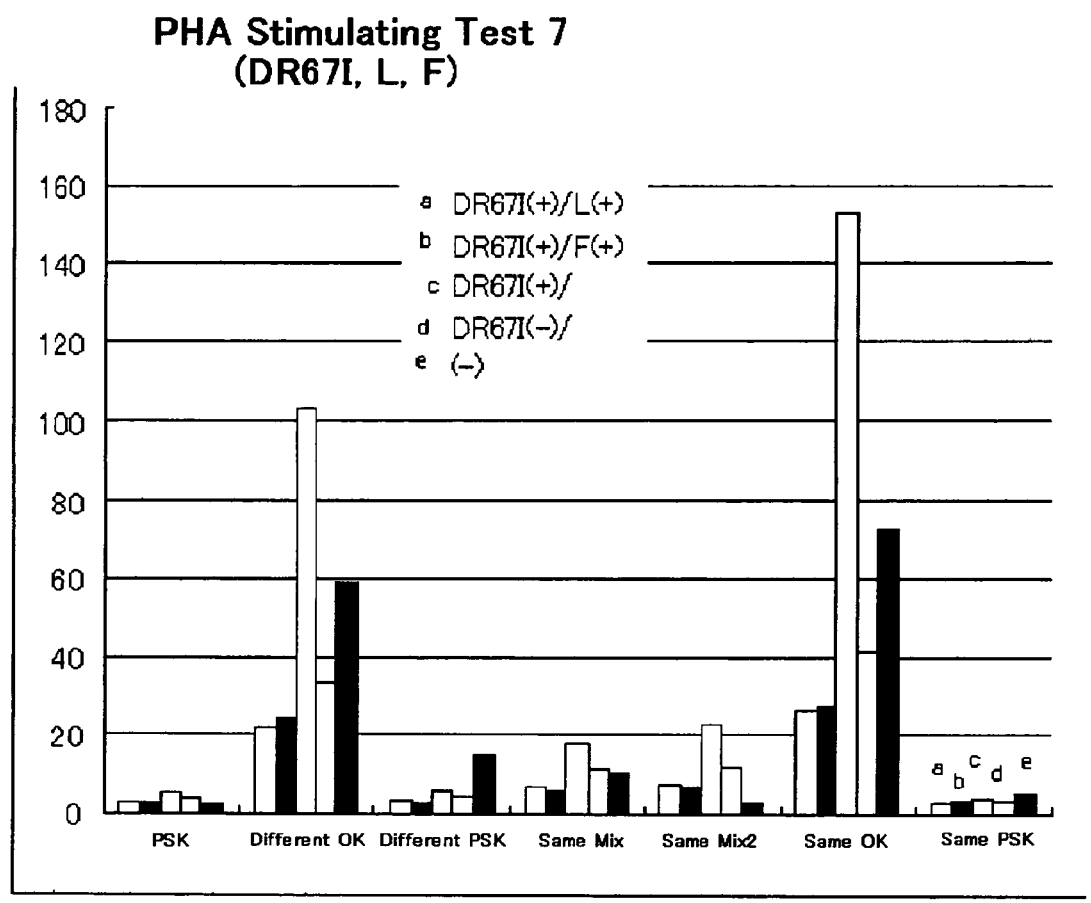
FIG. 19: Result of PHA stimulating test in patients with Ile, Leu, Phe at Position 67 on DRB1*.

FIG. 19
a: patients with Ile and Leu at Position 67 of DRB1*
b: patients with Ile and Phe at Position 67 of DRB1*
c: patients with Ile at Position 67 of DRB1*
d: patients with no Ile at Position 67 of DRB1*
    PSK: I-1 Group
    Different OK: II-2 Group
    Different PSK: I-3 Group
    Same Mix: II-1 Group
    Same Mix2: II-4 Group
    Same OK: II-3 Group
    Same PSK: I-2 Group FIG. 20
a: patients with neither Asp at Position 57 nor Val at Position 67 (DQB1*05031
b: patients with Asp at Position 57 and Val at Position 67 (DQ B 1 *05031 (+))
PSK: I-1 Group
Different OK: II-2 Group
Different PSK: I-3 Group
Same Mix: II-1 Group
Same Mix2: II-4 Group
Same OK: II-3 Group
Same PSK: I-2 Group FIG. 21
B: Heterozygote of vGUA and vGUG
G: Homozygote of vGUG
R: Homozygote of vGUA FIG. 22
B: Heterozygote of 1 CUG and 1 UUG
G: Homozygote of 1 UUG
R: Homozygote of 1 CUG FIG. 23
B: Heterozygote of kAAG and kAAA
G: Homozygote of kAAG
R: Homozygote of kAAA FIGS. 24, 25, 26
a: Homozygote of yUAU
b: Heterozygote of yUAC and yUAU
c: Homozygote of yUAC FIG. 27-75, 85-129
Upper case letters shown on the Figures are single character codes of the amino acids FIG. 76-84
Lower case letters shown on Figures are single character codes of the amino acids

DETAILED DESCRIPTION

Genes specified in this invention are either one of DRB1*gene, DQB1*gene, and DPB1*gene of HLA. Variations of the amino acids coded on the diversity positions of those genes have important meanings. Variations of such amino acids effect interactions with several amino acids. Variations of the amino acids can be used as a marker for screening of effective cancer curative medicines.

1. Positions of Note of the Amino Acid Sequences of Each Genes are as Follows:
1) Positions of the amino acid sequences of DQB1*gene of HLA Class II: −21, (−9), −6, −5, −4, 3, 9, 14, (19), 23, (26), 30, 37, 38, 45, 53, 55, 56, 57, 66, 67, 70, 71, 74, 77, 84, (85), 86, 87, (89), (90), (116), 125, 130, 140, 182, 197, 220, 221, and 224.
Bracketed numbers have $2^{nd}$ level of importance or to tend to have predominance over others.
2) Positions of the amino acid sequences of DRB1*gene of HLA Class II: −25, −24, −17, −16, −1, 9, 10, 11, 13, (14), 16, (25), 26, 28, 30, 31, 32, 33, 37, 38, 40, (47), 57, 60, 67, 70, 71, 73, 74, 77, (78), 85, 86, 96, 98, 104, 120, 133, 142, 166, 231, and 233. Bracketed numbers have the same meanings as above.
3) Positions of the amino acid sequences of DPB1*gene of HLA Class II: 8, 9, 11, 35, 36, 55, 56, 57, 65, 69, 76 84, 85, 86, and 87. 2. Amino acid variations in the amino acid sequences of DQB1*gene at Position 3, 14, 19, 26, 30, 66, 67, 71, 77, 87, 116, 125, 185, 203, and 224 have functions to restrict and control the metastases of cancer cells. Especially, the variations such as (LM: single character codes of the amino acid) and (LL) at Position 14, (GLY) at Position 26, (DE) at Position 66, (IV) at Position 67, (RT) and (RR) at Position 67, (FLY) and (YY) at Position 87, (LV) at Position 116, (SS) at Position 125, (IT) at Position 185, (IV) at Position 203, and (RR) at Position 224 indicate significant tendency. The term "significant tendency" means, for example, that experimental results indicate a stronger than average positive correlation between the amino acid sequence position number and functions to restrict and control the metastases of cancer cells.

3. Amino acid variations in the amino acid sequences of DQB1*gene at Position −5, 9, 30, 57, 66, 67, 86, 87, and 130 are found to have important relationship with the immunotherapy. Especially, the variations such as (PP) at Position −5, (LY) and (YY) at Position 9, (HSY) and (HY) at Position 30, (AA) at Position 57, (EE) and (DE) at Position 66, (VV) and (IV) at Position 67, (EG) at Position 86, (LY) at Position 87, and (QR) at Position 130 indicate significant tendency. The terms "important relationship" and "significant tendency" mean, for example, that the noted amino acid positions have a positive correlation with effective immunotherapy and that experimental results indicate a stronger than average positive correlation between the amino acid sequence position number and functions to restrict and control the metastases of cancer cells, respectively. Furthermore, the terms "the same," "different," "significantly different," "longer," "shorter," or the like, refer to the statistical probability that the values of the items being compared or referred to are the same, different, significantly different, etc.

4. Amino acid variations in the amino acid sequences of DQB1*gene at Position (−5), 9, 30, 37, 38, 66, 67, 86, 87, and 130 are found to have important relationship with the chemotherapy. Especially, the variations such as (PP) at Position −5, (LY) and (YY) at Position 9, (HY) at Position 30, (DY) at Position 37, (AV) at Position 38, (DE) and (EE) at Position 66, (IV) and (VV) at Position 67, (EG) at Position 86, (LY) at Position 87, and (QR) and (RR) at Position 130 indicate significant tendency. The terms "important relationship" and "significant tendency" mean, for example, that the noted amino acid positions have a positive correlation with effective immunotherapy and that experimental results indicate a stronger than average positive correlation between the amino acid sequence position number and functions to restrict and control the metastases of cancer cells, respectively.

5. Amino acid variations in the amino acid sequences of DRB1*gene at Position −24, 14, (25), 26, 28, (77, 78), and 86 are found to have functions to restrict and control the metastases of cancer cells. Especially, the variations such as (FL) at Position −24, (EK) at Position 14, (QR) at Position 25, (FLY) at Position 26, (DEH) at Position 28, (VY) at Position 78, and (GV) at Position 86 indicate significant tendency. The term "significant tendency" means, for example, that experimental results indicate a stronger than average positive correlation between the amino acid sequence position number and functions to restrict and control the metastases of cancer cells.

6. Amino acid variations in the amino acid sequences of DRB1*gene at Position −17, 9, 11, 13, 26, 31, 33, 37, 40, 47, 57, 67, 71, 74, 166, and 231 are found to have important relationship with the immunotherapy. Especially, the variations such as (AA) at Position −17, (KW) at Position 9, (DP) at Position 11, (FS) at Position 13, (FL) at Position 26, (FF) at Position 31, (HN) and (HH) at Position 33, (NS)

at Position 37, (FF) at Position 40, (AV) at Position 57, (FIL) and (FL) at Position 67, (ER) at Position 71, (AE) at Position 74, (RR) at Position 166, and (QQ) at Position 231 indicate significant tendency. The terms "important relationship" and "significant tendency" mean, for example, that the noted amino acid positions have a positive correlation with effective immunotherapy and that experimental results indicate a stronger than average positive correlation between the amino acid sequence position number and functions to restrict and control the metastases of cancer cells, respectively.

7. Amino acid variations in the amino acid sequences of DRB1*gene at Position 37, (47), 57, 60, 71, 73, 74, and 77 are found to have important relationship with the chemotherapy. Especially, the variations such as (LY) at Position 37, (FY) at Position 47, (AV) at Position 57, (YY) at Position 60, (FIL) and (FI) at Position 67, (AA) at Position 71, (AG) and (AA) at Position 73, (AL) at Position 74, and (TT) at Position 77 indicate significant tendency. The terms "important relationship" and "significant tendency" mean, for example, that the noted amino acid positions have a positive correlation with effective chemotherapy and that experimental results indicate a stronger than average positive correlation between the amino acid sequence position number and functions to restrict and control the metastases of cancer cells, respectively.

8. Amino acid variations in the amino acid sequences of DPB1*gene at Position 36 and 55 are found to have important functions to block and control the metastases of cancer cells. Especially, the variation such as (AE vs. AA) at Position 55 indicate significant tendency. The term "important function" means, for example, that the noted amino acid positions have a positive correlation with effective functions to restrict, block, and control the metastases of cancer cells.

9. Amino acid variations in the amino acid sequences of DPB1*gene at Position 9 and 69 are found to have important relationship with the immunotherapy. Especially, the variations such as (FY) (FF) at Position 9 and (KK) at Position 69 indicate significant tendency. The term "important function" means, for example, that the noted amino acid positions have a positive correlation with effective immunotherapy to block and control the metastases of cancer cells.

10. Amino acid variations in the amino acid sequences of DPB1*gene at Position 35, 36, and 76 are found to have important relationship with the chemotherapy. Especially, the variations such as (FF) at Position 35, (VV) at Position 36, and (MV) at Position 76 indicate significant tendency. The term "important function" means, for example, that the noted amino acid positions have a positive correlation with effective chemotherapy to block and control the metastases of cancer cells.

The method provided teaches easy screening of cancer curative medicines by inspecting interactions with the above amino acids positions. Methods for drug-designing by comparison of three-dimensional structures of the candidate compounds, based on the three-dimensional structures and each amino acid's positions and variations, are provided. Effectiveness of the cancer treatment medications can be measured by selecting from the conditions which allow interaction with three-dimensional structures by positions and variations of each amino acid with the candidate compounds, estimating the interaction, and detecting signals from interaction.

New compounds identified from the above information and methods should be effective cancer medicines. The term "effective" means that experimental data indicates a positive correlation exists between a cancer medicine and reduction or lack of growth of cancer cells and/or tumors or reduction in the rate of cancer metastases. Medicines for anti-metastases can contain the compounds according to one of topics 1, 2, 5, or 8. Medicines for immunotherapy can contain the compounds according to one of topics 1, 3, 6, or 9. Medicines used for chemotherapy can contain the compounds according to one of topic 1, 4, 7, or 10.

Information is provided about gene variations suitable for effective cancer treatments. The information relating to the relationship, or statistical correlation, between amino acid positions and variations provides methods of measuring the significance, or effectiveness, of anticancer treatments. For example, examining the genes or the amino acid variations coded by the genes of patients enables the estimation of the rate of metastases of cancer cells and the effectiveness of the immunotherapy, the chemotherapy, or the cancer resection, alone. When using at least one of the below amino acid variations of DRB1*gene, DQB1*gene, or DPB1*gene of HLA as a marker, it is possible to provide statistically significant or statistically meaningful examination methods.

1) Positions of the amino acid sequences of HLA Class II, DQB1*gene: −21, −6, −5, −4, 3, 9, 14, (19), 23, 30, 37, 38, 45, 53, 55, 56, 57, 66, 67, 70, 71, 74, 77, 84, (85), 86, 87, (89, 90, 116), 125, 130, 140, 182, 197, 220, 221, and 224.

2) Positions of the amino acid sequences of HLA Class II, DRB1*gene: −25, −24, −17, −16, −1, 9, 10, 11, 13, 14, 16, (25), 26, 28, 30, 31, 32, 33, 37, 38, 40, (47), 57, 60, 67, 70, 71, 73, 74, 77, (78), 85, 86, 96, 98, 104, 120, 133, 142, 166, 231, and 233.

3) Positions of the amino acid sequences of HLA Class II, DPB1*gene: 8, 9, 11, 35, 36, 55, 56, 57, 65, 69, 76, 84, 85, 86, and 87.

4) Base variations of HLA Class II, DQB1*gene: CCU and CCC at Position −23, CCU and CCC at Position −15, AAC and AAU at Position 19, ACG and ACC at Position 21, GUA or GUG at Position 27 (Val), GCA and GCG at Position 38, AAC and AAU at Position 62, CGG and CGA at Position 72, ACC, ACG and AGA at Position 77, GUA and GUG at Position 78, CUG and UUG at Position 91 (Leu), GAC and GAU at Position 135, GCC, GCU, ACC and ACU at Position 140, GAC and GAU at Position 169, CUC and CUG at Position 210, CUC and CUU at Position 213, and CUU and CUG at Position 215.

5) Base variations of HLA Class II, DRB1*gene: GCG and GCU at Position −16, AAA or AAG at Position 12 (Lys), CAC/GAA or CAC/GAG at Position 28, CAA/CAA or CAA/CAG at Position 34, GAC, GAU, GCC, GCU, and GCG at Position 57, GAG, GCC, GAG, GCU and GCG at Position 58, GAA and GAG at Position 69, CGG, CGC, and CGU at Position 72, UAC or UAU at Position 78 (Tyr), GUC and GUU at Position 95, GUG and GUA at Position 101, GCA and GCC at Position 104, CGG and CGA at Position 166, and ACA, AUG, and ACG at Position 181.

Additionally, reagent kits to measure diversity of the amino acids or the base sequences of these specified genes can be provided. Clinical measuring reagents which estimate the results of the treatments accurately can be provided.

WORKING EXAMPLES

The following are the details of clinical results of the invention. It is, however, not limited to the reported cases only.

Methods used herein are as follows:

1) Genetic polymorphisms are based on the public literature. (WHO HLA Nomenclature Committee For Factors of the HLA system, IMGT/HLA Sequence Database, http://www.ebi.ac.uk/imgt/HLA/align.html, Tissue Antigens, 1998; 51:417-466, incorporated herein by reference in its entirety)

2) Clinical experiments, including 344 patients with the cancer resection alone, 394 patients with anticancer chemotherapy after the cancer resection (therapy: fluoropyrimidines such as 5-FU, mitomycin or adriamycin), and 241 patients with immunotherapy after the cancer resection (therapy: immuneopotentiator such as PSK or OK432).

3) Standard methods were used for collecting genes from the patients, identifying genes, and specifying diverse amino acids and base sequences. (MCH & IRS, Supplement Vol. 1 73-95, 1994. Tissue Antigens 39:187-202, 1992. 38;53-59, 1991, 38:60-71, 1991, 40;100-103, 1992, all of which are incorporated herein by reference in their entireties). For amplification of genomic DNA, for example, an automated PCR thermal sequencer can be used, as described in Tissue Antigens, 38:53-59, 1991. Analyses positions were from −29 to 237th on DRB1*, −32 to 237th on DQB1*, and −29 to 229th on DPB1*.

4) Metastases of all kinds of cancers included 1649 cases, of which 504 cases had metastases and 1145 cases did not have metastases. "Metastases" as used herein refer to lymph node metastases and remote metastases.

5) Analysis of influence of the variations of the amino acids on metastases and the treatment was performed as followings: after a provision of the treatments described at 2), the follow-up research of the patients was conducted for about 10 years, and the statistical analysis of the mortality rate was carried out. The amino acid positions which are distinguishable with a statistically significant difference by the amino acid types (types of amino acids: heterozygote or homozygote) have been identified for each given treatment (the cancer resection alone, anticancer chemotherapy after cancer resection, and anticancer immunotherapy after cancer resection). In the summary tables, the results are organized by the types of amino acids, effect on metastases, and the treatment effect at each amino acid position.

[Clinical Cases]

[Results of Clinical Cases]

FIG. 1: Table shows the base sequence of DQB1*gene and corresponding amino acids to analyze polymorphic amino acids at Position 57 and 67. As a result, Asp, Ala, Ser, and Val are found at Position 57 while Ile and Val are found at Position 67.

FIGS. 2 and 3 show the base sequence of DRB1*gene and corresponding amino acids to analyze polymorphic amino acids at Position 57 and 67. As a result, Asp, Ala, Ser, and Val are found at Position 57 while Ile, Leu, and Phe are found at Position 67.

FIG. 4 shows the accumulated survival curves in patients with DQRB1*05031 gene (Asp at Position 57, Val at Position 67) ("1" group) and the "a" group without DQRB1* 05031 gene among patients with DQB1*gene cluster with the stomach cancer resection alone. The vertical axis indicates the accumulated survival rate (Kaplan-Meier Method) (1.0=100% survived) while the lateral axis shows the number of survived days. As the result, there is only a slight difference at the 1825$^{th}$ day (5$^{th}$ year) between the 2 groups, but shows a good survival rate at the 7$^{th}$ and 8$^{th}$ year for the "b" group with (+) (the patient group with DQRB1*05031 gene). Thus, it can be concluded that the patients with DQRB1*05031 gene (Asp at Position 57, Val at Position 67) have slightly better survival rate after stomach cancer resection. (DQB1*05031(−) (n=306), (+) (n=38))

FIG. 5 shows the accumulated survival curves in patients with DQRB*105031 gene ("b" group) (Asp at Position 57, Val at Position 67) and the "a" group without DQRB1*gene among patients with DQB1*gene cluster with anticancer chemotherapy after cancer resection. Medications used for anticancer chemotherapy in this report are treatments with prescription anticancer chemicals well known in the clinical field, such as, for example, 5-FU, Adriamycin, and others. As clearly shown in the figure, the (+) (b) patient group is not suitable for the chemotherapy. Thus, if verifying existence of DQRB1*05031 gene (Asp at Position 57, Val at Position 67) by gene examination before beginning the treatments, prescribing such chemical treatments to those patients can be avoided. In contrast, the chemotherapy is suitable for the patients without DQRB1*05031 gene (Asp at Position 67, other than Val at Position 67). Moreover, if the effective examination of the anticancer chemotherapy is given to these (−) patients, the effectiveness rate would improve drastically (DQB1*05031(−) (n=356), (+) (n=38))

FIG. 6 shows the accumulated survival curves in patients with DQRB*105031 gene ("b" group) (Asp at Position 57, Val at Position 67) and the "a" group without DQRB1*gene among patients with DQB1*gene with anticancer immunotherapy after cancer resection. Medications used for anticancer immunotherapy in this report are treatments with prescription anticancer immune materials well known in the clinical field, such as, for example, krestin (PSK), OK432, and others. The figure clearly shows that the survival rate of the (+) (b) patient group is statistically longer (log rank test $p<0.05$) than that of the (−) (a) patient group without such gene. Five year-survival rates were 90% and 50% in patients with positive and negative DQRB*105031 gene, respectively. Thus, if patients could be confirmed as not having DQRB1*05031 gene (Asp at Position 57, other than Val at Position 67), the immunotherapy is not a recommended treatment for them. If the immunotherapy treatment is given only to the (+) patients or excluding the (−) patients, the effectiveness rate would improve. (DQB1*05031(−) (n=233), (+) (n=18))

From FIGS. 5 and 6, it is clear that the (+) patients and the (−) patients have opposite outcomes from the anticancer treatments. It is possible to select patients who respond positively to therapies by using this gene as a marker and to provide the most appropriate treatments to those patients. In other words, "order-made" treatment is possible.

FIG. 7 shows the accumulated survival curves in patients with Asp at Position 57 (group b (+)) and the patient (group a (−)) without Asp at Position 57 among patients with DRB1* of DRB1*gene cluster with stomach cancer resection alone. About at the 8$^{th}$ year, the (−) patients have a slightly better statistically significant result, and patients without this gene have a better survival rate.

FIG. 8 shows the accumulated survival curves in patients with Asp at Position 57 (group b (+)) and the patient (group a (−)) without Asp at Position 57 on DRB1* of DRB1*gene cluster with anticancer chemotherapy after stomach cancer resection. The result means that there is no statistically significant relation between (+) and (−) and the anticancer chemotherapy.

FIG. 9 shows the accumulated survival curves in patients with Asp at Position 57 (group b (+)) and the patient (group a (−)) without Asp at Position 57 on DRB1* of DRB1*gene cluster with the anticancer immunotherapy after stomach cancer resection. The effect is statistically significantly better treatment results in patients with Asp at Position 57 with anticancer immunotherapy.

FIG. 10 shows the accumulated survival curves in patients with Ile at Position 67(group b(+)) and the patient (group a (−)) without Ile at Position 67 on DRB1* of DRB1*gene cluster with stomach cancer resection alone. The result means that there is no statistically significant difference between (+) and (−) patients.

FIG. 11 shows the accumulated survival curves in patients with le at Position 67(group b (+)) and the patient (group a (−)) without Ile at Position 67 on DRB1* of DRB1*gene cluster with the anticancer chemotherapy after stomach cancer resection. The result shows that chemotherapy is statistically effective on (+) patients. Thus, the treatment effect of the anticancer chemotherapy would improve by selection of the patients with Ile at position 67.

FIG. 12 shows the accumulated survival curves in patients with Ile at Position 67(group b (+)) and the patient (group a (−)) without Ile at Position 67 on DRB1* of DRB1*gene cluster with the anticancer immunotherapy after stomach cancer resection. The result shows that immunotherapy is effective on (−) patients. Thus, the rate of treatment effectiveness of the anticancer chemotherapy would improve by selection of the patients without Ile at position 67.

FIG. 13 shows the accumulated survival curves in patients (group c: DR67I (+)) with Ile at Position 67, patients (group d: DR67I (−)) without Ile, patients (group b: DR67I(+)/F (+)) with Ile and Phe, and patients (group a: DR67I(+)/L(+)) with Ile and Leu on DRB1* of DRB1*gene cluster with the stomach cancer resection alone.

FIG. 14 shows the accumulated survival curves in patients (group c: DR67I (+)) with Ile at Position 67, patients (group d: DR67I (−)) without Ile, patients (group b: DR67I(+)/F(+)) with Ile and Phe, and patients (group a: DR67I(+)/L(+)) with Ile and Leu on DRB1* of DRB1*gene cluster. The patients were treated with the anticancer chemotherapy after the cancer resection. The result indicates that the anticancer chemotherapy is statistically effective on patients of DR67I(+)/F(+) and DR67I(+), that is, patients with Ile but not Leu at the position 67.

FIG. 15 shows the accumulated survival curves in patients (group c: DR67I (+)) with Ile at Position 67, patients (group d: DR67I (−)) without Ile, patients (group b: DR67I(+)/F(+)) with Ile and Phe, and patients (group a: DR67I(+)/L(+)) with Ile and Leu on DRB1* of DRB1*gene cluster. The patients were treated with the anticancer immunotherapy after the cancer resection. The results show patient group a is not suitable for the anticancer immunotherapy, and such immunotherapy would seriously damage patients with Leu at Position 67. Thus, the anticancer immunotherapy should not be given to the patients with Leu at Position 67. Since DR67I (−) and DR67I (+) draw the same curve, the patients with Ile at Position 67 on DRB1 are suitable for the chemotherapy.

FIG. 16 shows the accumulated survival curves in patients (group a: Asp at Position 57 and Ile at Position 67), patients (group b: Asp at Position 57 and other than Ile at Position 67), patients (group c: other than Asp at Position 57 and Ile at Position 67), and patients (group d: neither Asp nor Ile at Position 57 and 67) on DRB1* of DRB1*gene cluster patients with the stomach cancer resection alone.

FIG. 17 shows the accumulated survival curves in patients (group a: Asp at Position 57 and Ile at Position 67), patients (group b: Asp at Position 57 and other thanile at Position 67), patients (group c: other than Asp at Position 57 and Ile at Position 67), and patient (group d: neither Asp nor Ile at Position 57 and 67) on DRB1* of the DRB1*gene cluster patients with the anticancer chemotherapy after the stomach cancer resection. The result indicates that the presence of Ile at Position 67 is statistically significant and important for anticancer chemotherapy, and anticancer chemotherapy should not be given to the patients without Ile at Position 67. The efficacy of medicines for anticancer chemotherapy is such that chemotherapy treatment should be carried out in patients with Ile at Position 67 and avoided in the patients without it.

FIG. 18 shows the accumulated survival curves in patients (group a: Asp at Position 57 and Ile at Position 67), patients (group b: Asp at Position 57 and other than Ile at Position 67), patients (group c: other than Asp at Position 57 and Ile at Position 67), and patients (group d: neither Asp nor Ile at Position 57 and 67) on DRB1* of the DRB1*gene cluster patients with the anticancer immunotherapy after the cancer resection. The result indicates that an existence of Asp at Position 57, but not Ile at Position 67, is statistically significant and important for the anticancer immunotherapy. The efficacy of medicines for anticancer immunotherapy is such that immunotherapy treatment should be carried out in patients without Ile at Position 67 but with Asp at Position 57.

The above analyses show that effective treatment for cancer patients can be dependent upon the amino acids that are in Position 57 and 67 on both DRB1*gene and DQB*1 gene. It is possible to choose the appropriate therapy and to provide appropriate medications after resections (e.g., surgery) by identifying and recognizing the amino acids of the patients. Also, this invention demonstrates that the amino acids in Position 57 and 67 on DRB1*gene and DQB*1 gene can be used as markers to select patients who respond to anticancer therapy, thereby enhancing treatment efficacy.

[Experimental Results]

Figure 20:
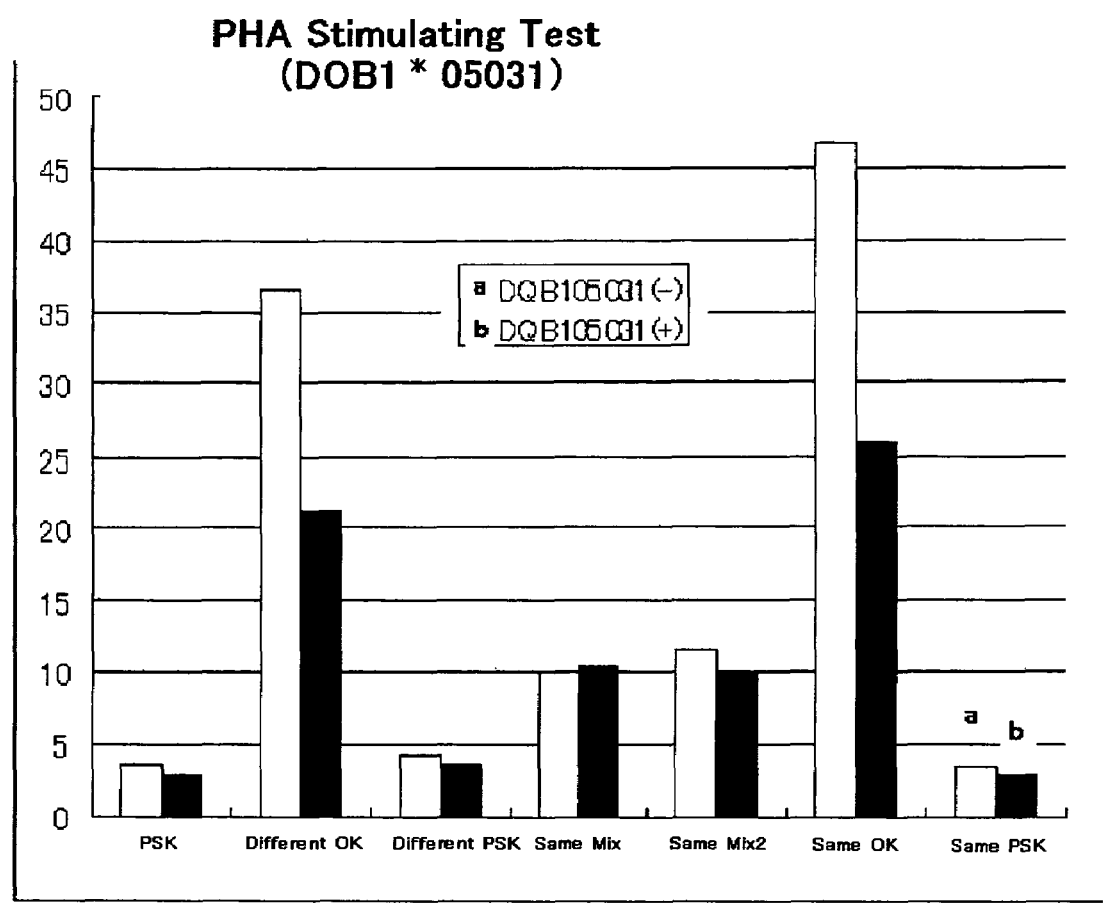
FIG. 20: Result of PHA stimulating test in patients with the presence of DQB1*05031.

The phytohemagglutinin (PHA) Stimulating Test (lymphocyte proliferation reaction in stomach cancer cases) was performed as follows. Results are shown in FIGS. 19 and 20. Stimulation index was calculated as follows; the Ficollo-Conray gravity centrifugation was used to separate lymphocytes from peripheral blood with heparin. RPMI-1640 was added to adjust to $6.0 \times 10^6$/ml. It was separated into 0.1 ml/well on a 96-hole U-base microplate (corning #2850) for the stimulating test. The I Group was added with PSK (1 mg/ml, 0.1 ml/well), the II Group was added with OK-432 (1/200 KE/ml, 0.1 ml/well), and the III Group was on medium only. The I Group was separated into 3 aliquots and tested: the I-1 Group (indicated as PSK on FIGS. 19 and 20) was incubated for 5 days, the I-2 Group (indicated as Same PSK on Figures) for 2 more days of incubation upon adding 0.1 mg/well of PSK after the first 3-day incubation, and the I-3 Group (indicated as Different PSK on Figures) for 2 more days of incubation upon adding 0.005 KE/well of OK432 after the first 3-day incubation. Similarly, the II Group was subdivided and classified into the II-1 Group (indicated as Same Mix), the II-2 Group (indicated as Different OK), and the II-3 Group (indicated as Same OK). Among this group, a double amount of OK432 was added to the II-4 Group (indicated as Mix2). The III Group was incubated for 5 days.

Then, 1 micro Ci/well of $^3$H-thymidine was added to the samples and incubated for 24 hours to measure lymphocytes on the harvest scintillation counter.

FIG. 19 shows results of the PHA stimulating test in patients with Ile, Leu, and Phe at Position 67 of DRB1*gene. The purpose of this test is to determine levels of immune responses. The vertical axis is for SI and the lateral axis is for variable stimulus. These are, from left, the a Group [Position 67: Ile (+) and Leu (+)], the b Group [Position 67: Ile (+) and Phe [Position 67: other than Ile, Leu, or Phe] DESCRIPTION OF GROUPS B, C, AND D APPEAR TO BE INCOMPLETE. FIG. 20 shows that twice the stimulus was necessary to give sufficient activation. Such activation, and the necessary stimulus, depends on the types of the amino acids at Position 67. It is important to have Ile at Position 67 while response to the stimulus is weak even if Leu and Phe exist. The results of this experiment and the results of the anticancer chemotherapy experiment (patients with Ile at Position 67, referring to FIG. 14) prove that the anticancer chemotherapy is effective on the patients with high immune response.

FIG. 20 shows the result of the PHA stimulating test in patients with/without Asp at Position 57 and Val at Position 67 of DQB*1 gene (i.e. DQB1*05031 patients). The vertical axis is for SI and lateral axis is for the methods used for stimulation. The left side of the coupled bars is the a Group and the right side represents the b Group. Similar reactions to the stimulus are noted. The patients with Asp at Position 57 but not Val at Position 67 (a Group) are more immune responsive than the patients with Asp at Position 57 and Val at Position 67 (b Group). The results from this experiment and the fact that the anticancer immunotherapy is effective to the patient with Asp at Position 57 and Val at Position 67 (referring to FIG. 6) proves that anticancer immunotherapy is not effective on the patients with high immune response.

Working Example 1

Table 1 shows statistical analysis of the polymorphic amino acids on DQB1*gene. It shows the results of the amino acid variations at Position 3, 14, 19, 26, 30, 38, 53, 57, 66, 67, 77, 85, 86, 87, 89, 90, 116, 125, 140, 182, 185, 203, 220, and 221, the effectiveness of the anticancer immunotherapy and the anticancer chemotherapy, the metastases (total), lymph node metastases, and remote metastases. Letters in the brackets shown in the position of the amino acid columns represent single character codes of the amino acids which may be combined. For example, Position 30 (HSY) means that amino acids may be H, S, or Y. "H" (with the same H for the complementary amino acid) in the immunotherapy of (HSY) column means that there is a tendency for immunotherapy to be effective on patients with H at that position, while "HY hetero•" means that there is a statistically significant tendency for Immunotherapy to be effective on patients with H and Y, different kinds of the amino acids variation. "hetero" is an abbreviation of "heterozygote," and marked with "•" means that there is a statistically significant tendency of the figures. In addition, "Y homo•*" in the column indicates that there is a statistically significant tendency for Immunotherapy to be effective on patients with Y at Position 30 (with the same Y for the complementary amino acid. "homo" is an abbreviation of "homozygote").

"AV hetero •*" in the 38 (AV) row and in the Chemotherapy column shows that there is a statistically significant tendency for Chemotherapy to be effective on patients with A at Position 38 and V for the complementary amino acid. "V homo" in the Chemotherapy column shows that there is a statistically significant tendency for anticancer chemotherapy to be effective on patients with V at Position 38 (with the same amino acid for the complementary amino acid).

"V hetero •*" in the 57(ADSV) row and in the Immunotherapy column shows that there is a statistically significant tendency for anticancer immunotherapy to be effective on patients with V at Position 57 and A, D, or S for the complementary amino acids. Hereafter, the meaning of each gene is shown by same relation.

"PS 34.2" in the 3 (PS) row and in the Metastases (total) column shows that the complementary amino acids are P and S, and the rate of metastases is 34.2% in total and is increasing. "PP 26.8" means that the complementary of the amino acids are same P and P, and the rate of metastases is 26.8% in total on a decreasing trend. Additionally, the mark represents statistical significance in the figures.

The results show that cancer metastases has statistically significant relationship with Positions 3, 14, 19, 26, 30, 77, 87, 116, 125, and 203 of DQB1*gene, and either homozygotic or heterozygotic type of the complementary amino acids at corresponding positions has important effects on the metastases. It is likely to have cancer metastases in patients with heterozygotes at Position 3 and 19 and homozygotes at Position 14, 26, 30, 77, 87, 116, 125, and 203. In particular, LL homozygote at Position 14 and 26, RR homozygote at Position 77, YY homozygote at Position 87, II homozygote at Position 116, SS homozygote at Position 125, and VV homozygote at Position 203 shows statistically significant differences of the effect. Therefore, the possibility of providing the means of suppressing cancer metastases using these amino acids as a marker is shown.

There is a statistically significant relationship between the effectiveness of Immunotherapy and Position 30, 57, 66, 67, 85, 86, and 87 of DQB1*gene. Especially, Y homozygote and heterozygote at Position 30, H heterozygote on Position 30, V heterozygote on Position 57 have statistically significant results. Position 38, 66, 67, 86, and 87 has a statistically significant relationship with the Chemotherapy. Especially, A heterozygote and V heterozygote on Position 38, D heterozygote and E heterozygote on Position 66, I heterozygote and V heterozygote on Position 67, A homozygote on Position 86, and F homozygote on Position 87 shows statistically significant results. Therefore, the possibility of providing the means of the anticancer chemotherapy and the anticancer immunotherapy in cancer treatment using these amino acids as a marker is shown.

Differences between the Working Examples and the statistical analysis report can be explained as follows:

The survival rates were examined when applying the priority demand and 1 year after. All cancers were treated as one group on applying the priority demand, but it was separated into the stomach cancer cases and the other cancer cases in this experiment. Since all positions of cancer cases published at present were examined for this report, there was some difference in the result. Moreover, since the lymph node metastases and the metastases of remote organs (liver, lungs and others) were divided and examined on the priority demands for the metastases, there was some difference.

Working Example 2

Table 2 shows the results of statistics analysis of the polymorphic amino acids on DRB1*gene. A table shows the relationship between the effectiveness of the anticancer immunotherapy and the chemotherapy, tendency of cancer metastases (total), tendency of lymph node metastases, and tendency of remote metastases, and the amino acid variations at Position 14, 25, 26, 28, 30, 33, 47, 57, 67, 71, 73, 74, 77, 78, and 86.

There is an important statistically significant relationship between the cancer metastases and Position 14, 25, 26, 28, 77, 78, and 86 of DRB1*gene. Also, either homozygote or heterozygote of complementary amino acids at the corresponding positions has an important influence on the metastases. Patients having homozygotes at Position 14, 25, 26, 28, and 78 tend to have cancer metastases. In particular, FY heterozygote at Position 26, GG homozygote and GV heterozygote at Position 86 show statistically significant results. It is possible to control cancer metastases by using these amino acids as a marker.

Position 33, 47, 57, 67, 73, 74, and 78 on DRB1*gene have relationship with effectiveness of the anticancer immunotherapy. In particular, H homozygote at Position 33, AD heterozygote at Position 57, L homozygote at Position 67, and A or E homozygote at Position 74 are statistically notable. Position 47, 57, 67, 71, 73, 74, and 78 on DRB1*gene have a statistically significant relationship with effectiveness of the anticancer chemotherapy. In particular, F homozygote at Position 47, I homozygote at Position 67, A homozygote at Position 71, A homozygote at Position 73, L homozygote at Position 74, and Y homozygote at Position 78 are statistically notable. It is possible to provide the means for the anticancer chemotherapy and the immunotherapy by using these amino acids as a marker.

Working Example 3

Table 3 shows the results of statistics analysis of amino acid polymorphisms on DPB1*gene. The table shows the relationship between the effectiveness tests for the anticancer chemotherapy and the immunotherapy, the tendency of cancer metastases (total), the tendency of lymph node metastases, and the tendency of remote metastases against the amino acid variations of the amino acid sequences on Position 8, 9, 11, 35, 36, 55, 56, 57, 69, and 76.

There is an important statistically significant relationship between the cancer metastases and Position 8, 11, 36, and 55 on DPB1*gene. Also, either the homozygote or the heterozygote of complementary amino acids at the corresponding positions has an important statistically significant influence for the metastases. Patients having a homozygote at Position 8 and 11 and a heterozygote at Position 36 and 55 tend to have cancer metastases. In particular, AE heterozygote at Position 55 shows statistically significant results. It is possible to control cancer metastases by using these amino acids as a marker. Position 9, 35, 36, 56, 57, 69, and 70 on DPB1*gene and the anticancer immunotherapy have a significant relationship with effectiveness of the anticancer immunotherapy. In particular, FY heterozygote at Position 9 and K homozygote at Position 69 are statistically notable. Position 9, 35, 36, 56, 57, 69, and 76 on DPB1*gene have a statistically significant relationship with effectiveness of the anticancer chemotherapy. In particular, F homozygote at Position 35, AV heterozygote at Position 36, and I homozygote at Position 76 are statistically notable. It is possible to provide the means and determine the effectiveness for the anticancer chemotherapy and the immunotherapy by using these amino acids as a marker.

Working Example 4

It is confirmed that the differences in the base sequence on genes affect the effectiveness of anticancer treatments by the following statistics processing. The corresponding base sequences are GUA or GUG of the base sequences at Position 27 (Val) on DQB1 gene of HLA Class II, CUG or UUG of the base sequences at Position 91 (Leu) on DQB1 gene of HLA Class II, and AAA or AAG of the base sequences at Position 12 (Lys), and UAC or UAU at Position 78 (Tyr).

Figure 21:
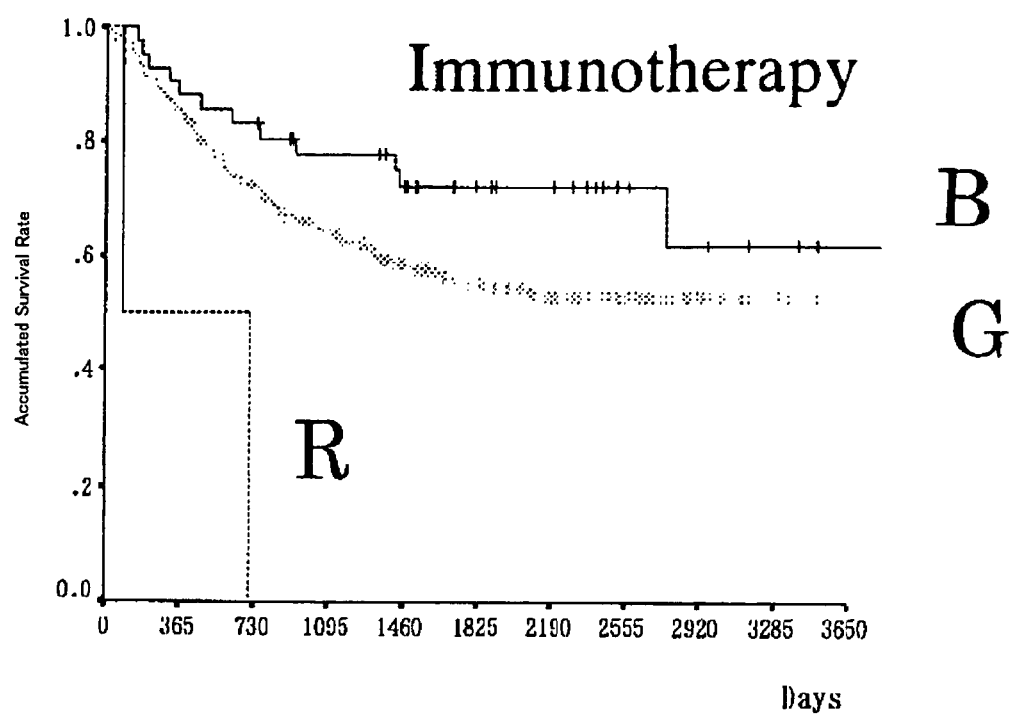
FIG. 21: Graph showing effectiveness of immunotherapy in patients with GUA or GUG at Position 27 (Val) of the amino acid sequence of DQB1*gene cluster of HLA Class II. The vertical axis shows accumulated survival rate, while the cross axis shows survived days.

FIG. 21 shows that GUA or GUG at Position 27 (Val) of the base sequences on DQB1*gene has a statistically significant relationship with the response to immunotherapy. Immunotherapy is not effective for vGUG homozygote but is for vGUG homozygote or vGUA and vGUG heterozygote. The result means that the patients who respond to immunotherapy can be determined by measuring the base sequence of Position 27 (Val) on DQB1*gene.

Figure 22:
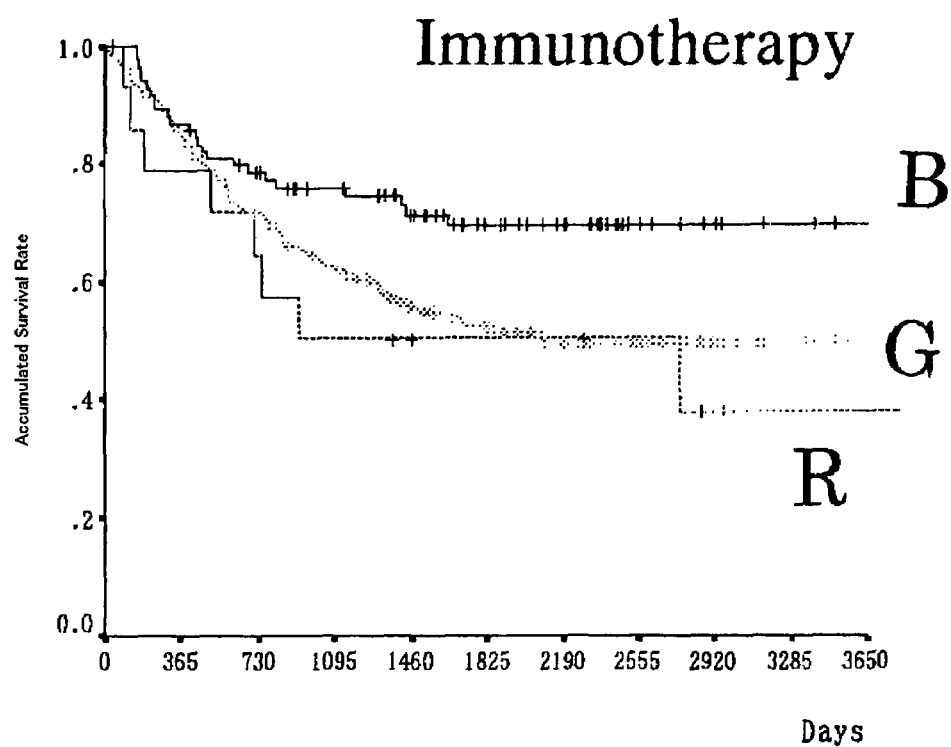
FIG. 22: Graph showing effectiveness of immunotherapy in patients with CUG or UUG at Position 91 (Leu) of the amino acid sequence of DQB1*gene cluster of HLA Class II. The vertical axis shows accumulated survival rate, while the lateral axis shows survived days.

FIG. 22 shows that CUG or UUG at Position 91 (Leu) of the base sequences on DQB1*gene has a statistically significant relationship with the response to immunotherapy. Immunotherapy is not effective for 1UUG homozygote or 1CUG homozygote but is for 1CUG and 1UUG heterozygote. As a result, it can be predicted which patients respond to immunotherapy by examining the base sequence of Position 91 (Leu) on DQB1*gene.

Figure 23:
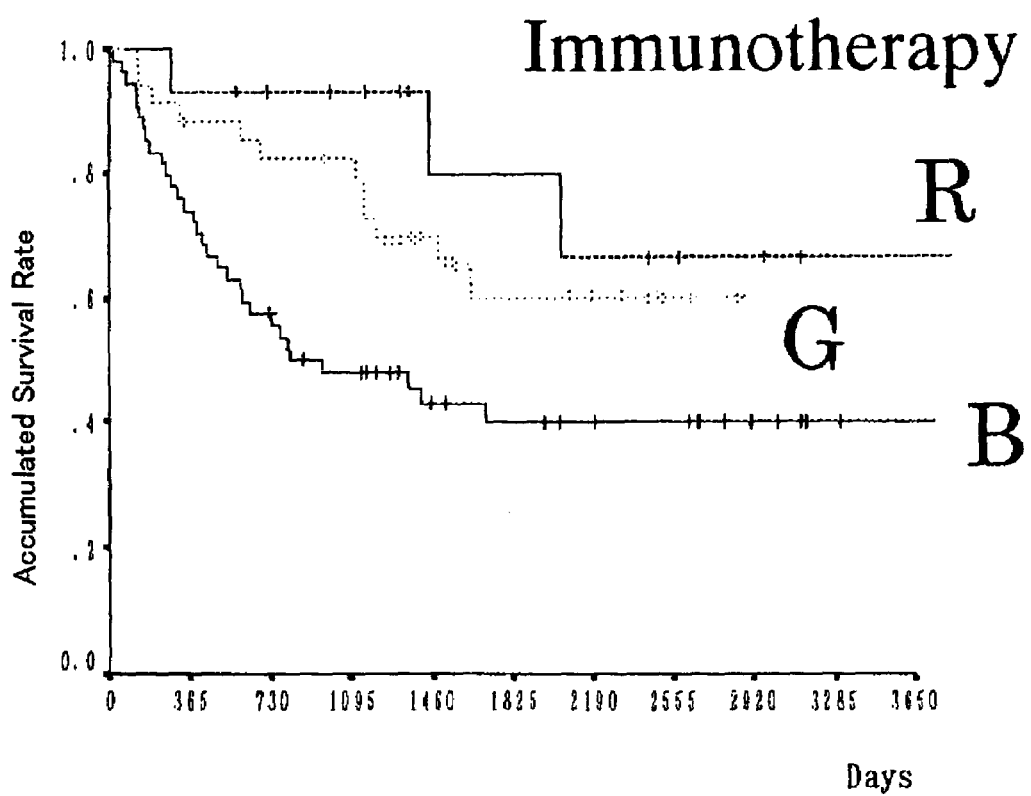
FIG. 23: Graph showing effectiveness of immunotherapy in patients with AAA or AAG at Position 12 (Lys) of the amino acid sequence of DQB1*gene cluster of HLA Class II. The vertical axis shows accumulated survival rate, while the cross axis shows survived days.

FIG. 23 shows that AAG or AAA at Position 12 (Lys) of the base sequence on DRB1*gene has a statistically significant relationship with the response to immunotherapy with a significant difference. Immunotherapy is effective on kAAA homozygote or kAAG homozygote but not for kAAA and kAAG heterozygote. The result means that the patients who respond to immunotherapy can be determined by examining the base sequence of Position 12 (Lys) on DRB1*gene.

Figure 24:
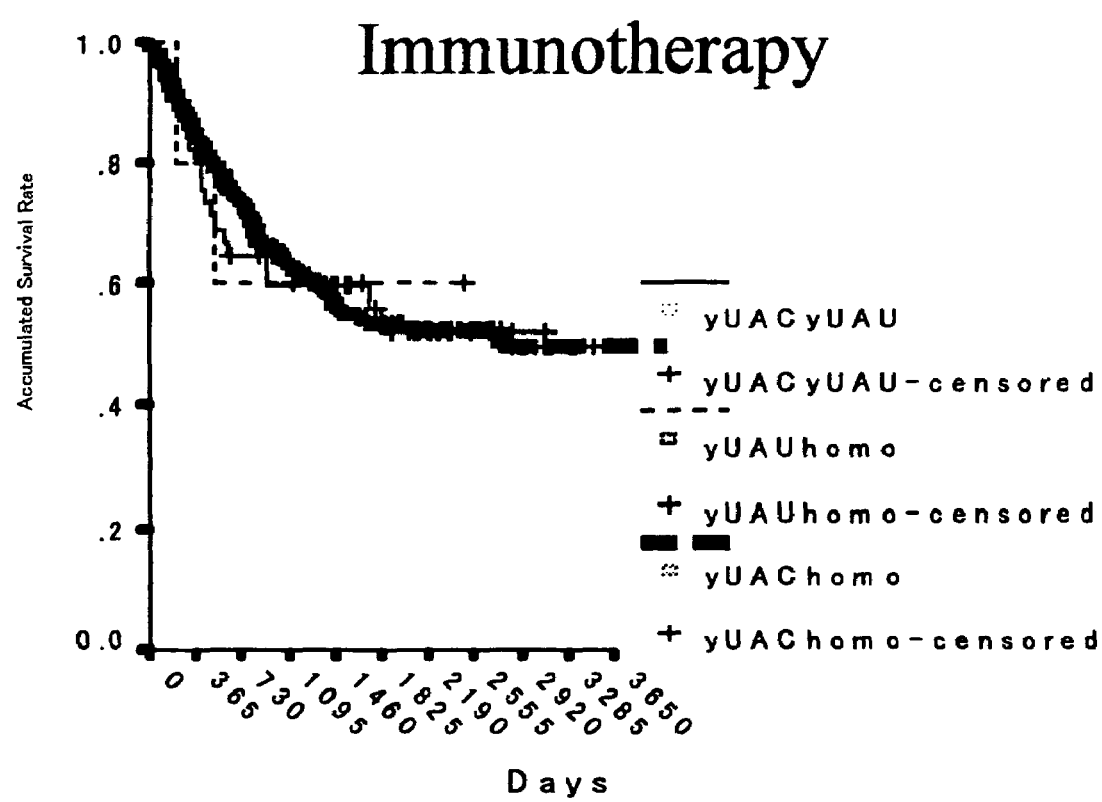
FIG. 24: Graph showing effectiveness of immunotherapy in patients with UAC or UAU at Position 78 (Tyr) of DRB1*. The vertical axis shows accumulated survival rate, while the cross axis shows survived days.

FIG. 24 shows that there is no influence on the effectiveness of the immunotherapy group by either UAC or UAU at Position 78 (Tyr) of the base on DRB1*.

Figure 25:
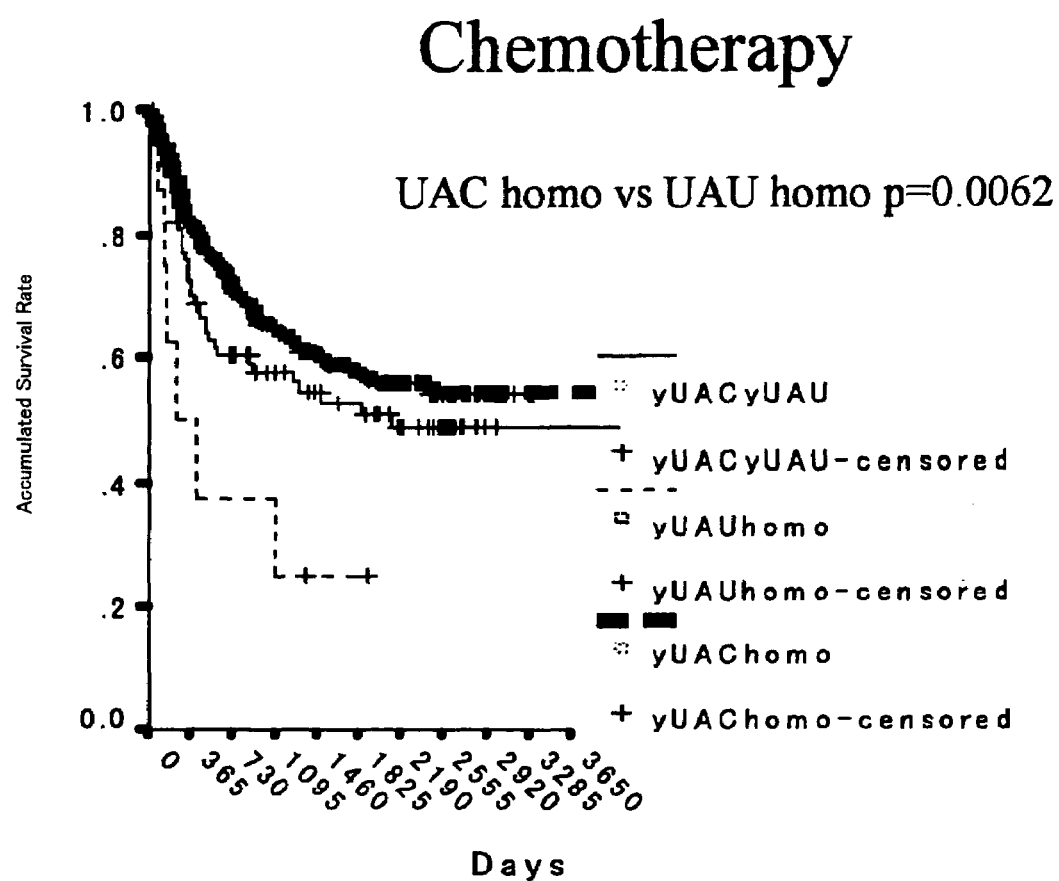
FIG. 25: Graph showing effectiveness of chemotherapy in patients with UAC or UAU at Position 78 (Tyr) of DRB1*. The vertical axis shows accumulated survival rate, while the cross axis shows survived days.

FIG. 25 shows UAC or UAU at Position 78 (Tyr) of the base sequence on DRB*1 gene has a statistically significant relationship with response to chemotherapy. Chemotherapy is effective on yUAC homozygote or yUAC and yUAU heterozygote but not on yUAU homozygote with therapy. The result means that the patients who respond to chemotherapy can be determined by examining the base sequence of Position 78 (Tyr) on DRB1*gene.

Figure 26:
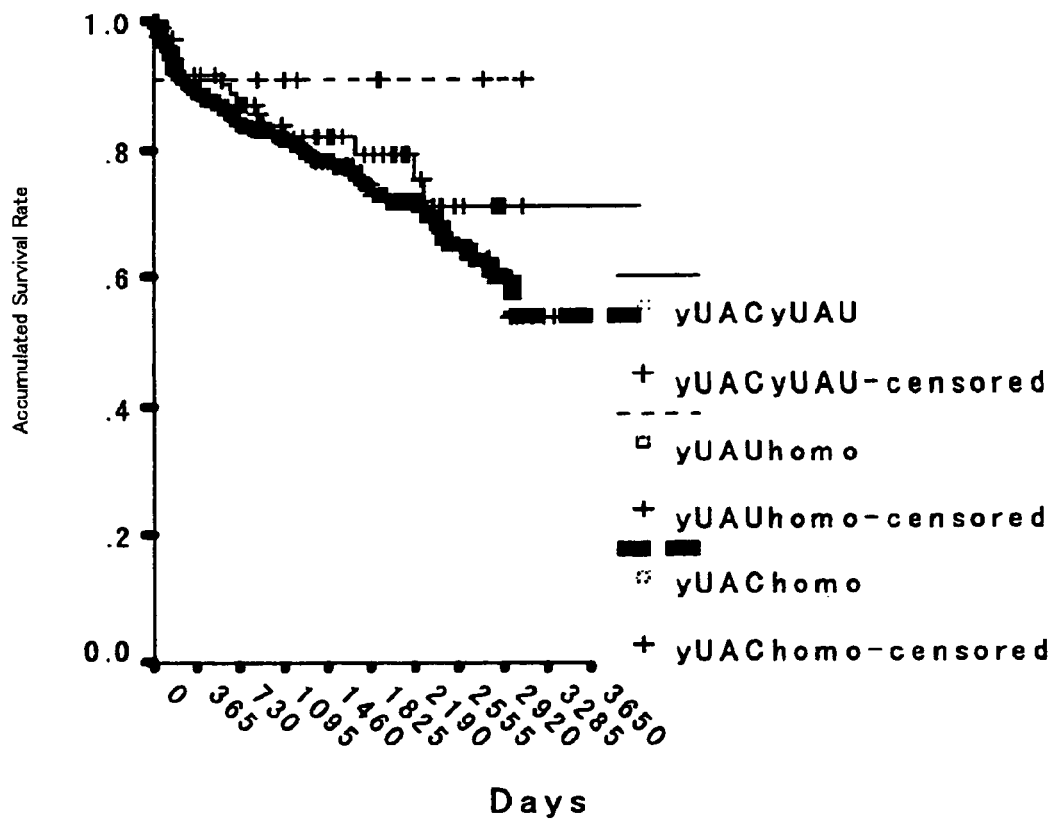
FIG. 26: Graph showing effectiveness of stomach cancer resection alone in patients with the resections UAC or UAU at Position 78 (Tyr) of DRB1*. The vertical axis shows accumulated survival rate, while the cross axis shows survived days.

FIG. 26 shows UAC or UAU at Position 78 (Tyr) of the base on DRB*1 gene has a statistically significant relationship with the response to chemotherapy. The effectiveness of cancer resection alone for yUAU homozygote and for yUAC and yUAU heterozygote in patients is confirmed. Thus, examining the base sequence at Position 78 (Tyr) of the base sequence on DRB*1 gene enables the prediction of the patients who respond to resection alone. Results shown in FIG. 21 to 26 and 76 to 84 prove that the genes and the proteins coded by the genes have a close statistically significant relationship (recognized as the Gene Code Table (triplets)), and thousands of human genes treat the uncoded RNA (noncoding RNA: ncRNA), which are not coded to the proteins, as the end products. Data contained herein from the inventions is the first to confirm this using human cases.

Working Example 5

(Relationship Between Polymorphism on Each Gene and Treatment in the Specified Positions)

With respect to the variations of the amino acids of the specific part of the polymorphic amino acids of DQB1*, DRB1*, and DPB1*genes in all cases, the variations of the amino acids and the medical treatment effect of treatments [The cancer resection alone (no adjuvant therapy), anticancer chemotherapy after the cancer resection (Chemotherapy), and anticancer immunotherapy after the cancer resection (Immunotherapy)] were confirmed. (Graphs include the survival rate for the vertical axis (1.0=100%) and survived days for the lateral axis.) The base data was collected from the above clinical cases.

1) DQ9 (All Cases)

Figure 27:
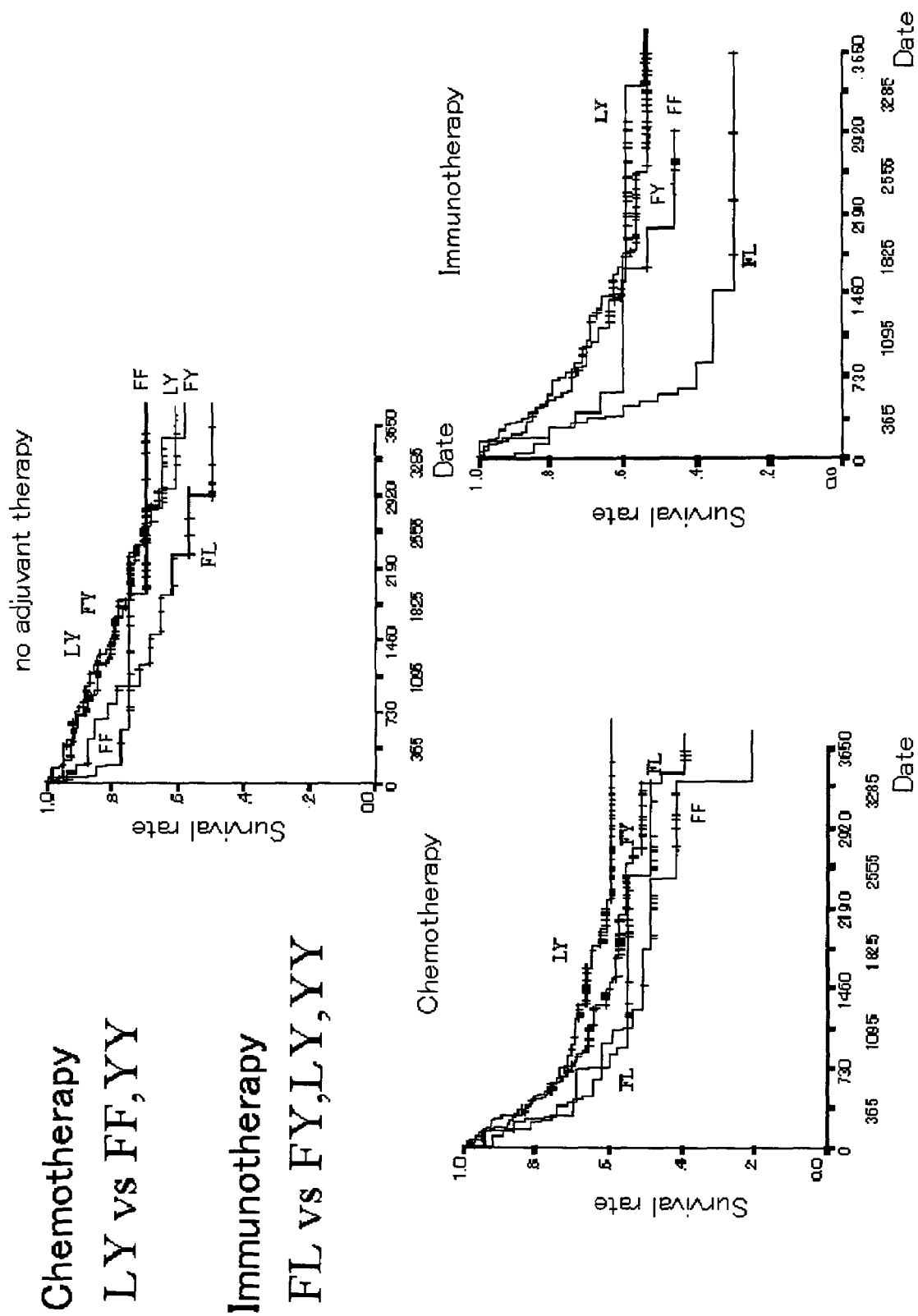
FIG. 27: Result of the treatment effects in all cancer cases and the variations of the amino acid sequences at Position 9 of DQB1*.

The remarkable point of FIG. 27 is that the immunotherapy after the cancer resection (Immunotherapy) is not suitable for patients with the variation FL (Single character code of the amino acid) at Position 9 of the amino acid sequence on DQB1*gene.

2) DQ67 (All Cases)

Figure 28:
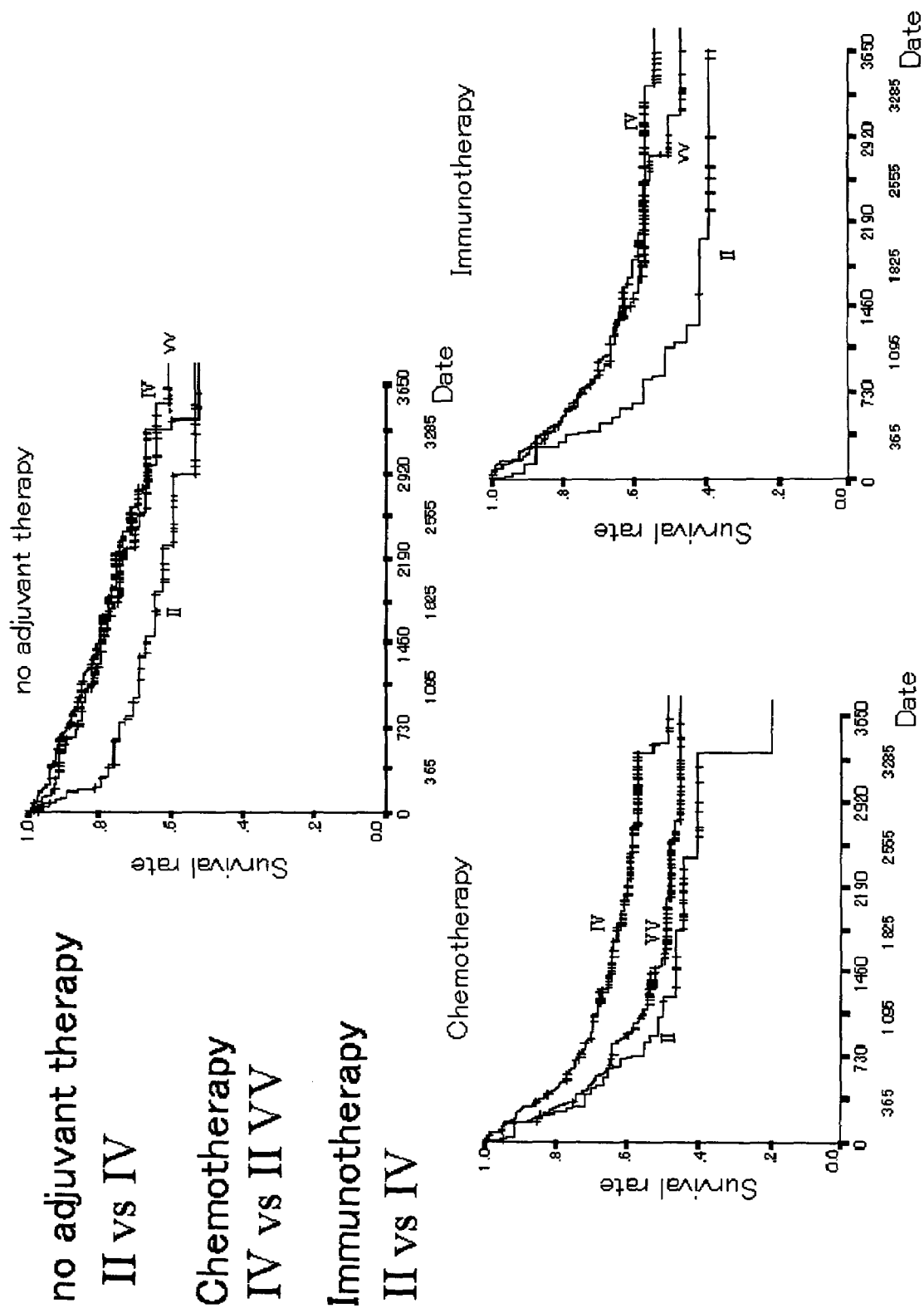
FIG. 28: Result of the treatment effects in all cancer cases and the variations of the amino acid sequences at Position 67 of DQB1*.

FIG. 28 shows that none of the treatments [The cancer resection alone (no adjuvant therapy), anticancer chemotherapy after the cancer resection (Chemotherapy), and anticancer immunotherapy after the cancer resection (Immunotherapy)] is suitable for the patients with II at Position 67 of the amino acid sequence on DQB1*gene.

3) DR9 (All Cases)

Figure 29:
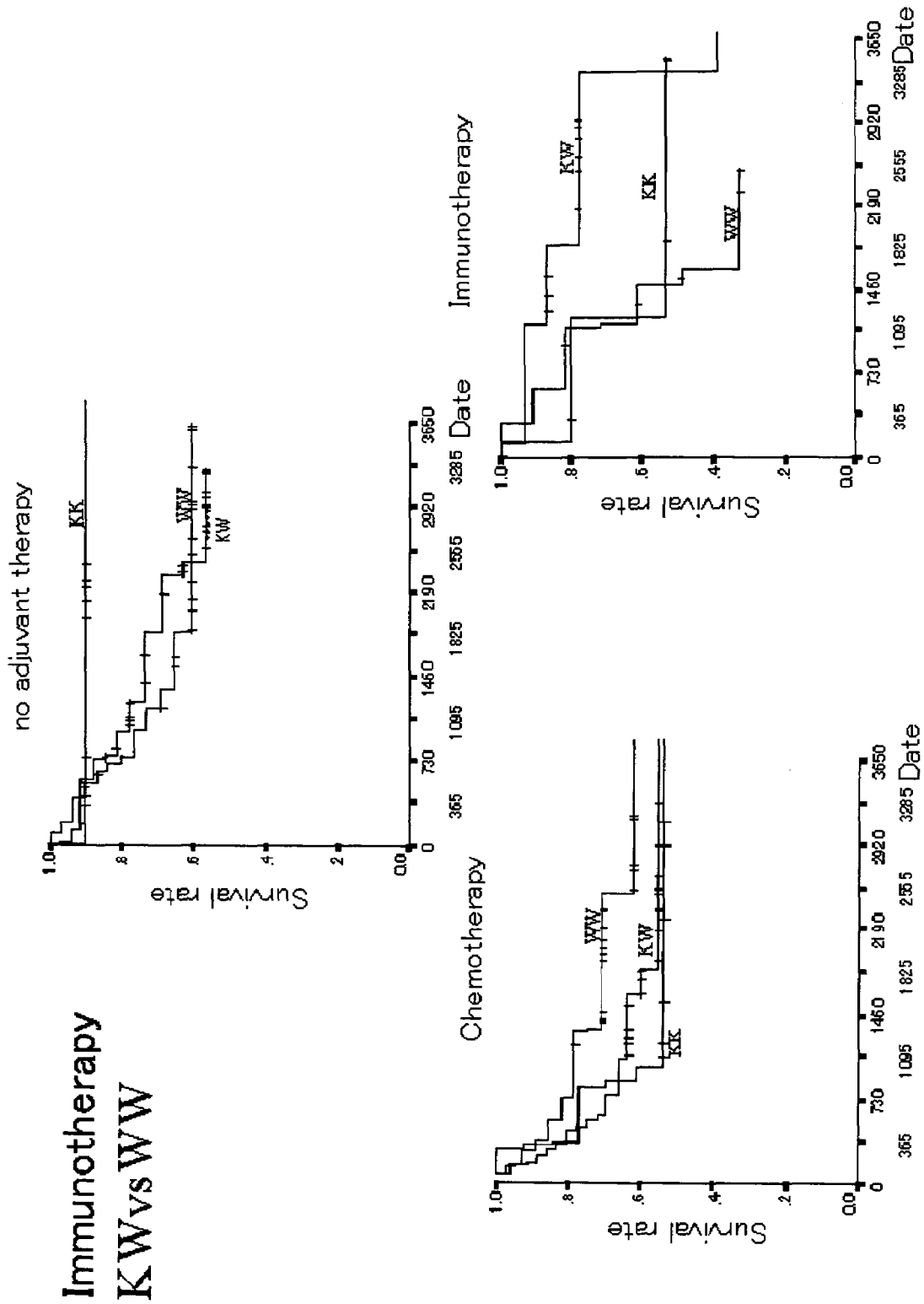
FIG. 29: Result of the treatment effects in all cancer cases and the variations of the amino acid sequences at Position 9 of DRB1*.

FIG. 29 shows that the cancer resection alone (no adjuvant therapy) is suitable for patients with KK at Position 9 of the amino acid sequence on DRB1*gene. Also, anticancer immunotherapy after the cancer resection (Immunotherapy) is suitable for patients with KW.

4) DR37 (All Cases)

Figure 30:
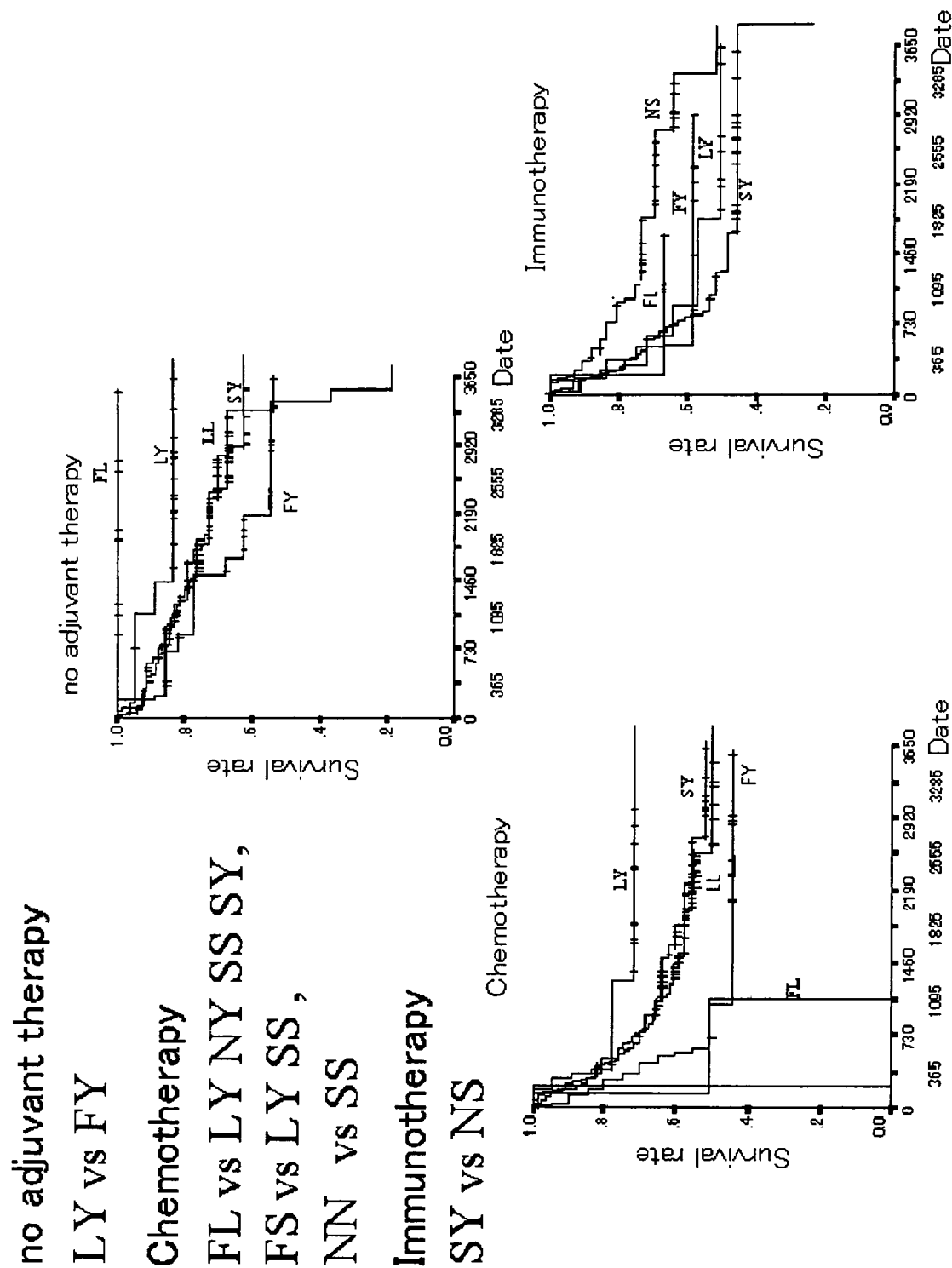
FIG. 30: Result of the treatment effects in all cancer cases and the variations of the amino acid sequences at Position 57 of DRB1*.

FIG. 30 shows that the cancer resection alone (no adjuvant therapy) is suitable for patients with FL at Position 37 of the amino acid sequence on DRB1*gene. Also, the cancer resection alone (no adjuvant therapy) and anticancer chemotherapy after the cancer resection (Chemotherapy) are suitable for patients with LY.

5) DR57 (All Cases)

Figure 31:
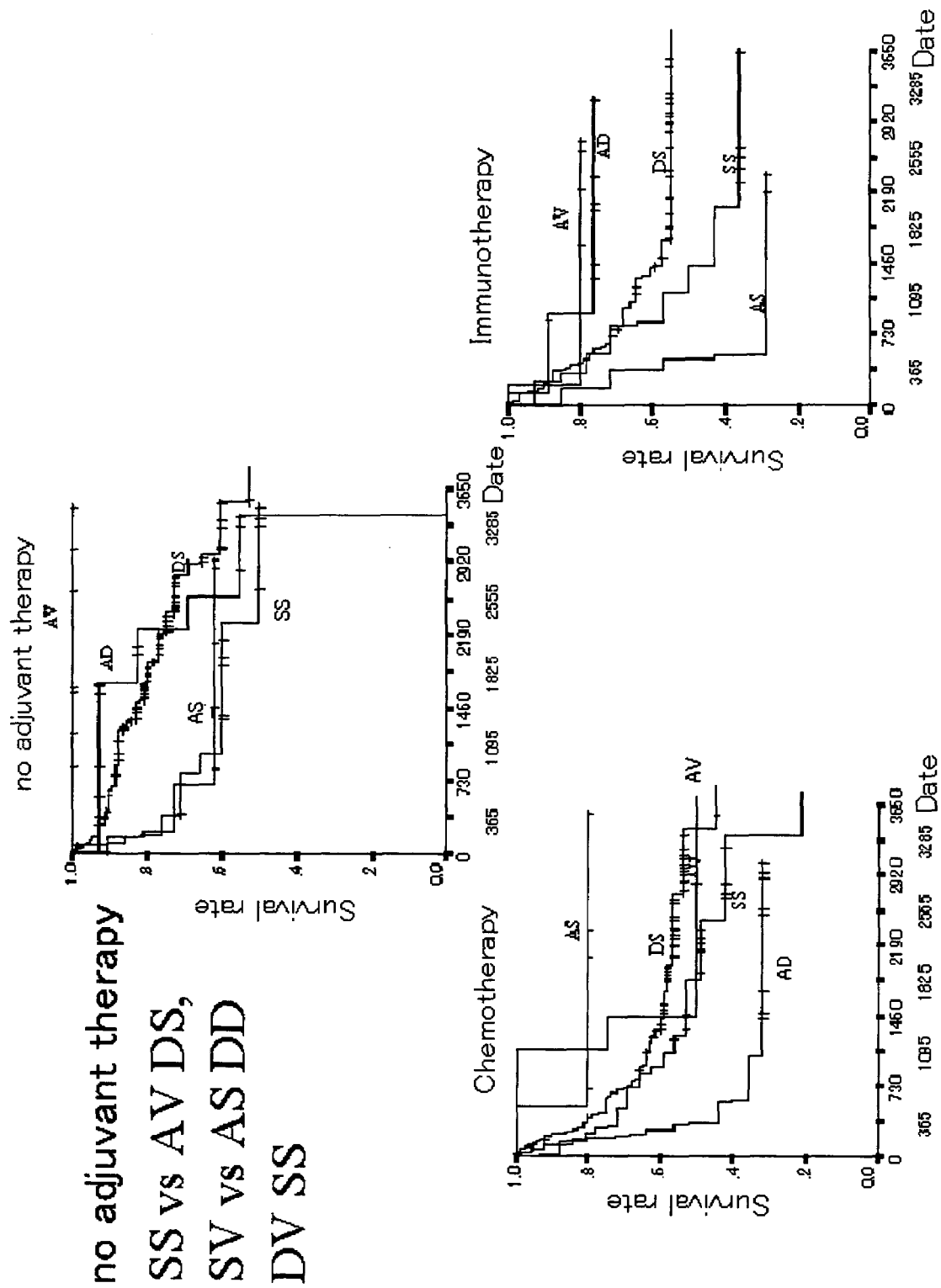
FIG. 31: Result of the treatment effects in all cancer cases and the variations of the amino acid sequences at Position 9 of DRB1*.

FIG. 31 shows that the cancer resection alone (no adjuvant therapy) and anticancer immunotherapy after the resection (Immunotherapy) are suitable for patients with AV at Position 57 of the amino acid sequence on DRB1*gene. Also, anticancer immunotherapy after the resection (Immunotherapy) is suitable for patients with AD, while anticancer chemotherapy after the resection (Chemotherapy) is suitable for patients with AS.

6) DR67 (All Cases)

Figure 32:
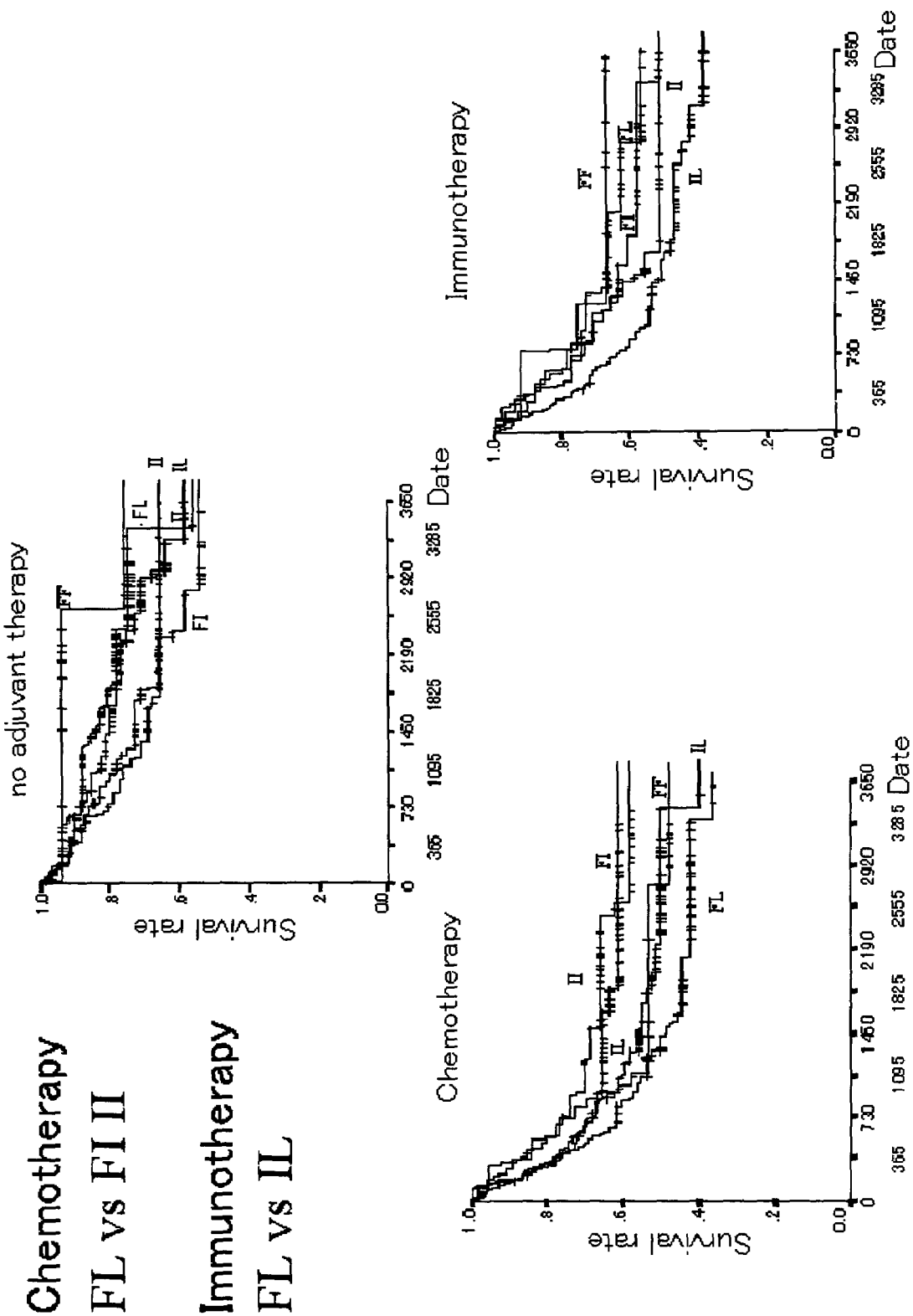
FIG. 32: Result of the treatment effects in all cancer cases and the variations of the amino acid sequences at Position 67 of DRB1*.

FIG. 32 shows that the cancer resection alone (no adjuvant therapy) is suitable for patients with FF at Position 67 of the amino acid sequence on DRB1*gene.

7) DR74 (All Cases)

Figure 33:
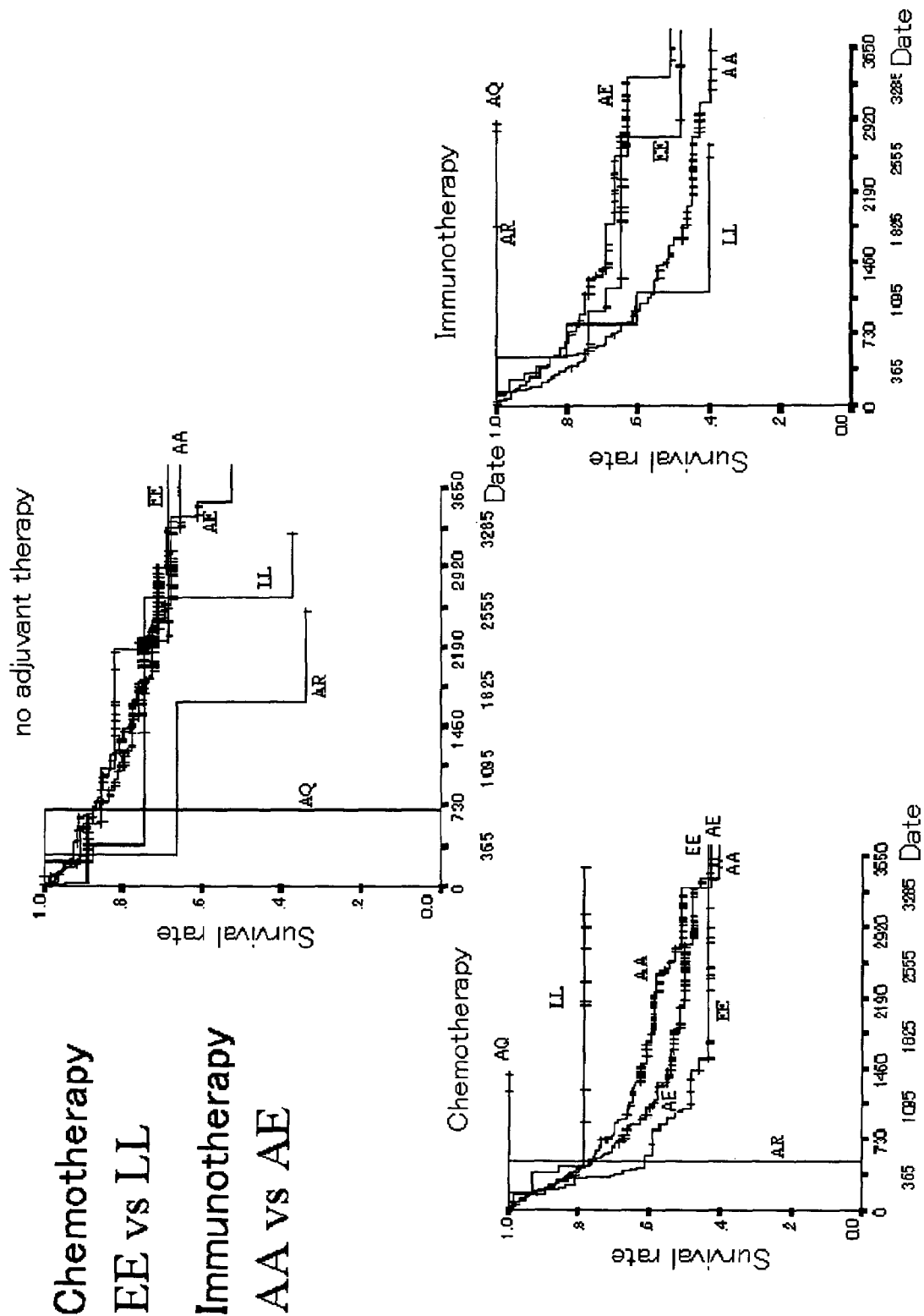
FIG. 33: Result of the treatment effects in all cancer cases and the variations of the amino acid sequences at Position 74 of DRB1*.

FIG. 33 shows that the cancer resection alone (no adjuvant therapy) is suitable for patients with AQ at Position 74 of the amino acid sequence on DRB1*gene. Anticancer chemotherapy after the resection (Chemotherapy) and anticancer immunotherapy after the resection (Immunotherapy) are suitable for patients with AQ at Position 74. Anticancer immunotherapy after the resection (Immunotherapy) is not suitable, but anticancer chemotherapy after the resection (Chemotherapy) is suitable for Patients with LL. Anticancer immunotherapy after the cancer resection (Immunotherapy) is suitable for patients with AR.

Working Example 6

(Relationship Analysis Among Polymorphisms, Treatment and the Specified Positions on Each Gene in Stomach Cancer Patients)

With respect to the variations of the amino acids of the specific part of the polymorphic amino acids of DQB1*, DRB1*, and DPB1*genes in stomach cancer cases, the variations of the amino acids and the medical effect of treatments [The cancer resection alone (no adjuvant therapy), anticancer chemotherapy after the cancer resection (Chemotherapy), and anticancer immunotherapy after the cancer resection (Immunotherapy)] were confirmed. (Graphs include the survival rate for the vertical axis (1.0=100%) and survived days for the lateral axis.) The base data was collected from the previous clinical cases.

1) DQ9 (Stomach Cancer)

Figure 34:
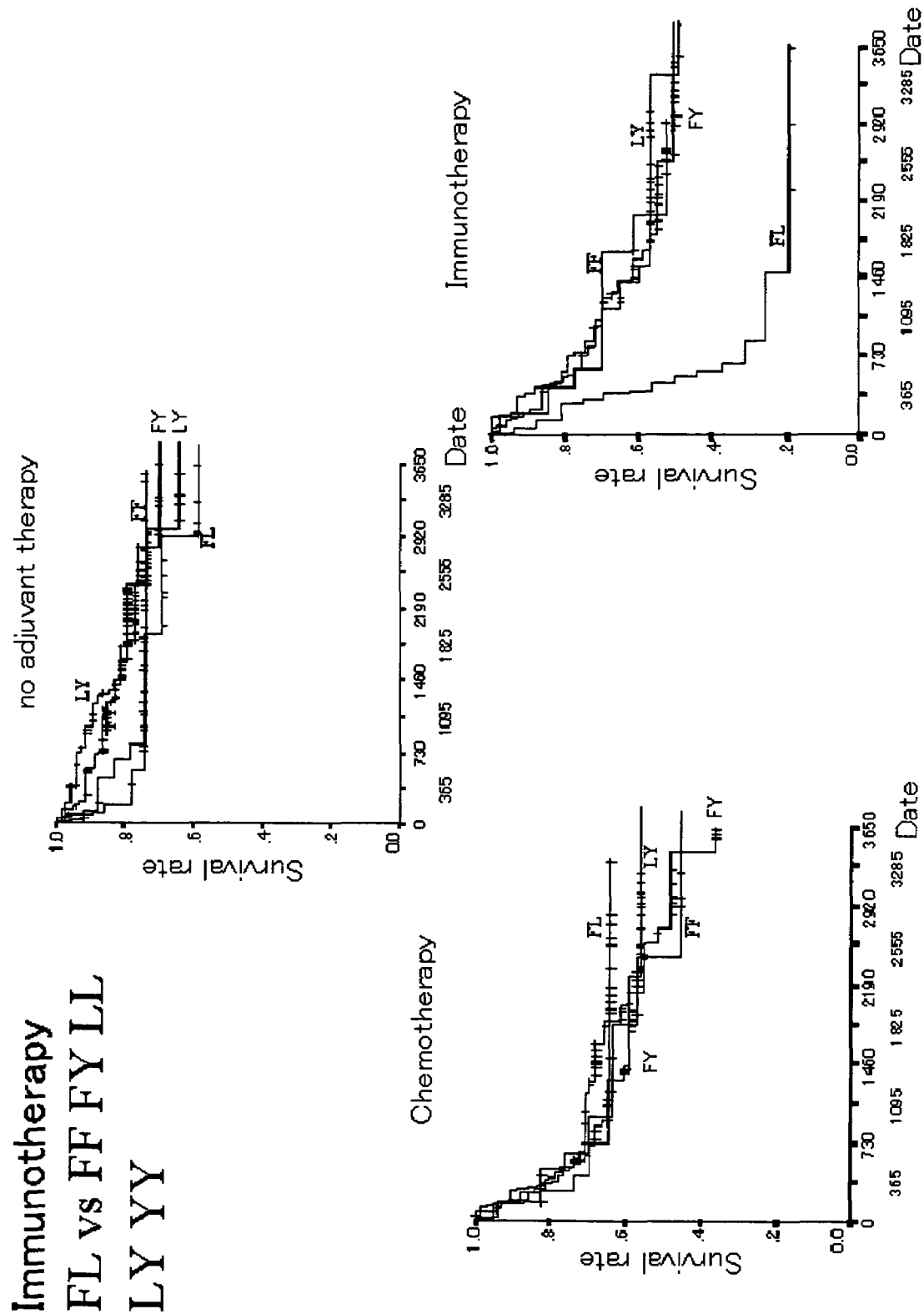
FIG. 34: Result of the treatment effects in stomach cancer cases and the variations of the amino acid sequences at Position 9 of DQB1*.

FIG. 34 shows that the patients with the anticancer immunotherapy after the cancer resection (Immunotherapy) is not suitable for patients with FL at Position 9 of the amino acid sequence on DQB1*gene.

2) DQ67 (Stomach Cancer)

Figure 35:
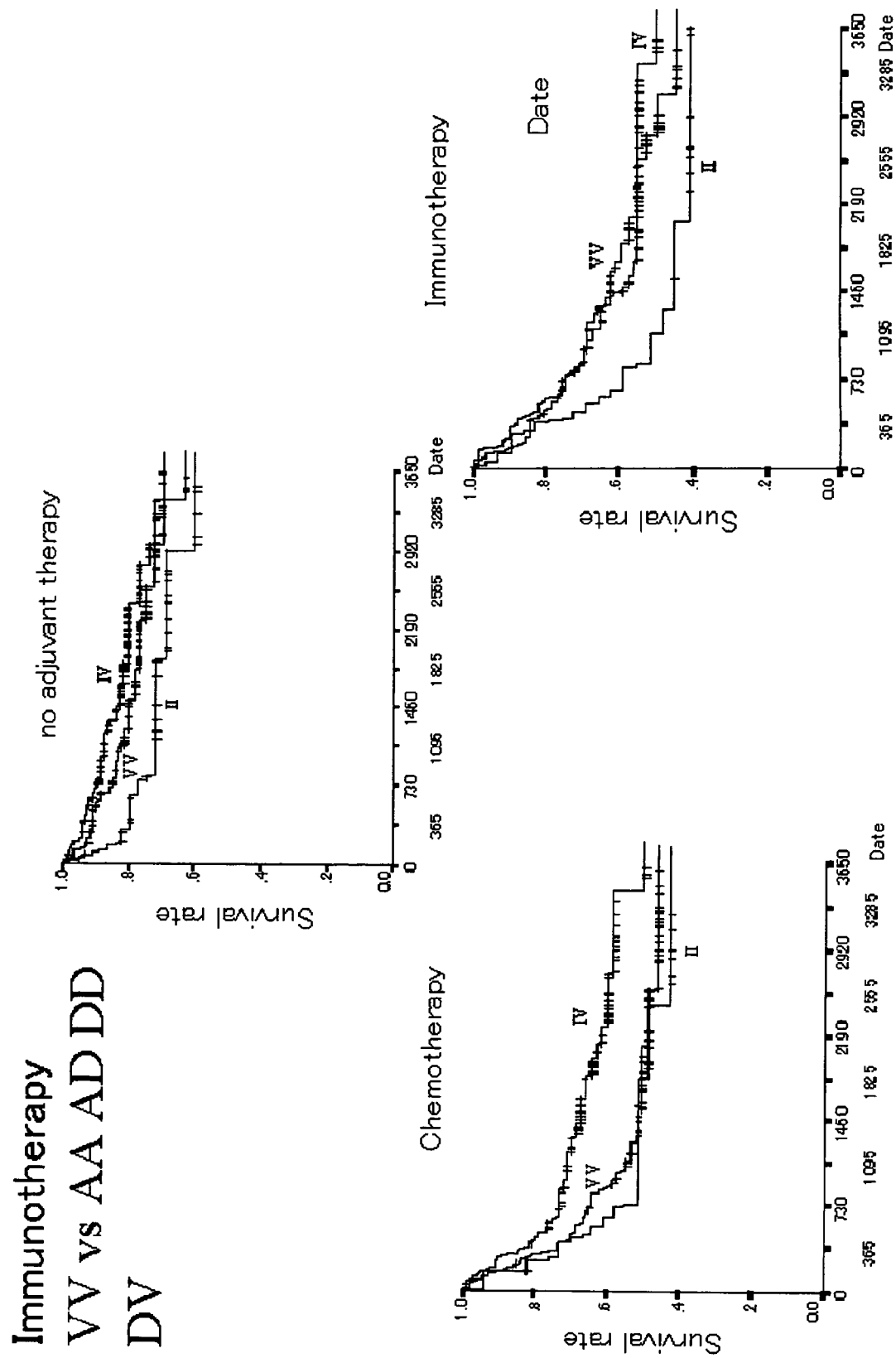
FIG. 35: Result of the treatment effects in stomach cancer cases and the variations of the amino acid sequences at Position 67 of DQB1*.

FIG. 35 shows that the anticancer immunotherapy after the cancer resection (Immunotherapy) is not suitable for patients with II at Position 67 of the amino acid sequence on DQB1*gene. The anticancer chemotherapy after the cancer resection (Chemotherapy) IV is suitable for patients with II at Position 6.

10) DR9 (Stomach Cancer)

Figure 36:
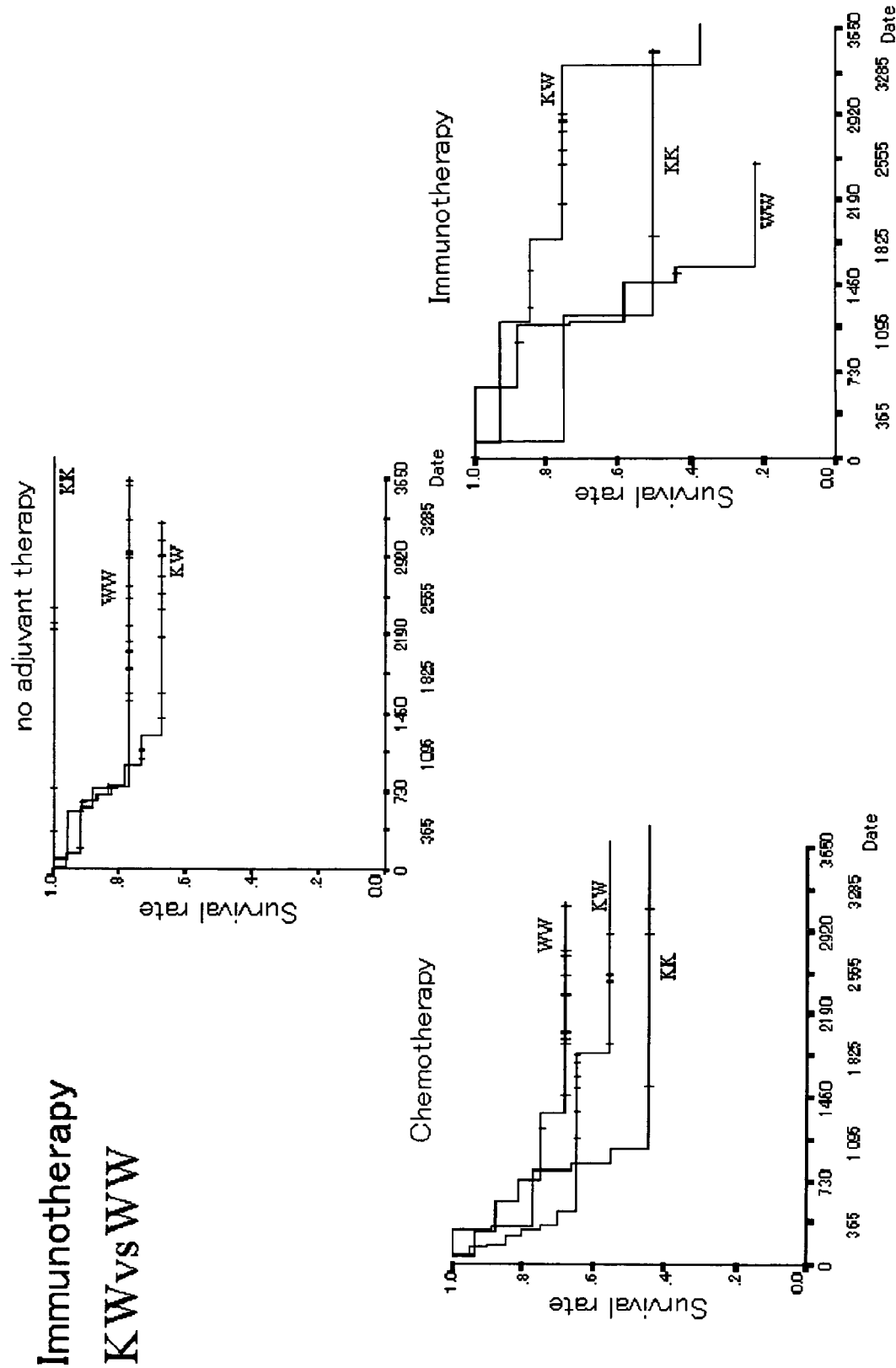
FIG. 36: Result of the treatment effects in stomach cancer cases and the variations of the amino acid sequences at Position 9 of DRB1*.

FIG. 36 indicates that anticancer chemotherapy after the cancer resection (Chemotherapy) is not suitable, but the cancer resection alone (no adjuvant therapy) is suitable for patients with KK at Position 9 of the amino acid sequence on DRB1*gene.

11) DR37 (Stomach Cancer)

Figure 37:
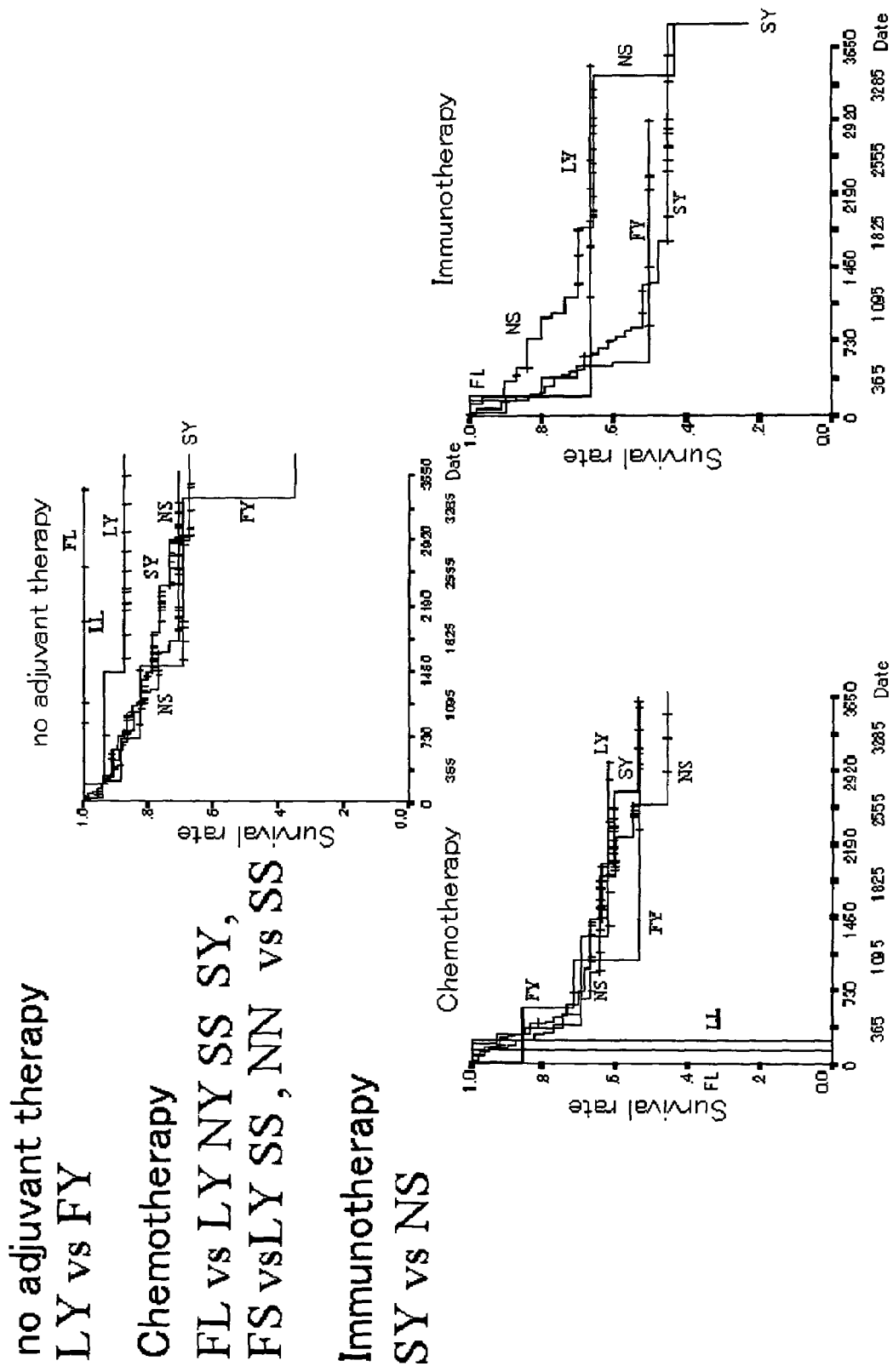
FIG. 37: Result of the treatment effects in stomach cancer cases and the variations of the amino acid sequences at Position 37 of DRB1*.

FIG. 37 shows that the cancer resection alone (no adjuvant therapy) is suitable for patients with FL and LL at Position 37 of the amino acid sequence on DRB1*gene.

12) DR57 (Stomach Cancer)

Figure 38:
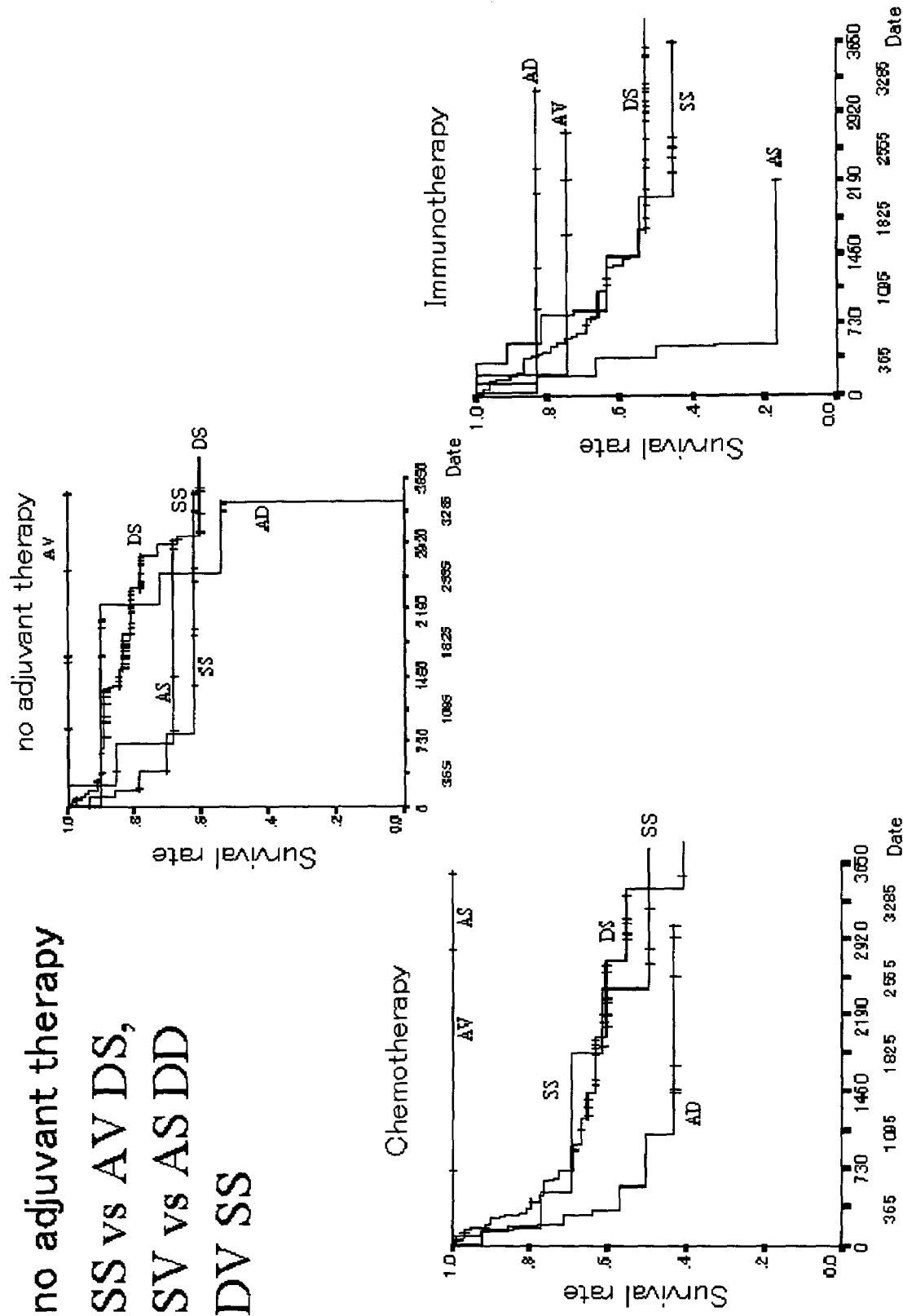
FIG. 38: Result of the treatment effects in stomach cancer cases and the variations of the amino acid sequences at Position 57 of DRB1*.

FIG. 38 shows that the cancer resection alone (no adjuvant therapy) and the anticancer chemotherapy after the cancer resection (Chemotherapy) are suitable for patients with AV at Position 57 of the amino acid sequence on DRB1*gene. Also, the anticancer immunotherapy after the cancer resection (Immunotherapy) is not suitable but the anticancer chemotherapy after the cancer resection (Chemotherapy) is suitable for patients with AS.

13) DR67 (Stomach Cancer)

Figure 39:
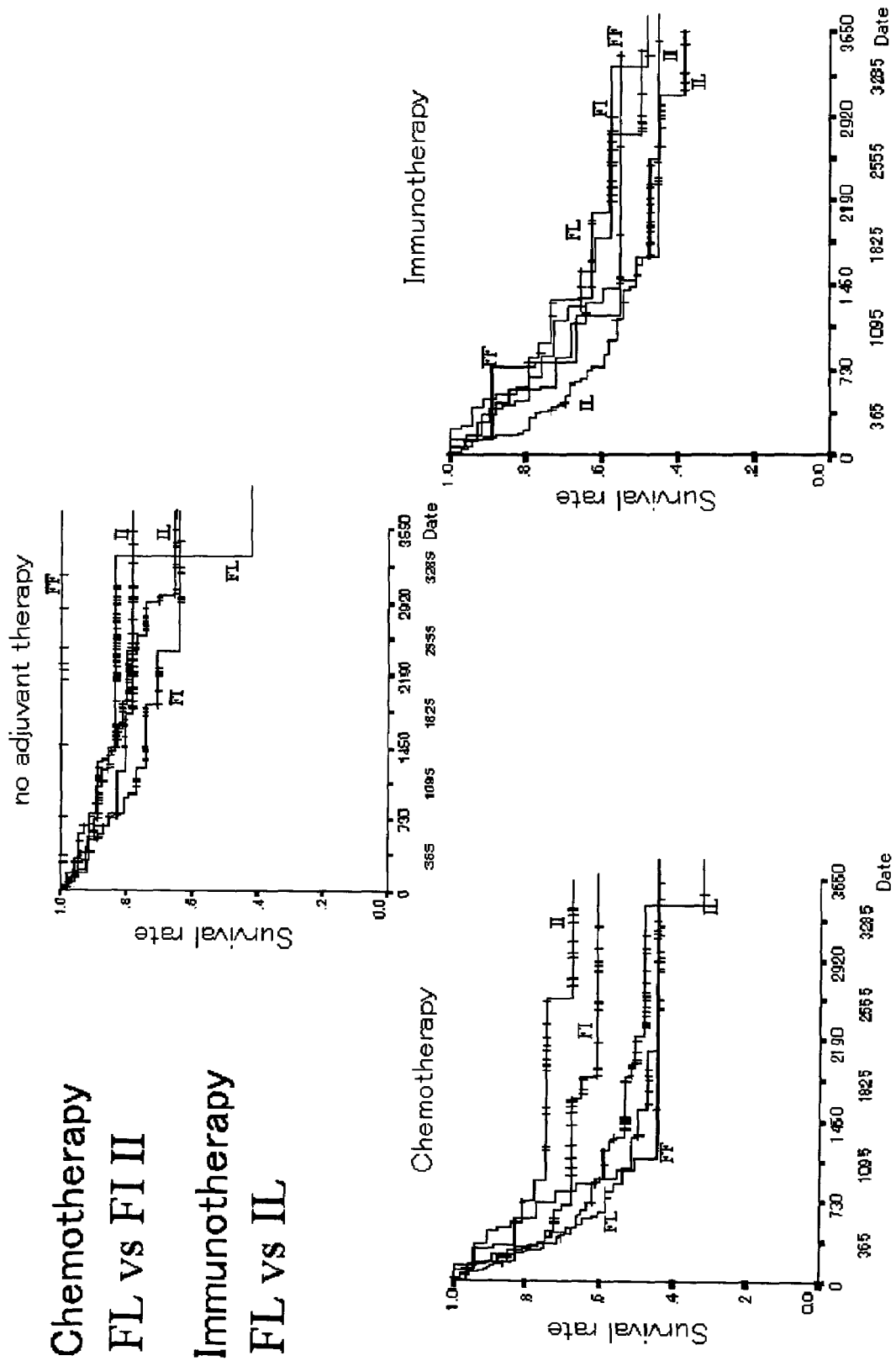
FIG. 39: Result of the treatment effects in stomach cancer cases and the variations of the amino acid sequences at Position 67 of DRB1*.

FIG. 39 shows that the cancer resection alone (no adjuvant therapy) is suitable for patients with FF at Position 67 of the amino acid sequence on DRB1*gene.

14) DR74 (Stomach Cancer)

Figure 40:
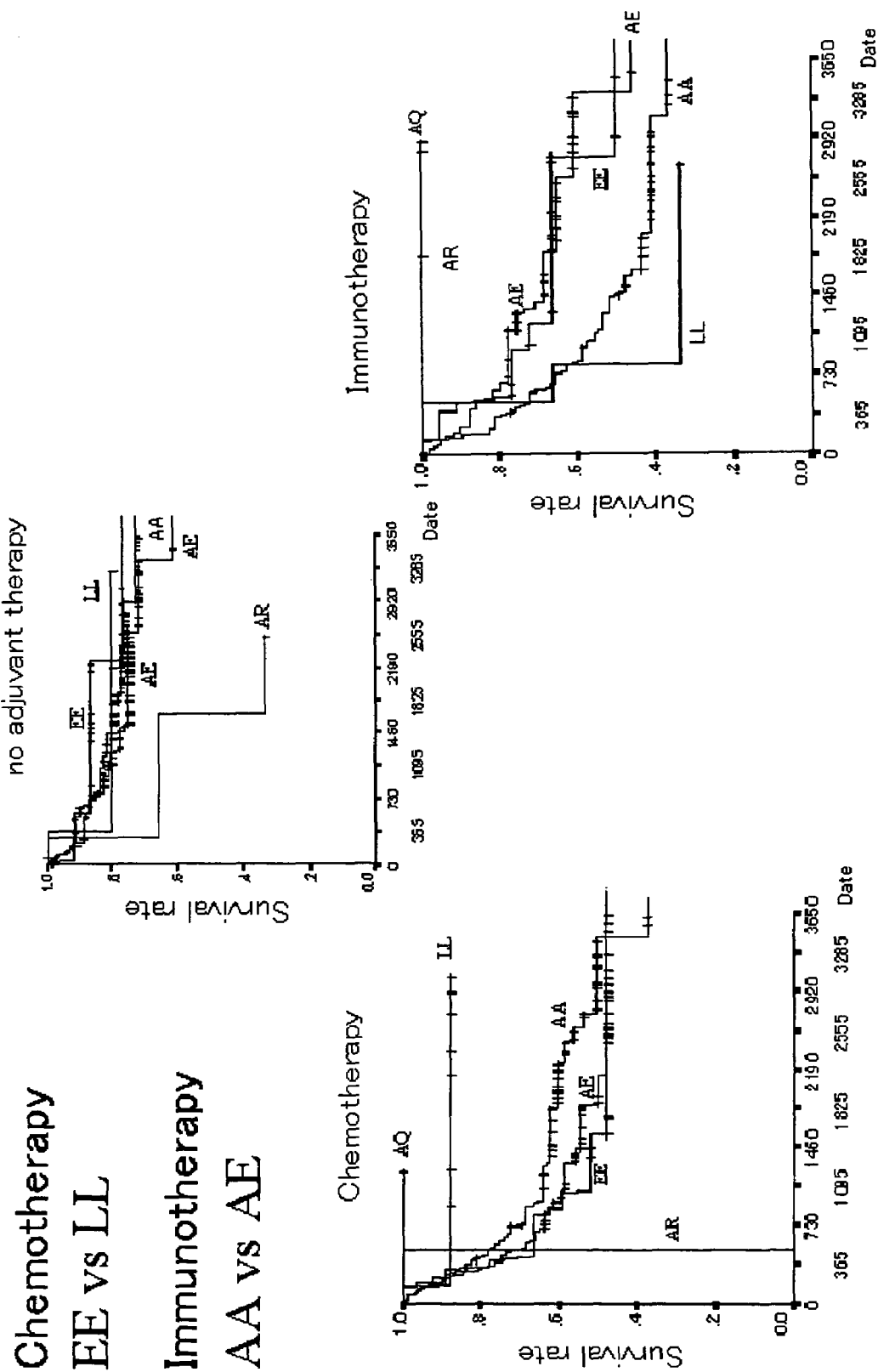
FIG. 40: Result of the treatment effects in stomach cancer cases and the variations of the amino acid sequences at Position 74 of DQB1*.

FIG. 40 shows that cancer resection alone (no adjuvant therapy) and the anticancer chemotherapy after the cancer resection (Chemotherapy) are not suitable for patients with AR at Position 74 of the amino acid sequence on DRB1*gene, while the anticancer immunotherapy after the cancer resection (Immunotherapy) is suitable for them. Cancer resection alone (no adjuvant therapy) and the anticancer immunotherapy after cancer resection (Immunotherapy) are suitable for patients with AQ. The anticancer immunotherapy after cancer resection (Immunotherapy) is not suitable but the anticancer chemotherapy after cancer resection (Chemotherapy) is suitable for patients with LL.

Working Example 7

The treatment effects (5-year survival rate) with the amino acid variations of the specific part of the polymorphic amino acids of each DPB1*, DQB1* and DRB1*gene were analyzed. Data from a previous clinical example were used.

FIG. 41 shows the best survival rate (5-year survival) of the amino acid variations of the specific parts (polymorphic parts) of the amino acids of DRB1*, DQB1*, and DPB1*genes with the cancer resections alone. Positions marked with @* in table are the positions with a statistically significant difference. Displayed as "APR-25=RR 0.8333" means the 5-year survival rate of 83.33% in patients with the RR of the amino acid variations at Position −25 (QR) on DRB1*gene. This table shows that the cancer resection alone is advantageous to patients with the amino acid variations such as (DS) at Position 11, (GH) at Position 13, (FL) at Position 26, (AV) at Position 57, (IL) at Position 67, (HY) at Position 96, (RR) at Position 133, and (VV) at Position 142 on the DR gene with a significant statistical difference. On DQB1*gene, the cancer resection alone is advantageous to patients with the amino acid variations such as (SS) at Position 3, (VV) at Position 4, (TT) at Position 6, (YY) at Position 37, (EE) at Position 66, (IV) at Position 67, (LV) at Position 75, and (SS) at Position 197 with a significant statistical difference. On DPB1*gene, the cancer resection alone is advantageous to patients with the amino acid variations of (AD) at Position 55 and (EK) at Position 69 with a significant statistical difference.

FIG. 42 shows the best survival rate (5-year survival) with the amino acid variation of the specific parts (polymorphic parts) of the amino acids of DRB1*, DQB1*, and DPB1*genes with the anticancer chemotherapy after cancer resection. Positions marked with @* in the table are positions with a statistically significant difference. Displayed as "APR-25=RR 0.8571" means the best 5-year survival rate of 85.71% in patients with the RR of the amino acid variations (QR) at Position −25 on DRB1*gene. This table shows that anticancer chemotherapy after cancer resection is advantageous to patients with the variations such as (LY) at Position 37, (AV) at Position 57, and anticancer chemotherapy after the cancer resection is advantageous to patients with amino acid variations such as (YY) at Position 60, and (FI) at Position 67, with a significant statistical difference. On DQB1*gene, anticancer chemotherapy after the cancer resection is advantageous to patients with the amino acid variations such as (LY) at Position 9, (DY) at Position 37, (DE) at Position 66, and (IV) at Position 67 with a significant statistical difference.

FIG. 43 shows the best survival rate (5-year survival) with the amino acid variation of the specific parts (polymorphic parts) on DRB1*, DQB1*, and DPB1*genes with the immunotherapy after the cancer resection. Positions marked with @* in table are positions with a statistically significant difference. Displayed as "APR-25=RR 0.7143" means that the best 5-year survival rate of patients with the variation of RR is 71.43% at Position −25 (QR) of DRB1*gene. This table shows that anticancer immunotherapy after cancer resection is advantageous to patients with amino acid variations such as the DR genes of (AA) at Position −17, (KW) at Position 9, (DP) at Position 11, (FS) at Position 13, (FL) at Position 26, (FF) at Position 31, (FI) at Position 31, (HH) at Position 3, (NS) at Position 37, (FF) at Position 40, (AV) at Position 57, (ER) at Position 71, (AE) at Position 74, and (QQ) at Position 231 with statistically significant difference. On DQB1*gene, the anticancer immunotherapy after the cancer resection is advantageous to patients with amino acid variations such as (PP) at Position −5, (YY) at Position 9, (HY) at Position 30, (AA) at Position 57, (EE) at Position 66, (VV) at Position 67, (EG) at Position 86, (LY) at Position 87, and (QR) at Position 310.

Working Example 8

I. The analysis of equivalence of the polymorphic amino acid of DPB1*gene by the survival rate (=number of the survived patients/number of the total treated patients) over 5 years is shown. FIG. 44 shows the influence of the amino acid polymorphism of each amino acid position with the difference in therapy after cancer resection on survival rate in the stomach cancer cases (upper) and the other cancer cases (lower).

For example, the survival rates of both stomach and other cancer cases are the same in patients with A or V at Position 36 on the sequence with all treatments; the cancer resection alone (no adjuvant therapy), the anticancer chemotherapy after the cancer resection (Chemotherapy), and the anticancer immunotherapy after the cancer resection (Immunotherapy).

In stomach cancer cases, I on DP65 (Position 65 on the amino acid sequence) and L on DP65 also show the same result. Both E and K on DP69 have the same tendency; the survival rate of EK (heterozygote) is significantly longer than that of EE (homozygote) or E (−) ["E (−)" means it does not have E] with the cancer resection alone (no adjuvant therapy). That is, the cancer resection alone is sufficient for the patients with EK (heterozygote) on DP69, compared with the patients with EE (homozygote) or E (−) on DP69. Also, the survival rate of KE (heterozygote) is significantly longer than that of KK (homozygote) or K (−) with the cancer resection alone. That is, the cancer resection alone is sufficient for the patients with EK (heterozygote) on the DP69, compared with KK (homozygote) and K (−) on DP69. There were no statistical relations between E and K on DP69 with the anticancer chemotherapy after the cancer resection (Chemotherapy). The survival rate of E (−) or EK (heterozygote) is significantly longer than that of EE (homozygote) with the anticancer immunotherapy after the cancer resection (Immunotherapy). That is, the anticancer immunotherapy is more effective on the patients with E (−) and EK (heterozygote) on DP69, compared with EE (homozygote). The survival rate of K (−) or EK (heterozygote) is significantly longer than that of KK (homozygote). Thus, the anticancer immunotherapy after the cancer resection is effective on patients with K (−) and EK (heterozygote), compared with KK (homozygote) on DP69. The survival rates in stomach cancer cases are the same with any treatments [the cancer resection alone (no adjuvant therapy), the anticancer chemotherapy after the cancer resection (Chemotherapy), and the anticancer immunotherapy after the cancer resection (Immunotherapy)]when it is L on DP8, V on DP8, F on DP9, G on DP 1, and L on DP11. It can be concluded that there is little difference among the polymorphic amino acids. The survival rate of H (−) or HH (homozygote) on DP9H is statistically significantly longer than that of HF (heterozygote) with stomach cancer resection with the anticancer immunotherapy (Immunotherapy). It follows that the anticancer immunotherapy after the cancer resection is more effective on the stomach cancer patients with H (−) or HH (homozygote), as compared with HF (heterozygote).

Given the above results, the influence of the polymorphic amino acids of DPB1* gene at position 69 and 9 is important in the anticancer treatments for stomach cancer patients. Also, it is clear that other polymorphisms are effective on the treatments and their results even if involving different positions (e.g., positions 8, 9, and 11). With cancers other than stomach cancers, the survival rate of IL (heterozygote) is significantly longer than that of II (homozygote) on DP65 I and L with the cancer resection alone (no adjuvant therapy). In the other words, the patients with IL (heterozygote) are suitable for tumor resection alone, compared with the patients with II (homozygote). Other treatment results are the same with the polymorphism on the DP65 with cancers other than stomach cancer. The survival rate of E and K on the DP69 does not differ much with the treatments [tumor resection alone (no adjuvant therapy), the anticancer chemotherapy after the cancer resection (Chemotherapy), and the anticancer immunotherapy after the cancer resection (Immunotherapy)] and is the same with cancer cases other than stomach cancers. Among L on the DP8, V on the DP8, F on the Dp9, G on the DP11, and L on the DP11, the same results are shown with the treatments of no adjuvant therapy, Chemotherapy, and Immunotherapy. The survival rate of LL (homozygote) or LV (heterozygote) on DP8 is longer than that of L (−) with the cancer resection alone (no adjuvant therapy). The survival rate of FF (homozygote) and FH (heterozygote) is longer than that of F (−) with the cancer resection alone (no adjuvant therapy). The survival rate of GG (homozygote) and GL (heterozygote) on DP11 is longer than that of G (−). The same results are shown in the anticancer chemotherapy (Chemotherapy) and the anticancer immunotherapy (Immunotherapy) after the cancer resections. There were no statistically significant differences between V on the DP8 and L on DP9 in treatment results. With cancers other than stomach cancers, the survival rates of HF (heterozygote) and H (−) is significantly longer than that of HH (homozygote) with the cancer resection alone (no adjuvant therapy) while the same results are shown in the chemotherapy (Chemotherapy) and the immunotherapy (Immunotherapy) after the cancer resections.

These results revealed that the polymorphic amino acids at position 65, 8, 9, and 11 have statistically significant effects on the treatments with patients of cancers other than stomach cancers.

II. The Analysis of Equivalence of the Polymorphic Amino Acid on DRB1*Gene by the Survival Rate (5-year) are Shown in FIG. 45 to 49. ("Same" Indicated in the Tables Means That Survival Rates Draw the Same Survival Curves Among Homozygote, Heterozygote and Without.)

(Stomach Cancer Cases)

From FIG. 45 to 49, the survival rates of patients with DR-25K [Amino acid is K at Position −25 of the amino acid sequence on DRB1*gene, and so forth] and DR-25R, DR-24A and DR-24L, DR-17A and DR-17T, DR-16A and DR16V, DR-1S and DR-1A, and DR4Q and DR4R are the same regardless of types of the treatments (no adjuvant therapy, Chemotherapy, or Immunotherapy) in stomach cancer cases. The survival rates of patients with DR9K, DR11D, DR26Y, DR28H, and DR30G are the same regardless of types of the treatments (no adjuvant therapy, Chemotherapy, or Immunotherapy). With DR9E, the survival rate of EE (homozygote) or EK (heterozygote) are significantly longer than that of E (−) with the cancer resections alone (no adjuvant therapy). The survival rate of E (−) or EE (homozygote) is significantly longer than that of EK (heterozygote) with the chemotherapy after the cancer resection (Chemotherapy). The survival rate of EE (homozygote) or E (−) (heterozygote) is significantly longer than that of EK survival rate with the anticancer immunotherapy after the cancer resection. The survival rates of patients with DR10Q and DR10Y are the same regardless of types of the treatments (no adjuvant therapy, Chemotherapy, and Immunotherapy). Also, the survival rates are the same in patients with DR10E, DR31V, DR38A, DR40Y, DR166Q, and DR166R. The survival rate of E (−) of DR10 is significantly longer than that of EQ or EY (heterozygote) with the cancer resections alone (no adjuvant therapy). Similarly, the survival rates with the cancer resection alone (no adjuvant therapy) and the anticancer immunotherapy (Immunotherapy) are significantly longer in the patients with V (−) on DR31 compared with VF or VI, A (−) on DR38 compared with AL, Y (−) on DR40 compared with YF, Q (−) on DR166 compared with QR, and R (−) on DR166 compared with RQ. However, these results are the same with the anticancer chemotherapy after the cancer resection. The results of DR11S, DR12K, and DR12T are equivalent. The results on DR11G, DR13Y, DR14E, DR14K, DR25Q, DR25R, and DR30L are equivalent. With the cancer resection alone (no adjuvant therapy), DR11V with all different kinds of the amino acid sequences results in the same rate (Same in the Fig.). The survival rate of V (−) or VV (homozygote) is significantly longer than that of VP (heterozygote) with the anticancer chemotherapy after the resection (Chemotherapy). The survival rate of W (homozygote) is significantly longer than that of V (−) or VP (heterozygote) with the anticancer immunotherapy after the cancer resection (Immunotherapy). The results on DP11P and DR13R are equivalent. The results on DR13F, DR31F, and DR311 are equivalent. The survival rates of DR13H at any amino acid sequences are the same as with the cancer resections alone (no adjuvant therapy) (Same in the Figure). The survival rate of H (−) or HH (homozygote) is significantly longer than (heterozygote) such as HS, HR, and HY with the anticancer chemotherapy after the cancer resection (Chemotherapy). The survival rate of HH (homozygote) is significantly longer than that of H (−) and (heterozygote) such as HS, HR, and HY with the anticancer immunotherapy after the cancer resection (Immunotherapy). The result of DR13S is equivalent. The result of DR26L is the same with other polymorphic amino acids with the anticancer chemotherapy after the resection (Chemotherapy). The survival rate of L (−) or LF (heterozygote) is significantly longer than that of LL (homozygote) with the anticancer chemotherapy (Chemotherapy). The survival rate of LF (heterozygote) or L (−) is significantly longer than that of LL (homozygote) with the anticancer immunotherapy after the cancer resection (Immunotherapy). The result of DR26F is equivalent. The results of DR28H and DR30G are equivalent. The survival rate of EE (homozygote) is significantly longer than that of ED (heterozygote) or E (−) of DR28E with the cancer resection alone (no adjuvant therapy). The survival rate of E (−) or ED (heterozygote) is significantly longer than that of EE (homozygote) with the anticancer chemotherapy after the resection (Chemotherapy). The results on 1) DR28D, 2) DR30H, DR37L, DR38L, DR85A, and DR85V, 3) DR31V, DR38A, DR40F, and DR40Y, and 4) DR32H and DR32Y are equivalent to each other in the groups. On DR33H and DR33N the same tendency is shown, and the survival rate of DR33H is the same with the cancer resection alone (no adjuvant therapy). The survival rate of H (−) or HH (homozygote) is significantly longer than that of HN (heterozygote) with the anticancer chemotherapy (Chemotherapy). In contrast, with the immunotherapy, the survival rate of HH (homozygote) or H (−) is significantly longer than that of HN (heterozygote). Similarly, all the survival rates of DR33N are the same with the cancer resection alone (no adjuvant therapy). The survival rate of N (−) or NN (homozygote) is significantly longer than that of HN (heterozygote) with the anticancer chemotherapy after the resection (Chemotherapy) The survival rate of NN (homozygote) or N (−) is significantly longer than that of HN (heterozygote) with the anticancer immunotherapy after the cancer resection (Immunotherapy). The results of DR37F and DR37S and for DR47F and DR47Y are equivalent. The survival results on DR57A are also equivalent with the cancer resection alone (no adjuvant therapy). The survival rate of A (−) is longest, and, next, that of AS (heterozygote) is significantly longer than that of AA (homozygote) with the anticancer chemotherapy (Chemotherapy). The survival rate of AS (heterozygote) is statistically significantly longer than that of A (−) with the anticancer immunotherapy after the resection (Immunotherapy). The results on DR57S are the same with the cancer resection alone (no adjuvant therapy). The survival rate of S (−) or AS (heterozygote) on DR57S are significantly longer than that of SS (homozygote) with the anticancer chemotherapy (Chemotherapy). The survival rate of S (−) or AS (heterozygote) is statistically significantly longer than that of SS (homozygote) with the cancer resections after the anticancer immunotherapy (Immunotherapy). It shows equivalent results of DR58A and DR58E. The results of DR60H are the same. The survival rate of II (homozygote) is significantly longer than that of IL (heterozygote) and I (−) on DR67I with the cancer resection alone (no adjuvant therapy). The survival rate of II (homozygote) is statistically significantly longer than that of IL (heterozygote) and I (−) with the anticancer chemotherapy (Chemotherapy). The survival rate of I (−) is significantly longer than that of II (homozygote) and IL (heterozygote) with the anticancer immunotherapy (Immunotherapy). The survival rate of LI (heterozygote) or L (−) is significantly longer than that of LL (homozygote) on DR67L with the cancer resection alone (no adjuvant therapy). The survival rate of L (−) or LL (homozygote) is statistically significantly longer than that of LI (heterozygote) with the anticancer chemotherapy (Chemotherapy). The survival rate of LL (homozygote) is statistically significantly longer than that of LI (heterozygote) or L (−) with the anticancer immunotherapy (Immunotherapy). The survival rate of (heterozygote) or DD (homozygote) is statistically significantly longer than that of D (−) on DR70D with the cancer resection alone (no adjuvant therapy). The survival rate of DD (homozygote) is statistically significantly longer than that of (heterozygote) and D (−) with the anticancer chemotherapy after the cancer resection (Chemotherapy). The survival rate of DD (homozygote) is statistically significantly longer than that of (heterozygote) and D (−) with the immunotherapy after the resection (Immunotherapy). The results of DR73A, DR73G, DR74R, DR74N, DR77N, and DR77T are equivalent. The survival rates with the cancer resection alone (no adjuvant therapy) are significantly longer in patients with AA (homozygote) on DR73 than AG (heterozygote), RR (homozygote) on DR74 than RN (heterozygote), and NN (homozygote) on DR77 than NT (heterozygote). The survival rates with the chemotherapy after the cancer resection (Chemotherapy) are significantly longer in patients with AA (homozygote) on DR73 than AG (heterozygote), RR (homozygote) on DR74 than RN (heterozygote), and NN (homozygote) on DR77 against NT (heterozygote). In contrast, the survival rate with the anticancer immunotherapy after the cancer resection (Immunotherapy) is significantly longer in patients with AG (heterozygote) than AA (homozygote) on DR73, RN (heterozygote) than RN (homozygote) on DR74, and NT (heterozygote) than NN (homozygote) on DR77.

The survival rates with the cancer resection alone (no adjuvant therapy) are statistically significantly longer in patients with G (−) or GG (homozygote) than GA (heterozygote) on DR73, N (−) or NN (homozygote) than NR (heterozygote) on DR74, and T (−) or TT (homozygote) than TN (heterozygote) on DR77. It is the same result with the anticancer chemotherapy after the cancer resection (Chemotherapy). The survival rates with the anticancer immunotherapy after the cancer resection (Immunotherapy) are significantly longer in patients with GA or G (−) than GG (homozygote) on DR73, NR (heterozygote) or N (−) than NN (homozygote) on DR74, and TN (heterozygote) or T (−) than TT (homozygote) on DR77. With the cancer resection alone (no adjuvant therapy), the survival rate with A (−) and (heterozygote) such as AR and AN is statistically significantly longer than that of AA (homozygote). The same result is shown in anticancer chemotherapy after the resection (Chemotherapy). The survival rates of A (−) and (heterozygote) such as AR and AN is significantly longer than that of AA (homozygote) with anticancer immunotherapy after the cancer resection (Immunotherapy). The results are equivalent on 1) DR78V and DR78Y, DR85A and DR85V, and DR86G and DR86V, 2) DR96Q, 3) DR98E, DR98K, DR10A, and DR10S, 4) DR120S and DR120N, 5) DR133L, DR133R, DR14M, and DR14V, and 6) DR149H and DR149Q. The survival rate of Q (−) of DR166Q is significantly longer than that of QR (heterozygote) with the cancer resection alone (no adjuvant therapy). The same result is shown in the anticancer chemotherapy after the resection (Chemotherapy). The survival rate of Q (−) is statistically significantly longer than that of QR (heterozygote) with the anticancer immunotherapy after the cancer resection (Immunotherapy). The survival rate of R (−) on DR166R is statistically significantly longer than that of RQ (heterozygote) with the cancer resection alone (no adjuvant therapy), while it is the same with the anticancer chemotherapy after the resection (Chemotherapy). The survival rate of R (−) is significantly longer than that of RQ (heterozygote) with the immunotherapy after the cancer resection (Immunotherapy). The survival rates of DR180L and 180V, 189R and 189S, 231P and 231Q, and 233R and 233T are equivalent.

These results indicate that regarding DRB1*gene Position 9, 10, 11, 13, 26, 28, 31, 33, 38, 40, 57, 67, 70, 73, 74, 77, and 166 of the amino acid sequence are important in each treatment. Also, several positions where the polymorphic amino acids are equivalent are confirmed.

Equivalent Survival Rate in Cases of Cancers Other Than Stomach Cancer

Equivalence is confirmed for 1) DR-25K and -25R, DR-24F and -24L, DR-17A and -17T, DR-16A and -16V, DR-1S and -1A, DR4Q and 4R, DR10Q and 10Y, 33H and 33N, 38L and 38V, 47F and 47Y, 58A and 58E, 78V and 78Y, 85A and 85V, 120N and 120S, 149Q and 149H, 166Q and 166R, 180L and 180V, 189R and 189S, 231P and 231Q, and 233T, 2) DR9K, 11D, 26Y, 28H, and 30G, 3) DR11S, 12K, and 12T 4) DR11G, 13Y, 14E, 14K, 25Q, 25R, and 30L, 5) DR28H and 30G, 6) DR30H, 37L, 38L, 85A, and 85V, 7) DR31V, 38A, 40F, and 40Y, 8) DR73A, 73G, 74R, 74N, 77T, and 77N, 9) DR98E, 98K, 10A, and 10S, 10) DR133L, 133R, 14V, and 14M.

On DR9W, the survival rate of WW (heterozygote) or W (−) is statistically significantly longer than that of WK (heterozygote) with the cancer resection alone (no adjuvant therapy), the survival rate of WW is statistically significantly longer than that of WK or W (−) with the anticancer chemotherapy after the cancer resection (Chemotherapy), and the survival rate of KW and WW is statistically significantly longer than that of W (−) with the anticancer immunotherapy after the cancer resection (Immunotherapy). The results of DR11P and 13R are equivalent. On DR11, the survival rate of PG/PS (heterozygote) or P (−) is significantly longer than that of PP (homozygote) with both the cancer resection alone (no adjuvant therapy) and the anticancer chemotherapy after the cancer resection (Chemotherapy), while the survival rate of PP (homozygote) is statistically significantly longer than that of PG/PS (heterozygote) with the anticancer immunotherapy after the cancer resection (Immunotherapy). On DR13, the survival rate of RY/RS (heterozygote) or R (−) is significantly longer than that of RR (homozygote) with both the cancer resection alone (no adjuvant therapy) and the anticancer chemotherapy after the cancer resection (Chemotherapy), while the survival rate of RR is statistically significantly longer than that of RY (heterozygote) or R (−) with the anticancer immunotherapy after the cancer resection (Immunotherapy). On DR13S, the survival rate of SS or S (−) is statistically significantly longer than that of SR (heterozygote) with the cancer resection alone (no adjuvant therapy), while the survival rate of R or S (−) is statistically significantly longer than that of SS with the anticancer chemotherapy after the cancer resection (Chemotherapy), and the survival rate of SR or S (−) is significantly longer than that of SS with the anticancer immunotherapy after the cancer resection (Immunotherapy). On DR26F, the survival rate is statistically the same with the cancer resection alone, while the survival rate of F (−) or FY (heterozygote) is significantly longer than that of FF (homozygote) with the anticancer chemotherapy after the cancer resection (Chemotherapy), and the survival rate of FF (homozygote) or HY (heterozygote) is statistically significantly longer than F (−) with the anticancer immunotherapy after the cancer resection (Immunotherapy). On DR28D, the survival rate with the cancer resection alone (no adjuvant therapy) is statistically the same, but the survival rate of D (−) or DH (heterozygote) is longer than that of DD (homozygote) with the anticancer chemotherapy after the resection (Chemotherapy), while the survival rate of DD or D (−) is significantly longer than that of DH with the anticancer immunotherapy after the resection (Immunotherapy). On DR32H, the survival rate of HH (homozygote) or H (−) is statistically significantly longer than that of HY (heterozygote) with the cancer resection alone (no adjuvant therapy), while the survival rate of H (−) or HY (heterozygote) is statistically significantly longer than that of HH (homozygote) with both the anticancer chemotherapy after the cancer resection (Chemotherapy) and the anticancer immunotherapy after the cancer resection (Immunotherapy). On DR32Y, the survival rate of YY (homozygote) or Y (−) is statistically significantly longer than that of YH (heterozygote) with the cancer resection alone (no adjuvant therapy), while the survival rate of Y (−) or YH (heterozygote) is significantly longer than that of YY (homozygote) with both the anticancer chemotherapy after the cancer resection (Chemotherapy) and the anticancer immunotherapy after the cancer resection (Immunotherapy). The results on DR32H and 32Y are equivalent. On DR37F, the survival rate is the same with no treatment after the cancer resection alone (no adjuvant therapy), while F (−) is significantly longest, and, next, the survival rate of FS (heterozygote) is statistically significantly longer than that of FF with the anticancer chemotherapy after the cancer resection (Chemotherapy), and the survival rate of FS (heterozygote) is significantly longer than that of F (−) with the anticancer immunotherapy after the cancer resection (Immunotherapy). On DR37S, the survival rate of S (−) or SF (heterozygote) is significantly longer than that of SS (homozygote) with the cancer resection alone (no adjuvant therapy), while the survival rate of SS (homozygote) is statistically significantly longer than that of SF (heterozygote) or S (−) with the anticancer chemotherapy after the cancer resection (Chemotherapy), and the survival rate is significantly longer than that of SS (homozygote) with the anticancer immunotherapy after the cancer resection (Immunotherapy). On DR57A, the survival rate is statistically the same with the cancer resection alone (no adjuvant therapy), while the survival rate with the anticancer chemotherapy after the cancer resection (Chemotherapy) of A (−) is significantly longest, and, next, that of AS (heterozygote) is significantly longer than that of AA (homozygote), and the survival rate with the anticancer immunotherapy after the resection (Immunotherapy) of AS (heterozygote) is statistically significantly longer than that of A (−). On DR57S, the survival rate is the same with the cancer resection alone (no adjuvant therapy), while the survival rate of SA or S (−) is significantly longer than with the chemotherapy after the cancer resection (Chemotherapy) and has higher rates than with SS with the immunotherapy after the cancer resection (Immunotherapy). On DR60H, the survival rate is statistically the same with the cancer resection alone (no adjuvant therapy), while the survival rate with the chemotherapy provided after the cancer resection (Chemotherapy) of H (−) significantly longest, and, next, that of (heterozygote) is significantly longer than that of HH (homozygote), and the survival rate with the anticancer immunotherapy after the resection (Immunotherapy) of (heterozygote) is significantly longer than that of H (−). On DR71A, the survival rate of A (−) or (heterozygote) is statistically significantly longer than that of AA (homozygote) with the cancer resection alone (no adjuvant therapy), while the survival rate of (heterozygote) or A (−) is significantly longer than that of AA (homozygote) with the anticancer chemotherapy after the cancer resection (Chemotherapy), and the survival rate is the same with the anticancer chemotherapy after the cancer resection (Immunotherapy). On DR74L, the survival rate of (heterozygote) such as LR and LN or L (−) is significantly longer than that of LL (homozygote) with the cancer resection alone (no adjuvant therapy), while the survival rate of LL or L (−) is significantly longer than that of (heterozygote) with the anticancer chemotherapy after the cancer resection (Chemotherapy), and the survival rate of (homozygote) is significantly longer than that of (heterozygote) or L (−) with the anticancer immunotherapy after the cancer resection (Immunotherapy). On DR86G, the survival rate is the same with the cancer resection alone (no adjuvant therapy), while the survival rate with the anticancer chemotherapy after the cancer resection (Chemotherapy) of GV (heterozygote) or GG (homozygote) is significantly longer than that of G (−), and the survival rate with the anticancer immunotherapy after the cancer resection (Immunotherapy) of (homozygote) or (heterozygote) is significantly longer than that of G (−). On DR86V, the survival rate is the same with the cancer resection alone (no adjuvant therapy), while the survival rate with the anticancer chemotherapy after the resection (Chemotherapy) of VG (heterozygote) or VV (homozygote) is significantly longer than that of V (−), and the survival rate with the anticancer immunotherapy after the cancer resection (Immunotherapy) of (heterozygote) or (homozygote) is significantly longer than that of V (−). On DR96Q, the survival rate of Q (−) or (heterozygote) is significantly longer than that of QQ (homozygote) with the cancer resection alone (no adjuvant therapy), while the survival rate is the same with the anticancer chemotherapy after the cancer resection (Chemotherapy), and the survival rate of Q (−) is significantly longer than that of (homozygote) with the anticancer immunotherapy after the cancer resection (Immunotherapy). On DR98E, the survival rate of EK (heterozygote) or EE (homozygote) is significantly longer than that of E (−) with the cancer resection alone (no adjuvant therapy), and the survival rate is the same with the anticancer chemotherapy after the cancer resection (Chemotherapy), while the survival rate of E (−) or (heterozygote) is significantly longer than that of (homozygote) with the anticancer immunotherapy after the cancer resection (Immunotherapy). On DR98K, the survival rate of KE (heterozygote) or KK (homozygote) is significantly longer than that of K (−) with the cancer resection alone (no adjuvant therapy), while the survival rate is the same with the anticancer chemotherapy after the cancer resection (Chemotherapy), and the survival rate of K (−) or (heterozygote) is significantly longer than that of (homozygote) with the anticancer immunotherapy after the cancer resection (Immunotherapy). On DR10A, the survival rate of AS (heterozygote) or AA (homozygote) is significantly longer than that of A (−) with the cancer resection alone (no adjuvant therapy), while the survival rate is the same with the anticancer chemotherapy after the cancer resection (Chemotherapy), and the survival rate of A (−) or (heterozygote) is significantly longer than that of (homozygote) with the anticancer immunotherapy after the cancer resection (Immunotherapy). On DR10S, the survival rate of SA (heterozygote) or SS (homozygote) is significantly longer than that of S (−) with the cancer resection alone (no adjuvant therapy), while the survival rate is the same with the anticancer chemotherapy after the cancer resection (Chemotherapy), and survival rate of S (−) or (heterozygote) is significantly longer than that of (homozygote) with the anticancer immunotherapy after the cancer resection (Immunotherapy). On DR133L, the survival rate of L (−) or LR (heterozygote) is significantly longer than that of LL (homozygote) with the cancer resection alone (no adjuvant therapy), while the survival rate is the same with both the anticancer chemotherapy after the cancer resection (Chemotherapy) and the anticancer immunotherapy after the cancer resection (Immunotherapy). On DR133R, the survival rate of R (−) or RL (heterozygote) is significantly longer than that of RR (homozygote) with the cancer resection alone and the survival rate is the same with both the anticancer chemotherapy after the cancer resection (Chemotherapy) and the anticancer immunotherapy after the cancer resection (Immunotherapy). On DR14V, the survival rate of V (−) or VM (heterozygote) is significantly longer than that of VV (homozygote), while the survival rate is the same with both the anticancer chemotherapy (Chemotherapy) and the anticancer immunotherapy after the cancer resections (Immunotherapy).

On DR233R, the survival rate is the same with the cancer resection alone (no adjuvant therapy), while the survival rate with the anticancer chemotherapy after the cancer resection (Chemotherapy) of RT (heterozygote) or R (−) is significantly longer than that of RR (homozygote), and the survival rate with the anticancer immunotherapy after the cancer resection (Immunotherapy) is the same with R (−) or (heterozygote) and is statistically longer than that of (homozygote).

These results indicate that the amino acid sequences at Position 9, 10, 11, 13, 14, 26, 28, 32, 37, 57, 60, 71, 74, 86, 96, 98, 133, and 233 on DR gene are important or statistically significant in each treatment. Also, the positions where the polymorphic amino acids have equivalent significance are confirmed.

III. FIGS. 50 and 51 Display the Result of the 5-Year Survival Rate Relating to the Amino Acid Polymorphism of DQB*1 Gene.

(Patients with Stomach Cancers)

Equivalences are confirmed in the following 4 groups: 1) DQ14L and 14M, 23L and 23R, 38A and 38V, 45E and 45G, 53L and 53Q, 55P and 55R, and 56L and 56P, 2) DQ28S, 28T, 30S, 37I, 46V, 46E, 47F, 47Y, 53P, 52L, and 55L, 3) DQ3P, 3S, 9L, 37D, and 4) DQ66D, 66E, 67I, and 67V. On DQ30Y, the survival rate of YH (heterozygote) is significantly longest, and that of Y (−) is significantly longer than that of YY (homozygote) with the anticancer immunotherapy after the cancer resection (Immunotherapy). On DQ30H, the survival rate of HY (heterozygote) is significantly longest, and that of H (−) is significantly longer than that of HH (heterozygote) with anticancer immunotherapy after the cancer resection (Immunotherapy). On DQ38A, the survival rate of AY (heterozygote) is significantly longer than that of A (−) or AA (homozygote) with the anticancer chemotherapy after the cancer resection (Chemotherapy). On DQ38V the survival rate of VH (heterozygote) is significantly longer than that of V (−) or VV (homozygote) with the anticancer chemotherapy after the cancer resection (Chemotherapy). On DQ57V, the survival rate of (heterozygote) is significantly longer than that of V (−) and VV (homozygote) with the anticancer immunotherapy after the cancer resection (Immunotherapy). On DQ66D, the survival rate of DE (heterozygote) is significantly longer than that of D (−) or DD (homozygote) with the anticancer chemotherapy after the cancer resection (Chemotherapy). On DQ66E, the survival rate of ED (heterozygote) is significantly longer than that of E (−) or EE (homozygote) with the anticancer chemotherapy after the cancer resection (Chemotherapy). On DQ67I, the survival rate of IV (heterozygote) is significantly longer than that of I (−) or II (homozygote) with the anticancer chemotherapy after the cancer resection (Chemotherapy). On DQ67V, the survival rate of VI (heterozygote) is significantly longer than that of V (−) or VV (homozygote) with the anticancer chemotherapy after the cancer resection (Chemotherapy).

These results indicate that Positions at 30, 38, 57, 66, and 67 on the amino acid sequences of DQB*1 gene are important and statistically significant in each stomach cancer treatment. Also, the positions where the polymorphic amino acids have equivalent significance are confirmed.

(Patients of Cancers Other Than Stomach Cancer)

Equivalences are confirmed in the following 4 groups: 1) DQ14L and 14M, 23L and 23R, 45E and 45G, 53L and 53Q, 55P and 55R, and 56L and 56P, 2) DQ28S, 28T, 30S, 37I, 46E, 46V, 47F, 47Y, 52L, 52P, and 55L, 3) DQ3P, 3S, 9L, and 37D, and 4) DQ66D, 66E, 67I, and 67V.

On DQ3P, the survival rate of P (−) or PS (heterozygote) is significantly longer than that of PP (homozygote) with the cancer resection alone (no adjuvant therapy). On DQ3S, the survival rate of S (−) or PS (heterozygote) is significantly longer than that of SS (homozygote) with the cancer resection alone (no adjuvant therapy). On DQ9L, the survival rate of L (−) or (heterozygote) such as LF/LY is significantly longer than that of LL (homozygote) with the cancer resection alone (no adjuvant therapy). On DQ37D, the survival rate of D (−) or DI (heterozygote) is significantly longer than that of DD (homozygote) with the cancer resection alone (no adjuvant therapy). On DQ9F, the survival rate of FY (heterozygote) or F (−) is significantly longer than that of FF (homozygote) with the anticancer immunotherapy after the cancer resection (Immunotherapy). On DQ9Y, the survival rate of YF (heterozygote) or YY (homozygote) is significantly longer than that of Y (−) with both the cancer resection alone (no adjuvant therapy) and the anticancer chemotherapy after the cancer resection (Chemotherapy). On DQ38A, the survival rate of AV (heterozygote) and AA (homozygote) is significantly longer than that of A (−) with the cancer resection alone (no adjuvant therapy). On DQ38V, the survival rate of VA (heterozygote) or VV (homozygote) is significantly longer than that of V (−) with the cancer resection alone (no adjuvant therapy). On DQ66D, the survival rate of DE (heterozygote) or D (−) is significantly longer than that of DD (homozygote) with the anticancer chemotherapy after the cancer resection (Chemotherapy). On DQ67I, the survival rate of IV (heterozygote) or I (−) is significantly longer than that of II (homozygote) with the anticancer chemotherapy after the cancer resection (Chemotherapy). On DQ66E, the survival rate of ED (heterozygote) or E (−) is significantly longer than that of EE (homozygote) with the anticancer chemotherapy after the cancer resection (Chemotherapy). On DQ67V, the survival rate of VI (heterozygote) and V (−) is significantly longer than that of VV (homozygote) with the anticancer chemotherapy after the cancer resection (Chemotherapy).

These results indicate that Positions at 3, 9, 37, 38, 66, and 67 on the amino acid sequences on DQ gene play an important and statistically significant role in each treatment for cancers other than stomach cancers. Also, several positions where the polymorphic amino acids have equivalent significance are confirmed.

Working Example 9

In FIG. 52 to 75, the polymorphic amino acids at the amino acid sequences on each gene (DRB1*, DQB1* and DPB1*) and prognosis of the variations [5-year survival rates in all cancer cases (not categorize them according to treatments)], treatment effects, 5-year survival rate, and other possible effects are shown. Basic data is based on the above clinical cases. (e.g. In a row marked "arp-1" and in a column of "Prognosis", "A, S homo, hetero>(−)" in FIG. 52 indicate "AA homozygote, SS homozygote, AS heterozygote>(−)". Shadowed cells indicate the results with statistically significant differences.)

In the row of "arp-25" in the Figure, data of the amino acid at Position −25 is shown. In the "Diversity" column, a polymorphism (e.g. KR) of the amino acid at each position is shown. "Equivalence" column shows whether the amino acid has equivalence (e.g. K=R: equivalence). In the "Prognosis", "Total (homozygote)" and "Total" column, the prognoses in all cases with presence/absence/homozygote/heterozygote of polymorphic amino acid on the amino acid sequence positions are shown. In the "Prognosis", "Total", and a blank cell column, the survival rate of the best amino acid variations for good prognosis in all cases is shown. (e.g. "RR78.8" means that the 5-year survival rate of the patients with RR homozygote variation in the corresponding sequence is 78.8%, and the prognosis is good.) In the "Prognosis", "Total (+) vs. (−)", and "Stomach" column, only stomach cancer patients are totaled, and the prognoses by the presence or absence of the polymorphic amino acid are shown. (e.g. F (−)>(+) means that the prognosis in stomach cancer cases of the patients without F is better than that of the patients with F.) In the "Prognosis", "Total (homozygote)", and "Stomach" column, only stomach cancer patients are totaled, and prognoses with presence/absence/homozygote/ heterozygote of polymorphic amino acid are shown. (e.g. "V heterozygote>(−)" means that the prognosis of the patients with (heterozygote) such as VG/VD/VL is better than that of the patients without heterozygote.

In the "Prognosis", "Stomach" and a blank cell column, only stomach cancer patients are totaled, and the survival rate of the best amino acid variations for good prognosis in all cases is shown. (e.g. "RR71.4" means that the 5-year survival rate of the patients with RR variation in the sequence is 71.4%, and the prognosis is good.) In the "Prognosis", "Total (+) vs. (−)", and "Other cancer" column, only patients of cancers other than stomach cancers are totaled, the prognosis with the presence or absence of the polymorphic amino acid is shown. (e.g. A(+)>(−) means that the prognosis of the patients with A is better than that of the patients without A in other cancers cases. In the "Prognosis", "Total (homozygote)", and "Other Cancer" column, only patients of cancers other than stomach cancers are totaled, and prognosis with presence/absence/homozygote/ heterozygote of polymorphic amino acids are shown. (e.g. "A, S homozygote, heterozygote>(−)" means that the prognosis of the patients with AA (homozygote), SS (homozygote), or AS (heterozygote) is better than that of the patients without A or S. In the "Prognosis", "Other Cancers", and a blank cell column, only patients of cancers other than stomach cancers are totaled, and the survival rate of the best amino acid variations for good prognosis in all cases is shown. (e.g. "RR100" means that the 5-year survival rate of the patients with RR variation in the sequence is 100%, and the prognosis is good.) In the "Treatment Effect", "Total (+) vs. (−)", and "Total" column, all kinds of cancer including stomach cancer and other cancers patients are totaled, the polymorphic amino acids presence and treatment effects of the post-treatments after the cancer resections [the cancer resection alone (no adjuvant therapy), and the anticancer chemotherapy after the cancer resection (Chemotherapy), and the anticancer immunotherapy after the cancer resection (Immunotherapy)] are compared and examined. (e.g. "Immunotherapy E (−)>(+)" means that the amino acids of the specific sequence position has EQY and the treatment effect of the patients without E (E(−)) is better than that of the patients with E with the anticancer immunotherapy after the cancer resection (Immunotherapy).

In the "Treatment Effect", "Total (homozygote)" and "Total" column, all kinds of cancer including stomach cancer and other cancers patients are totaled, and treatment effects with presence/absence/homozygote/heterozygote of polymorphic amino acids are shown. (e.g. "Immunotherapy E (−)>heterozygote" means that the amino acids of the specific sequence position has EQY and the treatment effect of the patients without E is better than that of the patients with (heterozygote) such as EQ and EY with the anticancer immunotherapy after the cancer resection (Immunotherapy). In the "Treatment Effect", "All Cases", and a blank cell column, the survival rate of the best amino acid variations for good prognosis in all cases is shown. (e.g. "AA71.4" means that the 5-year survival rate of the patients with AA variation in the sequence t is 71.4%, and the anticancer immunotherapy after the cancer resection (Immunotherapy) is effective on the patients.) In the "Treatment Effect", "Total (+) vs. (−)", "Stomach" column, stomach cancer patients is totaled, and treatment effects with the polymorphic amino acids presence and the type of the post-treatments after the cancer resections are compared and examined. (e.g. "Immunotherapy E (−)> (+)" means that the treatment effect of the patients without E in the sequence is better than that of the patients with E with the anticancer immunotherapy after the cancer resection (Immunotherapy) in stomach cancer cases.) In the "Treatment Effect", "Total (homozygote)", and "Stomach" column, stomach cancer patients are totaled, and the treatment effects of each treatment with presence/absence/homozygote/heterozygote of polymorphic amino acids are shown. (e.g. "Immunotherapy E (−), homozygote>heterozygote" means that the amino acids of the specific sequence position has EKW, and the treatment effect of the patients with E or EE (homozygote) is better than that of the patients with (heterozygote) such as EK and EW with the anticancer immunotherapy after the cancer resection (Immunotherapy).) In the "Treatment Effect", "Stomach Cancer", and a blank cell column, stomach cancer patients are totaled, and the survival rate of the best amino acid variations for good prognosis in all cases is shown. (e.g. "KW84.6" means the 5-year survival rate of the stomach cancer patients with KW variation in the sequence is 84.6%, and the anticancer immunotherapy after the cancer resection (Immunotherapy) is effective on the patients.) In the "Treatment Effect", "Total (+) vs. (−)", "Other Cancer" column, cancers other than stomach cancer patients are totaled, and treatment effects with the polymorphic amino acids presence and the type of the post-treatments after the cancer resections are compared and examined. (e.g. "Chemotherapy Y (+)>(−)" means that the treatment effect of patients with Y is better, or more effective, than that of the patients without Y with the anticancer chemotherapy after the cancer resection (Chemotherapy). In the "Treatment Effect", "Total (homozygote)" and "Other Cancer" column, cancers other than stomach cancers are totaled, and the treatment effects with presence/absence/homozygote/heterozygote of polymorphic amino acids are shown. (e.g. "Chemotherapy H (–), heterozygote>homozygote" means that the amino acids of the specific sequence position has HY, and the treatment effect of the patients without H or HY (heterozygote) is better than that of the patients with HH (homozygote) with the anticancer chemotherapy after the cancer resection (Chemotherapy). In the "Treatment Effect", "Other Cancers", and a blank cell column, the survival rate of the best amino acid variations for good prognosis in all cases is shown. (e.g. "HY55.6" means that 5-year survival rate of the patients with HY variation in the sequence is 55.6% in other cancer cases, the anticancer chemotherapy after the cancer resection (Chemotherapy) is effective on the patients.)

The "DR" and "Cancer in Family" column shows the particular amino acids at the specified amino acid sequences of the family with a history of having cancer patients. ("Cancer in Family" means that the patients have cancer patients within their 2 degrees of consanguinity.) Marked '#' indicates that no significance is found in this case study, although there was in the previous study. Marked 'O' means that there is significant difference of the amino acid variation in the column. (e.g. "AV 38.7" means significant difference that the variation of AV of the specified amino acid sequence has 38.7% while AA has 0%. It means that the families of the patients of AV tend to have more cancer patients.)

The "DR" and "Metastases" column indicates the tendency of the cancer metastases. ("Metastases" in this report refers cancer metastases to lymph nodes, liver, and lungs.) Marked 'O' means that there is the significant difference in the column, while marked '#' means not much difference although there was in the previous case. (e.g. "FL80" means that since metastases are observed in 80% of patients with FL amino acid variation while it is 22.9% with LL variation, there is significant difference between them. Patients with an FL variation tend to have more cancer metastases.)

In "DR" and "Total t" (Ratio of advanced cancer) column, the rates of advanced cancer patients are shown. Marked 'O' means that there is the significant difference in the column, while marked '#' means that there is not much difference, even though there was in the previous case. (e.g. "FT 22.6" means that advanced cancer is seen in 22.6% of the patients with FT amino acid variation, while in the patients with FF or GR variations there is not advanced cancer but early stage cancers only (early stage cancers is invasive cancers to mucosa or submucosa with few or no lymph node metastases. Advanced cancer mentioned in this report means other cancer cases.), In "DR" and "Smoking" column, the rate of smokers is shown ("Smoker" is defined as the patient who has a smoking habit before the treatments and keeps the habit.) Marked 'O' means that there is the significant difference, while marked '#' means that there is not much difference, even though there was in the previous case. (e.g. "AS 73.3" means that 77.3% of patients with AS amino acid variation are smokers while 44.4% for AA variation significant difference is noted between the groups.

I. DRB1*Gene (Influences of Polymorphic Amino Acids at the Specific Positions of DRB1*Gene on Prognosis and Treatment Effects)

Prognosis Analysis of DRB1*Gene in All Cancer Cases (FIG. 52 to 54)

At Position –25, the prognosis of K (–) or RR (homozygote) is significantly better than that of KR (heterozygote). At Position –17, the prognosis of AA (homozygote) is significantly better than that of AT (heterozygote) and also T (–) than TA (heterozygote). At Position 24, the prognosis of F (–) is significantly better than that of F (+). At Position –16, the prognosis of A (–) is significantly better than that of AV (heterozygote) and also VV (homozygote) than AV (heterozygote). Since the survival rate of HQ variation is 71.5%, the prognosis is significantly good. At Position 11, the prognosis of V (–) is significantly better than that of (heterozygote) such as VD, VG, VL, VP, and VS. Since the survival rates of GV and LL variations are 100%, the prognosis is significantly good. At Position 57, the prognosis of (heterozygote) such as SA, SD, SV, or S (–) is significantly better than that of SS (homozygote). At Position 71, the prognosis of K (–) is significantly better than that of (heterozygote) such as KA, KE and KR. At Position 120, the prognosis of N (–) is significantly better than that of NS (heterozygote). At Position 30, since the survival rate of CC variation is 100%, the prognosis is significantly good.

Prognosis Analysis of DRB1*Gene in Stomach Cancer Cases (FIG. 52 to 56)

At Position –24, the prognosis of F (–) is significantly better than that of F (+). At Position 11, the prognosis of (heterozygote) such as VD, VG, VP, VL, or VS is significantly better than that of V (–). At Position 16, the prognoses of (heterozygote) such as QH and QY are significantly better than that of than QQ (homozygote). Since the survival rate of HQ variation is 83%, the prognosis is good. At Position 26, the prognosis of (heterozygote) such as LF and LY is significantly better than that of LL (homozygote). At Position 30, given the survival rate of CC, the prognosis is good. At Position 71, the prognosis of K (–) is significantly better than that of K (+). The prognosis of K (–) is significantly better than that of (heterozygote) such as KA, KE, and KR. Since the survival rate of EK variation is 75%, the prognosis is significantly good. Since the survival rate of AQ at Position 74 is 100%, the prognosis is significantly good. At Position 233, the prognosis of T (–) is significantly better than that of T (+). The prognosis of RR (homozygote) or TT (homozygote) is significantly better than that of RT (heterozygote), R (–), and T (–).

Prognosis Analysis of DRB1*Gene in Other Cancers Cases (FIG. 52 to 54) (FIG. 55 to 57)

At Position –1, the prognosis of A (+) is significantly better than that of A (–). The prognosis of S (–) is significantly better than that of S (+), while the prognosis of AA (homozygote), SS (homozygote), or AS (heterozygote) is significantly better than that of S (–). Since the survival rate of AA is 90.9%, the prognosis is significantly good. At Position 11, the prognosis of (heterozygote) such as PDPV, PL, PS, or PG is significantly better than that of PP (homozygote). Since the survival rate of LL is 100%, the prognosis is significantly good. At Position 3, the prognosis of F (+) is significantly better than that of than F (–). The prognosis of (heterozygote) such as FG, FH, FR, FS, and FY is significantly better than that of F (–). The prognosis of R (heterozygote) is significantly better than that of RR (homozygote). The prognosis of S (heterozygote) or S (–) is significantly better than that of SS (homozygote). Since the survival rate of FR is 74.2%, the prognosis is significantly good. At Position 16, since the survival rate of QY is 100%, the prognosis is significantly good. At Position 26, the prognosis of F (heterozygote) is significantly better than that of FF (homozygote). At Position 31, the prognosis of I (+) is significantly better than that of I (–). The prognosis of F (heterozygote) is significantly better than that of FF (homozygote). The prognosis of I (heterozygote) is significantly better than that of I (–). At Position 37, the prognosis of F (–) or F (heterozygote) is significantly better than that of FF (homozygote). Since the survival rate of FL is 83.3%, the prognosis is significantly good. At Position 57, the prognosis of S (heterozygote) or S (–) is significantly better than that of SS (homozygote). Since the survival rate of AV is 88.9%, the prognosis is significantly good. Since the survival rate of KR at Position 71 is 78.8%, the prognosis is significantly good. Since the survival rate of ER at Position 74 is 100%, the prognosis is significantly good. At Position 96, the prognosis of Q (–) or Q (heterozygote) is significantly better than that of QQ (homozygote). Since the survival rate of EE is 100%, the prognosis is significantly good. At Position 133, the prognosis of R (+) is significantly better than that of R (–). At Position 142, the prognosis of V (+) is significantly better than that of V (–). At Position 233, the prognosis of R (heterozygote), T (heterozygote), or T (–) is significantly better than that of TT (homozygote).

Treatment Effect Analysis of DRB1*Gene in All Cancer Cases (FIG. 55 to 57)

Position –17: Since the survival rate of AA is 71.4%, the treatment effect of the anticancer immunotherapy after the cancer resection (Immunotherapy) is significantly good. Position 9: Since the survival rate of KW is 86.7%, the treatment effect is significantly good with the anticancer immunotherapy after the cancer resection (Immunotherapy). Position 10: The treatment effect of E (–) is significantly better than that of E (+) with the anticancer immunotherapy after the cancer resection (Immunotherapy). The treatment effect of E (–) is significantly better than that of E (heterozygote) with the anticancer immunotherapy after the cancer resection (Immunotherapy). Position 11: The treatment effect of V (homozygote) or V (–) is significantly better than that of V (heterozygote) with the anticancer immunotherapy after the cancer resection (Immunotherapy). Since the survival rate of DS is 83.4% and that of DV is 79.6%, the treatment effect is significantly good with the cancer resection alone (no adjuvant therapy). Since the survival rate of DP is 84.6%, the treatment effect is significantly good with the anticancer immunotherapy after the cancer resection (Immunotherapy). Position 13: The treatment effect of S (heterozygote) is significantly better than that of S (–) or S (homozygote) with the anticancer immunotherapy after the cancer resection (Immunotherapy). Since the survival rate of GH is 89.9%, the treatment effect is significantly good with the cancer resection alone (no adjuvant therapy). Since the survival rate of FS is 81.9%, the treatment effect is significantly good with the cancer resection alone (no adjuvant therapy). Position 26: The treatment effect of L (+) is significantly better than that of L (–) with the anticancer chemotherapy after the cancer resection (Chemotherapy). The treatment effect of L (heterozygote) is significantly better than that of L (–) or L (homozygote) with the anticancer chemotherapy after the cancer resection (Chemotherapy). The treatment effect of L (heterozygote) or L (–) is significantly better than that of L (homozygote) with the anticancer immunotherapy after the cancer resection (Immunotherapy). Since the survival rate of FL is 87%, the treatment effect is significantly good with the cancer resection alone (no adjuvant therapy). Since the survival rate of FL is 61.4, the treatment effect is significantly good with the anticancer immunotherapy after the cancer resection (Immunotherapy). Position 28: The treatment effect of E (heterozygote) or E (–) is significantly better than that of E (homozygote) with the anticancer immunotherapy after the cancer resection (Immunotherapy). Position 30: The treatment effect of H (+) is significantly better than that of H (–) with the cancer resection alone (no adjuvant therapy). The treatment effect of R (–) is significantly better than that of R (+) with the anticancer immunotherapy after the cancer resection (Immunotherapy). The treatment effect of R (–) is significantly better than that of R (heterozygote) with the anticancer immunotherapy after the cancer resection (Immunotherapy). Position 31: The treatment effect of V (–) is significantly better than that of V (+) with the anticancer immunotherapy after the cancer resection (Immunotherapy). The treatment effect of V (–) is significantly better than that of V (heterozygote) with the anticancer immunotherapy after the cancer resection (Immunotherapy). Since the survival rate of FF is 55.5% and that of FI is 60.7%, the treatment effect is significantly good with the anticancer immunotherapy provided after the cancer resection (Immunotherapy). Position 37: The treatment effect of F (–) is significantly better than that of F (+) with the anticancer chemotherapy after the cancer resection (Chemotherapy). The treatment effect of L (+) is significantly better than that of L (–) with the cancer resection alone (no adjuvant therapy). The treatment effect of N (+) is significantly better than that of N (–) with the anticancer immunotherapy after the cancer resection (Immunotherapy). The treatment effect of F (–) is significantly better than that of F (heterozygote) or F (homozygote) with the anticancer chemotherapy after the cancer resection (Chemotherapy). The treatment effect of N (heterozygote) or N (homozygote) is significantly better than that of N (–) with the anticancer immunotherapy after the cancer resection (Immunotherapy). Since the survival rate of LY is 70.9%, the treatment effect is significantly good with the anticancer chemotherapy after the cancer resection (Chemotherapy). Since the survival rate of NS is 72.5%, the treatment effect is significantly good with the anticancer immunotherapy after the cancer resection (Immunotherapy). Position 38: The treatment effect of A (–) is significantly better than that of A (+) with the anticancer immunotherapy after the cancer resection (Immunotherapy). The treatment effect of L (+) is significantly better than that of L (–) when the cancer resection alone is given (no adjuvant therapy). The treatment effect of A (–) is significantly better than that of A (heterozygote) with the anticancer immunotherapy after the cancer resection (Immunotherapy). Position 40: The treatment effect of Y (–) is significantly better than that of Y (+) with the anticancer immunotherapy after the cancer resection (Immunotherapy). The treatment effect of F (homozygote) is significantly better than that of F (heterozygote) with the anticancer immunotherapy after the cancer resection (Immunotherapy). The treatment effect of Y (–) is significantly better than that of Y (heterozygote) with the anticancer immunotherapy after the cancer resection (Immunotherapy). The treatment effective rate is 57.5% for FF with the anticancer immunotherapy after the cancer resection (Immunotherapy). Position 57: The treatment effect of A (–) is significantly better than that of A (+) with the anticancer chemotherapy after the cancer resection (Chemotherapy). The treatment effect of S (heterozygote) or S (–) is significantly better than that of S (homozygote) when the cancer resection alone is given (no adjuvant therapy). Since the survival rate of SV is 92.2%, the treatment effect is significantly good with the cancer resection alone (no adjuvant therapy). Since the survival rate of DD is 60.3%, the treatment effect is significantly good with the anticancer chemotherapy after the cancer resection (Chemotherapy). Since the survival rate of AD is 76.25, the treatment effect is significantly good with the anticancer immunotherapy after the cancer resection (Immunotherapy). Position 60: The treatment effect of H (–) is significantly better than that of H (+) with the anticancer chemotherapy after the cancer resection (Chemotherapy). Since the survival rate of YY is 56.8%, the treatment effect is significantly good with the anticancer chemotherapy after the cancer resection (Chemotherapy). Position 67: The treatment effect of I (−) is significantly better than that of I (+) with the anticancer immunotherapy after the cancer resection (Immunotherapy). The treatment effect of L (−) is significantly better than that of L (+) with the anticancer chemotherapy after the cancer resection (Chemotherapy). The treatment effect of I (−) is significantly better than that of I (homozygote) or I (heterozygote) with the anticancer immunotherapy after the cancer resection (Immunotherapy). The treatment effect of L (heterozygote) is significantly better than that of L (−) or L (homozygote) with the cancer resection alone (no adjuvant therapy). The treatment effect of L (−) is significantly better than that of L (heterozygote) or L (homozygote) with the anticancer chemotherapy after the cancer resection (Chemotherapy). Since the survival rate of IL is 82.8%, the treatment effect is significantly good with the cancer resection alone (no adjuvant therapy). Since the survival rate of FI is 63.4%, the treatment effect is significantly good with the anticancer chemotherapy after the cancer resection (Chemotherapy). Since the survival rate of FL is 68%, the treatment effect is significantly good with the anticancer immunotherapy after the cancer resection (Immunotherapy). Position 70: The treatment effect of R (−) is significantly better than that of R (+) with the anticancer chemotherapy after the cancer resection (Chemotherapy). Position 71: The treatment effect of K (−) is significantly better than that of K (+) with the cancer resection alone (no adjuvant therapy). The treatment effect of A (heterozygote) or A (−) is significantly better than that of A (homozygote) with the cancer resection alone (no adjuvant therapy). The treatment effect of E (heterozygote) or E (−) is significantly better than that of E (homozygote) with the cancer resection alone (no adjuvant therapy). Since the survival rate of RR is 81.8%, the treatment effect is significantly good with the cancer resection alone (no adjuvant therapy). Since the survival rate of ER is 73.7%, the treatment effect is significantly good with the anticancer immunotherapy after the cancer resection (Immunotherapy). Position 74: The treatment effect of E (−) is significantly better than that of E (+) with the anticancer chemotherapy after the cancer resection (Chemotherapy). The treatment effect of E (+) is significantly better than that of E (−) with the anticancer immunotherapy after the cancer resection (Immunotherapy). A (heterozygote) or A (−) have better treatment effects than A (homozygote) with the anticancer immunotherapy after the cancer resection (Immunotherapy). The treatment effect of E (heterozygote) or E (homozygote) is significantly better than that of E (−) with the anticancer immunotherapy after the cancer resection (Immunotherapy). Position 85: The treatment effect of A (+) is significantly better than that of A (−) with the cancer resection alone (no adjuvant therapy). Position 96: Q (−) and Q (heterozygote) have better treatment effects than Q (homozygote) when with the cancer resection alone (no adjuvant therapy). Since the survival rate of HY is 81.8%, the treatment effect is significantly good with the cancer resection alone (no adjuvant therapy). Position 120: The treatment effect of N (homozygote) is significantly better than that of N (−) or N (heterozygote) with the anticancer immunotherapy after the cancer resection (Immunotherapy). The treatment effect of S (−) is significantly better than that of S (homozygote) or S (heterozygote) with the anticancer immunotherapy after the cancer resection (Immunotherapy). Position 133: Since the survival rate of RR is 73.9%, the treatment effect is significantly good with the cancer resection alone (no adjuvant therapy). Position 142: Since the survival rate of VV is 79.9%, the treatment effect is significantly good with the cancer resection alone (no adjuvant therapy). Position 166: The treatment effect of Q (−) is significantly better than that of Q (+) with the anticancer immunotherapy after the cancer resection (Immunotherapy). The treatment effect of Q (−) is significantly better than that of Q (heterozygote) with the anticancer immunotherapy after the cancer resection (Immunotherapy). The treatment effect of R (−) is significantly better than that of R (heterozygote) with the anticancer immunotherapy after the cancer resection (Immunotherapy). Since the survival rate of RR is 57.5%, the treatment effect is significantly good with the anticancer immunotherapy after the cancer resection (Immunotherapy). Position 231: The treatment effect of P (−) is significantly better than that of P (+) with the anticancer immunotherapy after the cancer resection (Immunotherapy). The treatment effect of P (−) is significantly better than that of P (heterozygote) with the anticancer immunotherapy after the cancer resection (Immunotherapy). The treatment effect of Q (heterozygote) is significantly better than that of Q (homozygote) with the anticancer immunotherapy after the cancer resection (Immunotherapy). Since the survival rate of QQ is 57.5%, the treatment effect is significantly good with the anticancer immunotherapy after the cancer resection (Immunotherapy).

Treatment Effect Analysis of DRB1*Gene in Stomach Cancer Cases (FIG. 55 to 57)

Position 9: The treatment effect of E (−) or E (homozygote) is significantly better than that of E (heterozygote) with the anticancer immunotherapy after the cancer resection (Immunotherapy). Since the survival rate of KW is 84.6%, the treatment effect is significantly good with the anticancer immunotherapy after the cancer resection (Immunotherapy). Position 10: The treatment effect of E (−) yields better results than E (+) with the anticancer immunotherapy after the cancer resection (Immunotherapy). The treatment effect of E (−) is significantly better than that of E (heterozygote) with the anticancer immunotherapy after the cancer resection (Immunotherapy). Position 11: The treatment effect of V (homozygote) or V (−) is significantly better than that of V (heterozygote) with the anticancer immunotherapy after the cancer resection (Immunotherapy). Position 13: The treatment effect of H (homozygote) or H (−) is significantly better than that of H (heterozygote) with the anticancer immunotherapy after the cancer resection (Immunotherapy). Position 26: The treatment effect of L (heterozygote) or L (−) is significantly better than that of L (homozygote) with the anticancer chemotherapy after the cancer resection (Chemotherapy). The treatment effect of L (heterozygote) or L (−) is significantly better than that of L (homozygote) with the anticancer immunotherapy after the cancer resection (Immunotherapy). Since the survival rate of LY is 66.7%, the treatment effect is significantly good with the anticancer immunotherapy after the cancer resection (Immunotherapy). Position 28: The treatment effect of E (heterozygote) or E (−) is significantly better than that of E (homozygote) with the anticancer immunotherapy after the cancer resection (Immunotherapy). Since the survival rate is of EH is 68.6%, the treatment effect is significantly good with the anticancer immunotherapy after the cancer resection (Immunotherapy). Position 30: The treatment effect of R (−) is significantly better than that of R (+) with the anticancer immunotherapy after the cancer resection (Immunotherapy). Position 31: The treatment effect of V (−) is significantly better than that of V (+) with the anticancer immunotherapy after the cancer resection (Immunotherapy). The treatment effect of V (−) is significantly better than that of V (heterozygote) with the anticancer immunotherapy after the cancer resection (Immunotherapy). Position 33: The treatment effect of N (−) is significantly better than that of N (+) with the anticancer immunotherapy after the cancer resection (Immunotherapy). The treatment effect of H (homozygote) h is significantly better than that of H (−) or H (heterozygote) with the anticancer immunotherapy after the cancer resection (Immunotherapy). The treatment effect of N (−) is significantly better than that of N (homozygote) or N (heterozygote) with the anticancer immunotherapy after the cancer resection (Immunotherapy). Since the survival rate 87.5% for HH, the treatment effect is significantly good with the anticancer immunotherapy after the cancer resection (Immunotherapy). Position 37: Since the survival rate of NS is 69.1%, the treatment effect is significantly good with the anticancer immunotherapy after the cancer resection (Immunotherapy). Position 38: The treatment effect of A (−) is significantly better than that of A (+) with the anticancer immunotherapy after the cancer resection (Immunotherapy) and better than A (heterozygote) with the anticancer immunotherapy after the cancer resection (Immunotherapy). Position 40: The treatment effect of Y (−) is significantly better than that of Y (heterozygote) with the anticancer immunotherapy after the cancer resection (Immunotherapy). Position 57: Since the survival rate of SV is 100%, the treatment effect is significantly good with the cancer resection alone (no adjuvant therapy). Since the survival rate of AD is 83.3%, the treatment effect is significantly good with the anticancer immunotherapy after the cancer resection (Immunotherapy). Position 67: The treatment effect of I (homozygote) is significantly better than that of I (heterozygote) or I (−) with the anticancer chemotherapy after the cancer resection (Chemotherapy). The treatment effect of L (−) or L (homozygote) is significantly better than that of L (heterozygote) with the anticancer chemotherapy after the cancer resection (Chemotherapy). Since the survival rate of II is 74.8%, the treatment effect is significantly good with the anticancer chemotherapy after the cancer resection (Chemotherapy). Position 70: The treatment effect of D (heterozygote) is significantly better than that of D (homozygote) or D (−) with the cancer resection alone (no adjuvant therapy). Position 71: The treatment effect of K (−) is significantly better than that of K (+) with the cancer resection alone (no adjuvant therapy). Since the survival rate of ER is 91.7%, the treatment effect is significantly good with the cancer resection alone (no adjuvant therapy). Since the survival rate of AA is 77.8%, the treatment effect is significantly good with the anticancer chemotherapy after the cancer resection (Chemotherapy). Position 73: The treatment effect of G (−) is significantly better than that of G (+) with the anticancer chemotherapy after the cancer resection (Chemotherapy). The treatment effect of A (homozygote) is significantly better than that of A (heterozygote) with the anticancer chemotherapy after the cancer resection (Chemotherapy). The treatment effect of G (−) is significantly better than that of G (heterozygote) with the anticancer chemotherapy after the cancer resection (Chemotherapy). Since the survival rate of AA is 58%, the treatment effect is significantly good with the anticancer chemotherapy after the cancer resection (Chemotherapy). Position 74: The treatment effect of R (−) is significantly better than that of R (+) with the anticancer chemotherapy after the cancer resection (Chemotherapy). The treatment effect of A (heterozygote) or A (−) is significantly better than that of A (homozygote) with the anticancer immunotherapy after the cancer resection (Immunotherapy). The treatment effect of A (−) is significantly better than that of A (heterozygote) with the anticancer chemotherapy after the cancer resection (Chemotherapy). Since the survival rate of EL is 90.9%, the treatment effect is significantly good with the cancer resection alone (no adjuvant therapy). Since the survival rate of AL is 66.1%, the treatment effect is significantly good with the anticancer chemotherapy after the cancer resection (Chemotherapy). Since the survival rate of AE is 67.5%, the treatment effect is significantly good with the anticancer immunotherapy after the cancer resection (Immunotherapy). Position 78: The treatment effect of N (−) is significantly better than that of N (+) with the anticancer chemotherapy after the cancer resection (Chemotherapy). The treatment effect of N (−) is significantly better than that of N (heterozygote) with the anticancer chemotherapy after the cancer resection (Chemotherapy). The treatment effect of T (homozygote) is significantly better than that of T (heterozygote) with the anticancer chemotherapy after the cancer resection (Chemotherapy). Since the survival rate of TT is 58%, the treatment effect is significantly good with the anticancer chemotherapy after the cancer resection (Chemotherapy). Position 166: The treatment effect of Q (−) is significantly better than that of Q (heterozygote) with the anticancer immunotherapy after the cancer resection (Immunotherapy). The treatment effect of R (−) is significantly better than that of R (heterozygote) with the anticancer immunotherapy after the cancer resection (Immunotherapy). Since the survival rate of RR is 55.2%, the treatment effect is significantly good with the anticancer immunotherapy after the cancer resection (Immunotherapy). Position 231: The treatment effect of P (−) is significantly better than that of P (heterozygote) with the anticancer immunotherapy after the cancer resection (Immunotherapy). The treatment effect of Q (heterozygote) is significantly better than that of Q (homozygote) with the anticancer immunotherapy after the cancer resection (Immunotherapy).

Treatment Effect Analysis of DRB1*Gene in Other Cancer Cases (FIG. 59 to 61)

Position −1: Since the survival rate of AA is 100%, the treatment effect is significantly good with the cancer resection alone (no adjuvant therapy). Position 9: The treatment effect of W (heterozygote) or W (−) is significantly better than that of W (homozygote) with the cancer resection alone (no adjuvant therapy). Since the survival rate of KW is 88.9%, the treatment effect is significantly good with the cancer resection alone (no adjuvant therapy). Position 11: The treatment effect of P (heterozygote) or P (−) is significantly better than that of P (homozygote) with the cancer resection alone (no adjuvant therapy). Position 13: The treatment effect of R (heterozygote) or R (−) is significantly better than that of R (homozygote) with the cancer resection alone (no adjuvant therapy). The treatment effect of S (heterozygote) or S (−) is significantly better than that of S (homozygote) with the anticancer chemotherapy after the cancer resection (Chemotherapy). The treatment effect of S (heterozygote) is significantly better than that of S (−) or S (homozygote) with the anticancer immunotherapy after the cancer resection (Immunotherapy). Since the survival rate of FR is 90%, the treatment effect is significantly good with the cancer resection alone (no adjuvant therapy). Since the survival rate of FR is 72%, the treatment effect is significantly good with the anticancer chemotherapy after the cancer resection (Chemotherapy). Since the survival rate of FS is 100%, the treatment effect is significantly good with the anticancer immunotherapy after the cancer resection (Immunotherapy). Position 26: The treatment effect of F (−) or F (heterozygote) is significantly better than that of F (homozygote) with the anticancer chemotherapy after the cancer resection (Chemotherapy). Position 28: Since the survival rate of EE is 100%, the treatment effect is significantly good with the anticancer chemotherapy after the cancer resection (Chemotherapy). Position 32: The treatment effect of Y (+) is significantly better than that of Y (−) with both the anticancer immunotherapy after the cancer resection (Immunotherapy) and the anticancer chemotherapy after the cancer resection (Chemotherapy). The treatment effect of H (−) is significantly better than that of H (+) with the anticancer chemotherapy after the cancer resection (Chemotherapy). The treatment effect of H (−) or H (heterozygote) is significantly better than that of H (homozygote) with the anticancer chemotherapy after the cancer resection (Chemotherapy). The treatment effect of Y (heterozygote) or Y (homozygote) is significantly better than that of Y (−) with both the anticancer chemotherapy after the cancer resection (Chemotherapy) and the anticancer immunotherapy after the cancer resection (Immunotherapy). Since the survival rate of HY is 55.6%, the treatment effect is significantly good with both the anticancer chemotherapy after the cancer resection (Chemotherapy) and the anticancer immunotherapy after the cancer resection (Immunotherapy). Position 37: The treatment effect of F (−) or F (heterozygote) is significantly better than that of F (homozygote) with the anticancer chemotherapy after the cancer resection (Chemotherapy). The treatment effect of S (heterozygote) or S (−) is significantly better than that of S (homozygote) with the cancer resection alone (no adjuvant therapy). Since the survival rate of YY is 81.3% the treatment effect is significantly good with the cancer resection alone (no adjuvant therapy). Since the survival rate of FS is 100%, the treatment effect is significantly good with the anticancer chemotherapy after the cancer resection (Chemotherapy). Since the survival rate of NS is 80%, the treatment effect is significantly good with the anticancer immunotherapy after the cancer resection (Immunotherapy). The same results are found at Position 57, 60, 67, 71, 74, 86, 96, 98, 104, 113, 142, and 233, therefore it is proved that the polymorphic amino acids on the specific positions have important significance in the treatments [the cancer resection alone (no adjuvant therapy), the anticancer chemotherapy after the cancer resection (Chemotherapy), and the anticancer immunotherapy after the cancer resection (Immunotherapy)].

Other Analysis of DRB1*Gene (FIG. 58 to 60)

Polymorphic amino acids at Position 85 have significance in Cancer in Family. Polymorphic amino acids at Position 24 have significance in the cancer metastases. Polymorphic amino acids at Position 13, 16, and 33 have significance in advanced cancers. Polymorphic amino acids at Position 1 have significance in smoking and cancers.

II. DPB1*Gene (Influence of Polymorphic Amino Acids at the Specific Positions of DPB1*Gene on Prognosis and Treatment Effects)

Prognosis Analysis of DPB1*Gene in All Cancer Cases (FIG. 61 to 62)

From the figures, the polymorphic amino acids which have significant treatment effect is not confirmed.

Prognosis Analysis of DPB1*Gene in Stomach Cancer Cases (FIG. 61 to 62)

From the figures, it is confirmed that the polymorphic amino acids at Position 35 have significance in prognosis in stomach cancer cases.

Prognosis Analysis of DPB1*Gene in Other Cancer Cases (FIG. 61 to 62)

From the figures, it is confirmed that the polymorphic amino acids at Position 8, 9, 11, 69, and 76 have significance in prognosis in other cancer cases (other than stomach cancer cases).

Treatment Effect Analysis of DPB1*Gene in All Cancer Cases (FIG. 61 to 62)

From the figures, it is confirmed that the polymorphic amino acids at Position 55 and 69 have significance in treatment effects in all cancer cases. The treatment effect of the cancer resection alone (no adjuvant therapy) is significantly good in all cases.

Treatment Effect Analysis of DPB1*Gene in Stomach Cancer Cases (FIG. 63 to 64)

From the figures, it is confirmed that the polymorphic amino acids at Position 9, 35, 36, 55, 69, and 76 of the polymorphic amino acids have significance in treatment effects in stomach cancer cases. The treatment effects are confirmed in the cancer resection alone (no adjuvant therapy), the anticancer chemotherapy after the cancer resection (Chemotherapy), and the anticancer immunotherapy after the cancer resection (Immunotherapy).

Treatment Effect Analysis of DPB1*Gene in Other Cancer Cases (FIG. 63 to 64) (FIG. 65 to 66)

From the figures, it is confirmed that the polymorphic amino acids at Position 8, 9, 11, 55, 56, 57, 65, 69, 76, 84, 85, and 86 have significance in treatment effects in other cancer cases (other than stomach cancers). The treatment effect is significantly good with the cancer resection alone (no adjuvant therapy).

The polymorphic amino acids at Position 8, 11, 57, 76, 84, 85, 86, and 87 have significance in the rate of malignant cancers. The polymorphic amino acids at Position 55 have significance in cancer metastases. The polymorphic amino acids at Position 69 have significance in a relationship between smoking and cancer. The polymorphic amino acids at Position 55 and 69 have significance in age (below 50 years old)

III. DQB1*Gene (Influences of Polymorphic Amino Acids on the Specific Positions of DQB1*Gene on Prognosis and Treatment Effects)

Prognosis Analysis of DQB1*Gene in All Cancer Cases (FIG. 67 to 69)

From the figures, it is confirmed that the polymorphic amino acids at Position 9, 55, 56, 57, 66, 67, 70, 71, and 74 have significance in prognosis in all cancer cases.

Prognosis Analysis of DQB1*Gene in Stomach Cancer Cases (FIG. 67 to 69)

From the figures, it is confirmed that the polymorphic amino acids at Position −5, 9, 55, 66, and 67 have significance in prognosis in stomach cancer cases.

Prognosis Analysis of DQB1*Gene in Other Cancer Cases (FIG. 67 to 69)

From the figures, it is confirmed that the polymorphic amino acids at Position 9, 23, 56, 66, 67, 70, 71, 86, and 87 of the polymorphic amino acids have significance in prognosis in other cancer cases (other than stomach cancer cases).

Treatment Effect Analysis of DQB1*Gene in All Cancer Cases (FIG. 67 to 69) (FIG. 70 to 72)

From the figures, it is confirmed that in all cancer cases the polymorphic amino acids at Position −21, −6, −5, −4, 3, 9, 30, 57, 66, 67, 86, 87, and 130 have significance in treatment effects with the cancer resection alone (no adjuvant therapy), the anticancer chemotherapy after the cancer resection (Chemotherapy), and the anticancer immunotherapy after the cancer resection (Immunotherapy).

Treatment Effect Analysis of DQB1*Gene in Stomach Cancer Cases (FIG. 70 to 72)

From the figures, it is confirmed that in stomach cancer cases the polymorphic amino acids at Position −21, −6, −5, −4, 9, 30, 38, 57, 66, 67, 86, 87, and 197 have significance in treatment effects with the cancer resection alone (no adjuvant therapy), the anticancer chemotherapy after the cancer resection (Chemotherapy), and the anticancer immunotherapy after the cancer resection (Immunotherapy).

Treatment Effect Analysis of DQB1*Gene in Other Cancer Cases (FIG. 70 to 72)

From the figures, it is confirmed that in other cancer cases (excluding stomach cancer cases) the polymorphic amino acids at Position −5, −3, 9, 37, 38, 66, 67, 70, 71, 86, 87, and 197 significance in treatment effects with the cancer resection alone (no adjuvant therapy), the anticancer chemotherapy after the cancer resection (Chemotherapy), and the anticancer immunotherapy after the cancer resection (Immunotherapy).

Other Analysis of DQB1*Gene (FIG. 73 to 75)

From the figures, it is confirmed that polymorphic amino acids at Position 45, 53, 55, 84, 140, 182, 220, and 221 have significance in Cancer in Family.

[Performed Case 10]

Relational Analysis of Variation in the Base Sequences of the Specific Amino Acid Position of DQB1*, DRB1*, and DPB1*Gene with Treatment Effects FIG. 76-84 shows, from left, Nucleic Acid (Position of Amino Acid Sequence, "−16" means the pre-area of the gene and "4" means Position 4.), Number of Diversity (Number of polymorphic amino acids at the position, "3" means that 3 kinds of amino acids exist), Total (total number of stomach cancer and other cancer cases), Stomach (Stomach cancer cases), Other cancer (other cancer cases), Treatment Effect [rate of 5-year survival (Total Case, Stomach Cancer, Other Cancer)], Cancer In Family (family with history of having cancer patients), Alcohol (patients with a habit of drinking alcohol), Metastases (patients with cancer metastases), and Smoking (patients with a habit of smoking). For example, "aGCGaGCG>aGCGaGCU" under DRB1*gene (column: −16 and row: Total Stomach) means that the lower-case alphabet "a" is the single character code of the amino acid which is followed with the corresponding base sequence GCG. Thus, it means that on the whole homozygote is more significant than heterozygote. Also, "kAAAkAAA>kAAGkAAG>kAAAkAAG" under DRB1*gene (column: 12, row: stomach cancer treatment effect) means that the lower-case alphabet "k" is a single character code of the amino acid which is followed with the corresponding base sequence AAA or AAG. Both kAAA-kAAA and kAAGkAAG are homozygotic while kAAA-kAAG is heterozygotic. Thus, it indicates that the treatment effects of kAAAkAAA and kAAGkAAG (homozygote) are significantly better than that of kAAAkAAG (heterozygote) with the anticancer immunotherapy after the cancer resection (Immunotherapy). And so forth, the relationship of the base sequences with the treatments [the cancer resection alone (no adjuvant therapy), the anticancer chemotherapy after the cancer resection (Chemotherapy), and the anticancer immunotherapy after the cancer resection (Immunotherapy)] are shown. Data was collected from the above clinical data analysis.

I. Effect of the Polymorphic Amino Acids of DRB1*Gene and Corresponding Base Sequence on Prognosis in Total, Treatment Effect, and Otherwise.

Analysis of DRB1*Gene in All Cancer Cases (FIG. 76 to 77)

From the figures, it is confirmed that the polymorphic base sequence of the amino acid at Position 104 has significance in all cancer cases.

Analysis of DRB1*Gene in Stomach Cancer Cases (FIG. 76 to 77)

From the figures, it is confirmed that the polymorphic base sequences of the amino acid at Position −16a, 28hc, and 72r have significance in stomach cancer cases.

Analysis of DRB1*Gene in Other Cancer Cases (FIG. 76 to 77)

From the figures, it is confirmed that the polymorphic base sequences of the amino acid at Position 57d, 58ea, and 181tm have significance in other cancer cases.

Treatment Effect Analysis of DRB1*Gene in All Cancer Cases (FIG. 76 to 77)

From the figures, it is confirmed that in all cancer cases the polymorphic base sequences of the amino acid at Position 12k, 58a, 72r, 78y, and 166r have significance in treatment effects with the cancer resection alone (no adjuvant therapy), the anticancer chemotherapy after the cancer resection (Chemotherapy), and the anticancer immunotherapy provided after the cancer resection (Immunotherapy).

Treatment Effect Analysis of DRB1*Gene in Stomach Cancer Cases (FIG. 76 to 77)

From the figures, it is confirmed that in stomach cancer cases the polymorphic base sequences of the amino acid at Position 12k and 72r have significance in treatment effects with the cancer resection alone (no adjuvant therapy), the anticancer chemotherapy after the cancer resection (Chemotherapy), and the anticancer immunotherapy after the cancer resection (Immunotherapy).

Treatment Effect Analysis of DRB1*Gene in Other Cancer Cases (FIG. 76 to 77)

From the figures, it is confirmed that in other cancer cases the polymorphic base sequences of the amino acid at Position 12k, 34q, 57da, 101v, and 166r have significance in treatment effects with the cancer resection alone (no adjuvant therapy) and the anticancer chemotherapy after the cancer resection (Chemotherapy).

Other Analysis of DRB1*Gene (FIG. 78 to 79)

From the figures, it is confirmed that the polymorphic base sequence of the amino acid has significance at Position 72r in family history, at Position 28e in drinking, and at Position 95v in cancer metastases.

II. Effect of the Polymorphic Amino Acids of DQB1*Gene and Corresponding Base Sequence on Prognosis in Total, Treatment Effect, and Other Analysis Analysis of DQB1*Gene in All and Stomach Cancer Cases (FIG. 80 to 81)

From the figures, the significance of the polymorphic base sequence is not confirmed.

Analysis of DQB1*Gene in Other Cancer Cases (FIG. 80 to 81)

From the figures, it is confirmed that the polymorphic base sequences of the amino acid at Position 2 lt, 38a, 62n, 77t, and 78v have significance in other cancer cases.

Treatment Effect Analysis of DQB1*Gene in All Cancer Cases (FIG. 80 to 81)

From the figures, it is confirmed that the polymorphic base sequence of the amino acid at Position 27v has significance in treatment effects of the anticancer immunotherapy after the cancer resection (Immunotherapy) in all cancer cases.

Treatment Effect Analysis of DQB1*Gene in Stomach Cancer Cases (FIG. 80 to 81)

From the figures, it is confirmed that the polymorphic base sequences of the amino acid at Position −23 and −15 have significance in treatment effects of the cancer resection alone (no adjuvant therapy) in stomach cancer cases.

Treatment Effect Analysis of DQB1*Gene in Other Cancer Cases (FIG. 82 to 83)

From the figures, it is confirmed that the polymorphic base sequences of the amino acid at Position 19n, 2 it, 38a, 72r, 77r, and 104a have significance in treatment effects of the cancer resection alone (no adjuvant therapy), the anticancer chemotherapy after the cancer resection (Chemotherapy), and the anticancer immunotherapy after the cancer resection (Immunotherapy) in other cancer cases.

Other Analysis of DB1*Gene (FIG. 82 to 83)

From the figures, it is confirmed that the polymorphic base sequences of the amino acid have significance at Position 140t and 210l in drinking, at Position 91l, 135d, 147l, 169d, 213l, and 215l in cancer metastases, and at Position 19n and 72r in smoking.

III. Effect of the Polymorphic Amino Acids of DPB1*Gene and Corresponding Base Sequence on Prognosis in Total, Treatment Effect, and Other Analysis In all cases, significant differences in variation are not confirmed. (FIG. 84)

[Performed Case 11]

Relations of the Amino Acids on Each Genes with the Treatments

FIG. 85 to 99 show the relationship (Compatibility) of the amino acids on the genes with the cancer resection alone (no adjuvant therapy), the anticancer chemotherapy after the cancer resection (Chemotherapy), and the anticancer immunotherapy after the cancer resection (Immunotherapy). Basic data was collected from the above clinical cases. The tables show, from the left, Position, Polymorphic Amino Acid, Treatment, and Amino Acids. For example, on DP gene, the amino acid at Position −29 is M (single character code), and M is the most appropriate for the all treatments. Since at Position 8 L and V can be present as polymorphisms, the L and V amino acids at the position have the same treatment effects as with all treatments.

I. Optimum Amino Acid of DPB1*Gene (FIG. 85 to 89)

Polymorphisms are found at Position 8, 9, 11, 35, 36, 55, 56, 57, 65, 69, 76, 84, 85, 86, 87, 96, 170, and 178. Particularly important positions are Position 36, 55, 57, 65, 69, 76, 84, 85, 87, and 178, having significance in the treatments [the cancer resection alone (no adjuvant therapy), the anticancer chemotherapy after the cancer resection (Chemotherapy), and the anticancer immunotherapy after the cancer resection (Immunotherapy)].

II. Optimum Amino Acid of DQB1*Gene (FIG. 90 to 94)

Polymorphisms are found at Position −27, −21, −18, −10, −9, −6, −5, −4, 3, 9, 13, 14, 23, 26, 28, 30, 37, 38, 45, 46, 47, 52, 53, 55, 56, 57, 66, 67, 70, 71, 74, 75, 77, 84, 85, 86, 87, 89, 90, 116, 125, 126, 130, 140, 167, 182, 185, 197, 203, 220, 221, and 224.

Particularly important positions are Position −21, −6, −5, −4, 3, 9, 13, 14, 23, 30, 37, 45, 53, 56, 57, 66, 67, 71, 74, 75, 77, 84, 85, 86, 87, 89, 90, 116, 125, 126, 130, 140, 167, 182, 185, 197, 220, 221, 224, having significance in the treatments [the cancer resection alone (no adjuvant therapy), the anticancer chemotherapy after the cancer resection (Chemotherapy), and the anticancer immunotherapy after the cancer resection (Immunotherapy)].

III. Optimum Amino Acid of DRB1*Gene (FIG. 95 to 99)

Polymorphisms are found at Position −25, −24, −17, −16, −1, 4, 9, 10, 11, 12, 13, 14, 16, 25, 26, 28, 30, 31, 32, 33, 37, 38, 40, 47, 57, 58, 60, 67, 70, 71, 73, 74, 77, 78, 85, 86, 96, 98, 104, 120, 133, 140, 142, 149, 164, 166, 180, 181, 189, 231, and 233. Particularly important positions are Position −25, −17, −16, −1, 4, 9, 10, 11, 13, 16, 26, 31, 32, 33, 37, 38, 40, 57, 60, 67, 70, 73, 74, 78, 85, 86, 96, 98, 104, 120, 133, 140, 142, 149, 166, 189, and 231, having significance in the treatments [the cancer resection alone (no adjuvant therapy), the anticancer chemotherapy after the cancer resection (Chemotherapy), and the anticancer immunotherapy after the cancer resection (Immunotherapy)].

[Performed Case 12]

Other Analysis (FIG. 100 to 129)

Statistical analysis about the polymorphisms on DPB1*, DRB1*, and DQB1*genes with respective treatment effects (controlling cancer metastases and being hard to develop to malignant tumor) are carried out. By statistical analysis about the relationships of the amino acid variations on the polymorphic positions with treatment effects, the significance of corresponding positions in the treatment effects are confirmed. This analysis enables choosing the most appropriate treatments for the patients by knowing the diverse amino acids at the polymorphic positions, and analysis of three-dimensional structure of the amino acids can be useful in drug designing. For example, three-dimensional structural analysis by pinpointing the specific amino acids which could suppress cancer metastases is very useful as a method for screening new medicines. Also, there is no doubt that this analysis provides very important significance for gene diagnosis. Signs with brackets in figures mean that the result of either amino acid is the same and there is little significance of diversity. Also, shaded cells in figures mean the positioning at the same level.

Optimum Amino Acids of DPB1*Gene to Inhibit Cancer Metastases (FIG. 100 to 104)

Position 55 is the most important position for variation of optimum amino acids for inhibiting cancer metastases. Also, all signs with brackets at Position 8, 9, 11, 35, 36, 56, 57, 65, 69, 76, 84, 85, 86, 87, 96, 170, and 178 mean that relation between the polymorphic amino acids and inhibiting cancer metastases is the same.

Optimum Amino Acids of DQB1*Gene to Inhibit Cancer Metastases (FIG. 105 to 109)

Position 14, 77, 87, 116, 125, 203, and 224 are the most important position for variation of optimum amino acids for inhibiting cancer metastases.

Optimum Amino Acids of DRB1*Gene to Inhibit Cancer Metastases (FIG. 110 to 114)

Position −24 is the most important position for variation of optimum amino acids for inhibiting cancer metastases.

Optimum Amino Acids of DPB1*Gene to Suppress Development of Malignant Tumors (FIG. 115 to 119)

Position 8, 11, 57, 76, 84, 85, 86, and 87 are the most important position for variation of optimum amino acids for suppressing development of malignant tumors.

Optimum Amino Acids of DQB1*Gene to Suppress Development of Malignant Tumors (FIG. 120 to 124)

Position 86 is the most important position for variation of optimum amino acids for suppressing development of malignant tumors.

Optimum Amino Acids of DRB1*Gene to Suppress Development of Malignant Tumors (FIG. 125 to 129)

Optimum amino acids have suppressing development of malignant tumors have no especially important positions but significance as to optimum amino acids for suppressing development to advanced cancers at Position 13, 16, and 33.

INDUSTRIAL APPLICABILITY

In accordance with the teaching herein, there are provided methods of developing new cancer curative medicines, cancer treatments, and diagnosis of cancer by analyzing polymorphisms at specific positions of DRB1*, DPB1*, and DQB1*genes. Since the relationship of the specific positions of the polymorphic amino acid variations with respect to the effect of cancer treatments together with immune ability is clearly realized, very useful means for cancer treatments as cancer treatment sensitivity (patients on whom cancer curative medicines tend to effect), cancer metastasis (patients having more cancer metastases), and more personalized cancer treatment are provided by using variations at the position as markers. It is also useful for developing new medicines with computer graphic technology, and also it improves the extreme efficiency in the efficiency parameters.

TABLE 1

| DQ Gene | | Rate of Metastases (Total)(%) | | Rate of Lymph Node Metastases(%) | | Rate of Remote Metastases(%) | |
|---|---|---|---|---|---|---|---|
| Treatment Method | | | | | | | |
| Immunotherapy | Chemotherapy | Increase | Decrease | Increase | Decrease | Increase | Decrease |
| 3(PS) | | PS 34.2 | PP 26.8 | | | | |
| 14(LM) | | LL 47.8% | LM 24.5 | LL 36.4% | LM 19.2 | LL 20% | LM 9.6 |
| 19(NS) | | NS 34.2 | NN 26.8 | | | | |
| 26(GLY) | | | | LL 30% | GL 20.1 | | |
| 30(HSY) | H homozygote, HY heterozygote %, Y homozygote % | HH 38.9 | HY 26.9 | | | | |
| 38(AV) | | AV heterozygote %. V homozygote | | | | | |
| 53(LQ) | | | | | | | |
| 57(ADSV) | V heterozygote % | | | | | | |
| 66(DE) | E homozygote | E homozygote, DE heterozygote % E homozygote | | | | DD 18.9% | DE 11.7 |
| 67(IV) | V homozygote | I homozyogote, IV heterozygote % | | | | II 18.9% | IV 11.7 |
| 77(RT) | | | RR 44% | RT 24.5 | RR 33.3 | RT 19.3 | RR 18.5 | RT 9.6 |
| 85(LV) | G homozygote | | | | | | |
| 86(AEG) | E homozygote | A homozygote % | | | | | |
| 87(FLY) | L homozygote, Y homozygote | F homozygote % | YY 39.7% | LY 24.3 | | | |

TABLE 1-continued

| DQ Gene | | Rate of Metastases (Total)(%) | | Rate of Lymph Node Metastases(%) | | Rate of Remote Metastases(%) | |
|---|---|---|---|---|---|---|---|
| Treatment Method | | | | | | | |
| Immunotherapy | Chemotherapy | Increase | Decrease | Increase | Decrease | Increase | Decrease |
| 89(GT) | | | | | | | |
| 90(IT) | | | | | | | |
| 116(LV) | | II 47.8% | IV 24.5 | II 36.4% | IV 19.2 | II 20% | IV 9.6 |
| 125(AGS) | | SS 47.8% | AS 23.9 | | | | |
| 140(AT) | | | | | | | |
| 182(NS) | | | | | | | |
| 185(IT) | | | | | | IT 15.3% | TT 10 |
| 203(IV) | | VV 34.4 | IV 27 | | | VV 15.6 | IV 11 |
| 220(HR) | | | | | | | |
| 221(HQ) | | | | | | | |

TABLE 2

| DR Gene | | Rate of Metastases (Total)(%) | | Rate of Lymph Node Metastases(%) | | Rate of Remote Metastases(%) | |
|---|---|---|---|---|---|---|---|
| Treatment Method | | | | | | | |
| Immunotherapy | Chemotherapy | Increase | Decrease | Increase | Decrease | Increase | Decrease |
| 14(EK) | | EE 30.7 | EK 0 | | | | |
| 25(QR) | | RR 30.7 | QR 0 | | | | |
| 26(FLY) | | YY 45.7 | LY 21.6 | | | FY 17.7% | LY 5.6 |
| 28(DEH) | | HH 47.1 | DE 25.3 | | | | |
| 30(CGLRY) | | | | | | | |
| 33(HN) | H homozygote % | | | | | | |
| 47(FY) | Y/F or Y homozygote | F homozygote % | | | | | |
| 57(ADSV) | AD heterozygote % | AA, AS, AV | | | | | |
| 67(FIL) | L homozygote % | I homozygote % | | | | | |
| 71(AEKR) | | A homozygote % | | | | | |
| 73(AG) | AG heterozygote % | A homozygote % | | | | | |
| 74(AELQR) | A or E homozygote % | L homozygote % | | | | | |
| 77(NT) | | | | | | NT 27.3 | TT 13.1 |
| 78(VY) | YV heterozygote | Y homozygote % | VV 47.1 | YY 29.8 | VV 41.2 | YY 23.3 | |
| 86(VG) | | | GG 31.5 | VV 21.5 | GV 25.3% | VV 14.4 | GG 15.3% | VV 10.3 |

TABLE 3

| DP Gene | | Rate of Metastases (Total)(%) | | Rate of Lymph Node Metastases(%) | | Rate of Remote Metastases(%) | |
|---|---|---|---|---|---|---|---|
| Treatment Method | | | | | | | |
| Immunotherapy | Chemotherapy | Increase | Decrease | Increase | Decrease | Increase | Decrease |
| 8(LV) | | | | VV 37.5 | LV 22.6 | | |
| 9(FHY) | FY hetero % | YY homo | | | | | |
| 11(GL) | | | | LL 37.5 | GL 22.4 | | |
| 35(FLY) | FL hetero | FF homo % | | | | | |
| 36(AV) | A homo | AV hetero % | AV 36.1 | AA 10 | | | | |
| 55(ADE) | | | AE 44.8% | AA 10 | | | | |
| 56(AE) | A homo | E homo | | | | | |
| 57(DE) | E homo | DE hetero | | | | | |
| 69(KE) | K homo % | E homo | | | | | |
| 76(IMV) | M homo | I homo % | | | | | |

The invention claimed is:

1. A method for selecting treatments for a cancer patient, comprising:

collecting genomic DNA from the patient;

amplifying the HLA DQB1* (Major histocompatibility complex, class II, DQ beta 1) gene from the genomic DNA using an automated PCR thermal sequencer;

identifying the amino acids at positions 57 and 67 of the amino acid sequence encoded by the HLA DQB1* (Major histocompatibility complex, class II, DQ beta 1) gene of the patient;

determining anti-cancer immunotherapy after cancer resection to have statistically significant probability of prolonging the cancer patient's survival, by determining that Asp is at position 57 and Val is at position 67 of the amino acid sequence encoded by the HLA DQB1* (Mayor histocompatibility complex, class II, DQ beta 1) gene; and selecting anti-cancer immunotherapy after cancer resection, as a treatment for the patient;

wherein the cancer of the patient is stomach cancer.

* * * * *